US008663616B2

(12) United States Patent
Butterick et al.

(10) Patent No.: US 8,663,616 B2
(45) Date of Patent: Mar. 4, 2014

(54) ENZYMATIC PERACID GENERATION FOR USE IN ORAL CARE PRODUCTS

(75) Inventors: Lisa A. Butterick, Swedesboro, NJ (US); Scott D. Cunningham, Chadds Ford, PA (US); Robert DiCosimo, Chadds Ford, PA (US); Kari A. Fosser, Wilmington, DE (US); Tanja Maria Gruber, Media, PA (US); Sharon L. Haynie, Philadelphia, PA (US); Mark S. Payne, Wilmington, DE (US); Pierre E. Rouviere, Wilmington, DE (US); Hong Wang, Kennett Square, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 177 days.

(21) Appl. No.: 13/330,261

(22) Filed: Dec. 19, 2011

(65) Prior Publication Data

US 2012/0328534 A1 Dec. 27, 2012

Related U.S. Application Data

(60) Provisional application No. 61/424,903, filed on Dec. 20, 2010.

(51) Int. Cl.
*A61L 9/00* (2006.01)
*C12P 7/40* (2006.01)
*C12N 9/96* (2006.01)
*C12N 9/18* (2006.01)

(52) U.S. Cl.
USPC ........... 424/76.1; 435/136; 435/188; 435/197

(58) Field of Classification Search
None
See application file for complete search history.

(56) References Cited

U.S. PATENT DOCUMENTS

| | | | |
|---|---|---|---|
| 3,901,819 A | 8/1975 | Nakagawa et al. |
| 3,974,082 A | 8/1976 | Weyn |
| 4,138,476 A | 2/1979 | Simonson et al. |
| 4,444,886 A | 4/1984 | Esders et al. |
| 5,116,575 A | 5/1992 | Badertscher et al. |
| 5,279,816 A | 1/1994 | Church et al. |
| 5,296,161 A | 3/1994 | Wiersema et al. |
| 5,302,375 A | 4/1994 | Viscio |
| 5,364,554 A | 11/1994 | Stanislowski et al. |
| 5,398,846 A | 3/1995 | Corba et al. |
| 5,490,988 A | 2/1996 | Beggs et al. |
| 5,552,018 A | 9/1996 | Devenyns |
| 5,624,634 A | 4/1997 | Brougham et al. |
| 5,683,724 A | 11/1997 | Hei et al. |
| 5,871,714 A | 2/1999 | Budny |
| 6,183,807 B1 | 2/2001 | Gutsmann et al. |
| 6,210,639 B1 | 4/2001 | Vlass et al. |
| 6,221,341 B1 | 4/2001 | Montgomery |
| 6,264,925 B1 | 7/2001 | Fuglsang et al. |
| 6,265,366 B1 | 7/2001 | Bonett et al. |
| 6,280,747 B1 | 8/2001 | Philippe et al. |
| 6,319,888 B2 | 11/2001 | Wei et al. |
| 6,391,840 B1 | 5/2002 | Thompson et al. |
| 6,545,047 B2 | 4/2003 | Gutzmann et al. |
| 6,635,286 B2 | 10/2003 | Hei et al. |
| 6,706,256 B2 | 3/2004 | Lawler et al. |
| 6,740,311 B2 | 5/2004 | White et al. |
| 6,830,745 B1 | 12/2004 | Budny |
| 7,189,385 B2 | 3/2007 | Montgomery |
| 7,220,405 B2 | 5/2007 | Huang et al. |
| 7,285,264 B2 | 10/2007 | O'Brien et al. |
| 7,384,787 B2 | 6/2008 | Kazlauskas et al. |
| 7,510,859 B2 | 3/2009 | Wieland et al. |
| 7,632,919 B2 | 12/2009 | Cunningham et al. |
| 7,662,587 B1 | 2/2010 | Cheng et al. |
| 7,700,716 B2 | 4/2010 | Cunningham et al. |
| 7,709,601 B2 | 5/2010 | Cunningham et al. |
| 7,754,460 B2 | 7/2010 | Amin et al. |
| 7,807,141 B2 | 10/2010 | Huang et al. |
| 7,858,581 B2 | 12/2010 | Cunningham et al. |
| 7,906,617 B2 | 3/2011 | Cunningham et al. |
| 7,910,347 B1 | 3/2011 | Dicosimo et al. |

(Continued)

FOREIGN PATENT DOCUMENTS

| | | |
|---|---|---|
| EP | 491782 B1 | 12/1993 |
| EP | 453097 B1 | 12/1995 |
| EP | 451972 B1 | 5/1996 |
| EP | 450800 B1 | 6/1996 |
| EP | 479600 B1 | 8/1997 |
| EP | 1689859 B1 | 3/2011 |
| WO | 0107009 A1 | 2/2001 |

OTHER PUBLICATIONS

Vincent et al, Multifunctinal xylooligosaccharide/cephalosporin C deacetylase revealed by the hemameric structure of the *Bacillus subtilis* enzyme at 1.9 A resolution, J.Mol.Biol., 2003, 330, 593-606, Science Direct.

Tomme et al., Characterization and affinity applications of cellulose-binding domains, J. of Chromatography B, 1998, 715, 283-296, Elsevier.

Han et al., Screening of Cellulose Binding Motif (CMB) from phage peptides library, Acta Biochimica et Biophysica Sinica, 1998, 30, 263-266.

(Continued)

*Primary Examiner* — Tekchand Saidha
*Assistant Examiner* — MD. Younus Meah

(57) ABSTRACT

Disclosed herein are compositions and methods to treat an oral cavity surface with a peracid-based benefit agent. The peracid benefit agent can be use for oral surface bleaching, whitening, disinfecting, destaining, deodorizing, decreasing or removing biofilm, and combinations thereof. The peracid is enzymatically generated from a carboxylic acid ester substrate using a CE-7 carbohydrate esterase having perhydrolytic activity (perhydrolase) in the presence of a source of peroxygen. A fusion protein comprising the perhydrolase coupled to a peptidic component having affinity for an oral cavity surface, either directly or through an optional linker, may be used to target the perhydrolytic activity to the oral cavity surface.

26 Claims, No Drawings

(56) References Cited

U.S. PATENT DOCUMENTS

| | | | |
|---|---|---|---|
| 7,923,233 B1 | 4/2011 | Dicosimo et al. | |
| 7,927,854 B1 | 4/2011 | Dicosimo et al. | |
| 7,928,076 B2 | 4/2011 | Cunningham et al. | |
| 7,932,072 B1 | 4/2011 | Dicosimo et al. | |
| 7,960,528 B1 | 6/2011 | Dicosimo et al. | |
| 2002/0098524 A1 | 7/2002 | Murray et al. | |
| 2005/0008526 A1 | 1/2005 | Bianchetti et al. | |
| 2005/0054752 A1 | 3/2005 | O'Brien et al. | |
| 2005/0069501 A1 | 3/2005 | Abrahim et al. | |
| 2005/0139608 A1 | 6/2005 | Muehlhausen et al. | |
| 2005/0158253 A1 | 7/2005 | Budny | |
| 2005/0226839 A1 | 10/2005 | Huang et al. | |
| 2005/0281773 A1* | 12/2005 | Wieland et al. | 424/70.14 |
| 2006/0161121 A1 | 7/2006 | Klaveness et al. | |
| 2006/0171885 A1 | 8/2006 | Janssen et al. | |
| 2007/0042924 A1 | 2/2007 | Dicosimo et al. | |
| 2007/0065387 A1 | 3/2007 | Beck et al. | |
| 2007/0082832 A1 | 4/2007 | Dicosimo et al. | |
| 2007/0105740 A1 | 5/2007 | Dicosimo et al. | |
| 2007/0184999 A1 | 8/2007 | Dicosimo et al. | |
| 2007/0196305 A1 | 8/2007 | Wang et al. | |
| 2008/0145353 A1 | 6/2008 | Amin et al. | |
| 2008/0176299 A1 | 7/2008 | Dicosimo et al. | |
| 2008/0176783 A1* | 7/2008 | DiCosimo et al. | 510/374 |
| 2008/0280810 A1 | 11/2008 | O'Brien et al. | |
| 2009/0005590 A1 | 1/2009 | Dicosimo et al. | |
| 2009/0311198 A1 | 12/2009 | Concar et al. | |
| 2010/0041752 A1 | 2/2010 | Dicosimo et al. | |
| 2010/0048448 A1 | 2/2010 | Dicosimo et al. | |
| 2010/0086510 A1 | 4/2010 | Ben-Bassat et al. | |
| 2010/0086534 A1 | 4/2010 | Dicosimo et al. | |
| 2010/0086535 A1 | 4/2010 | Dicosimo et al. | |
| 2010/0086621 A1 | 4/2010 | Ben-Bassat et al. | |
| 2010/0087528 A1 | 4/2010 | Dicosimo et al. | |
| 2010/0087529 A1 | 4/2010 | Dicosimo et al. | |
| 2010/0158823 A1 | 6/2010 | Cheng et al. | |
| 2010/0158846 A1 | 6/2010 | Fahnestock et al. | |
| 2010/0158847 A1 | 6/2010 | Fahnestock et al. | |
| 2010/0247589 A1 | 9/2010 | Fahnestock et al. | |
| 2010/0298231 A1 | 11/2010 | Schneider et al. | |
| 2010/0298240 A1 | 11/2010 | Schneider et al. | |
| 2010/0298241 A1 | 11/2010 | Schneider et al. | |
| 2010/0298531 A1 | 11/2010 | Schneider et al. | |
| 2010/0298532 A1 | 11/2010 | Schneider et al. | |
| 2010/0298533 A1 | 11/2010 | Schneider et al. | |
| 2010/0298534 A1 | 11/2010 | Schneider et al. | |
| 2010/0298535 A1 | 11/2010 | Schneider et al. | |
| 2010/0310495 A1 | 12/2010 | Schneider et al. | |
| 2011/0081693 A1 | 4/2011 | Dicosimo et al. | |
| 2011/0236335 A1 | 9/2011 | Dicosimo et al. | |
| 2011/0250673 A1 | 10/2011 | Dicosimo et al. | |

OTHER PUBLICATIONS

Hahn et al., Some New Hair Removal: Part 1, New depilation methods, Leder, 1967, 18, 184-192.

Guillen et al., Carbohydrate-binding domains: multiplicity of biological roles, Appl. Microbiolo. Biotechnology, 2010, 85, 1241-1249, Springer.

Muyldermans, Single domain camel antibodies: current status, Molecular Biotechnology, 2001, 74, 277-302, Elsevier.

Hosse et al., A new generation of protein display scaffolds for molecular recognition, Protein Science, 2006, 15, 14-27, Cold spring Harbor Laboratory Press.

Binz et al., Engineering novel binding proteins from nonimmunoglobulin domains, Nature Biotechnology, 2005, 23(10), 1257-1268, Nature Publishing Group.

Cantarel et al., The carbohydrate-active enzymes database : an expert resource for glycogenomics, Nucleic Acids Research, 2009, 37, D233-D238.

Kirk et al., Metal Free Haloperoxidases: Fact or Artifact?, Angew Chem. Int. Ed. 1999, 38, 977-979.

Bernhardt et al., Molecular basis of perhydrolase activity in serine hydrolases, Angew.chem.Int.Ed., 2005, 44, 2742-2746; Wiley-VCH Verlag GmbH & Co.

Lillie et al., Metachromatic basophilia of keratin after oxidation-cleavage of disulfide bonds, J. HistochemCytochem, 1954, 2, 95-102.

U.S. Appl. No. 61/318,016, filed Mar. 26, 2010, Dicosimo.
U.S. Appl. No. 13/330,105, filed Dec. 19, 2011, Chisholm.
U.S. Appl. No. 13/330,171, filed Dec. 19, 2011, Dicosimo.
International Search Report, PCT/US2011/065912, Mail date Sep. 27, 2012.

* cited by examiner

ENZYMATIC PERACID GENERATION FOR USE IN ORAL CARE PRODUCTS

CROSS-REFERENCE TO RELATED APPLICATIONS

This application claims benefit of U.S. Provisional Patent Application No. 61/424,903, filed Dec. 20, 2010, which is incorporated by reference herein in its entirety.

FIELD OF THE INVENTION

This invention relates to the field of personal care products comprising at least one peracid as an oral care benefit agent. The peracid is enzymatically produced in the presence of at least one suitable carboxylic acid ester substrate and a source of peroxygen. Specifically, an enzyme catalyst having perhydrolytic activity is used to produce a peracid benefit agent for use in an oral care product. The perhydrolytic enzyme may be in the form of a fusion protein (a "targeted perhydrolase") engineered to contain at least one peptidic component having affinity for an oral cavity surface such that the enzymatically produced peracid is produced on or near the desired surface.

BACKGROUND OF THE INVENTION

Peroxycarboxylic acids ("peracids") are effective antimicrobial agents. Methods to clean, disinfect, and/or sanitize hard surfaces, food products, living plant tissues, and medical devices against undesirable microbial growth have been described (e.g., U.S. Pat. No. 6,545,047; U.S. Pat. No. 6,183,807; U.S. Pat. No. 6,518,307; U.S. Pat. No. 5,683,724; and U.S. Pat. No. 6,635,286). Peracids have also been reported to be useful in preparing bleaching compositions for laundry detergent applications (e.g., U.S. Pat. No. 3,974,082; U.S. Pat. No. 5,296,161; and U.S. Pat. No. 5,364,554).

Oral care compositions comprising a peracid have also been disclosed. U.S. Pat. No. 5,302,375 to Viscio, D., discloses oral compositions for whitening teeth comprising peracetic acid dissolved in a vehicle, wherein the peracetic acid is generated within the vehicle in situ by combining water, acetylsalicylic acid, and a water soluble alkali metal percarbonate. U.S. Pat. No. 5,279,816 to Church et al. discloses the use of a composition comprising peracetic acid to whiten stained or discolored teeth. U.S. Pat. Nos. 6,221,341 and 7,189,385 to Montgomery, R., disclose peroxy acid toothwhitening compositions suitable for use in a method to whiten teeth. More specifically, a peracetic acid composition is produced by combining a hydrogen peroxide precursor, an acetic acid ester of glycerin, and water to generate, via chemical perhydrolysis, peracetic acid. Enzymatic perhydrolysis is not described.

U.S. Patent Application Publication No. 2009-0311198 to Concar et al. discloses an oral composition comprising an *M. smegmatis* enzyme having perhydrolytic activity to bleach teeth. The use of a CE-7 perhydrolase to produce a peracid benefit agent is not disclosed. Concar et al. is also silent on the use of a targeted perhydrolytic enzyme in an oral care composition.

The inclusion of specific variant subtilisin Carlsberg proteases having perhydrolytic activity in a body care product is disclosed in U.S. Pat. No. 7,510,859 to Wieland et al. Perhydrolytic enzymes beyond the specific variant proteases are not described nor are there any working examples demonstrating the enzymatic production of peracid as a personal care benefit agent.

U.S. Patent Application Publication Nos. 2008-0176783 A1; 2008-0176299 A1; 2009-0005590 A1; and 2010-0041752 A1 to DiCosimo et al. disclose enzymes structurally classified as members of the CE-7 family of carbohydrate esterases (i.e., cephalosporin C deacetylases [CAHs] and acetyl xylan esterases [AXEs]) that are characterized by significant perhydrolytic activity for converting carboxylic acid ester substrates (in the presence of a suitable source of peroxygen, such as hydrogen peroxide) into peroxycarboxylic acids at concentrations sufficient for use as a disinfectant and/or a bleaching agent. Some members of the CE-7 family of carbohydrate esterases have been demonstrated to have perhydrolytic activity sufficient to produce 4000-5000 ppm peracetic acid from acetyl esters of alcohols, diols, and glycerols in 1 minute and up to 9000 ppm between 5 minutes and 30 minutes once the reaction components were mixed (DiCosimo et al., U.S. 2009-0005590 A1). U.S. Patent application publication No. 2010-0087529 A1 describes variant CE-7 enzymes having improved perhydrolytic activity. Although the CE-7 perhydrolases have exceptional perhydrolytic activity, their use in personal care products has not been disclosed. As such, a problem to be solved is to provide personal care compositions and methods comprising the use of at least one CE-7 perhydrolase for the production of a peracid benefit agent.

Peracids are strong oxidizing agents that may be reactive towards a variety of materials, including materials not targeted for the desired benefit. As such, certain personal care applications may benefit from the ability to target/focus the peracid benefit agent to the desired body surface by localizing peracid production on or near the desired target body surface. Enzymatic peracid production may benefit by targeting the perhydrolase to the body surface. An additional benefit can be achieved by targeting the perhydrolase to a delivery material so as to limit enzyme concentration and exposure of the user.

Oral care compositions and/or methods of treating an oral care surface with an enzyme coupled to an oral cavity material have been reported. U.S. Pat. No. 4,138,476 to Simonson et al. discloses a process for treating plaque comprising the use of a glucan-degrading enzyme covalently coupled, via a complexing reagent, to a phosphate carrier group having affinity for the surface of a tooth. The enzymatic degradation of the glucan deposits is said to promote dissolution and dispersion of plaque material.

U.S. Patent Application Publication No. 2005-0158253, U.S. Pat. No. 6,830,745 to Budny et al. discloses a two-component composition comprising an anchor enzyme complex to enzymatically degrade biofilm structures and a second anchor enzyme component capable of acting directly upon bacteria. The biofilm-degrading enzymes are those that directly degrade the exopolysaccharide backbone structures.

U.S. Pat. No. 5,871,714 to Budny, J., discloses a composition for controlling bacterial growth/colonization (e.g., reducing dental plaque) comprising an enzyme that degrades the plaque matrix coupled to an anchor molecule. The use of a targeted perhydrolase is not disclosed.

U.S. Pat. No. 5,490,988 and EP 0479,600 B1 to Beggs et al. discloses the use of antibody fragments as a means for binding to a target site, wherein a therapeutic agent is connected through an additional peptide appended to the antibody fragment to attach the therapeutic agent to the target site. An oral care product is disclosed comprising a modified antibody fragment having affinity to an antigenic component of bacteria in dental plaque to delivery a therapeutic agent. The therapeutic agent may be a cytotoxic agent produced by an enzyme or a combination of enzymes, such as an oxidase in combination with a peroxidase to form oxidized halides. The use of a targeted perhydrolase to produce a peracid benefit agent is not described.

EP 0450,800 B1 to Beggs et al, discloses the utilization of two different enzymes working together to attack species occurring in the oral microflora. The first enzyme generates an intermediate product that is used as a substrate for the second enzyme to produce an agent active against a target within the mouth. Each enzyme is attached to an antibody or antibody fragment having affinity to a target surface within the mouth, whereby in use the enzymes are coupled to the target site in proximity to each other. Exemplified is a combination of a glucose oxidase to produce hydrogen peroxide which then may be converted by a peroxidase, in the presence of a halide or thiocyanate, to produce a hypohalite or hypothiocyanate, respectively. The use of a targeted perhydrolase to produce a peracid benefit agent is not described.

EP 0451,972 B1 to Beggs et al. describes a product comprising a two enzymes, the product comprising a first enzyme for generating an active agent against a target and a second enzyme for generating an intermediate which is a substrate for the first enzyme; said product further comprising a linking means (i.e., an antibody or antibody fragment) attached or attachable to both enzymes to couple the enzymes together, thereby forming a complex which binds to a target cell. Exemplified is an oxidase (capable of generating hydrogen peroxide) coupled to a peroxidase which catalyzes the formation of a hypohalite or hypothiocyanate active agent.

EP 0453,097 B1 to Beggs et al. describes the delivery of an active agent to a target site using a plurality of antibodies or antibody fragments which can self assemble to form a bridge between the agent and the target site. The active agent is glucose oxidase or a combination of a glucose oxidase and a peroxidase. The use of targeted perhydrolase to produce a peracid benefit agent is not described.

The use of antibodies, antibody fragments ($F_{ab}$), single chain fused variable region antibodies (scFc), Camelidae antibodies, and large scaffold display proteins as peptidic affinity materials may not be suitable for some personal care applications due to their size and cost. As such, there remains a need in certain low cost cosmetic applications to use shorter, less expensive peptidic affinity materials for targeted delivery of a benefit agent.

The use of shorter, biopanned peptides having strong affinity for a body surface to target a cosmetic benefit agent to a body surface has been described (U.S. Pat. Nos. 7,220,405; 7,309,482; 7,285,264 and 7,807,141; U.S. Patent Application Publication Nos. 2005-0226839 A1; 2007-0196305 A1; 2006-0199206 A1; 2007-0065387 A1; 2008-0107614 A1; 2007-0110686 A1; 2006-0073111 A1; 2010-0158846; 2010-0158847; and 2010-0247589; and published PCT applications WO2008/054746; WO2004/048399, and WO2008/073368). U.S. Pat. No. 7,807,141 to Huang et al. discloses peptide-based oral care surface reagents suitable to couple an oral care benefit agent to a tooth surface. The use of a peptidic material having affinity for an oral cavity surface to couple an active CE-7 perhydrolase (i.e., "targeted perhydrolases") for the production of a peracid benefit agent has not been described.

As such, an additional problem to be solved is to provide compositions and methods suitable to target enzymatic peracid production to an oral cavity surface.

SUMMARY OF THE INVENTION

Methods and compositions comprising components to enzymatically produce and deliver a peracid-based benefit agent to an oral cavity surface are provided.

In one embodiment, oral care compositions and methods are provided that use a CE-7 perhydrolase to enzymatically produce a peracid benefit agent for use in oral care applications such as oral cavity surface bleaching, teeth whitening, disinfecting, destaining, deodorizing, treating dental caries, preventing of dental caries, reducing oral bacteria associated with dental caries, and treating or removing oral biofilms (e.g., dental plaque).

In one embodiment, a method is provided comprising:
1) providing a set of reaction components comprising:
   a) at least one substrate selected from the group consisting of:
      i) esters having the structure

wherein X=an ester group of the formula $R_6C(O)O$
   $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
   $R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;
   m is an integer ranging from 1 to the number of carbon atoms in $R_5$; and
   wherein said esters have solubility in water of at least 5 ppm at 25° C.,
      ii) glycerides having the structure

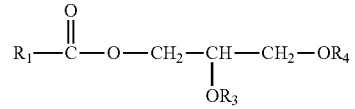

wherein $R_1$=C1 to C7 straight chain or branched chain alkyl optionally substituted with an hydroxyl or a C1 to C4 alkoxy group and $R_3$ and $R_4$ are individually H or $R_1C(O)$;
      iii) one or more esters of the formula

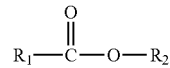

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; and
      iv) acetylated saccharides selected from the group consisting of acetylated monosaccharides, acetylated disaccharides, and acetylated polysaccharides;

b) a source of peroxygen; and
c) an enzyme catalyst having perhydrolytic activity, wherein said enzyme catalyst comprises an enzyme having a CE-7 signature motif that aligns with a reference sequence SEQ ID NO: 2 using CLUSTALW, said signature motif comprising:
   i) an RGQ motif at positions corresponding to positions 118-120 of SEQ ID NO:2;
   ii) a GXSQG motif at positions corresponding to positions 179-183 of SEQ ID NO:2; and
   iii) an HE motif at positions corresponding to positions 298-299 of SEQ ID NO:2; and
2) combining the reaction components of (1) under suitable reaction condition whereby at least one peracid is enzymatically produced; and
3) contacting an oral cavity surface with the at least one peracid whereby the oral cavity surface receives a peracid-based benefit selected from the group consisting of bleaching, teeth whitening, disinfecting, destaining, deodorizing, decreasing or removing biofilm, and combinations thereof.

In one embodiment, the oral cavity surface is tooth enamel, tooth pellicle, a soft tissue within the oral cavity (e.g. gums, tongue), or an oral cavity biofilm (e.g., oral plaque).

In another embodiment, compositions and methods are provided comprising the use of a fusion protein (i.e., a "targeted perhydrolase") comprising a perhydrolytic enzyme and a peptidic component having affinity for an oral cavity surface, wherein the two components may be optionally separated by a peptide spacer.

In one embodiment, a method is provided comprising:
1) providing a set of reaction components comprising:
   a) at least one substrate selected from the group consisting of:
      i) esters having the structure

[X]$_m$R$_5$ wherein X=an ester group of the formula R$_6$C(O)O
   R$_6$=C1 to C7 linear, branched or cyclic hydrocarbyl moiety, optionally substituted with hydroxyl groups or C1 to C4 alkoxy groups, wherein R$_6$ optionally comprises one or more ether linkages for R$_6$=C2 to C7;
   R$_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in R$_5$ individually comprises no more than one hydroxyl group or no more than one ester group or carboxylic acid group; wherein R$_5$ optionally comprises one or more ether linkages;
   m is an integer ranging from 1 to the number of carbon atoms in R$_5$; and
   wherein said esters have solubility in water of at least 5 ppm at 25° C.;
      ii) glycerides having the structure

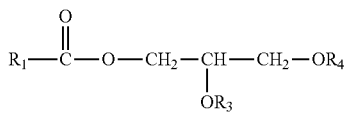

wherein R$_1$=C1 to C7 straight chain or branched chain alkyl optionally substituted with an hydroxyl or a C1 to C4 alkoxy group and R$_3$ and R$_4$ are individually H or R$_1$C(O);

iii) one or more esters of the formula

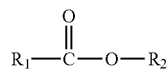

wherein R$_1$ is a C1 to C7 straight chain or branched chain alkyl optionally substituted with an hydroxyl or a C1 to C4 alkoxy group and R$_2$ is a C1 to C10 straight chain or branched chain alkyl, alkenyl, alkynyl, aryl, alkylaryl, alkylheteroaryl, heteroaryl, (CH$_2$CH$_2$O)$_n$, or (CH$_2$CH(CH$_3$)—O)$_n$H and n is 1 to 10; and
      iv) acetylated saccharides selected from the group consisting of acetylated monosaccharides, acetylated disaccharides, and acetylated polysaccharides;
b) a source of peroxygen; and
c) an enzyme catalyst having perhydrolytic activity, wherein said enzyme catalyst comprises a fusion protein having the following general structure:

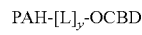

PAH-[L]$_y$-OCBD or

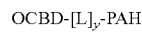

OCBD-[L]$_y$-PAH wherein
   PAH is the enzyme having perhydrolytic activity;
   OCBD is a peptidic component having affinity for the oral cavity surface; and
   L is an optional peptide linker ranging from 1 to 100 amino acids in length; and
   y is 0 or 1;
2) combining the reaction components of (1) under suitable reaction condition whereby at least one peracid is enzymatically produced; and
3) contacting an oral cavity surface with the at least one peracid whereby the oral cavity surface receives a peracid-based benefit selected from the group consisting of bleaching, teeth whitening, disinfecting, destaining, deodorizing, decreasing or removing biofilm, and combinations thereof.

The fusion protein may comprise a perhydrolytic enzyme selected from the group consisting of lipases, proteases, esterases, acyl transferases, aryl esterases, carbohydrate esterases, and combinations thereof.

In one embodiment, the fusion protein comprises a perhydrolytic aryl esterase (ArE) from *Mycobacterium smegmatis*. In another embodiment, the fusion protein comprises a perhydrolytic enzyme having an amino acid sequence with at least 95% identity to the S54V *Mycobacterium smegmatis* aryl esterase provided as SEQ ID NO: 460.

In one embodiment, the fusion protein comprises a perhydrolytic esterase from *Pseudomonas fluorescens*. In another embodiment, the fusion protein comprises a perhydrolytic enzyme having an amino acid sequence with at least 95% identity to the *Pseudomonas fluorescens* esterase provided as SEQ ID NO: 477.

In another embodiment, the fusion protein comprises a perhydrolytic enzyme having an amino acid sequence selected from the group consisting of SEQ ID NOs: 424, 425, 426, 427, 428, 429, 430, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 476, 477, 478, and 479.

In another embodiment, the fusion protein comprises a CE-7 perhydrolase having a CE-7 signature motif that aligns with a reference sequence SEQ ID NO: 2 using CLUSTALW, said signature motif comprising:

i) an RGQ motif at positions corresponding to positions 118-120 of SEQ ID NO:2;
ii) a GXSQG motif at positions corresponding to positions 179-183 of SEQ ID NO:2; and
iii) an HE motif at positions corresponding to positions 298-299 of SEQ ID NO:2.

In another embodiment, the peptidic component having affinity for an oral cavity surface is preferably a single chain peptide comprising at least one oral cavity surface-binding peptide. In yet a further embodiment, the oral cavity surface-binding peptide is a peptide having affinity for tooth enamel, tooth pellicle or both tooth enamel and tooth pellicle.

In another embodiment, a fusion protein is provided comprising the following general structure:

PAH-[L]$_y$-OCBD or

OCBD-[L]$_y$-PAH wherein
1) PAH is an enzyme having perhydrolytic activity;
2) OCBD is a peptidic component having affinity for an oral cavity surface;
3) L is an optional peptide linker ranging from 1 to 100 amino acids in length; and
4) y is 0 or 1.

In another embodiment, a fusion protein is provided comprising the general structure:

PAH-[L]$_y$-OCBD or

OCBD-[L]$_y$-PAH wherein
a) PAH is a CE-7 carbohydrate esterase having perhydrolytic activity; the PAH having a CE-7 signature motif that aligns with a reference sequence SEQ ID NO: 2 using CLUSTALW, said signature motif comprising:
  i) an RGQ motif at positions corresponding to positions 118-120 of SEQ ID NO:2;
  ii) a GXSQG motif at positions corresponding to positions 179-183 of SEQ ID NO:2; and
  iii) an HE motif at positions corresponding to positions 298-299 of SEQ ID NO:2; and
b) OCBD is a peptidic component having affinity for an oral cavity surface;
c) L is an optional peptide linker ranging from 1 to 100 amino acids in length; and
d) y is 0 or 1.

In another embodiment, an oral care product is provided comprising:
1) an enzyme catalyst comprising any of the above perhydrolytic fusion proteins;
2) at least one substrate selected from the group consisting of:
  a) esters having the structure

[X]$_m$R$_5$ wherein X=an ester group of the formula R$_6$C(O)O
  R$_6$=C1 to C7 linear, branched or cyclic hydrocarbyl moiety, optionally substituted with hydroxyl groups or C1 to C4 alkoxy groups, wherein R$_6$ optionally comprises one or more ether linkages for R$_6$=C2 to C7;

R$_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in R$_5$ individually comprises no more than one hydroxyl group or no more than one ester group or carboxylic acid group; wherein R$_5$ optionally comprises one or more ether linkages;
  m is an integer ranging from 1 to the number of carbon atoms in R$_5$; and
  wherein said esters have solubility in water of at least 5 ppm at 25° C.;
  b) glycerides having the structure

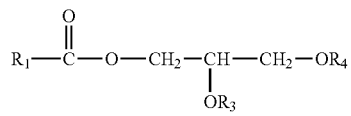

wherein R$_1$=C1 to C7 straight chain or branched chain alkyl optionally substituted with an hydroxyl or a C1 to C4 alkoxy group and R$_3$ and R$_4$ are individually H or R$_1$C(O);
  c) one or more esters of the formula

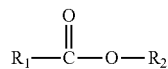

wherein R$_1$ is a C1 to C7 straight chain or branched chain alkyl optionally substituted with an hydroxyl or a C1 to C4 alkoxy group and R$_2$ is a C1 to C10 straight chain or branched chain alkyl, alkenyl, alkynyl, aryl, alkylaryl, alkylheteroaryl, heteroaryl, (CH$_2$CH$_2$O)$_n$, or (CH$_2$CH(CH$_3$)—O)$_n$H and n is 1 to 10; and
  d) acetylated saccharides selected from the group consisting of acetylated monosaccharides, acetylated disaccharides, and acetylated polysaccharides;
3) a source of peroxygen; and
4) an orally-acceptable carrier medium.

In another embodiment, an oral care product is provided comprising:
1) an enzyme catalyst having perhydrolytic activity, wherein said enzyme catalyst comprises an enzyme having a CE-7 signature motif that aligns with a reference sequence SEQ ID NO: 2 using CLUSTALW, said signature motif comprising:
  a) an RGQ motif at positions corresponding to positions 118-120 of SEQ ID NO:2;
  b) a GXSQG motif at positions corresponding to positions 179-183 of SEQ ID NO:2; and
  c) an HE motif at positions corresponding to positions 298-299 of SEQ ID NO:2; and
2) at least one substrate selected from the group consisting of:
  a) esters having the structure

[X]$_m$R$_5$ wherein X=an ester group of the formula R$_6$C(O)O
  R$_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m is an integer ranging from 1 to the number of carbon atoms in $R_5$; and wherein said esters have solubility in water of at least 5 ppm at 25° C.;

b) glycerides having the structure

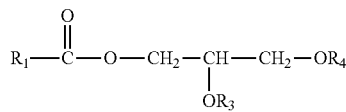

wherein $R_1$=C1 to C7 straight chain or branched chain alkyl optionally substituted with an hydroxyl or a C1 to C4 alkoxy group and $R_3$ and $R_4$ are individually H or $R_1C(O)$;

c) one or more esters of the formula

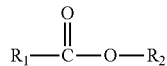

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)\text{—}O)_nH$ and n is 1 to 10; and d) acetylated saccharides selected from the group consisting of acetylated monosaccharides, acetylated disaccharides, and acetylated polysaccharides;

3) a source of peroxygen; and
4) an orally acceptable carrier medium.

In another embodiment, an isolated polypeptide having affinity for an oral cavity surface is provided, said polypeptide having an amino acid sequence selected from the group consisting of SEQ ID NOs 399, 400, 401, 402, 403, 404, 405, 406, 407, 408, 409, 410, 412, 413, 414, 415, 416, 417, 418, 419, 420, 421, and 422.

In another embodiment, the use of a CE-7 carbohydrate esterase having perhydrolytic activity in an oral care product to produce an efficacious concentration of at least one peracid to bleach, whiten, disinfect, destain, deodorize or remove biofilm from an oral cavity material/surface is also provided.

In another embodiment, the use of a peracid generation composition is provided comprising:

a) an enzyme catalyst having perhydrolytic activity, wherein said enzyme catalyst comprises an enzyme having a CE-7 signature motif that aligns with a reference sequence SEQ ID NO: 2 using CLUSTALW, said signature motif comprising:
  i) an RGQ motif at positions corresponding to positions 118-120 of SEQ ID NO:2;
  ii) a GXSQG motif at positions corresponding to positions 179-183 of SEQ ID NO:2; and
  iii) an HE motif at positions corresponding to positions 298-299 of SEQ ID NO:2; and b) at least one substrate selected from the group consisting of:
  1) esters having the structure $[X]_mR_5$ wherein X=an ester group of the formula $R_6C(O)O$
  $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
  $R_5$=a C1 to C6 linear, branched, or cyclic hydrocarbyl moiety or a five-membered cyclic heteroaromatic or six-membered cyclic aromatic or heteroaromatic moiety optionally substituted with hydroxyl groups;
  wherein each carbon atom in $R_5$ individually comprises no more than one hydroxyl group or no more than one ester group or carboxylic acid group;
  wherein $R_5$ optionally comprises one or more ether linkages;
  m is an integer ranging from 1 to the number of carbon atoms in $R_5$; and
  wherein said esters have solubility in water of at least 5 ppm at 25° C.;

2) glycerides having the structure

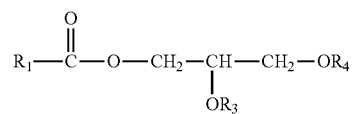

wherein $R_1$=C1 to C7 straight chain or branched chain alkyl optionally substituted with an hydroxyl or a C1 to C4 alkoxy group and $R_3$ and $R_4$ are individually H or $R_1C(O)$;

3) one or more esters of the formula

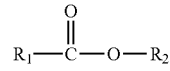

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)\text{—}O)_nH$ and n is 1 to 10; and d) acetylated saccharides selected from the group consisting of acetylated monosaccharides, acetylated disaccharides, and acetylated polysaccharides; and c) a source of peroxygen;

whereby a peracid is formed upon mixing simultaneously, or in a step-wise manner (but in no particular order), (a), (b), and (c); for the treatment or prevention of dental caries, gingivitis, oral candidiasis, or periodontitis.

In another embodiment, the use of fusion protein comprising the following general structure in an oral cavity product is provided comprising:

PAH-[L]$_y$-OCBD or

OCBD-[L]$_y$-PAH wherein
1) PAH is an enzyme having perhydrolytic activity having an amino acid sequence with at least 95% amino acid identity to SEQ ID NO: 460;

2) OCBD is a peptidic component having affinity for an oral cavity surface;
3) L is a peptide linker ranging from 1 to 100 amino acids in length; and
4) y is 0 or 1.

Several of the ester substrates described herein (Table 20) were particularly susceptible to chemical perhydrolysis when reacted with hydrogen peroxide to produce peracetic acid. In another embodiment, a personal care product is provided comprising a peracid precursor selected from the group consisting of 1, 2,3,5-tetra-O-acetyl-ribofuranose; 1,2,3,4-tetra-O-acetyl-ribopyranose; 2-acetamido-2-deoxy-1,3,4,6-tetraacetyl-β-D-glucopyranose; β-D-glucopyranose, 1,2,3,4-tetraacetate; 2,3,4,6-tetraacetyl-β-D-glucopyranose; 1,3,4,6-tetra-O-acetyl-mannopyranose; and α-D-mannopyranose pentaacetate. In a preferred embodiment, the personal care product is an oral care product.

In another embodiment, a method is also provided comprising:
 a) providing a set of reaction components comprising
  i) a peracid precursor selected form the group consisting of 1, 2,3,5-tetra-O-acetyl-ribofuranose; 1,2,3,4-tetra-O-acetyl-ribopyranose; 2-acetamido-2-deoxy-1,3,4,6-tetraacetyl-β-D-glucopyranose; (3-D-glucopyranose, 1,2,3,4-tetraacetate; 2,3,4,6-tetraacetyl-β-D-glucopyranose; 1,3,4,6-tetra-O-acetyl-mannopyranose; and α-D-mannopyranose pentaacetate; and
  ii) a source of peroxygen;
 b) contacting a body surface with an effective amount of peracetic acid produced by combining the set of reaction components in the presence of water; whereby the peracetic acid provides a benefit to the body surface. In a preferred aspect, the body surface in the above method is an oral cavity tissue, such as teeth and/or gums.

BRIEF DESCRIPTION OF THE BIOLOGICAL SEQUENCES

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO: 1 is the nucleic acid sequence encoding a cephalosporin C deacetylase from *Bacillus subtilis* ATCC® 31954™.

SEQ ID NO: 2 is the amino acid sequence of a cephalosporin C deacetylase from *Bacillus subtilis* ATCC® 31954™.

SEQ ID NO: 3 is the nucleic acid sequence encoding a cephalosporin C deacetylase from *Bacillus subtilis* subsp. *subtilis* strain 168.

SEQ ID NO: 4 is the amino acid sequence of a cephalosporin C deacetylase from *Bacillus subtilis* subsp. *subtilis* strain 168.

SEQ ID NO: 5 is the nucleic acid sequence encoding a cephalosporin C deacetylase from *B. subtilis* ATCC®6633™.

SEQ ID NO: 6 is the acid sequence of a cephalosporin C deacetylase from *B. subtilis* ATCC® 6633™.

SEQ ID NO: 7 is the nucleic acid sequence encoding a cephalosporin C deacetylase from *B. licheniformis* ATCC® 14580™.

SEQ ID NO: 8 is the deduced amino acid sequence of a cephalosporin C deacetylase from *B. licheniformis* ATCC® 14580™.

SEQ ID NO: 9 is the nucleic acid sequence encoding an acetyl xylan esterase from *B. pumilus* PS213.

SEQ ID NO: 10 is the deduced amino acid sequence of an acetyl xylan esterase from *B. pumilus* PS213.

SEQ ID NO: 11 is the nucleic acid sequence encoding an acetyl xylan esterase from *Clostridium thermocellum* ATCC®27405™.

SEQ ID NO: 12 is the deduced amino acid sequence of an acetyl xylan esterase from *Clostridium thermocellum* ATCC®27405™.

SEQ ID NO: 13 is the nucleic acid sequence encoding an acetyl xylan esterase from *Thermotoga neapolitana*.

SEQ ID NO: 14 is the amino acid sequence of an acetyl xylan esterase from *Thermotoga neapolitana*.

SEQ ID NO: 15 is the nucleic acid sequence encoding an acetyl xylan esterase from *Thermotoga maritima* MSBB.

SEQ ID NO: 16 is the amino acid sequence of an acetyl xylan esterase from *Thermotoga maritima* MSBB.

SEQ ID NO: 17 is the nucleic acid sequence encoding an acetyl xylan esterase from *Thermoanaerobacterium* sp. JW/SL YS485.

SEQ ID NO: 18 is the deduced amino acid sequence of an acetyl xylan esterase from *Thermoanaerobacterium* sp. JW/SL YS485.

SEQ ID NO: 19 is the nucleic acid sequence of a cephalosporin C deacetylase from *Bacillus* sp. NRRL B-14911. It should be noted that the nucleic acid sequence encoding the cephalosporin C deacetylase from *Bacillus* sp. NRRL B-14911 as reported in GENBANK® Accession number ZP_01168674 appears to encode a 15 amino acid N-terminal addition that is likely incorrect based on sequence alignments with other cephalosporin C deacetylases and a comparison of the reported length (340 amino acids) versus the observed length of other CAH enzymes (typically 318-325 amino acids in length; see U.S. Patent Application Publication No. US-2010-0087528-A1; herein incorporated by reference). As such, the nucleic acid sequence as reported herein encodes the cephalosporin C deacetylase sequence from *Bacillus* sp. NRRL B-14911 without the N-terminal 15 amino acids reported under GENBANK® Accession number ZP_01168674.

SEQ ID NO: 20 is the deduced amino acid sequence of the cephalosporin C deacetylase from *Bacillus* sp. NRRL B-14911 encoded by the nucleic acid sequence of SEQ ID NO: 19.

SEQ ID NO: 21 is the nucleic acid sequence encoding a cephalosporin C deacetylase from *Bacillus halodurans* C-125.

SEQ ID NO: 22 is the deduced amino acid sequence of a cephalosporin C deacetylase from *Bacillus halodurans* C-125.

SEQ ID NO: 23 is the nucleic acid sequence encoding a cephalosporin C deacetylase from *Bacillus clausii* KSM-K16.

SEQ ID NO: 24 is the deduced amino acid sequence of a cephalosporin C deacetylase from *Bacillus clausii* KSM-K16.

SEQ ID NO: 25 is the nucleic acid sequence encoding a *Bacillus subtilis* ATCC® 29233™ cephalosporin C deacetylase (CAH).

SEQ ID NO: 26 is the deduced amino acid sequence of a *Bacillus subtilis* ATCC® 29233™ cephalosporin C deacetylase (CAH).

SEQ ID NO: 27 is the deduced amino acid sequence of a *Thermotoga neapolitana* acetyl xylan esterase variant from U.S. Patent Application Publication No. 2010-0087529 (incorporated herein by reference in its entirety), where the Xaa residue at position 277 is Ala, Val, Ser, or Thr.

SEQ ID NO: 28 is the deduced amino acid sequence of a *Thermotoga maritime* MSB8 acetyl xylan esterase variant from U.S. Patent Application Publication No. 2010-0087529, where the Xaa residue at position 277 is Ala, Val, Ser, or Thr.

SEQ ID NO: 29 is the deduced amino acid sequence of a *Thermotoga lettingae* acetyl xylan esterase variant from U.S. Patent Application Publication No. 2010-0087529, where the Xaa residue at position 277 is Ala, Val, Ser, or Thr.

SEQ ID NO: 30 is the deduced amino acid sequence of a *Thermotoga petrophila* acetyl xylan esterase variant from U.S. Patent Application Publication No. 2010-0087529, where the Xaa residue at position 277 is Ala, Val, Ser, or Thr.

SEQ ID NO: 31 is the deduced amino acid sequence of a *Thermotoga* sp. RQ2 acetyl xylan esterase variant derived from "RQ2(a)" from U.S. Patent Application Publication No. 2010-0087529, where the Xaa residue at position 277 is Ala, Val, Ser, or Thr.

SEQ ID NO: 32 is the deduced amino acid sequence of a *Thermotoga* sp. RQ2 acetyl xylan esterase variant derived from "RQ2(b)" from U.S. Patent Application Publication No. 2010-0087529, where the Xaa residue at position 278 is Ala, Val, Ser, or Thr.

SEQ ID NO: 33 is the deduced amino acid sequence of a *Thermotoga lettingae* acetyl xylan esterase.

SEQ ID NO: 34 is the deduced amino acid sequence of a *Thermotoga petrophila* acetyl xylan esterase.

SEQ ID NO: 35 is the deduced amino acid sequence of a first acetyl xylan esterase from *Thermotoga* sp. RQ2 described herein as "RQ2(a)".

SEQ ID NO: 36 is the deduced amino acid sequence of a second acetyl xylan esterase from *Thermotoga* sp. RQ2 described herein as "RQ2(b)".

SEQ ID NO: 37 is the codon optimized nucleic acid sequence encoding a *Thermoanearobacterium saccharolyticum* cephalosporin C deacetylase.

SEQ ID NO: 38 is the deduced amino acid sequence of a *Thermoanearobacterium saccharolyticum* cephalosporin C deacetylase.

SEQ ID NO: 39 is the nucleic acid sequence encoding the acetyl xylan esterase from *Lactococcus lactis* (GENBANK® accession number EU255910).

SEQ ID NO: 40 is the amino acid sequence of the acetyl xylan esterase from *Lactococcus lactis* (GENBANK® accession number ABX75634.1).

SEQ ID NO: 41 is the nucleic acid sequence encoding the acetyl xylan esterase from *Mesorhizobium loti* (GENBANK® accession number NC_002678.2).

SEQ ID NO: 42 is the amino acid sequence of the acetyl xylan esterase from *Mesorhizobium loti* (GENBANK® accession number BAB53179.1).

SEQ ID NO: 43 is the nucleic acid sequence encoding the acetyl xylan esterase from *Geobacillus stearothermophilus* (GENBANK® accession number AF038547.2).

SEQ ID NO: 44 is the amino acid sequence of the acetyl xylan esterase from *Geobacillus stearothermophilus* (GENBANK® accession number AAF70202.1).

SEQ ID NO: 45 is the nucleic acid sequence encoding a variant acetyl xylan esterase (variant "A3") having the following substitutions relative to the wild-type *Thermotoga maritima* acetyl xylan esterase amino acid sequence: (F24I/S35T/Q179L/N275D/C277S/S308G/F317S).

SEQ ID NO: 46 is the amino acid sequence of the "A3" variant acetyl xylan esterase.

SEQ ID NO: 47 is the nucleic acid sequence encoding the N275D/C277S variant acetyl xylan esterase.

SEQ ID NO: 48 is the amino acid sequence of the N275D/C277S variant acetyl xylan esterase.

SEQ ID NO: 49 is the nucleic acid sequence encoding the C277S/F317S variant acetyl xylan esterase.

SEQ ID NO: 50 is the amino acid sequence of the C277S/F317S variant acetyl xylan esterase.

SEQ ID NO: 51 is the nucleic acid sequence encoding the S35T/C277S variant acetyl xylan esterase.

SEQ ID NO: 52 is the amino acid sequence of the S35T/C277S variant acetyl xylan esterase.

SEQ ID NO: 53 is the nucleic acid sequence encoding the Q179L/C277S variant acetyl xylan esterase.

SEQ ID NO: 54 is the amino acid sequence of the Q179L/C277S variant acetyl xylan esterase.

SEQ ID NO: 55 is the nucleic acid sequence encoding the variant acetyl xylan esterase 843H9 having the following substitutions relative to the wild-type *Thermotoga maritima* acetyl xylan esterase amino acid sequence: (L8R/L125Q/Q176L/V183D/F247I/C277S/P292L).

SEQ ID NO: 56 is the amino acid sequence of the 843H9 variant acetyl xylan esterase.

SEQ ID NO: 57 is the nucleic acid sequence encoding the variant acetyl xylan esterase 843F12 having the following substitutions relative to the wild-type *Thermotoga maritima* acetyl xylan esterase amino acid sequence: K77E/A 266E/C277S.

SEQ ID NO: 58 is the amino acid sequence of the 843F12 variant acetyl xylan esterase.

SEQ ID NO: 59 is the nucleic acid sequence encoding the variant acetyl xylan esterase 843C12 having the following substitutions relative to the wild-type *Thermotoga maritima* acetyl xylan esterase amino acid sequence: F27Y/I149V/A266V/C277S/I295T/N302S.

SEQ ID NO: 60 is the amino acid sequence of the 843C12 variant acetyl xylan esterase.

SEQ ID NO: 61 is the nucleic acid sequence encoding the variant acetyl xylan esterase 842H3 having the following substitutions relative to the wild-type *Thermotoga maritima* acetyl xylan esterase amino acid sequence: L195Q/C277S.

SEQ ID NO: 62 is the amino acid sequence of the 842H3 variant acetyl xylan esterase.

SEQ ID NO: 63 is the nucleic acid sequence encoding the variant acetyl xylan esterase 841A7 having the following substitutions relative to the wild-type *Thermotoga maritima* acetyl xylan esterase amino acid sequence: Y110F/C277S.

SEQ ID NO: 64 is the amino acid sequence of the 841A7 variant acetyl xylan esterase.

SEQ ID NOs: 65-221, 271, and 368 are a non-limiting list of amino acid sequences of peptides having affinity for hair.

SEQ ID NO: 217-269 are the amino acid sequences of peptides having affinity for skin.

SEQ ID NOs: 270-271 are the amino acid sequences of peptides having affinity for nail.

SEQ ID NOs 272-382 are the amino acid sequences of peptides having affinity to an oral cavity surface. SEQ ID NOs: 272-291 and 312-382 have affinity for tooth pellicle. SEQ ID NOs 292-311 have affinity for tooth enamel.

SEQ ID NOs: 383-396 are the amino acid sequences of peptide linkers/spacers.

SEQ ID NO: 397 if the nucleic acid sequence of expression plasmid pLD001.

SEQ ID NO: 398 is the nucleic acid sequence of a sequencing primer.

SEQ ID NOs: 399-410 are the amino acid sequences of tooth enamel-binding and tooth pellicle-binding peptides from Example 2.

SEQ ID NO: 411 is the amino acid sequence of tooth-binding peptides DenP03 with a C-terminal lysine as shown in Table 4.

SEQ ID NOs: 412-422 are the amino acid sequence of tooth enamel-binding peptides and tooth pellicle-binding peptides with a C-terminal lysine as shown in Table 4.

SEQ ID NO: 423 is the amino acid sequence of peptide HC263.

SEQ ID NO: 424 is the amino acid sequence of *Thermotoga maritima* variant C277S also referred to in the present application as enzyme "EZ-1".

SEQ ID NO: 425-430 and 437-467 and 479 are the amino acid sequences of various perhydrolase constructs as disclosed in Table 5 and/or Table 6.

SEQ ID NOS: 431-436 and 468-475 are the amino acid sequences of various targeting sequences disclosed in Example 4.

SEQ ID NO: 476 is the amino acid sequence of a *Thermotoga maritime* variant HTS-007-D5 having the following substitutions: C277T/R296P.

SEQ ID NO: 477 is the amino acid sequence of a *Pseudomonas fluorescens* esterase having perhydrolytic activity (U.S. Pat. No. 7,384,787; "L29P" variant. Note that the numbering of the substitution is followed from the cited patent which did not include the initial methionine residue. SEQ ID NO: 477 comprises the L29P substitution at residue position number 30 as the initial methionine is included in the present sequence).

SEQ ID NO: 478 is the amino acid sequence of the wild type *Mycobacterium smegmatis* aryl esterase (U.S. Pat. No. 7,754,460).

DETAILED DESCRIPTION OF THE INVENTION

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, "contacting" refers to placing a composition in contact with the target body surface for a period of time sufficient to achieve the desired result (target surface binding, peracid based effects, etc). In one embodiment, "contacting" may refer to placing a composition comprising (or capable of producing) an efficacious concentration of peracid in contact with a target body surface for a period of time sufficient to achieve the desired result. In another embodiment, "contacting" may also refer to the placing at least one component of a personal care composition, such as one or more of the reaction components used to enzymatic perhydrolysis, in contact with a target body surface. Contacting includes spraying, treating, immersing, flushing, pouring on or in, mixing, combining, painting, coating, applying, affixing to and otherwise communicating a peracid solution or a composition comprising an efficacious concentration of peracid, a solution or composition that forms an efficacious concentration of peracid or a component of the composition that forms an efficacious concentration of peracid with the body surface.

As used herein, the terms "substrate", "suitable substrate", and "carboxylic acid ester substrate" interchangeably refer specifically to:

(a) one or more esters having the structure $$[X]_m R_5$$

wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety or a cyclic five-membered heteroaromatic or six-membered cyclic aromatic or heteroaromatic moiety optionally substituted with a hydroxyl group; wherein each carbon atom in $R_5$ individually comprises no more than one hydroxyl group or no more than one ester group, and wherein $R_5$ optionally comprises one or more ether linkages;

m is an integer ranging from 1 to the number of carbon atoms in $R_5$, said one or more esters having solubility in water of at least 5 ppm at 25° C.; or (b) one or more glycerides having the structure

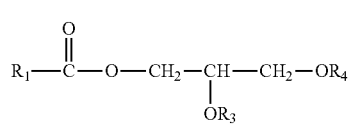

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or (c) one or more esters of the formula

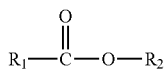

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10; or (d) one or more acetylated monosaccharides, acetylated disaccharides, or acetylated polysaccharides; or (e) any combination of (a) through (d).

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane; 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the terms "acetylated sugar" and "acetylated saccharide" refer to mono-, di- and polysaccharides comprising at least one acetyl group. Examples include, but are not limited to glucose pentaacetate; xylose tetraacetate; acetylated xylan; acetylated xylan fragments; β-D-ribofuranose-1,2,3,5-tetraacetate; tri-O-acetyl-D-galactal; and tri-O-acetyl-glucal.

As used herein, the terms "hydrocarbyl", "hydrocarbyl group", and "hydrocarbyl moiety" is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,5-pentandiol; 1,6-pentanediol; 1,2-hexanediol; 2,5-hexanediol; 1,6-hexanediol; and mixtures thereof, refer to said compounds comprising at least one ester group of the formula RC(O)O, wherein R is a C1 to C7 linear hydrocarbyl moiety. In one embodiment, the carboxylic acid ester substrate is selected from the group consisting of propylene glycol diacetate (PGDA), ethylene glycol diacetate (EDGA), and mixtures thereof.

As used herein, the term "propylene glycol diacetate" is synonymous with 1,2-diacetoxypropane, propylene diacetate, 1,2-propanediol diacetate, and all other synonyms of CAS Registry Number 623-84-7.

As used herein, the term "ethylene glycol diacetate" is synonymous with 1,2-diacetoxyethane, ethylene diacetate, glycol diacetate, and all other synonyms of CAS Registry Number 111-55-7.

As used herein, the terms "suitable enzymatic reaction mixture", "components suitable for in situ generation of a peracid", "suitable reaction components", "suitable aqueous reaction mixture", "reaction mixture", and "peracid-generating components" refer to the materials and water in which the reactants and the perhydrolytic enzyme catalyst come into contact. The peracid-generating components will include at least enzyme having perhydrolytic activity, preferably wherein the perhydrolytic enzyme is at least one CE-7 perhydrolase (optionally in the form of a fusion protein targeted to a body surface), at least one suitable carboxylic acid ester substrate, a source of peroxygen, and water (aqueous solution comprising a source of peroxygen, for example, hydrogen peroxide). In one embodiment, any perhydrolytic enzyme not belonging to the CE-7 class of carbohydrate esterases will, by proviso, be used in the form of a fusion protein having at least one peptide component having affinity for a target surface, preferably an oral cavity surface.

As used herein, the term "perhydrolysis" is defined as the reaction of a selected substrate with peroxide to form a peracid. Typically, inorganic peroxide is reacted with the selected substrate in the presence of a catalyst to produce the peroxycarboxylic acid. As used herein, the term "chemical perhydrolysis" includes perhydrolysis reactions in which a substrate (a peroxycarboxylic acid precursor) is combined with a source of hydrogen peroxide wherein peroxycarboxylic acid is formed in the absence of an enzyme catalyst. As used herein, the term "enzymatic perhydrolysis" includes perhydrolysis reactions in which a carboxylic acid ester substrate (a peracid precursor) is combined with a source of hydrogen peroxide and water whereby the enzyme catalyst catalyzes the formation of peracid.

As used herein, the term "perhydrolase activity" refers to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 μmol of peroxycarboxylic acid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (such as by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. In one embodiment, the perhydrolase catalyst may be immobilized non-covalently or covalently in or on an oral care strip (e.g., a whitening strip) or dental tray. The immobilized enzyme may be coupled directly to the polymeric support and/or a component within the oral care strip or dental tray (e.g., titanium dioxide, hydroxyapatite, an orally acceptable adhesive, polyethylene, polypropylene, etc.). In a further embodiment, the non-covalent immobilization to the strip or dental tray may be through the use of a peptidic binding domain having strong affinity for a material in or on the strip or tray (e.g., a fusion protein comprising a perhydrolytic enzyme coupled through an optional peptide spacer to a peptidic binding domain). In another embodiment, the dental tray is deformable tray. In yet a further embodiment, the perhydrolase catalyst is immobilized in or on the deformable tray after the formation of the dental impression.

As used herein, "acetyl xylan esterases" refers to an enzyme (E.C. 3.1.1.72; AXEs) that catalyzes the deacetylation of acetylated xylans and other acetylated saccharides. As illustrated herein, several enzymes classified as acetyl xylan esterases are provided having significant perhydrolytic activity.

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Mitsushima et al., (1995) *Appl. Env. Microbiol.* 61 (6):2224-2229). The amino acid sequences of several cephalosporin C deacetylases having significant perhydrolytic activity are provided herein.

As used herein, the term "*Bacillus subtilis* ATCC® 31954™" refers to a bacterial cell deposited to the American Type Culture Collection (ATCC) having international depository accession number ATCC® 31954™. As described herein, an enzyme having significant perhydrolase activity from *B. subtilis* ATCC® 31954™ is provided as SEQ ID NO: 2 (see United States Patent Application Publication No. 2010-0041752).

As used herein, the term "*Thermotoga maritime* MSB8" refers to a bacterial cell reported to have acetyl xylan esterase activity (GENBANK® NP_227893.1; see U.S. Patent Application Publication No. 2008-0176299). The amino acid sequence of the enzyme having perhydrolase activity from *Thermotoga maritime* MSB8 is provided as SEQ ID NO: 16.

As used herein, an "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1: Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

As used herein, the terms "signature motif" and "diagnostic motif" refer to conserved structures shared among a family of enzymes having a defined activity. The signature motif can be used to define and/or identify the family of structurally-related enzymes having similar enzymatic activity for a defined family of substrates. The signature motif can be a single contiguous amino acid sequence or a collection of discontiguous, conserved motifs that together form the signature motif. Typically, the conserved motif(s) is represented by an amino acid sequence. In one embodiment, the perhydrolytic enzyme comprises a CE-7 carbohydrate esterase signature motif.

As used herein, the term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding Sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

As used herein, the term "expression" refers to the transcription and stable accumulation of sense (mRNA) or antisense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g., plasmid) genes. Host organisms containing the transformed nucleic acid molecules are referred to as "transgenic", "recombinant" or "transformed" organisms.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Accelrys Software Corp., San Diego, Calif.), BLASTP, BLASTN, BLASTX (Altschul et al., *J. Mol. Biol.* 215:403-410 (1990)), and DNASTAR (DNASTAR, Inc. 1228 S. Park St. Madison, Wis. 53715 USA), CLUSTALW (for example, version 1.83; Thompson et al., *Nucleic Acids Research,* 22 (22):4673-4680 (1994)), and the PASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

The term "body surface" refers to any surface of the human body that may serve as the target for a benefit agent, such as a peracid benefit agent. The present methods and compositions are directed to oral care applications and products. As such, the body surface comprises an oral cavity material/surface. In one embodiment, the oral cavity material comprises tooth enamel, tooth pellicle, soft tissues such as the cheeks, tongue, and gums, and oral cavity biofilms (e.g., oral plaque).

As used herein, the term "biological contaminants" refers to one or more unwanted and/or pathogenic biological entities including, but not limited to, microorganisms, spores, viruses, prions, and mixtures thereof. In one embodiment, a process is provided to enzymatically produce an efficacious concentration of at least one peracid useful to reduce and/or eliminate the presence of the biological contaminants.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants, which may include biological contaminants within a human oral cavity, such as microorganisms associated with dental caries, gingivitis, oral candidiasis, or periodontitis. As used herein, the term "disinfection" refers to the act or process of disinfecting. As used herein, the term "antiseptic" refers to a chemical agent that inhibits the growth of disease-carrying microorganisms. In one aspect, the biological contaminants are pathogenic microorganisms.

As used herein, the term "sanitary" means of or relating to the restoration or preservation of health, typically by removing, preventing or controlling an agent that may be injurious to health. As used herein, the term "sanitize" means to make sanitary. As used herein, the term "sanitizes" refers to a sanitizing agent. As used herein the term "sanitization" refers to the act or process of sanitizing.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peracids can have biocidal activity. Typical alternative biocides may include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable microorganisms after treatment is at least a 3-$\log_{10}$ reduction, more preferably at least a 4-$\log_{10}$ reduction, and most preferably at least a 5-$\log_{10}$ reduction. In another aspect, the minimum biocidal concentration is at least a 6-$\log_{10}$ reduction in viable microbial cells.

As used herein, "cleaning compositions" and "cleaning formulations" refer to compositions that find use in the removal of undesired compounds from teeth (mouthwashes, toothpastes, etc.). The term encompasses any materials/compounds selected for the particular type of cleaning composition desired and the form of the product (e.g., liquid, paste, gel, emulsion, granule, or spray composition), as long as the composition is compatible with the perhydrolase and other enzyme(s) used in the composition.

As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Oral care compositions that find use in conjunction with the perhydrolases of the present invention are well known in the art (See e.g., U.S. Pat. Nos. 5,601,750; 6,379,653; and 5,989,526, all of which are incorporated herein by reference, in their entirety).

As used herein, "pharmaceutically-acceptable" means that drugs, medicaments and/or inert ingredients which the term describes are suitable for use in contact with the tissues of humans and other animals without undue toxicity, incompatibility, instability, irritation, allergic response, and the like, commensurate with a reasonable benefit/risk ratio.

As used herein, "personal care products" means products used in the cleaning, bleaching and/or disinfecting of hair, skin, scalp, and teeth, including, but not limited to shampoos, body lotions, shower gels, topical moisturizers, toothpaste, toothgels, mouthwashes, mouthrinses, anti-plaque rinses, and/or other topical cleansers. In some particularly preferred embodiments, these products are utilized on humans, while in other embodiments, these products find use with non-human animals (e.g., in veterinary applications).

As used herein, the terms "tooth whitening" and "tooth bleaching" are used interchangeably, to refer to improving the brightness (e.g., whitening) of a tooth or teeth. It is intended that the term encompass any method suitable for whitening teeth, including the present invention, as well as chemical treatment, mild acid treatment, abrasive tooth whitening, and laser tooth whitening. In particularly preferred embodiments, the present invention provides a perhydrolase and perhydrolase-containing compositions suitable for whitening teeth.

As used in herein, "intrinsic stains" in teeth refer to the resulting color from chromogens within the enamel and underlying dentin. The intrinsic color of human teeth tends to become more yellow with aging, due to the thinning of the enamel and darkening of the underlying yellow dentin. Removal of intrinsic stain usually requires the use of peroxides or other oxidizing chemicals, which penetrate the enamel and decolorize the internal chromogens.

In contrast to intrinsic stains, "extrinsic stains" form on the surface of the teeth when exogenous chromogenic materials bind to the enamel, usually within the pellicle naturally coating the teeth. Most people accumulate some degree of unsightly extrinsic stains on their teeth over time. This staining process is promoted by such factors as: (1) the ingestion of tannin-containing foods and beverages such as coffee, tea, or red wine; (2) the use of tobacco products; and/or (3) exposure to certain cationic substances (e.g., tin, iron, and chlorhexidine). These substances tend to adhere to the enamel's hydroxyapatite structure, which leads to tooth discoloration and a concomitant reduction in tooth whiteness. Over a period of years, extrinsic stains may penetrate the enamel layer and result in intrinsic stains.

As used herein, the term "deodorize" means to eliminate or prevent offensive odor.

As used herein, the term "destain" or "destaining" refers to the process of removing a stain from an oral cavity surface. The stain(s) may be intrinsic stains, extrinsic stains, or a combination thereof.

As used herein, "enhanced performance" in a perhydrolase-containing composition is defined as increasing cleaning of bleach-sensitive stains compared to other compositions, as determined using standard methods in the dental art. In particular embodiments, the perhydrolase of the present invention provides enhanced performance in the oxidation and removal of colored stains. In further embodiments, the perhydrolase of the present invention provides enhanced performance in the removal and/or decolorization of stains.

As used herein, "effective amount of perhydrolase enzyme" refers to the quantity of perhydrolase enzyme necessary to achieve the enzymatic activity required in the specific application. Such effective amounts are readily ascertained by one of ordinary skill in the art and are based on many factors, such as the particular enzyme variant used, the cleaning application, the specific composition of the cleaning composition, and whether a liquid or non-liquid (e.g., emulsion) composition is required, and the like.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates. As described herein, the concentration of the hydrogen peroxide provided by the peroxygen compound in the aqueous reaction formulation is initially at least 0.1 mM or more upon combining the reaction components. In one embodiment, the hydrogen peroxide concentration in the aqueous reaction formulation is at least 0.5 mM. In one embodiment, the hydrogen peroxide concentration in the aqueous reaction formulation is at least 1 mM. In another embodiment, the hydrogen peroxide concentration in the aqueous reaction formulation is at least 10 mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more. The molar ratio of the hydrogen peroxide to enzyme substrate, e.g., triglyceride, ($H_2O_2$:substrate) in the aqueous reaction formulation may be from about 0.002 to 20, preferably about 0.1 to 10, and most preferably about 0.5 to 5.

As used herein, the term "oligosaccharide" refers to compounds containing between 2 and at least 24 monosaccharide units linked by glycosidic linkages. The term "monosaccharide" refers to a compound of empirical formula $(CH_2O)_n$, where $n \geq 3$, the carbon skeleton is unbranched, each carbon atom except one contains a hydroxyl group, and the remaining carbon atom is an aldehyde or ketone at carbon atom 1. The term "monosaccharide" also refers to intracellular cyclic hemiacetal or hemiketal forms.

As used herein, the term "excipient" refers to inactive substance used as a carrier for active ingredients in a formulation. The excipient may be used to stabilize the active ingredient in a formulation, such as the storage stability of the active ingredient. Excipients are also sometimes used to bulk up formulations that contain active ingredients. As described herein, the "active ingredient" may be an enzyme having perhydrolytic activity, a peracid produced by the perhydrolytic enzyme under suitable reaction conditions, or a combination thereof.

The term "substantially free of water" will refer to a concentration of water in a formulation that does not adversely impact the storage stability of the enzyme or an enzyme powder when present in the carboxylic acid ester. The carboxylic acid ester may contain a very low concentration of water, for example, triacetin typically has between 180 ppm and 300 ppm of water. In one embodiment, the perhydrolytic enzyme is stored in the carboxylic acid ester substrate that is substantially free of water. In a further embodiment, "substantially free of water" may mean less than 2000 ppm, preferably less than 1000 ppm, more preferably less than 500 ppm, and even more preferably less than 250 ppm of water in the formulation comprising the enzyme (or enzyme powder) and the carboxylic acid ester. In one embodiment, the perhydrolytic enzyme may be stored in an aqueous solution if the generation system is designed such that the enzyme is stable in the aqueous solution (for example, a solution that does not contain a significant concentration of a carboxylic acid ester substrate capable of being hydrolyzed by the enzyme during storage). In one embodiment, the perhydrolytic enzyme may be stored in a mixture comprising the carboxylic acid ester substrate that is substantially free of water and one or more buffers (e.g., sodium and/or potassium salts of bicarbonate, citrate, acetate, phosphate, pyrophosphate, methylphosphonate, succinate, malate, fumarate, tartrate, and maleate).

Enzymes Having Perhydrolytic Activity

Enzymes having perhydrolytic activity may include some enzymes classified as lipases, proteases, esterases, acyl transferases, aryl esterases, carbohydrate esterases, and combinations so long as the enzyme has perhydrolytic activity for one or more of the present substrates. Examples may include, but are not limited to perhydrolytic proteases (subtilisin Carlsberg variant; U.S. Pat. No. 7,510,859), perhydrolytic aryl esterases (*Pseudomonas fluorescens*; SEQ ID NO: 477; U.S. Pat. No. 7,384,787), the perhydrolytic aryl esterase/acyl transferase from *Mycobacterium smegmatis* (SEQ ID NOs: 460 and 478; U.S. Pat. No. 7,754,460; WO2005/056782; and EP1689859 B1), and perhydrolase carbohydrate esterases. In a preferred aspect, the perhydrolytic carbohydrate esterase is a CE-7 carbohydrate esterase.

In one embodiment, suitable perhydrolases may include enzymes comprising an amino acid sequence having at least 30%, 33%, 40%, 50%, 60%, 70%, 80%, 85%, 90%, 91%, 92%, 93%, 94%, 95%, 96%, 97%, 98%, or 99% amino acid identity to any of the amino acid sequences reported herein with the proviso that non-CE-7 perhydrolases are limited to targeted perhydrolase applications (i.e., perhydrolytic enzymes not belonging to the CE-7 carbohydrate esterase family are used in the form of a fusion protein comprising at least one peptidic targeting domain).

In another embodiment, the suitable perhydrolases may include enzymes comprising an amino acid sequence having at least 30%, 33%, 40%, 50%, 60%, 70%, 80%, 85%, 90%, 91%, 92%, 93%, 94%, 95%, 96%, 97%, 98%, or 99% amino acid identity to SEQ ID NO: 460, 477, and 478 with the proviso that non-CE-7 perhydrolases are limited to targeted perhydrolase applications (i.e., perhydrolytic enzymes not belonging to the CE-7 carbohydrate esterase family are used in the form of a fusion protein comprising at least one peptidic targeting domain). It is understood that percent identity comparisons and sequence alignments used to identify substantially similar perhydrolytic enzymes are conducted against the portion of fusion protein comprising the perhydrolytic enzyme (i.e., targeting domains and linkers not included).

In another embodiment, the fusion protein comprises a perhydrolytic enzyme having an amino acid sequence with at least 95% identity to the S54V *Mycobacterium smegmatis* aryl esterase provided as SEQ ID NO: 460.

In one embodiment, the fusion protein comprises a perhydrolytic esterase from *Pseudomonas fluorescens*. In another embodiment, the fusion protein comprises a perhydrolytic enzyme having an amino acid sequence with at least 95% identity to the *Pseudomonas fluorescens* esterase provided as SEQ ID NO: 477.

In another embodiment, the fusion protein comprises a perhydrolytic enzyme having an amino acid sequence selected from the group consisting of SEQ ID NOs: 424, 425, 426, 427, 428, 429, 430, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 476, 477, 478, and 479.

In another embodiment, substantially similar perhydrolytic enzymes may include those encoded by polynucleotide sequences that hybridize under highly stringent hybridization conditions (0.1×SSC, 0.1% SDS, 65° C. and washed with 2×SSC, 0.1% SDS followed by a final wash of 0.1×SSC, 0.1% SDS, 65° C.) to the polynucleotide sequences encoding any of the present perhydrolytic enzymes with the proviso that non-CE-7 perhydrolases are limited to targeted perhydrolase applications (i.e., perhydrolytic enzymes not belonging to the CE-7 carbohydrate esterase family are used in the form of a fusion protein comprising at least one peptidic targeting domain).

CE-7 Perhydrolases

In a preferred embodiment, the oral care compositions and method comprise enzymes having perhydrolytic activity that are structurally classified as members of the carbohydrate family esterase family 7 (CE-7 family) of enzymes (see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12). The CE-7 family of enzymes has been demonstrated to be particularly effective for producing peroxycarboxylic acids from a variety of carboxylic acid ester substrates when combined with a source of peroxygen (U.S. Pat. Nos. 7,794,378; 7,951,566; 7,723,083; and 7,964,378 and U.S. Patent Application Publication Nos.

2008-0176299, 2010-0087529, 2011-0081693, and 2011-0236335 to DiCosimo et al.; each incorporated herein by reference).

Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., *J. Mol. Biol.*, 330:593-606 (2003)). Perhydrolases comprising the CE-7 signature motif ("CE-7 perhydrolases") and/or a substantially similar structure are suitable for use in the compositions and methods described herein. Means to identify substantially similar biological molecules are well known in the art (e.g., sequence alignment protocols, nucleic acid hybridizations and/or the presence of a conserved signature motif). In one aspect, the perhydrolase includes an enzyme comprising the CE-7 signature motif and at least 20%, preferably at least 30%, more preferably at least 33%, more preferably at least 40%, more preferably at least 42%, more preferably at least 50%, more preferably at least 60%, more preferably at least 70%, more preferably at least 80%, more preferably at least 90%, and most preferably at least 90%, 91%, 92%, 93%, 94%, 95%, 96%, 97%, 98%, or 99% amino acid identity to one of the sequences provided herein.

As used herein, the phrase "enzyme is structurally classified as a CE-7 enzyme", "CE-7 perhydrolase" or "structurally classified as a carbohydrate esterase family 7 enzyme" will be used to refer to enzymes having perhydrolysis activity which are structurally classified as a CE-7 carbohydrate esterase. This family of enzymes can be defined by the presence of a signature motif (Vincent et al., supra). The signature motif for CE-7 esterases comprises three conserved motifs (residue position numbering relative to reference sequence SEQ ID NO: 2; the CE-7 perhydrolase from *B. subtilis* ATCC® 31954™):

a) Arg118-Gly119-Gln120;
b) Gly179-Xaa180-Ser181-Gln182-Gly183; and
c) His298-Glu299.

Typically, the Xaa at amino acid residue position 180 is glycine, alanine, proline, tryptophan, or threonine. Two of the three amino acid residues belonging to the catalytic triad are in bold. In one embodiment, the Xaa at amino acid residue position 180 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 267-269 of SEQ ID NO: 2) that may be used to further define a perhydrolase belonging to the CE-7 carbohydrate esterase family. In a further embodiment, the signature motif defined above may include an additional (fourth) conserved motif defined as:

Leu267-Xaa268-Asp269.

The Xaa at amino acid residue position 268 is typically isoleucine, valine, or methionine. The fourth motif includes the aspartic acid residue (bold) belonging to the catalytic triad (Ser181-Asp269-His298).

The CE-7 perhydrolases may be in the form of fusion proteins having at least one peptidic component having affinity for at least one body surface. In one embodiment, all alignments used to determine if a targeted perhydrolase (fusion protein) comprises the CE-7 signature motif will be based on the amino acid sequence of the perhydrolytic enzyme without the peptidic component having the affinity for a body surface.

A number of well-known global alignment algorithms (i.e., sequence analysis software) may be used to align two or more amino acid sequences representing enzymes having perhydrolase activity to determine if the enzyme is comprised of the present signature motif. The aligned sequence(s) are compared to the reference sequence (SEQ ID NO: 2) to determine the existence of the signature motif. In one embodiment, a CLUSTAL alignment (such as CLUSTALW) using a reference amino acid sequence (as used herein the perhydrolase sequence (SEQ ID NO: 2) from the *Bacillus subtilis* ATCC® 31954™) is used to identify perhydrolases belonging to the CE-7 esterase family. The relative numbering of the conserved amino acid residues is based on the residue numbering of the reference amino acid sequence to account for small insertions or deletions (for example, typically five amino acids of less) within the aligned sequence.

Examples of other suitable algorithms that may be used to identify sequences comprising the present signature motif (when compared to the reference sequence) include, but are not limited to, Needleman and Wunsch (*J. Mol. Biol.* 48, 443-453 (1970); a global alignment tool) and Smith-Waterman (*J. Mol. Biol.* 147:195-197 (1981); a local alignment tool). In one embodiment, a Smith-Waterman alignment is implemented using default parameters. An example of suitable default parameters include the use of a BLOSUM62 scoring matrix with GAP open penalty=10 and a GAP extension penalty=0.5.

A comparison of the overall percent identity among perhydrolases indicates that enzymes having as little as 33% amino acid identity to SEQ ID NO: 2 (while retaining the signature motif) exhibit significant perhydrolase activity and are structurally classified as CE-7 carbohydrate esterases. In one embodiment, suitable perhydrolases include enzymes comprising the CE-7 signature motif and at least 20%, preferably at least 30%, 33%, 40%, 50%, 60%, 70%, 80%, 85%, 90%, 91%, 92%, 93%, 94%, 95%, 96%, 97%, 98%, or 99% amino acid identity to SEQ ID NO: 2.

Examples of suitable CE-7 carbohydrate esterases having perhydrolytic activity include, but are not limited to, enzymes having an amino acid sequence such as SEQ ID NOs: 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, 64, 424, 437, and 476. In one embodiment, the enzyme comprises an amino acid sequence selected from the group consisting of 14, 16, 27, 28, 29, 30, 31, 32, 33, 34, 35, 36, 46, 48, 50, 52, 54, 56, 58, 60, 62, 64, 424, 437, and 476.

As used herein, the term "CE-7 variant", "variant perhydrolase" or "variant" will refer to CE-7 perhydrolases having a genetic modification that results in at least one amino acid addition, deletion, and/or substitution when compared to the corresponding enzyme (typically the wild type enzyme) from which the variant was derived; so long as the CE-7 signature motif and the associated perhydrolytic activity are maintained. CE-7 variant perhydrolases may also be used in the present compositions and methods. Examples of CE-7 variants are provided as SEQ ID NOs: 27, 28, 29, 30, 31, 32, 46, 48, 50, 52, 54, 56, 58, 60, 62, 64, 424, 437, and 476. In one embodiment, the variants may include SEQ ID NOs: 27, 28, 46, 48, 50, 52, 54, 56, 58, 60, 62, 64, 424, 437, and 476.

The skilled artisan recognizes that substantially similar CE-7 perhydrolase sequences (retaining the signature motifs) may also be used in the present compositions and methods. In one embodiment, substantially similar sequences are defined by their ability to hybridize, under highly stringent conditions with the nucleic acid molecules associated with sequences exemplified herein. In another embodiment, sequence alignment algorithms may be used to define substantially similar enzymes based on the percent identity to the DNA or amino acid sequences provided herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of highly stringent hybridization conditions is 0.1×SSC, 0.1% SDS, 65° C. and washed with 2×SSC, 0.1% SDS followed by a final wash 10, of 0.1% SSC, 0.1% SDS, 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the CLUSTAL method (such as CLUSTALW; for example version 1.83) of alignment (Higgins and Sharp, CABIOS, 5:151-153 (1989); Higgins et al., *Nucleic Acids Res.* 22:4673-4680 (1994); and Chema et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein END-GAP=−1, protein GAPDIST=4, and KTUPLE=1. In one embodiment, a fast or slow alignment is used with the default settings where a slow alignment is preferred. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

In one aspect, suitable isolated nucleic acid molecules encode a polypeptide having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to the amino acid sequences reported herein. In another aspect, suitable isolated nucleic acid molecules encode a polypeptide having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to the amino acid sequences reported herein; with the proviso that the polypeptide retains the CE-7 signature motif. Suitable nucleic acid molecules not only have the above homologies, but also typically encode a polypeptide having about 210 to 340 amino acids in length, about 300 to about 340 amino acids, preferably about 310 to about 330 amino acids, and most preferably about 318 to about 325 amino acids in length wherein each polypeptide is characterized as having perhydrolytic activity.

Targeted Perhydrolases

As used herein, the term "targeted perhydrolase" and "targeted enzyme having perhydrolytic activity" will refer to a fusion proteins comprising at least one perhydrolytic enzyme (wild type or variant thereof) fused/coupled to at least one peptidic component having affinity for a target surface, preferably a targeted body surface. The perhydrolytic enzyme within the targeted perhydrolase may be any perhydrolytic enzyme and may include lipases, proteases, esterases, acyl transferases, aryl esterases, carbohydrate esterases, and combinations so long as the enzyme has perhydrolytic activity for one or more of the present substrates. Examples may include, but are not limited to perhydrolytic proteases (e.g., subtilisin variant; U.S. Pat. No. 7,510,859), perhydrolytic esterases (e.g., *Pseudomonas fluorescens*; U.S. Pat. No. 7,384,787; SEQ ID NO: 477), and perhydrolytic aryl esterases (e.g., *Mycobacterium smegmatis*; U.S. Pat. No. 7,754,460;

WO2005/056782; and EP1689859 B1; SEQ ID NOs: 460 [S54V variant] and 478 [wild type]).

In one embodiment, the fusion protein comprises a perhydrolytic enzyme having an amino acid sequence with at least 95% identity to the S54V *Mycobacterium smegmatis* aryl esterase provided as SEQ ID NO: 460.

In one embodiment, the fusion protein comprises a perhydrolytic esterase from *Pseudomonas fluorescens*. In another embodiment, the fusion protein comprises a perhydrolytic enzyme having an amino acid sequence with at least 95% identity to the *Pseudomonas fluorescens* esterase provided as SEQ ID NO: 477.

In another embodiment, the fusion protein comprises a perhydrolytic enzyme having an amino acid sequence selected from the group consisting of SEQ ID NOs: 424, 425, 426, 427, 428, 429, 430, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 476, 477, 478, and 479.

As used herein the terms "peptidic component", "peptidic component having affinity for an oral cavity surface", and "OCBD" will refer to component of the fusion protein that is not part of the perhydrolytic enzyme comprising at least one polymer of two or more amino acids joined by a peptide bond; wherein the component has affinity for the target oral cavity surface.

In one embodiment, the peptidic component having affinity for a body surface may be an antibody, an Fab antibody fragment, a single chain variable fragment (scFv) antibody, a Camelidae antibody (Muyldermans, S., *Rev. Mol, Biotechnol.* (2001) 74:277-302), a non-antibody scaffold display protein (Hosse et al., *Prot. Sci.* (2006) 15 (1): 14-27 and Binz, H. et al. (2005) *Nature Biotechnology* 23, 1257-1268 for a review of various scaffold-assisted approaches) or a single chain polypeptide lacking an immunoglobulin fold. In another aspect, the peptidic component having affinity for a body surface is a single chain peptide lacking an immunoglobulin fold (i.e., a body surface-binding peptide or a body surface-binding domain comprising at least one body surface-binding peptide having affinity for an oral cavity surface). In a preferred embodiment, the peptidic component is a single chain peptide comprising one or more body surface-binding peptides having affinity for an oral cavity surface.

The peptidic component having affinity for an oral cavity surface may be separated from the perhydrolytic enzyme by an optional peptide linker. Certain peptide linkers/spacers are from 1 to 100 or 1 to 50 amino acids in length. In some embodiments, the peptide spacers are about 1 to about 25, 3 to about 40, or 3 to about 30 amino acids in length. In other embodiments are spacers that are about 5 to about 20 amino acids in length. Multiple peptide linkers may be used. In one embodiment, at least one peptide linker is present and may be repeated up to 10 times.

Peptides previously identified as having affinity for one body surface may have affinity for an oral care surface as well. As such, the fusion peptide may comprise at least one previously reported to have affinity for another body surface, such as hair (SEQ ID NOs 65-221, 271, and 368); skin (SEQ ID NOs: 217-269); or nail (SEQ ID NOs: 270-271). In one embodiment, the fusion peptide comprises at least one oral cavity surface-binding peptide from the group comprising SEQ ID NOs: 272-382 and 399-422. In one embodiment, the fusion peptide comprises at least one oral cavity surface-binding peptide selected from the group consisting of SEQ ID NOs: 272-382, 399-410, and 412-422; wherein SEQ ID NOs 272-291 and 312-382 have affinity for tooth pellicle; SEQ ID NOs: 292-311 have affinity for tooth enamel; and SEQ ID NOs 399-410 and 412-422 have affinity for tooth enamel or pellicle. Some of the body surface-binding peptides may have strong affinity for more than one body surface, and as such, may be used to target perhydrolytic enzymes to different body surfaces. In another embodiment, the fusion peptide may include any body surface-binding peptide designed to have electrostatic attraction to the target body surface (e.g., a body surface-binding peptide engineered to electrostatically bind to the target body surface).

In another embodiment the target surface is a material that is part of the packaging and/or method of delivery to the oral cavity. The peptidic component is selected for it affinity to a material or materials in use such as polymers, plastics and films. The targeted perhydrolase fusion protein design allows for the controlled delivery and removal of the perhydrolase from the user by maintaining it on a removable device such as, but not limited to, a mouth tray or strip.

Targeted CE-7 Perhydrolases

In a preferred embodiment, the "targeted perhydrolase" is a targeted CE-7 carbohydrate esterase having perhydrolytic activity. As used herein, the terms "targeted CE-7 perhydrolase" and "targeted CE-7 carbohydrate esterase" will refer to fusion proteins comprising at least one CE-7 perhydrolase (wild type or variant perhydrolase) fused/coupled to at least one peptidic component having affinity for a targeted surface, preferably a targeted body surface. The peptidic component having affinity for a body surface may be any of those describe above. In a preferred aspect, the peptidic component in a targeted CE-7 perhydrolase is a single chain peptide lacking an immunoglobulin fold (i.e., a body surface-binding peptide or a body surface-binding domain comprising at least one body surface-binding peptide having affinity for an oral cavity surface). In a preferred embodiment, the peptidic component is a single chain peptide comprising one or more body surface-binding peptides having affinity for an oral cavity surface.

The peptidic component having affinity for an oral cavity surface may be separated from the CE-7 perhydrolase by an optional peptide linker. Certain peptide linkers/spacers are from 1 to 100 or 1 to 50 amino acids in length. In some embodiments, the peptide spacers are about 1 to about 25, 3 to about 40, or 3 to about 30 amino acids in length. In other embodiments are spacers that are about 5 to about 20 amino acids in length. Multiple peptide linkers may be used.

As such, examples of targeted CE-7 perhydrolases may include, but are not limited to, any of the CE-7 perhydrolases having an amino acid sequence selected from the group consisting of SEQ ID NOs 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, 64, 424, 437, and 476 coupled to a peptidic component having affinity for an oral cavity surface. In a preferred embodiment, examples of targeted perhydrolases may include, but are not limited to, any of CE-7 perhydrolases having an amino acid sequence selected from the group consisting of SEQ ID NOs 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, 64, 424, 437, and 476 coupled to one or more body surface-binding peptides having affinity for an oral cavity surface (optionally through a peptide spacer).

In another embodiment, targeted CE-7 perhydrolases may comprise peptides previously identified as having affinity for one body surface may have affinity for an oral care surface as well. As such, the fusion peptide may comprise at least one previously reported to have affinity for another body surface, such as hair (SEQ ID NOs 65-221, 271, and 368); skin (SEQ ID NOs: 217-269); or nail (SEQ ID NOs: 270-271). In one embodiment, the fusion peptide comprises at least one oral cavity surface-binding peptide from the group comprising SEQ ID NOs: 272-382 and 399-422. In one embodiment, the CE-7 perhydrolase fusion peptide comprises at least one oral cavity surface-binding peptide selected from the group consisting of SEQ ID NOs: 272-382, 399-410, and 412-422; wherein SEQ ID NOs 272-291 and 312-382 have affinity for tooth pellicle; SEQ ID NOs: 292-311 have affinity for tooth enamel; and SEQ ID NOs 399-410 and 412-422 have affinity for tooth enamel or pellicle. Some of the body surface-binding peptides may have strong affinity for more than one body surface, and as such, may be used to target perhydrolytic enzymes to different body surfaces. In another embodiment, the CE-7 perhydrolase fusion peptide may include any body surface-binding peptide designed to have electrostatic attraction to the target body surface (e.g., a body surface-binding peptide engineered to electrostatically bind to the target body surface).

In another embodiment, the target surface is a material that is part of the packaging and or delivery to the oral cavity. The peptidic component is selected for it affinity to a material or materials in use such as polymers, plastics and films. The targeted CE-7 perhydrolase fusion protein design allows for the controlled delivery and removal of the perhydrolase from the user by maintaining it on a removable device such as a mouth tray or strip.

Peptides Having Affinity for a Body Surface

Single chain peptides lacking an immunoglobulin fold that are capable of binding to an oral cavity surface are referred to as "oral cavity surface-binding peptides" (OCBP) and may include, for example, peptides that bind to a tooth surface (tooth-binding peptides), peptides having affinity for a soft tissue such as the gums, or peptides having affinity for an orally-acceptable material that is safe for use in the oral cavity. The tooth-binding peptides may include peptides having affinity for tooth enamel ("tooth enamel-binding peptides") and peptides having affinity for tooth pellicle ("tooth pellicle-binding peptides").

A non-limiting list of peptides having affinity for at least one body surface are provided herein including those having affinity for hair (hair-binding peptides having an amino acid sequence selected from the group consisting of SEQ ID NOs: 65-221, 271, and 368), skin (skin-binding peptides comprise an amino acid sequence selected from the group consisting of SEQ ID NOs: 217-269), and nail (nail-binding peptides comprise an amino acid sequence selected from the group consisting of SEQ ID NOs: 270-271). Examples of peptides having affinity for an oral cavity surface (oral cavity-binding peptides) comprise an amino acid sequence selected from the group consisting of SEQ ID NOs: 272-382 and 399-422. In a preferred aspect, the peptides having affinity for an oral cavity surface are selected from the group consisting of SEQ ID NOs: 272-382, 399-410, and 412-422; wherein SEQ ID NOs 272-291 and 312-382 have affinity for tooth pellicle; SEQ ID NOs: 292-311 have affinity for tooth enamel; and SEQ ID NOs 399-410 and 412-422 having affinity for tooth enamel or pellicle.

In one embodiment, a peptide that may also have affinity for an oral cavity surface may include one or more of SEQ ID NOs. 65-382, 399-410, and 412-422. Preferably, the peptides used in the present compositions and methods are selected from the group consisting of SEQ ID NOs: 272-382, 399-410, and 412-422. In another embodiment, oral cavity surface-binding peptides may include skin-binding peptides for some surfaces with the oral cavity (e.g., gums). In another embodiment, the fusion peptide may include any body surface-binding peptide designed to have electrostatic attraction to the target body surface (e.g., a body surface-binding peptide engineered to electrostatically bind to the target body surface).

In another embodiment, the present compositions and methods comprise at least one oral cavity surface-binding peptide having an amino acid sequence selected from the group consisting of SEQ ID NOs 399-410 and 412-422.

In some embodiments, oral cavity surface-binding domains are comprised of oral cavity surface-binding peptides that are up to about 60 amino acids in length. In one embodiment the oral cavity surface-binding peptides are 5 to 60 amino acids in length. In other embodiments a surface-binding peptides are 7 to 50 amino acids in length or 7 to 30 amino acids in length. In still other embodiments are those oral cavity surface-binding peptides that are 7 to 27 amino acids in length.

While fusion peptides comprising oral cavity surface-binding peptides are certain embodiments of the invention, in other embodiments of the invention, it may be advantageous to use multiple oral cavity surface-binding peptides. The inclusion of multiple, i.e., two or more, oral cavity surface-binding peptides can provide a peptidic component that is, for example, even more durable than those binding elements including a single oral cavity surface-binding peptide. In some embodiments, the oral cavity surface-binding domains (that is, multiple, i.e., two or more, oral cavity surface-binding peptides) includes from 2 to about 50 or 2 to about 25 oral cavity surface-binding peptides. Other embodiments include those oral cavity surface-binding domains including 2 to about 10 or 2 to 5 oral cavity surface-binding peptides.

Multiple binding elements (i.e., oral cavity surface-binding peptides or oral cavity surface-binding domains) can be linked directly together or they can be linked together using peptide spacers. Certain peptide spacers/linkers are from 1 to 100 or 1 to 50 amino acids in length. In some embodiments, the peptide spacers are about 1 to about 25, 3 to about 40, or 3 to about 30 amino acids in length. In other embodiments are spacers that are 1 to about 20 or about 5 to about 20 amino acids in length.

Oral cavity surface-binding domains, and the shorter oral cavity surface-binding peptides of which they are comprised, can be identified using any number of methods known to those skilled in the art, including, for example, any known biopanning techniques such as phage display, bacterial display, yeast display, ribosome display, mRNA display, and combinations thereof. Typically a random or substantially random (in the event bias exists) library of peptides is biopanned against the target body surface to identify peptides within the library having affinity for the target body surface.

The generation of random libraries of peptides is well known and may be accomplished by a variety of techniques including, bacterial display (Kemp, D. J.; Proc. Natl. Acad. Sci. USA 78 (7):4520-4524 (1981), and Helfman et al., Proc. Natl. Acad. Sci. USA 80 (1):31-35, (1983)), yeast display (Chien et al., Proc Natl Acad Sci USA 88 (21):9578-82 (1991)), combinatorial solid phase peptide synthesis (U.S. Pat. No. 5,449,754, U.S. Pat. No. 5,480,971, U.S. Pat. No. 5,585,275, U.S. Pat. No. 5,639,603), and phage display technology (U.S. Pat. No. 5,223,409, U.S. Pat. No. 5,403,484, U.S. Pat. No. 5,571,698, U.S. Pat. No. 5,837,500); riboome display (U.S. Pat. No. 5,643,768; U.S. Pat. No. 5,658,754; and U.S. Pat. No. 7,074,557), and mRNA display technology (PROFUSION™; see U.S. Pat. Nos. 6,258,558; 6,518,018; 6,281,344; 6,214,553; 6,261,804; 6,207,446; 6,846,655; 6,312,927; 6,602,685; 6,416,950; 6,429,300; 7,078,197; and 6,436,665).

Binding Affinity

The peptidic component having affinity for the oral cavity surface comprises a binding affinity for an oral cavity surface of $10^{-5}$ molar (M) or less. In certain embodiments, the peptidic component is one or more oral cavity surface-binding peptides and/or binding domain(s) having a binding affinity for human hair, skin, nail or oral cavity of $10^{-5}$ molar (M) or less. In some embodiments, the binding peptides or domains will have a binding affinity value of $10^{-5}$ M or less in the presence of at least about 50-500 mM salt. The term "binding affinity" refers to the strength of the interaction of a binding peptide with its respective substrate, in this case, a human oral cavity surface (gums, teeth, etc). Binding affinity can be defined or measured in terms of the binding peptide's dissociation constant ("$K_D$"), or "$MB_{50}$."

"$K_D$" corresponds to the concentration of peptide at which the binding site on the target is half occupied, i.e., when the concentration of target with peptide bound (bound target material) equals the concentration of target with no peptide bound. The smaller the dissociation constant, the more tightly the peptide is bound. For example, a peptide with a nanomolar (nM) dissociation constant binds more tightly than a peptide with a micromolar (µM) dissociation constant. Certain embodiments of the invention will have a $K_D$ value of $10^{-5}$ or less.

"$MB_{50}$" refers to the concentration of the binding peptide that gives a signal that is 50% of the maximum signal obtained in an ELISA-based binding assay. See, e.g., Example 3 of U.S. Patent Application Publication 2005/022683; hereby incorporated by reference. The $MB_{50}$ provides an indication of the strength of the binding interaction or affinity of the components of the complex. The lower the value of $MB_{50}$, the stronger, i.e., "better," the interaction of the peptide with its corresponding substrate. For example, a peptide with a nanomolar (nM) $MB_{50}$ binds more tightly than a peptide with a micromolar (µM) $MB_{50}$. Certain embodiments of the invention will have a $MB_{50}$ value of $10^{-5}$ M or less.

In some embodiments, the peptidic component having affinity for a oral cavity surface may have a binding affinity, as measured by $K_D$ or $MB_{50}$ values, of less than or equal to about $10^{-5}$ M, less than or equal to about $10^{-6}$ M, less than or equal to about $10^{-7}$ M, less than or equal to about $10^{-8}$ M, less than or equal to about $10^{-9}$ M, or less than or equal to about $10^{-10}$ M.

In some embodiments, the oral cavity surface-binding peptides and/or oral cavity surface-binding domains may have a binding affinity, as measured by $K_D$ or $MB_{50}$ values, of less than or equal to about $10^{-5}$ M, less than or equal to about $10^{-6}$ M, less than or equal to about $10^{-7}$ M, less than or equal to about $10^{-8}$ M, less than or equal to about $10^{-9}$ M, or less than or equal to about $10^{-10}$ M.

As used herein, the term "strong affinity" will refer to a binding affinity having a $K_D$ or $MB_{50}$ value of less than or equal to about $10^{-5}$ M, preferably less than or equal to about $10^{-6}$ M, more preferably less than or equal to about $10^{-7}$ M, more preferably less than or equal to about $10^{-8}$ M, less than or equal to about $10^{-9}$ M, or most preferably less than or equal to about $10^{-10}$ M.

Multicomponent Peroxycarboxylic Acid Generation Systems

The design of systems and means for separating and combining multiple active components are known in the art and generally will depend upon the physical form of the individual reaction components. For example, multiple active fluids (liquid-liquid) systems typically use multi-chamber dispenser bottles or two-phase systems (e.g., U.S. Patent Application Publication No. 2005/0139608; U.S. Pat. No. 5,398,846; U.S. Pat. No. 5,624,634; U.S. Pat. No. 6,391,840; E.P. Patent 0807156B1; U.S. Patent Application. Pub. No. 2005/0008526; and PCT Publication No. WO 00/61713) such as found in some bleaching applications wherein the desired bleaching agent is produced upon mixing the reactive fluids. Other forms of multicomponent systems used to generate peroxycarboxylic acid may include, but are not limited to, those designed for one or more solid components or combinations of solid-liquid components, such as powders (e.g., U.S. Pat. No. 5,116,575), multi-layered tablets (e.g., U.S. Pat. No. 6,210,639), water dissolvable packets having multiple compartments (e.g., U.S. Pat. No. 6,995,125) and solid agglomerates that react upon the addition of water (e.g., U.S. Pat. No. 6,319,888).

In another embodiment, the carboxylic acid ester in the first component is selected from the group consisting of monoacetin, diacetin, triacetin, and combinations thereof. In another embodiment, the carboxylic acid ester in the first component is an acetylated saccharide. In another embodiment, the enzyme catalyst in the first component may be a particulate solid, a liquid or gel. In another embodiment, the first reaction component may be a solid tablet or powder Peroxycarboxylic acids are quite reactive and generally decrease in concentration over time. This is especially true for commercial pre-formed peroxycarboxylic acid compositions that often lack long term stability. Aqueous solutions of pre-formed peroxycarboxylic acids may also present handling and/or shipping difficulties, especially when shipping large containers and/or highly concentrated peroxycarboxylic acid solutions over longer distances. Further, pre-formed peroxycarboxylic acid solutions may not be able to provide the desired concentration of peroxycarboxylic acid for a particular target application. As such, it is highly desirable to keep the various reaction components separated, especially for liquid formulations.

The use of multi-component peroxycarboxylic acid generation systems comprising two or more components that are combined to produce the desired peroxycarboxylic acid has been reported. The individual components should be safe to handle and stable for extended periods of time (i.e., as measured by the concentration of peroxycarboxylic acid produced upon mixing). In one embodiment, the storage stability of a multi-component enzymatic peroxycarboxylic acid generation system may be measured in terms of enzyme catalyst stability.

Personal care products comprising a multi-component peroxycarboxylic acid generation formulation are provided herein that use an enzyme catalyst to rapidly produce an aqueous peracid solution having a desired peroxycarboxylic acid concentration. The mixing may occur immediately prior to use and/or at the site (in situ) of application. In one embodiment, the personal care product formulation will be comprised of at least two components that remain separated until use. Mixing of the components rapidly forms an aqueous peracid solution. Each component is designed so that the resulting aqueous peracid solution comprises an efficacious peracid concentration suitable for the intended end use. The composition of the individual components should be designed to (1) provide extended storage stability and/or (2) provide the ability to enhance formation of a suitable aqueous reaction formulation comprised of peroxycarboxylic acid.

The multi-component formulation may be comprised of at least two substantially liquid components. In one embodiment, the multi-component formulation may be a two-component formulation comprises a first liquid component and a second liquid component. The use of the terms "first" or "second" liquid component is relative provided that two different liquid components comprising the specified ingredients remain separated until use. At a minimum, the multi-component peroxycarboxylic acid formulation comprises (1) at least one enzyme catalyst having perhydrolysis activity, wherein said at least one enzyme is preferably classified as a CE-7 esterase, (2) a carboxylic acid ester substrate, and (3) a source of peroxygen and water wherein the formulation enzymatically produces the desired peracid upon combining the components.

The type and amount of the various ingredients used within two component formulation should to be carefully selected and balanced to provide (1) storage stability of each component, especially the perhydrolysis activity of the enzyme catalyst and (2) physical characteristics that enhance solubility and/or the ability to effectively form the desired aqueous peroxycarboxylic acid solution (e.g., ingredients that enhance the solubility of the ester substrate in the aqueous reaction mixture and/or ingredients that modify the viscosity and/or concentration of at least one of the liquid components [i.e., at least one cosolvent that does not have a significant, adverse effect on the enzymatic perhydrolysis activity]).

Various methods to improve the performance and/or catalyst stability of enzymatic peracid generation systems have been disclosed. U.S. Patent Application Publication No. 2010-0048448 A1 describes the use of at least one cosolvent to enhance solubility and/or the mixing characteristics of certain ester substrates. The present personal care compositions and methods may also use a cosolvent. In one embodiment, the component comprising the carboxylic acid ester substrate and the perhydrolase catalyst comprises an organic solvent having a Log P value of less than about 2, wherein Log P is defined as the logarithm of the partition coefficient of a substance between octanol and water, expressed as $P=[solute]_{octanol}/[solute]_{water}$. Several cosolvents having a log P value of 2 or less that do not have a significant adverse impact on enzyme activity are described. In another embodiment, the cosolvent is about 20 wt % to about 70 wt % within the reaction component comprising the carboxylic acid ester substrate and the enzyme. The reaction component comprising the carboxylic acid ester substrate and the enzyme may optionally comprise one or more buffers (e.g., sodium and/or potassium salts of bicarbonate, citrate, acetate, phosphate, pyrophosphate, methylphosphonate, succinate, malate, fumarate, tartrate, and maleate).

U.S. Patent Application Publication No. 2010-0086534 A1 describes the use of a two component system wherein the first component comprises a formulation of a liquid carboxylic acid ester and solid enzyme powder; wherein said enzyme powder comprises a formulation of (a) at least one CE-7 esterase having perhydrolysis activity and (b) at least one oligosaccharide excipient; and the second component comprises water having a source of peroxygen and a hydrogen peroxide stabilizer. The present personal care compositions and methods may use a two-component formulation similar to the system described in US 2010-0086534 A1. As such, an oligosaccharide excipient may be used to help stabilize enzyme activity. In one embodiment, the oligosaccharide excipient may have a number average molecular weight of at least about 1250 and a weight average molecular weight of at least about 9000. In another embodiment, the oligosaccharide excipient has have a number average molecular weight of at least about 1700 and a weight average molecular weight of at least about 15000. In another embodiment, the oligosaccharide is maltodextrin.

U.S. Patent Application Publication No. 2010-0086535-A1 also describes a two component system wherein the first component comprises a formulation of a liquid carboxylic acid ester and solid enzyme powder, said formulation comprising (a) an enzyme powder comprising at least one CE-7 esterase having perhydrolysis activity and at least one oligosaccharide excipient and at least one surfactant; and (b) at least one buffer, where in a preferred embodiment the buffer is added as a separate (i.e. separate from the enzyme powder) insoluble component to the carboxylic acid ester substrate; and the second component comprises water having a source of peroxygen and a hydrogen peroxide stabilizer. The present personal care compositions and methods may use a two component formulation similar to the system described in US 2010-0086535 A1. In one embodiment, the excipient may be an oligosaccharide excipient that has a number average molecular weight of at least about 1250 and a weight average molecular weight of at least about 9000. In another embodiment, the oligosaccharide excipient may have a number average molecular weight of at least about 1700 and a weight average molecular weight of at least about 15000. In another embodiment, the oligosaccharide is maltodextrin. In a further embodiment, the optional pH buffer is a bicarbonate buffer. In yet a further embodiment, the hydrogen peroxide stabilizer is TURPINAL® SL.

Enzyme Powders

In some embodiments, the personal care compositions may use an enzyme catalyst in form of a stabilized enzyme powder. Methods to make and stabilize formulations comprising an enzyme powder are described in U.S. Patent Application Publication Nos. 2010-0086534 and 2010-0086535.

In one embodiment, the enzyme may be in the enzyme powder in an amount in a range of from about 5 weight percent (wt %) to about 75 wt % based on the dry weight of the enzyme powder. A preferred weight percent range of the enzyme in the enzyme powder/spray-dried mixture is from about 10 wt % to 50 wt %, and a more preferred weight percent range of the enzyme in the enzyme powder/spray-dried mixture is from about 20 wt % to 33 wt %

In one embodiment, the enzyme powder may further comprise an excipient. In one aspect, the excipient is provided in an amount in a range of from about 95 wt % to about 25 wt % based on the dry weight of the enzyme powder. A preferred wt % range of excipient in the enzyme powder is from about 90 wt % to 50 wt %, and a more preferred wt % range of excipient in the enzyme powder is from about 80 wt % to 67 wt %.

In one embodiment, the excipient used to prepare an enzyme powder may be an oligosaccharide excipient. In one embodiment, the oligosaccharide excipient has a number average molecular weight of at least about 1250 and a weight average molecular weight of at least about 9000. In some embodiments, the oligosaccharide excipient has a number average molecular weight of at least about 1700 and a weight average molecular weight of at least about 15000. Specific oligosaccharides may include, but are not limited to, maltodextrin, xylan, mannan, fucoidan, galactomannan, chitosan, raffinose, stachyose, pectin, insulin, levan, graminan, amylopectin, sucrose, lactulose, lactose, maltose, trehalose, cellobiose, nigerotriose, maltotriose, melezitose, maltotriulose, raffinose, kestose, and mixtures thereof. In a preferred embodiment, the oligosaccharide excipient is maltodextrin. Oligosaccharide-based excipients may also include, but are not limited to, water-soluble non-ionic cellulose ethers, such as hydroxymethyl-cellulose and hydroxypropylmethylcellulose, and mixtures thereof. In yet a further embodiment, the excipient may be selected from, but not limited to, one or more of the following compounds: trehalose, lactose, sucrose, mannitol, sorbitol, glucose, cellobiose, α-cyclodextrin, and carboxymethylcellulose.

The formulations may comprise at least one optional surfactant, where the presence of at least one surfactant is preferred. Surfactants may include, but are not limited to, ionic and nonionic surfactants or wetting agents, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium lauryl sulfate, cholic acid or derivatives thereof, lecithins, phospholipids, block copolymers of ethylene glycol and propylene glycol, and non-ionic organosilicones. Preferably, the surfactant is a polyoxyethylene sorbitan fatty acid ester, with polysorbate 80 being more preferred.

When the formulation comprises an enzyme powder, the surfactant used to prepare the powder may be present in an amount ranging from about 5 wt % to 0.1 wt % based on the weight of protein present in the enzyme powder, preferably from about 2 wt % to 0.5 wt % based on the weight of protein present in the enzyme powder.

The enzyme powder may additionally comprise one or more buffers (e.g., sodium and/or potassium salts of bicarbonate, citrate, acetate, phosphate, pyrophosphate, methylphosphonate, succinate, malate, fumarate, tartrate, and maleate), and an enzyme stabilizer (e.g., ethylenediaminetetraacetic acid, (1-hydroxyethylidene)bisphosphonic acid)).

Spray drying of the formulation to form the enzyme powder is carried out, for example, as described generally in *Spray Drying Handbook*, 5$^{th}$ ed., K. Masters, John Wiley & Sons, Inc., NY, N.Y. (1991), and in PCT Patent Publication Nos. WO 97/41833 and WO 96/32149 to Platz, R. et al.

In general spray drying consists of bringing together a highly dispersed liquid, and a sufficient volume of hot air to produce evaporation and drying of the liquid droplets. Typically the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured by Buchi Ltd. (Postfach, Switzerland) or GEA Niro Corp. (Copenhagen, Denmark) will effectively produce particles of desired size. It will further be appreciated that these spray dryers, and specifically their atomizers, may be modified or customized for specialized applications, such as the simultaneous spraying of two solutions using a double nozzle technique. More specifically, a water-in-oil emulsion can be atomized from one nozzle and a solution containing an antiadherent such as mannitol can be co-atomized from a second nozzle. In other cases it may be desirable to push the feed solution though a custom designed nozzle using a high pressure liquid chromatography (HPLC) pump. Provided that microstructures comprising the correct morphology and/or composition are produced the choice of apparatus is not critical and would be apparent to the skilled artisan in view of the teachings herein.

The temperature of both the inlet and outlet of the gas used to dry the sprayed material is such that it does not cause degradation of the enzyme in the sprayed material. Such temperatures are typically determined experimentally, although generally, the inlet temperature will range from about 50° C. to about 225° C., while the outlet temperature will range from about 30° C. to about 150° C. Preferred parameters include atomization pressures ranging from about 20-150 psi (0.14 MPa-1.03 MPa), and preferably from about 30-40 to 100 psi (0.21-0.28 MPa to 0.69 MPa). Typically the atomization pressure employed will be one of the following (MPa) 0.14, 0.21, 0.28, 0.34, 0.41, 0.48, 0.55, 0.62, 0.69, 0.76, 0.83 or above.

In one embodiment, "substantially retains its enzymatic activity" is meant that the enzyme powder or a formulation of the enzyme powder in carboxylic acid ester retains at least about 75 percent of the enzyme activity of the enzyme in the enzyme powder or a formulation of the enzyme powder after an extended storage period at ambient temperature and/or after a short storage period at an elevated temperature (above ambient temperature) in a formulation comprised of a carboxylic acid ester and the enzyme powder as compared to the initial enzyme activity of the enzyme powder prior to the preparation of a formulation comprised of the carboxylic acid ester and the enzyme powder. The extended storage period is a period of time of from about one year to about two years at ambient temperature. In one embodiment, the short storage period at an elevated temperature is a period of time of from when, the formulation comprised of a carboxylic acid ester and the enzyme powder is produced at 40° C. to about eight weeks at 40° C. In another embodiment, the elevated temperature is in a range of from about 30° C. to about 52° C. In a preferred embodiment, the elevated temperature is in a range of from about 30° C. to about 40° C.

In some embodiments, the enzyme powder retains at least 75 percent of the enzyme activity after eight weeks storage at 40° C. in a formulation comprised of a carboxylic acid ester and the enzyme powder as compared to the initial enzyme activity of the enzyme powder prior to the preparation of a formulation comprised of the carboxylic acid ester and the enzyme powder at 40° C. In other embodiments, the enzyme powder retains at least 76, 77, 78, 79, 80, 81, 82, 83, 84, 85, 86, 87, 88, 89, 90, 91, 92, 93, 94, 95, 96, 97, 98, 99, or 100 percent of the enzyme activity of the at least one enzyme after eight weeks storage at 40° C. in a formulation comprised of a carboxylic acid ester and the enzyme powder as compared to the initial enzyme activity of the enzyme powder prior to the preparation of a formulation comprised of the carboxylic acid ester and the enzyme powder at 40° C. Preferably, perhydrolysis activity is measured as described in Examples 8-13 of U.S. Patent Application Publication No. 2010-0086510; but any method of measuring perhydrolysis activity may used.

A further improvement in enzyme activity over the stated periods of time can be achieved by adding a buffer having a buffering capacity in a pH range of from about 5.5 to about 9.5 to the formulation comprised of the carboxylic acid ester and the spray-dried enzyme powder as described in U.S. Patent Application Publication No. 2010-0086534. A suitable buffer may include, but is not limited to, sodium salt, potassium salt, or mixtures of sodium or potassium salts of bicarbonate, pyrophosphate, phosphate, methylphosphonate, citrate, acetate, malate, fumarate, tartrate maleate or succinate. Preferred buffers for use in the formulation comprised of the carboxylic acid ester and the spray-dried enzyme powder include the sodium salt, potassium salt, or mixtures of sodium or potassium salts of bicarbonate, pyrophosphate, phosphate, methylphosphonate, citrate, acetate, malate, fumarate, tartrate maleate or succinate.

In embodiments where a buffer may be present in the carboxylic acid ester and enzyme powder formulation, the buffer may be present in an amount in a range of from about 0.01 wt % to about 50 wt % based on the weight of carboxylic acid ester in the formulation comprised of carboxylic acid ester and enzyme powder. The buffer may be present in a more preferred range of from about 0.10% to about 10% based on the weight of carboxylic acid ester in the formulation comprised of carboxylic acid ester and enzyme powder. Further, in these embodiments, the comparison between perhydrolysis activity of the enzyme is determined as between an enzyme powder which retains at least 75 percent of the perhydrolysis activity of the at least one enzyme after eight weeks storage at 40° C. in a formulation comprised of a carboxylic acid ester, a buffer having a buffering capacity in a pH range of from about 5.5 to about 9.5, and the enzyme powder as compared to the initial perhydrolysis activity of the enzyme powder prior to the preparation of a formulation comprised of the carboxylic acid ester, the buffer having a buffering capacity in a pH range of from about 5.5 to about 9.5, and the enzyme powder.

It is intended that the dried enzyme powder be stored as a formulation in the organic compound that is a substrate for the at least one enzyme, such as triacetin. In the absence of added hydrogen peroxide, triacetin is normally hydrolyzed in aqueous solution by a CE-7 carbohydrate esterase to produce diacetin and acetic acid, and the production of acetic acid results in a decrease in the pH of the reaction mixture. One requirement for long term storage stability of the enzyme in triacetin is that there is not a significant reaction of the triacetin with any water that might be present in the triacetin; the specification for water content in one commercial triacetin (supplied by Tessenderlo Group, Brussels, Belgium) is 0.03 wt % water (300 ppm). Any hydrolysis of triacetin that occurs during storage of the enzyme in triacetin would produce acetic acid, which could result in a decrease in activity or inactivation of the CE-7 perhydrolases; the perhydrolases are typically inactivated at or below a pH of 5.0 (see U.S. Patent Application Publication No. 2009-0005590 to DiCosimo, R., et al.). The excipient selected for use in the present application must provide stability of the enzyme in the organic substrate for the enzyme under conditions where acetic acid might be generated due to the presence of low concentrations of water in the formulation. The dried enzyme powder may be stored as a formulation in the organic compound that is a substrate for the at least one enzyme, where the formulation additionally comprises an excipient and one or more buffers (e.g., sodium and/or potassium salts of bicarbonate, citrate, acetate, phosphate, pyrophosphate, methylphosphonate, succinate, malate, fumarate, tartrate, and maleate).

Suitable Reaction Conditions for the Enzyme-Catalyzed Preparation of Peracids from Carboxylic Acid Esters and Hydrogen Peroxide One or more enzymes having perhydrolytic activity may be used to generate an efficacious concentration of the desired peracid(s) in the present personal care compositions and methods. The desired peroxycarboxylic acid may be prepared by reacting carboxylic acid esters with a source of peroxygen including, but not limited to, hydrogen peroxide, zinc peroxide, sodium peroxide, urea peroxide, calcium peroxide, sodium perborate, sodium percarbonate or complexes of hydrogen peroxide, in the presence of an enzyme catalyst having perhydrolysis activity.

The perhydrolytic enzyme within the targeted perhydrolase may be any perhydrolytic enzyme and may include lipases, proteases, esterases, acyl transferases, aryl esterases, carbohydrate esterases, and combinations so long as the enzyme has perhydrolytic activity for one or more of the present substrates. Examples may include, but are not limited to perhydrolytic proteases (subtilisin variant; U.S. Pat. No. 7,510,859), perhydrolytic esterases (*Pseudomonas fluorescens*; U.S. Pat. No. 7,384,787; "L29P" variant SEQ ID NO: 477), and perhydrolytic aryl esterases (*Mycobacterium smegmatis*; U.S. Pat. No. 7,754,460; WO2005/056782; and EPI 689859 B1; SEQ ID NOs: 460 [S54V variant] and 478 [wild type]).

In one embodiment, the enzyme catalyst comprises at least one enzyme having perhydrolase activity, wherein said enzyme is structurally classified as a member of the CE-7 carbohydrate esterase family (CE-7; see Coutinho, P. M., and Henrissat, B., supra). In another embodiment, the perhydrolase catalyst is structurally classified as a cephalosporin C deacetylase. In another embodiment, the perhydrolase catalyst is structurally classified as an acetyl xylan esterase.

In one embodiment, the perhydrolase catalyst comprises an enzyme having perhydrolysis activity and a signature motif comprising:
a) an RGQ motif that aligns with amino acid residues 118-120 of SEQ ID NO: 2;
b) a GXSQG motif that aligns with amino acid residues 179-183 of SEQ ID NO: 2; and
c) an HE motif that aligns with amino acid residues 298-299 of SEQ ID NO: 2.

In a preferred embodiment, the alignment to reference SEQ ID NO: 2 is performed using CLUSTALW.

In a further embodiment, the CE-7 signature motif additional may comprise and additional (i.e., fourth) motif defined as an LXD motif at amino acid residues 267-269 when aligned to reference sequence SEQ ID NO:2 using CLUSTALW.

In another embodiment, the perhydrolase catalyst comprises an enzyme having perhydrolase activity, said enzyme having an amino acid sequence selected from the group consisting of SEQ ID NOs: 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, 64, 424, 437, and 476.

In another embodiment, the perhydrolase catalyst comprises an enzyme having perhydrolase activity, said enzyme having an amino acid sequence selected from the group consisting of SEQ ID NOs: 2, 4, 6, 8, 10, 12, 14, 16, 18, 20, 22, 24, 26, 27, 28, 29, 30, 31, 32, 33, 34, 35, 36, 38, 40, 42, 44, 46, 48, 50, 52, 54, 56, 58, 60, 62, 64, 424, 437, and 476 wherein said enzyme may have one or more additions, deletions, or substitutions so long as the signature motif is conserved and perhydrolase activity is retained.

As described above, the CE-7 perhydrolase may be a fusion protein having a first portion comprising CE-7 perhydrolase and a second portion comprising a peptidic component having affinity for a target body surface such that the perhydrolase is "targeted" to the desired body surface. In one embodiment, any CE-7 perhydrolase (as defined by the presence of the CE-7 signature motifs) may be fused to any peptidic component/binding element capable of targeting the enzyme to a body surface. In one aspect, the peptidic component having affinity for an oral cavity surface may include antibodies, antibody fragments ($F_{ab}$), as well as single chain variable fragments (scFv; a fusion of the variable regions of the heavy ($V_H$) and light chains ($V_L$) of immunoglobulins), single domain camelid antibodies, scaffold display proteins, and single chain affinity peptides lacking immunoglobulin folds. The compositions comprising antibodies, antibodies fragments and other immunoglobulin-derived binding elements, as well as large scaffold display proteins, are often not economically viable. As such, and in a preferred aspect, the peptidic component/binding element is a single chain affinity peptide lacking an immunoglobulin fold and/or immunoglobulin domain. Short single chain body surface-binding peptides may be empirically generated (e.g., positively charged polypeptides targeted to negatively charged surfaces) or generated using biopanning against a target body surface. Methods to identify/obtain affinity peptides using any number of display techniques (e.g., phage display, yeast display, bacterial display, ribosome display, and mRNA display) are well known in the art. Individual oral cavity surface-binding peptides may be coupled together, via optional spacers/linkers, to form larger binding "domains" (also referred to herein as binding "hands") to enhance attachment/localization of the perhydrolytic enzyme to the target oral cavity surface.

The fusion proteins may also include one or more peptide linkers/spacers separating the CE-7 perhydrolase enzyme the oral cavity surface-binding domain and/or between different oral cavity surface-binding peptides (e.g., when a plurality of oral cavity surface-binding peptides are coupled together to form a larger target oral cavity surface-binding domain). Multiple peptide linkers/spacers may be present and the number of linkers may be repeated up to 10 times. A non-limiting list of exemplary peptide spacers are provided by the amino acid sequences of SEQ ID NOs: 383-396 and those illustrated in Table 5.

Suitable peptides having affinity for an oral cavity surface are described herein, supra. Methods to identify additional oral cavity surface-binding peptides using any of the above "display" techniques are well known and can be used to identify additional oral cavity surface-binding peptides.

Suitable carboxylic acid ester substrates may include esters having the following formula:

(a) one or more esters having the structure

wherein
X is an ester group of the formula $R_6C(O)O$;
$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
$R_5$ is a C1 to C6 linear, branched, or cyclic hydrocarbyl moiety or a five-membered cyclic heteroaromatic moiety or six-membered cyclic aromatic or heteroaromatic moiety optionally substituted with a hydroxyl group; wherein each carbon atom in $R_5$ individually comprises no more than one hydroxyl group or no more than one ester group or carboxylic acid group, and wherein $R_5$ optionally comprises one or more ether linkages;
m is an integer ranging from 1 to the number of carbon atoms in $R_5$,
said one or more esters having solubility in water of at least 5 ppm at 25° C.; or
(b) one or more glycerides having the structure

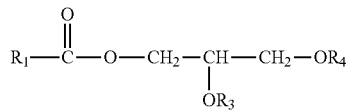

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or
(c) one or more esters of the formula

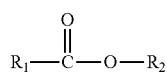

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; or
(d) one or more acetylated monosaccharides, acetylated disaccharides, or acetylated polysaccharides; or
(e) any combination of (a) through (d).

Suitable substrates may also include one or more acylated saccharides selected from the group consisting of acylated mono-, di-, and polysaccharides. In another embodiment, the acylated saccharides are selected from the group consisting of acetylated xylan; fragments of acetylated xylan; acetylated xylose (such as xylose tetraacetate); acetylated glucose (such as α-D-glucose pentaacetate; β-D-glucose pentaacetate; tetraacetate); β-D-galactose pentaacetate; sorbitol hexaacetate; sucrose octaacetate; β-D-ribofuranose-1,2,3,5-tetraacetate; β-D-ribofuranose-1,2,3,4-tetraacetate; tri-O-acetyl-D-galactal; tri-O-acetyl-D-glucal; β-D-xylofuranose tetraacetate, α-D-glucopyranose pentaacetate; β-D-glucopyranose-1,2,3,4-tetraacetate; β-D-glucopyranose-2,3,4,6-tetraacetate; 2-acetamido-2-deoxy-1,3,4,6-tetracetyl-β-D-glucopyranose; 2-acetamido-2-deoxy-3,4,6-triacetyl-1-chloride-α-D-glucopyranose; α-D-mannopyranose pentaacetate, and acetylated cellulose. In a preferred embodiment, the acetylated saccharide is selected from the group consisting of β-D-ribofuranose-1,2,3,5-tetraacetate; tri-O-acetyl-D-galactal; tri-O-acetyl-D-glucal; sucrose octaacetate; and acetylated cellulose.

In another embodiment, additional suitable substrates may also include 5-acetoxymethyl-2-furaldehyde; 3,4-diacetoxy-1-butene; 4-acetoxybenezoic acid; vanillin acetate; propylene glycol methyl ether acetate; methyl lactate; ethyl lactate; methyl glycolate; ethyl glycolate; methyl methoxyacetate; ethyl methoxyacetate; methyl 3-hydroxybutyrate; ethyl 3-hydroxybutyrate; and triethyl 2-acetyl citrate.

In another embodiment, suitable substrates are selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate, tri-O-acetyl-D-galactal; tri-O-acetyl-D-glucal; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,5-pentanediol; 1,6-pentanediol; 1,2-hexanediol; 2,5-hexanediol; 1,6-hexanediol; and mixtures thereof. In another embodiment, the substrate is a C1 to C6 polyol comprising one or more ester groups. In a preferred embodiment, one or more of the hydroxyl groups on the C1 to C6 polyol are substituted with one or more acetoxy groups (such as 1,3-propanediol diacetate; 1,2-propanediol diacetate; 1,4-butanediol diacetate; 1,5-pentanediol diacetate, etc.). In a further embodiment, the substrate is propylene glycol diacetate (PGDA), ethylene glycol diacetate (EGDA), or a mixture thereof.

In a further embodiment, suitable substrates are selected from the group consisting of monoacetin, diacetin, triacetin, monopropionin, dipropionin, tripropionin, monobutyrin, dibutyrin, and tributyrin. In yet another aspect, the substrate is selected from the group consisting of diacetin and triacetin. In a most preferred embodiment, the suitable substrate comprises triacetin.

In a preferred embodiment, the carboxylic acid ester is a liquid substrate selected from the group consisting of monoacetin, diacetin, triacetin, and combinations (i.e., mixtures) thereof. The carboxylic acid ester is present in the reaction formulation at a concentration sufficient to produce the desired concentration of peroxycarboxylic acid upon enzyme-catalyzed perhydrolysis. The carboxylic acid ester need not be completely soluble in the reaction formulation, but has sufficient solubility to permit conversion of the ester by the perhydrolase catalyst to the corresponding peroxycarboxylic acid. The carboxylic acid ester is present in the reaction formulation at a concentration of 0.05 wt % to 40 wt % of the reaction formulation, preferably at a concentration of 0.1 wt % to 20 wt % of the reaction formulation, and more preferably at a concentration of 0.5 wt % to 10 wt % of the reaction formulation.

The peroxygen source may include, but is not limited to, hydrogen peroxide, hydrogen peroxide adducts (e.g., urea-hydrogen peroxide adduct (carbamide peroxide)) perborate salts, percarbonate salts and peroxide salts. The concentration of peroxygen compound in the reaction formulation may range from 0.0033 wt % to about 50 wt %, preferably from 0.033 wt % to about 40 wt %, more preferably from 0.1 wt % to about 30 wt %.

The peroxygen source (i.e., hydrogen peroxide) may also be generated enzymatically using enzyme capable of producing and effective amount of hydrogen peroxide. For example, various oxidases can be used in the present compositions and methods to produce an effective amount of hydrogen peroxide including, but not limited to glucose oxidase, lactose oxidases, carbohydrate oxidase, alcohol oxidase, ethylene glycol oxidase, glycerol oxidase, and amino acid oxidase.

Many perhydrolase catalysts (whole cells, permeabilized whole cells, and partially purified whole cell extracts) have been reported to have catalase activity (EC 1.11.1.6). Catalases catalyze the conversion of hydrogen peroxide into oxygen and water. In one aspect, the perhydrolysis catalyst lacks catalase activity. In another aspect, a catalase inhibitor may be added to the reaction formulation. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM.

In another embodiment, the enzyme catalyst lacks significant catalase activity or may be engineered to decrease or eliminate catalase activity. The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In a preferred embodiment, the gene(s) encoding the endogenous catalase activity are down-regulated or disrupted (i.e., knocked-out). As used herein, a "disrupted" gene is one where the activity and/or function of the protein encoded by the modified gene is no longer present. Means to disrupt a gene are well-known in the art and may include, but are not limited to, insertions, deletions, or mutations to the gene so long as the activity and/or function of the corresponding protein is no longer present. In a further preferred embodiment, the production host is an *E. coli* production host comprising a disrupted catalase gene selected from the group consisting of katG and katE (see U.S. Patent Application Publication No. 2008-0176299). In another embodiment, the production host is an *E. coli* strain comprising a down-regulation and/or disruption in both katG and a katE catalase genes.

The concentration of the catalyst in the aqueous reaction formulation depends on the specific catalytic activity of the catalyst, and is chosen to obtain the desired rate of reaction. The weight of catalyst in perhydrolysis reactions typically ranges from 0.0001 mg to 10 mg per mL of total reaction volume, preferably from 0.001 mg to 2.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peroxycarboxylic acid generated by the combination of chemical perhydrolysis and enzymatic perhydrolysis of the carboxylic acid ester is sufficient to provide an effective concentration of peroxycarboxylic acid for the chosen personal care application. In another aspect, the present methods provide combinations of enzymes and enzyme substrates to produce the desired effective concentration of peroxycarboxylic acid, where, in the absence of added enzyme, there is a significantly lower concentration of peroxycarboxylic acid produced. Although there may in some cases be substantial chemical perhydrolysis of the enzyme substrate by direct chemical reaction of inorganic peroxide with the enzyme substrate, there may not be a sufficient concentration of peroxycarboxylic acid generated to provide an effective concentration of peroxycarboxylic acid in the desired applications, and a significant increase in total peroxycarboxylic acid concentration is achieved by the addition of an appropriate perhydrolase catalyst to the reaction formulation.

The concentration of peroxycarboxylic acid generated (e.g. peracetic acid) by the perhydrolysis of at least one carboxylic acid ester is at least about 0.1 ppm, preferably at least 0.5 ppm, 1 ppm, 5 ppm, 10 ppm, 20 ppm, 100 ppm, 200 ppm, 300 ppm, 500 ppm, 700 ppm, 1000 ppm, 2000 ppm, 5000 ppm or 10,000 ppm of peracid within 10 minutes, preferably within 5 minutes, of initiating the perhydrolysis reaction. The product formulation comprising the peroxycarboxylic acid may be optionally diluted with water, or a solution predominantly comprised of water, to produce a formulation with the desired lower concentration of peroxycarboxylic acid base on the target application. Clearly one of skill in the art can adjust the reaction components and/or dilution amounts to achieve the desired peracid concentration for the chosen personal care product.

In one aspect, the reaction time required to produce the desired concentration of peracid is not greater than about two hours, preferably not greater than about 30 minutes, more preferably not greater than about 10 minutes, and most preferably in about 5 minutes or less. In other aspects, an oral cavity surface is contacted with the peroxycarboxylic acid formed in accordance with the processes described herein within 5 minutes of combining the reaction components. In one embodiment, the target oral cavity surface is contacted with the peroxycarboxylic acid produced with the processes described herein within about 5 minutes to about 168 hours of combining said reaction components, or within about 5 minutes to about 48 hours, or within about 5 minutes to 2 hours of combining said reaction components, or any such time interval therein.

The peracid formed in accordance with the processes describe herein is used in a personal care product/application wherein the peracid is contacted with a target oral cavity surface to provide a peracid-based benefit to the oral cavity. In one embodiment, the process to produce a peracid for a target body surface is conducted in situ.

The temperature of the reaction may be chosen to control both the reaction rate and the stability of the enzyme catalyst activity. Clearly for certain personal care applications the temperature of the target body surface (e.g., 37° C. within the oral cavity) may be the temperature of the reaction. The temperature of the reaction may range from just above the freezing point of the reaction formulation (approximately 0° C.) to about 95° C., with a preferred range of 5° C. to about 75° C., and a more preferred range of reaction temperature of from about 5° C. to about 55° C.

The pH of the final reaction formulation containing peroxycarboxylic acid is from about 2 to about 9, preferably from about 3 to about 8, more preferably from about 5 to about 8, even more preferably about 5.5 to about 8, and yet even more preferably about 6.0 to about 7.5. The pH of the reaction, and of the final reaction formulation, may optionally be controlled by the addition of a suitable buffer including, but not limited to, phosphate, pyrophosphate, bicarbonate, acetate, or citrate. The concentration of buffer, when employed, is typically from 0.1 mM to 1.0 M, preferably from 1 mM to 300 mM, most preferably from 10 mM to 100 mM.

In another aspect, the enzymatic perhydrolysis reaction formulation may contain an organic solvent that acts as a dispersant to enhance the rate of dissolution of the carboxylic acid ester in the reaction formulation. Such solvents include, but are not limited to, propylene glycol methyl ether, acetone, cyclohexanone, diethylene glycol butyl ether, tripropylene glycol methyl ether, diethylene glycol methyl ether, propylene glycol butyl ether, dipropylene glycol methyl ether, cyclohexanol, benzyl alcohol, isopropanol, ethanol, propylene glycol, and mixtures thereof.

Single Step Vs. Multi-Step Application Methods

Typically the minimum set of reaction components to enzymatically produce a peracid benefit agent will include (1) at least one enzyme having perhydrolytic activity as described herein, such as a CE-7 perhydrolase (optionally in the form of a targeted fusion protein), (2) at least one suitable carboyxlic acid ester substrate, and (3) a source of peroxygen.

The peracid-generating reaction components of the personal care composition may remain separated until use. In one embodiment, the peracid-generating components are combined and then contacted with the target body surface whereby the resulting peracid-based benefit agent provides a benefit to the body surface. The components may be combined and then contacted with the target body surface or may be combined on the targeted body surface. In one embodiment, the peracid-generating components are combined such that the peracid is produced in situ.

A multi-step application may also be used. One or two of the individual components of the peracid-generating system (i.e., a sequential application on the body surface of at least one of the three basic reaction components) composition may be contacted with the oral cavity surface prior to applying the remaining components required for enzymatic peracid production. In one embodiment, the perhydrolytic enzyme is contacted with the oral cavity surface prior to contacting the oral cavity surface with the carboyxlic acid ester substrate and/or the source of peroxygen (i.e., a "two-step application"). In one embodiment, the enzyme having perhydrolytic activity is a targeted perhydrolase that is applied to the oral cavity surface prior to combining the remaining components necessary for enzymatic peracid production.

In a preferred embodiment, the enzyme having perhydrolytic activity is a "targeted CE-7 perhydrolase" (i.e., CE-7 fusion protein) that is applied to the oral cavity surface prior to combining the remaining components necessary for enzymatic peracid production (i.e., a two-step application method). The targeted perhydrolase is contacted with the oral cavity surface under suitable conditions to promote non-covalent bonding of the fusion protein to the oral cavity surface.

An optional rinsing step may be used to remove excess and/or unbound fusion protein prior to combining the remaining reaction components.

In a further embodiment, the perhydrolytic enzyme (optionally in the form of a fusion protein targeted to the oral cavity surface) and the carboxylic acid ester are applied to the target oral cavity surface prior to the addition of the source of peroxygen.

In a further embodiment, the perhydrolytic enzyme (optionally in the form of a fusion protein targeted to the oral cavity surface) and source of peroxygen (e.g., an aqueous solution comprising hydrogen peroxide) are applied to the oral cavity surface prior to the addition of the carboxylic acid ester substrate.

In a further embodiment, the carboxylic acid ester substrate and the source of peroxygen (e.g., an aqueous solution comprising hydrogen peroxide) are applied to the oral cavity surface prior to the addition of the perhydrolytic enzyme (optionally in the form of a fusion protein targeted to the oral cavity surface).

In yet another embodiment, any of the compositions or methods described herein can be incorporated into a kit for practicing the invention. The kits may comprise materials and reagents to facilitate enzymatic production of peracid. An exemplary kit comprises a substrate, a source of peroxygen, and an enzyme catalyst having perhydrolytic activity, wherein the enzyme catalyst can be optionally targeted to an oral cavity surface. Other kit components may include, without limitation, one or more of the following: sample tubes, solid supports, instruction material, and other solutions or other chemical reagents useful in enzymatically producing peracids, such as acceptable components or carriers.

Oral Care Compositions

Orally Acceptable Components/Carriers

The present compositions and method s may also include orally acceptable carriers as well as additional (i.e., in addition to the peracid-based benefit agent) oral care benefit agents. As used herein, the term "oral care benefit agent" is a general term applying to a compound or substance that provides a desired/beneficial effect or attribute to an oral surface. In one embodiment, benefit agents for oral surfaces may comprise (in addition to the peracid-based benefit agent) colorants including, but not limited to, white pigments such as titanium dioxide and white minerals such as hydroxyapatite or zircon. In another embodiment, oral care benefit agents may also include whitening agents and additional enzymes such as, for example, oxidases, peroxidases, proteases, lipases, glycosidases, esterases, and polysaccharide hydrolases. In another aspect, benefit agents may include anti-plaque agents, anti-stain agents, and antimicrobial agents. Antimicrobial agents may include, but are not limited to, antimicrobial peptides, magainins, cecropins, microbiocides, triclosan, chlorhexidine, cetylpyridinium chloride, quaternary ammonium compounds, chlorxylenol, chloroxyethanol, phthalic acid and its salts, thymol, and combinations thereof. Oral care benefit agents may also include anti-caries agents, such as sodium fluoride or sodium monofluorophosphate, and flavoring agents such as oil of wintergreen, peppermint, or spearmint, or methyl salicylate, eucalyptol, or vanillin. Oral care benefit agents may also include coolants, such as succinate-based coolant compounds, and salivating agents, to name a few. As is used herein, the term "salivating agent" refers to a material that promotes greater salivation in the user when present in the oral care composition. In one embodiment, the benefit agent is an orally-acceptable material approved for use in oral care products. In another embodiment, the orally-acceptable benefit agent is used to improve the cosmetic appearance of teeth.

A non-limiting list of components often used in an orally-acceptable carrier medium are described by White et al. in U.S. Pat. No. 6,740,311; Lawler et al. in U.S. Pat. No. 6,706, 256; Fuglsang et al. in U.S. Pat. No. 6,264,925; and Ibrahim et al. in U.S. Patent Application Publication No. 2005-0069501, each of which are incorporated herein by reference in their entirety. For example, the oral care composition may comprise one or more of the following: abrasives, surfactants, antioxidants, chelating agents, fluoride sources, thickening agents, buffering agents, solvents, humectants, carriers, bulking agents, anti-plaque agents, anti-staining agents, antimicrobial agents, anti-caries agents, anti-inflammatory agents, desensitizing agents, sweetening agents, flavoring agents, breath-freshening agents, coolants, nutrients, and salivating agents.

It will be appreciated that the components in the mixture are chosen such that the oral care composition retains the ability to enzymatically product the desired peracid benefit agent. Suitable mixtures of oral care systems disclosed herein may be determined by one skilled in the art using routine experimentation. The total concentration of the oral care benefit agents with the oral care formulation may be about 0.001% to about 90% by weight relative to the total weight of the oral care composition.

The oral care compositions may include, but are not limited to, toothpaste, dental cream, tooth gel or tooth powder, mouth wash, breath freshener, and dental floss. Additional embodiments include the application of the reaction components in a paste or gel that is applied in the oral environment via a mouth tray. One or more of the reaction components can also be deposited first on a plastic strip that is adhered to the enamel to deliver one or more of the reaction components to generate the peracid benefit agent. In the case of the deposition of the perhydrolase fusion on a delivery device such as a strip, the perhydrolase fusion can be designed to include binding elements with affinity for the material of the strip to aid in the deposition and retention of the perhydrolase to the strip during use and removal of the device after use.

Peracid-Based Oral Care Products to Reduce Microbes Associated with Diseases of the Oral Cavity or Remove Unwanted Biofilm.

Peracid-based oral care products may be used to reduce oral cavity bacteria associated with dental caries (such as *Streptococcus mutans*), gingivitis, oral candidiasis, or periodontitis. The peracid-based oral care products may be used to reduce or remove oral biofilm(s).

In one embodiment, the use of an enzyme having perhydrolytic activity in an oral care product to produce an efficacious concentration of at least one peracid is provided to bleach, whiten, disinfect, destain, deodorize or remove biofilm from an oral cavity surface.

In one embodiment, the enzyme having perhydrolytic activity is a targeted perhydrolase and may include lipases, proteases, esterases, acyl transferases, aryl esterases, carbohydrate esterases, and combinations so long as the enzyme has perhydrolytic activity for one or more of the present substrates. Examples may include, but are not limited to perhydrolytic proteases (e.g., subtilisin variant; U.S. Pat. No. 7,510,859), perhydrolytic esterases (e.g., *Pseudomonas fluorescens*; U.S. Pat. No. 7,384,787; SEQ ID NO: 477), and perhydrolytic aryl esterases (e.g., *Mycobacterium smegmatis*; U.S. Pat. No. 7,754,460; WO2005/056782; and EP1689859 B1; SEQ ID NOs: 460 [S54V variant] and 478 [wild type]).

In another embodiment, the use of a CE-7 carbohydrate esterase having perhydrolytic activity in an oral care product to produce an efficacious concentration of at least one peracid is provided to bleach, whiten, disinfect, destain, deodorize or remove biofilm from an oral cavity surface.

In another embodiment, the use the following peracid generation composition is also provided comprising:
a) an enzyme catalyst having perhydrolytic activity, wherein said enzyme catalyst comprises an enzyme having a CE-7 signature motif that aligns with a reference sequence SEQ ID NO: 2 using CLUSTALW, said signature motif comprising:
  i) an RGQ motif at positions corresponding to positions 118-120 of SEQ ID NO:2;
  ii) a GXSQG motif at positions corresponding to positions 179-183 of SEQ ID NO:2; and
  iii) an HE motif at positions corresponding to positions 298-299 of SEQ ID NO:2; and
b) at least one substrate selected from the group consisting of:
  1) esters having the structure

wherein X=an ester group of the formula $R_6C(O)O$
  $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
  $R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;
  M is an integer ranging from 1 to the number of carbon atoms in $R_5$; and
  wherein said esters have a solubility in water of at least 5 ppm at 25° C.;
  2) glycerides having the structure

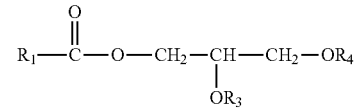

wherein $R_1$=C1 to C7 straight chain or branched chain alkyl optionally substituted with an hydroxyl or a C1 to C4 alkoxy group and $R_3$ and $R_4$ are individually H or $R_1C(O)$;
  3) one or more esters of the formula

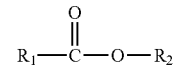

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10; and 4) acetylated saccharides selected from the group consisting of acetylated monosaccharides, acetylated disaccharides, and acetylated polysaccharides; and c) a source of peroxygen;

whereby a peracid formed upon mixing (a), (b), and (c); wherein the peracid generation formulation is used for the treatment or prevention of dental caries, gingivitis, oral candidiasis, or periodontitis.

HPLC Assay Method for Determining the Concentration of Peroxycarboxylic Acid and Hydrogen Peroxide.

A variety of analytical methods can be used in the present methods to analyze the reactants and products including, but not limited to, titration, high performance liquid chromatography (HPLC), gas chromatography (GC), mass spectroscopy (MS), capillary electrophoresis (CE), the analytical procedure described by U. Pinkernell et al., (*Anal. Chem.*, 69 (17):3623-3627 (1997)), and the 2,2'-azino-bis(3-ethylbenzothazoline)-6-sulfonate (ABTS) assay (U. Pinkernell et. al. *Analyst*, 122: 567-571 (1997) and Dinu et. al. *Adv. Funct. Mater.*, 20: 392-398 (2010)) as described in the present examples.

Determination of Minimum Biocidal Concentration of Peroxycarboxylic Acids

Certain personal care applications may be associated with the removal of unwanted microbes, such as those associated with body order, fungal infections, and the development of dental caries, to name a few. As such, one may want to measure the minimum biocidal concentration for the target personal care application. The method described by J. Gabrielson, et al. (*J. Microbiol. Methods* 50: 63-73 (2002)) can be employed for determination of the Minimum Biocidal Concentration (MBC) of peroxycarboxylic acids, or of hydrogen peroxide and enzyme substrates. The assay method is based on XTT reduction inhibition, where XTT ((2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to, viable plate counts, direct microscopic counts, dry weight, turbidity measurements, absorbance, and bioluminescence (see, for example Brock, Semour S., *Disinfection, Sterilization, and Preservation*, 5$^{th}$ edition, Lippincott Williams & Wilkins, Philadelphia, Pa., USA; 2001).

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, bacterial host strains include *Escherichia, Bacillus, Kluyveromyces*, and *Pseudomonas*. In a preferred embodiment, the bacterial host cell is *Bacillus subtilis* or *Escherichia coli*.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters which are useful to drive expression of the present cephalosporin C deacetylase coding region in the desired host cell are numerous and familiar to those skilled in the art. Virtually any promoter capable of driving these genes is suitable for the present invention including but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, araB, tet, trp, IP$_L$, F$_R$, T7, tac, and trc (useful for expression in *Escherichia coli*) as well as the amy, apr, npr promoters and various phage promoters useful for expression in *Bacillus*.

Termination control regions may also be derived from various genes native to the preferred host cell. In one embodiment, the inclusion of a termination control region is optional. In another embodiment, the chimeric gene includes a termination control region derived from the preferred host cell.

Industrial Production

A variety of culture methodologies may be applied to produce the perhydrolase catalyst. For example, large-scale production of a specific gene product over-expressed from a recombinant microbial host may be produced by batch, fed-batch, and continuous culture methodologies. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227-234 (1992).

Commercial production of the desired perhydrolase catalyst may also be accomplished with a continuous culture.

Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Recovery of the desired perhydrolase catalysts from a batch fermentation, fed-batch fermentation, or continuous culture, may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein by membrane filtration or centrifugation, and the resulting partially-purified enzyme catalyst solution concentrated by additional membrane filtration, then optionally mixed with an appropriate carrier (for example, maltodextrin, phosphate buffer, citrate buffer, or mixtures thereof) and spray-dried to produce a solid powder comprising the desired enzyme catalyst.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

General Methods

The following examples are provided to demonstrate preferred aspects of the invention. It should be appreciated by those of skill in the art that the techniques disclosed in the examples follow techniques to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods and examples.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.), Thermo Scientific (Pierce Protein Research Products) (Rockford, Ill.) or Sigma/Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "mg" means milligram(s), "µg" means microgram(s), "ng" means nanogram(s), "g" means gravity, "HPLC" means high performance liquid chromatography, "dd $H_2O$" means distilled and deionized water, "dcw" means dry cell weight, "ATCC" or "ATCC®" means the American Type Culture Collection (Manassas, Va.), "U" means unit(s) of perhydrolase activity, "rpm" means revolution(s) per minute, "Tg" means glass transition temperature, and "EDTA" means ethylenediaminetetraacetic acid.

Expression Vector pLD001

Plasmid pLD001 (SEQ ID NO: 397) has been previous reported as a suitable expression vector for *E. coli* (see U.S. Patent Application Publication No. 2010-0158823 A1 to Wang et al.; incorporated herein by reference).

The vector pLD001 was derived from the commercially available vector pDEST17 (Invitrogen, Carlsbad, Calif.). It includes sequences derived from the commercially available vector pET31b (Novagen, Madison, Wis.) that encode a fragment of the enzyme ketosteroid isomerase (KSI). The KSI fragment was included as a fusion partner to promote partition of the peptides into insoluble inclusion bodies in *E. coli*. The KSI-encoding sequence from pET31 b was modified using standard mutagenesis procedures (QuickChange II, Stratagene, La Jolla, Calif.) to include three additional Cys codons, in addition to the one Cys codon found in the wild type KSI sequence. In addition, all Asp codons in the coding sequence were replaced by Glu codons. The plasmid pLD001, given by SEQ ID NO: 397, was constructed using standard recombinant DNA methods, which are well known to those skilled in the art.

EXAMPLE 1

Effectiveness of Peracetic Acid as a Tooth Bleaching Agent

This example describes the use of peracetic acid to achieve a bleaching effect on model stained enamel surfaces. Bovine enamel incisors were obtained from SE Dental (Baton Rouge, La.). Teeth were sectioned and cut into enamel slabs approximately 7 mm on each side using a DREMEL® rotary saw (Robert Bosch Power Tool Corporation; Chicago, Ill.) with a diamond blade. The enamel slabs were cleaned and lightly polished to remove surface debris. The enamel was pretreated with a mixture of coffee and tea for 1-5 days in order to stain to a color similar to human stained teeth.

Each enamel block was hydrated in water for at least 1 hr prior to use. Color measurements for the substrate were obtained prior to exposure to test solutions. Solutions of peracetic acid were prepared from a 32% stock in 500 mM sodium phosphate buffer, pH 7.2. A solution of 2.5% $H_2O_2$ was also prepared in the same buffer. Multiple enamel blocks were exposed to each solution for 1 min followed by additional exposures of 5 min, 10 min, 15 min and 30 min. For each treatment, a fresh solution of peracetic acid and hydrogen peroxide was prepared from the stock solutions. After each treatment the enamel blocks were rinsed with water and measured with a Konica-Minolta 2600d spectrophotometer. Whiteness index was determined for each sample as listed in Table 1 and 2.

Whiteness index (WI) is defined by the International Commission on Illumination (CIE) and described in ASTM method E313-05 and calculated for D65/10 incident light as:

$$WI=Y+800*(0.3138-x)+1700*(0.3310-y)$$

Where Y, x, and y are the luminance factor and the chromaticity coordinates respectively of the enamel substrate.

TABLE 1

Comparison of Peracetic Acid Bleaching to Hydrogen Peroxide on Stained Bovine Enamel.

| | Whiteness Index | | | | | | |
|---|---|---|---|---|---|---|---|
| Sample | 0 min | 1 min | 6 min | 16 min | 31 min | 61 min | ΔWI |
| Buffer | −135.1 | −136.4 | −131.6 | −135.7 | −129.2 | −124.0 | 11.1 |
| 2.5% H₂O₂ | −127.5 | −127.2 | −124.5 | −118.4 | −103.6 | −84.9 | 42.6 |
| 0.5% PAA | −129.1 | −111.6 | −80.7 | −56.5 | −44.5 | −38.3 | 90.8 |

TABLE 2

Comparison of Peracetic Acid Bleaching to Hydrogen Peroxide on Stained Bovine Enamel at Various Concentrations.

| | Whiteness Index | | | | | | |
|---|---|---|---|---|---|---|---|
| Sample | 0 min | 1 min | 6 min | 16 min | 31 min | 61 min | ΔWI |
| Buffer | −100.8 | −98.6 | −100.0 | −97.1 | −89.5 | −84.0 | 16.8 |
| 2.5% H₂O₂ | −93.8 | −92.6 | −86.4 | −79.5 | −68.3 | −56.4 | 37.4 |
| 0.05% PAA | −103.4 | −97.1 | −93.1 | −70.1 | −59.0 | −34.7 | 68.7 |
| 0.2% PAA | −90.6 | −85.5 | −67.0 | −47.5 | −31.7 | −16.2 | 74.4 |
| 0.5% PAA | −97.5 | −86.6 | −64.1 | −46.4 | −32.7 | −24.7 | 72.8 |
| 1% PAA | −102.8 | −89.3 | | −36.0 | −20.6 | −5.1 | 97.7 |

The change in whiteness index to a more positive value indicated a whitening effect. Visual inspection of the samples also showed a perceptible whitening effect for peracetic acid treated samples compared to the buffer and hydrogen peroxide controls. This data demonstrates that peracetic acid is an effective bleaching agent and provides superior performance to hydrogen peroxide at lower concentrations.

EXAMPLE 2

Selection of Tooth Enamel and Pellicle Binding Peptides Using Standard Biopanning The purpose of this Example was to identify phage peptides that bind tooth enamel and pellicle using standard phage display biopanning.

Bovine enamel incisors were obtained from SE Dental (Baton Rouge, La.). The teeth were cut to approx. 5 mm squares and polished to remove surface debris. Enamel blocks were sterilized before use. Enamel blocks were embedded in a well plate contained molding material so as to only expose the enamel surface in the well. Pellicle was formed on additional enamel blocks by mounting the blocks on wax mounting for incubation in the mouth for 30 min to form a pellicle coated surface. The pellicle coated enamel substrates were brushed with a 1:2 slurry of COLGATE® MAXFRESH® toothpaste (Colgate-Palmolive, New York, N.Y.) and reincubated for an additional 30 min. A portion of the blocks were removed from the wax and embedded in a well plate while others were rebrushed before embedding in a well plate. The embedding process allowed for solution contact with only the enamel and pellicle-coated enamel surfaces.

The substrates were then incubated in blocking buffer for 1 hour at room temperature (~22° C.; 1 mg/mL Bovine Serum Albumin in Phosphate Buffered Saline pH 7.2 (Pierce BUPH™ #28372) with 0.1% TWEEN®20 (PBST), followed by 2 washes with PBST. Libraries of phage containing random peptide inserts ($10^{11}$ pfu) from 15 to 20 amino acids in length were added to each well. The final binding solution contained $10^{11}$ pfu phages, 10% UV treated whole saliva and 1 mg/mL BSA in 0.1% TWEEN®20 (PBST). After 30 minutes of incubation at 37° C. with shaking at 50 rpm, unbound phage were removed by aspirating the liquid out of each well followed by 6 washes with 1.0 mL PBST.

The enamel blocks were then transferred to clean tube and 1 mL of elution buffer consisting of 1 mg/mL BSA in 0.2 M glycine-HCl, pH 2.2, was added to each well and incubated for 10 min to elute the bound phages. Then, 167 µL of neutralization buffer consisting of 1 M Tris-HCl, pH 9.1, was added to each well. The phage particles, which were in the elution buffer as well as on the enamel blocks, were amplified by incubating with 20 mL diluted E. coli ER2738 cells, from an overnight culture diluted 1:100 in LB medium, at 37° C. for 4.5 h. After this time, the cell culture was centrifuged for 2 min and the upper 15 mL of the supernatant was transferred to a fresh tube, 2.5 mL of PEG/NaCl (20% polyethylene glycol-800, 2.5 M sodium chloride) was added, and the phage was allowed to precipitate overnight at 4° C. The precipitate was collected by centrifugation at 10,000×g at 4° C. and the resulting pellet was resuspended in 1 mL of PBS. This was the first round of amplified stock. The amplified first round phage stock was then titered according to the standard protocol. For subsequent rounds of biopanning, more than $2\times10^{11}$ pfu of phage stock from the previous round was used. Each additional round after the first also included an additional wash with human whole saliva (UV treated for 2 hours at room temperature), two washes with carbonate buffer pH 9.4 (Pierce BUPH™ Carbonate-Bicarbonate Buffer #28382), 2 washes with 50 mM phosphate buffer, pH 2.5 and followed by 2 washes with normal PBST.

After the 3rd round of biopanning and each subsequent round, 95 random single phage plaques were isolated and the single stranded phage genomic DNA was prepared using the Illustra Templiphi 500 Amplification Kit (GE Healthcare, Piscataway, N.J.) and sequenced at the DuPont Sequencing Facility using −96 gIII sequencing primer (5'-CCCTCATAGTTAGCGTAACG-3'; SEQ ID NO: 398). The displayed peptide is located immediately after the signal peptide of gene III. Based on the peptide sequences, 12 phage candidates were identified for further binding analysis as indicated in Table 3.

TABLE 3

Tooth Enamel-Binding and Pellicle-Binding Peptide Sequences.

| Sequence ID | Sequence | SEQ ID NO: |
|---|---|---|
| P301 | SNATMYNIQSHSHHQ | 399 |
| P302 | QAAQVHMMQHSRPTT | 400 |

TABLE 3-continued

Tooth Enamel-Binding and Pellicle-Binding Peptide Sequences.

| Sequence ID | Sequence | SEQ ID NO: |
|---|---|---|
| P303 | HDPYTMKSALRQSTS | 401 |
| P304 | DLGTFPNRTLKMAAH | 402 |
| P305 | DTIHPNKMKSPSSPL | 403 |
| P306 | GSNNHLPSTVPRLTV | 404 |
| P307 | SNPIPNFAHDLRHSKYNS | 405 |
| P308 | TKPPRTPTANTSRPHHNF | 406 |
| P309 | ANSGFPIWLQKYPWSEVQQE | 407 |
| P310 | ATPRLTPEAHHKAGNWYAS | 408 |
| P311 | ATPSQHRYGLMQNHAPNGIE | 409 |
| P312 | GMGSEVLSQYPQAPVG | 410 |

EXAMPLE 3

Characterization of Tooth-Binding Candidates on Enamel

The purpose of this example is to confirm the binding of peptide compositions on enamel surfaces using synthetically produced peptides.

A total of 11 synthetic peptides were manufactured using sequences obtained from Table 3. Peptides were obtained from SynBioSci Corp. (Livermore, Calif.) with biotin labeled lysine at the C-terminus.

Enamel substrates were prepared as described in Example 2. Each substrate was incubated for 1 h at room temperature (~22° C.) with 1 mL of blocking buffer, consisting of 1 mg/mL BSA in PBST (Pierce BUPH™ #28372 with 0.1% TWEEN® 20). The blocking buffer was removed by aspirating the liquid out of each well. The tube was rinsed 2 times with wash buffer consisting of PBST. The wells were filled with 500 μL of 20 μM peptide solution which was prepared by diluting in blocking buffer. The samples were incubated for 30 min with slow shaking at 37° C. The non-binding peptide was removed by washing 6 times with PBST. Then, 500 μL of horseradish peroxidase/streptavidin conjugate (Pierce #22127), diluted 1:1000 in PBST, was added and incubated for 1 h at room temperature (~22° C.). The conjugate solution was removed and the enamel blocks were washed 4 times with PBST.

Each enamel substrate was removed from the well and washed again in a 15-mL test tube with 10 mL of PBST. Each enamel substrate was then mounted in a clean well plate with only the enamel surface exposed. 200 μL of a QUANT-ABLU™ Substrate Solution (Thermo-Fisher, Rockford, Ill.; #1856187) was added directly to each enamel block. The solution was incubated for 20 min at room temperature. 200 μL of QUANTABLU™ Stop Solution (Thermo Fisher) was added. After mixing, 200 μL of solution was transferred to a clean 96-well black microcentrifuge plate. The fluorescence of the plate was measured with 325 nm excitation and 420 nm emission with no cutoff wavelength using a microplate spectrophotometer (Molecular Devices, Sunnyvale, Calif.). The resulting fluorescence values are given in Table 4. The analysis of the 11 pellicle/enamel binding candidates was compared to a known binding peptide, DenP03. Each sequence was tested with three replicate enamel substrates.

TABLE 4

Synthetic Peptide ELISA Results on Bovine Enamel for Binding Candidates Obtained from Biopanning.

| Peptide ID | Amino Acid Sequence | Avg Fluorescence 325/420 | SEQ ID NO |
|---|---|---|---|
| No peptide | — | 494.2 | — |
| DenP03 | TTYHYKNIYQESYQQRNPAVK (Biotin) | 3448.3 | 411 |
| DenP301 | SNATMYNIQSHSHHQK (Biotin) | 1098.4 | 412 |
| DenP302 | QAAQVHMMQHSRPTTK (Biotin) | 608.6 | 413 |
| DenP303 | HDPYTMKSALRQSTSK (Biotin) | 948.6 | 414 |
| DenP304 | DLGTFPNRTLKMAAHK (Biotin) | 642.8 | 415 |
| DenP305 | DTIHPNKMKSPSSPLK (Biotin) | 581.2 | 416 |
| DenP306 | GSNNHLPSTVPRLTVK (Biotin) | 1300.0 | 417 |
| DenP307 | SNPIPNFAHDLRHSKYNSK (Biotin) | 861.6 | 418 |
| DenP308 | TKPPRTPTANTSRPHHNFK (Biotin) | 12302.6 | 419 |
| DenP309 | ANSGFPIWLQKYPWSEVQQEK (Biotin) | 1729.5 | 420 |
| DenP311 | ATPSQHRYGLMQNHAPNGIEK (Biotin) | 795.3 | 421 |
| DenP312 | GMGSEVLSQYPQAPVGK (Biotin) | 2301.0 | 422 |

EXAMPLE 4

Construction of Perhydrolase and Perhydrolase Fusions

This example describes the design of an expression system for the production of perhydrolases targeted to enamel via enamel-binding sequences.

The genes encoding for fusions of an enzyme having perhydrolytic activity (a "perhydrolase") to enamel-binding domains were designed to have the polynucleotide sequence of the various enzymes listed in Table 5 fused at the 3'-end to the nucleotide sequence encoding various amino acid flexible linkers; each linker further fused to the enamel-binding domains or non-binding sequence controls as described in Table 6. The genes were codon-optimized for expression in *E. coli* and synthesized by DNA2.0 (Menlo Park, Calif.). The coding sequences were cloned in plasmids behind the T7 promoter (expression vector pLD001 (SEQ ID NO: 397)) or the pBAD promoter, between the NdeI and AscI restriction sites yielding plasmids. To express the fusion protein, the plasmids were transferred in an appropriate expression host:

E. coli strain BL21AI (Invitrogen, Carlsbad, Calif.) for constructs under the T7 promoter or in an AraBAD derivative of E. coli MG1655 for constructs under the pBAD promoter.

The non-targeted perhydrolase variants listed in Table 5 were cloned similarly. The preparation and recombinant expression of the *Thermotoga maritima* variants has previously been reported by DiCosimo et al. in U.S. Patent Application Publication No. 2010-0087529; hereby incorporated by reference.

Additional CE-7 perhydrolases from *Lactococcus lactis* (an acetyl xylan esterase; SEQ ID NO: 40), *Mesorhizobium loti* (an acetyl xylan esterase; SEQ ID NO: 42), and *Bacillus pumilus* (an acetyl xylan esterase; SEQ ID NO: 10) were cloned in a similar fashion. The cloning and expression of the CE-7 perhydrolases from *Lactococcus lactis*, *Mesorhizobium loti*, and *Bacillus pumilus* have been previously reported by DiCosimo et al. in U.S. Patent Application Publication No. 2011-0081693 and U.S. Pat. No. 7,951,566; each hereby incorporated by reference.

Perhydrolytic enzymes not belonging to the CE-7 family of perhydrolases were also cloned in a similar fashion. The *Mycobacterium smegmatis* aryl esterase ("ArE"; the wild type sequence is SEQ ID NO: 478; the S54V variant is provided as SEQ ID NO: 460) having perhydrolytic activity is described in U.S. Pat. No. 7,754,460. A *Pseudomonas fluorescens* esterase variant L29P ("Pfl"; SEQ ID NO: 477) having perhydrolytic activity is described in U.S. Pat. No. 7,384,787.

TABLE 5

Description and sequences for perhydrolase constructs.

| Enzyme ID | Abbrev Description | Sequence (SEQ ID NO:) |
|---|---|---|
| WT | T. maritime wild-type | MAFFDLPLEELKKYRPERYEEKDFDEFWEETLAESEKFPLDPVFERMESHLKTV EAYDVTFSGYRGQRIKGWLLVPKLEEEKLPCVVQYIGYNGGRGFPHDWLFWPS MGYICFVMDTRGQGSGWLKGDTPDYPEGPVDPQYPGFMTRGILDPRTYYYRRV FTDAVRAVEAAASFPQVDQERIVIAGGSQGGGIALAVSALSKKAKALLCDVPFLC HFRRAVQLVDTHPYAEITNFLKTHRDKEEIVFRTLSYFDGVNFAARAKIPALFSVG LMDNICPPSTVFAAYNYYAGPKEIRIYPYNNHEGGGSFQAVEQVKFLKKLFEKG (SEQ ID NO: 16) |
| C277S (EZ-1) | T. maritime C277S | MAFFDLPLEELKKYRPERYEEKDFDEFWEETLAESEKFPLDPVFERMESHLKTV EAYDVTFSGYRGQRIKGWLLVPKLEEEKLPCVVQYIGYNGGRGFPHDWLFWPS MGYICFVMDTRGQGSGWLKGDTPDYPEGPVDPQYPGFMTRGILDPRTYYYRRV FTDAVRAVEAAASFPQVDQERIVIAGGSQGGGIALAVSALSKKAKALLCDVPFLC HFRRAVQLVDTHPYAEITNFLKTHRDKEEIVFRTLSYFDGVNFAARAKIPALFSVG LMDNISPPSTVFAAYNYYAGPKEIRIYPYNNHEGGGSFQAVEQVKFLKKLFEKG (SEQ ID NO: 424) |
| C277T (EZ-12) | T. maritime C277T | MAFFDLPLEELKKYRPERYEEKDFDEFWEETLAESEKFPLDPVFERMESHLKTV EAYDVTFSGYRGQRIKGWLLVPKLEEEKLPCVVQYIGYNGGRGFPHDWLFWPS MGYICFVMDTRGQGSGWLKGDTPDYPEGPVDPQYPGFMTRGILDPRTYYYRRV FTDAVRAVEAAASFPQVDQERIVIAGGSQGGGIALAVSALSKKAKALLCDVPFLC HFRRAVQLVDTHPYAEITNFLKTHRDKEEIVFRTLSYFDGVNFAARAKIPALFSVG LMDNITPPSTVFAAYNYYAGPKEIRIYPYNNHEGGGSFQAVEQVKFLKKLFEKG (SEQ ID NO: 437) |
| HTS-007-D5 | T. maritime C277T/R296P | MAFFDLPLEELKKYRPERYEEKDFDEFWEETLAESEKFPLDPVFERMESHLKTV EAYDVTFSGYRGQRIKGWLLVPKLEEEKLPCVVQYIGYNGGRGFPHDWLFWPS MGYICFVMDTRGQGSGWLKGDTPDYPEGPVDPQYPGFMTRGILDPRTYYYRRV FTDAVRAVEAAASFPQVDQERIVIAGGSQGGGIALAVSALSKKAKALLCDVPFLC HFRRAVQLVDTHPYAEITNFLKTHRDKEEIVFRTLSYFDGVNFAARAKIPALFSVG LMDNITPPSTVFAAYNYYAGPKEIPIYPYNNHEGGGSFQAVEQVKFLKKLFEKG (SEQ ID NO: 476) |
| Bpu | B. pumilus wild-type | MQLFDLSLEELKKYKPKKTARPDFSDFWKKSLEELRQVEAEPTLESYDYPVKGV KVYRLTYQSFGHSKIEGFYAVPDQTGPHPALVRFHGYNASYDGGIHDIVNWALH GYATFGMLVRGQGGSEDTSVTPGGHALGWMTKGILSKDTYYYRGVYLDAVRAL EVIQSFPEVDEHRIGVIGGSQGGALAIAAAALSDIPKVVVADYPYLSNFERAVDVA LEQPYLEINSYFRRNSDPKVEEKAFETLSYFDLINLAGWVKQPTLMAIGLIDKITPP STVFAAYNHLETDKDLKVYRYFGHEFIPAFQTEKLSFLQKHLLLST (SEQ ID NO: 10) |
| Mlo | M. loti wild-type | MPFPDLIQPELGAYVSSVGMPDDFAQFWTSTIAEARQAGGEVSIVQAQTTLKAV QSFDVTFPGYGGHPIKGWLILPTHHKGRLPLVVQYIGYGGGRGLAHEQLHWAAS GFAYFRMDTRGQGSDWSVGETADPVGSTSSIPGFMTRGVLDKNDYYYRRLFTD AVRAIDALLGLDFVDPERIAVCGDSQGGGISLAVGGIDPRVKAVMPDVPFLCDFP RAVQTAVRDPYLEIVRFLAQHREKKAAVFETLNYFDCVNFARRSKAPALFSVALM DEVCPPSTVYGAFNAYAGEKTITEYEFNNHEGGQGYQERQQMTWLSRLFGVG (SEQ ID NO: 42) |
| Lla | L. lactis wild-type | MTKINNWQDYQGSSLKPEDFDKFWDEKINLVSNHQFEFELIEKNLSSKVVNFYHL WFTAIDGAKIHAQLIVPKNLKEKYPAILQFHGYHCDSGDWVDKIGIVAEGNVVLAL DCRGQGGLSQDNIQTMGMTMKGLIVRGIDEGYENLYYVRQFMDLITATKILSEFD FVDETNISAQGASQGGALAVACAALSPLIKKVTATYPFLSDYRKAYELGAEESAF EELPYWFQFKDPLHLREDWFFNQLEYIDIQNLAPRIKAEVIWILGGKDTVVPPITQ MAAYNKIQSKKSLYVLPEYGHEYLPKISDWLRENQ (SEQ ID NO: 40) |

TABLE 5-continued

Description and sequences for perhydrolase constructs.

| Enzyme ID | Abbrev Description | Sequence (SEQ ID NO:) |
|---|---|---|
| ArE | *M. smegmatis* S54V | MAKRILCFGDSLTWGWVPVEDGAPTERFAPDVRWTGVLAQQLGADFEVIEEGL VARTTNIDDPTDPRLNGASYLPSCLATHLPLDLVIIMLGTNDTKAYFRRTPLDIALG MSVLVTQVLTSAGGVGTTYPAPKVLVVSPPPLAPMPHPWFQLIFEGGEQKTTEL ARVYSALASFMKVPFFDAGSVISTDGVDGIHFTEANNRDLGVALAEQVRSLL (SEQ ID NO: 460) |
| Pfl | *P. fluorescens* L29P | MSTFVAKDGTQIYFKDWGSGKPVLFSHGWPLDADMWEYQMEYLSSRGYRTIAF DRRGFGRSDQPWTGNDYDTFADDIAQLIEHLDLKEVTLVGFSMGGGDVARYIAR HGSARVAGLVLLGAVTPLFGQKPDYPQGVPLDVFARFKTELLKDRAQFISDFNAP FYGINKGQVVSQGVQTQTLQIALLASLKATVDCVTAFAETDFRPDMAKIDVPTLVI HGDGDQIVPFETTGKVAAELIKGAELKVYKDAPHGFAVTHAQQLNEDLLAFLKR (SEQ ID NO: 477) |

TABLE 6

Perhydrolase Constructs With Targeting Sequences Produced for Use in Oral Care.

| Construct ID (SEQ ID NO:) | Abbrev. Description | Targeting Sequence*a* of the Fusion Protein (SEQ ID NO:) |
|---|---|---|
| EZ-1 (SEQ ID NO: 424) | C277S | N/A |
| EZ-2 (SEQ ID NO: 425) | C277S-link1-HC263-H6 | *GPGSGGAGSPGSAGGPGS*PSAQSQLPDKHSGLHERAPQRYGPEPE PEPEPIPEPPKEAPVVIEKPKPKPKPKPKPPAHDHKNQKETHQRHAA*G SGGGGS*PHHHHHH (SEQ ID NO: 431) |
| EZ-3 (SEQ ID NO: 426) | C277S-link2-H6 | *GS*HHHHHH (SEQ ID NO: 432) |
| EZ-4 (SEQ ID NO: 427) | C277S-link1-(GK)5 | *GPGSGGAGSPGSAGGPGS*GKGKGKGKGK (SEQ ID NO: 433) |
| EZ-5 (SEQ ID NO: 428) | C277S-link1-(GK)5-H6 | *GPGSGGAGSPGSAGGPGS*GKGKGKGKGKHHHHHH (SEQ ID NO: 434) |
| EZ-7 (SEQ ID NO: 429) | C277S-link1-DenP308-H6 | *GPGSGGAGSPGSAGGPGS*TKPPRTPTANTSRPHHNF*GSGGGGS*PH HHHHH (SEQ ID NO: 435) |
| EZ-9 (SEQ ID NO: 430) | C277S-link1-H6 | *GPGSGGAGSPGSAGGPGS*HHHHHH (SEQ ID NO: 436) |
| EZ-12 (SEQ ID NO: 437) | C277T | N/A |
| EZ-14 (SEQ ID NO: 438) | C277T-link1-DenP308-H6 | *GPGSGGAGSPGSAGGPGS*TKPPRTPTANTSRPHHNF*GSGGGGS*PH HHHHH (SEQ ID NO: 435) |
| EZ-15 (SEQ ID NO: 439) | C277T-link1-H6 | *GPGSGGAGSPGSAGGPGS*HHHHHH (SEQ ID NO: 436) |
| EZ-16 (SEQ ID NO: 440) | C277T-link1-HC263-H6 | *GPGSGGAGSPGSAGGPGS*PSAQSQLPDKHSGLHERAPQRYGPEPE PEPEPIPEPPKEAPVVIEKPKPKPKPKPKPPAHDHKNQKETHQRHAA*G SGGGGS*PHHHHHH (SEQ ID NO: 431) |
| EZ-17 (SEQ ID NO: 441) | C277T-link2-H6 | *GS*HHHHHH (SEQ ID NO: 432) |
| EZ-18 (SEQ ID NO: 442) | C277T-link1-(GK)5-H6 | *GPGSGGAGSPGSAGGPGS*GKGKGKGKGKHHHHHH (SEQ ID NO: 434) |
| EZ-19 (SEQ ID NO: 443) | C277S-EPEPE-link1-EPEPE-CXH201-H6 | EPEPE*GPGSGGAGSPGSAGGPGS*EPEPEWKTKKILLSRTRRIMRQVV RSVMHKIWHHHHHH (SEQ ID NO: 468) |

TABLE 6-continued

Perhydrolase Constructs With Targeting Sequences Produced for Use in Oral Care.

| Construct ID (SEQ ID NO:) | Abbrev. Description | Targeting Sequence<sup>a</sup> of the Fusion Protein (SEQ ID NO:) |
|---|---|---|
| EZ-20 (SEQ ID NO: 444) | C277S-EPEPEPEPEPE-link1-CXH201-H6 | EPEPEPEPEPE*GPGSGGAGSPGSAGGPGS*WKTKKILLSRTRRIMRQVVRSVMHKIWHHHHHH (SEQ ID NO: 469) |
| EZ-21 (SEQ ID NO: 445) | C277S-EPEPE-link1-EPEPE-CXHG2-H6 | EPEPE*GPSGGAGSPGSAGGPGS*EPEPEPLWRRITKRKLVRPVATLMWYWFTSKRHHHHHH (SEQ ID NO: 470) |
| EZ-22 (SEQ ID NO: 446) | C277S-EPEPEPEPEPE-Link1-CXHG2-H6 | EPEPEPEPEPE*GPGSGGAGSPGSAGGPGS*PLWRRITKRKLVRPVATLMWYWFTSKRHHHHHH (SEQ ID NO: 471) |
| EZ-23 (SEQ ID NO: 447) | C277S-EPEPE-Link1-EPEPE-CXH104-H6 | EPE*GPSGGAGSPGSAGGPGS*EPERMLSRILRMFVRILKRERLSQVRGLFVHHHHHH (SEQ ID NO: 472) |
| EZ-24 (SEQ ID NO: 448) | C277S-EPEPEPEPEPE-Link1-CXH104-H6 | EPEPEPE*GPSGGAGSPGSAGGPGS*RMLSRILRMFVRILKRERLSQVRGLFVHHHHHH (SEQ ID NO: 473) |
| EZ-25 (SEQ ID NO: 449) | C277S-EPEPE-Link1-EPEPE-CXHG102-H6 | EPEPEPE*GPGSGGAGSPGSAGGPGS*EPEPEPELRFLARRFLKLRRARKWWNAWKVWVTRHHHHHH (SEQ ID NO: 474) |
| EZ-26 (SEQ ID NO: 450) | C277S-EPEPEPEPEPEPE-Link1-CXHG102-H6 | EPEPEPEPEPEPE*GPGSGGAGSPGSAGGPGS*LRFLARRFLKLRRARKWWNAWKVWVTRHHHHHH (SEQ ID NO: 475) |
| EZ-27 (SEQ ID NO: 451) | Bpu-link1-H6 | *GPGSGGAGSPGSAGGPGS*HHHHHH (SEQ ID NO: 436) |
| EZ-28 (SEQ ID NO: 452) | Bpu-link1-HC263-H6 | *GPGSGGAGSPGSAGGPGS*PSAQSQLPDKHSGLHERAPQRYGPEPEPEPEPIPEPPKEAPVVIEKPKPKPKPKPKPPAHDHKNQKETHQRHAA*GSGGGGS*PHHHHHH (SEQ ID NO: 431) |
| EZ-29 (SEQ ID NO: 453) | Bpu-link1-DenP308-H6 | *GPGSGGAGSPGSAGGPGS*TKPPRTPTANTSRPHHNF*GSGGGGS*PHHHHHH (SEQ ID NO: 435) |
| EZ-30 (SEQ ID NO: 454) | Mlo-link1-H6 | *GPGSGGAGSPGSAGGPGS*HHHHHH (SEQ ID NO: 436) |
| EZ-31 (SEQ ID NO: 455) | Mlo-link1-HC263-H6 | *GPGSGGAGSPGSAGGPGS*PSAQSQLPDKHSGLHERAPQRYGPEPEPEPEPIPEPPKEAPVVIEKPKPKPKPKPKPPAHDHKNQKETHQRHAA*GSGGGGS*PHHHHHH (SEQ ID NO: 431) |
| EZ-32 (SEQ ID NO: 456) | Mlo-link1-DenP308-H6 | *GPGSGGAGSPGSAGGPGS*TKPPRTPTANTSRPHHNF*GSGGGGS*PHHHHH (SEQ ID NO: 435) |
| EZ-33 (SEQ ID NO: 457) | Lla-link1-H6 | *GPGSGGAGSPGSAGGPGS*HHHHHH (SEQ ID NO: 436) |
| EZ-34 (SEQ ID NO: 458) | Lla-link1-HC263-H6 | *GPGSGGAGSPGSAGGPGS*PSAQSQLPDKHSGLHERAPQRYGPEPEPEPEPIPEPPKEAPVVIEKPKPKPKPKPKPPAHDHKNQKETHQRHAA*GSGGGGS*PHHHHHH (SEQ ID NO: 431) |
| EZ-35 (SEQ ID NO: 459) | Lla-link1-DenP308-H6 | *GPGSGGAGSPGSAGGPGS*TKPPRTPTANTSRPHHNF*GSGGGGS*PHHHHH (SEQ ID NO: 435) |
| EZ-36 (SEQ ID NO: 460) | *M. smegmatis* ArE S54V | N/A |
| EZ-37 (SEQ ID NO: 461) | ArE-link1-H6 | *GPGSGGAGSPGSAGGPGS*HHHHHH (SEQ ID NO: 436) |

TABLE 6-continued

Perhydrolase Constructs With Targeting Sequences
Produced for Use in Oral Care.

| Construct ID (SEQ ID NO:) | Abbrev. Description | Targeting Sequence[a] of the Fusion Protein (SEQ ID NO:) |
|---|---|---|
| EZ-38 (SEQ ID NO: 462) | ArE-link1-HC263-H6 | *GPGSGGAGSPGSAGGPGS*PSAQSQLPDKHSGLHERAPQRYGPEPE PEPEPIPEPPKEAPVVIEKPKPKPKPKPKPPAHDHKNQKETHQRHAA*G SGGGGS*PHHHHHH (SEQ ID NO: 431) |
| EZ-39 (SEQ ID NO: 463) | ArE-link1-(GK)5-H6 | *GPGSGGAGSPGSAGGPGS*GKGKGKGKGKHHHHHH (SEQ ID NO: 434) |
| EZ-40 (SEQ ID NO: 464) | ArE-link1-DenP308-H6 | *GPGSGGAGSPGSAGGPGS*TKPPRTPTANTSRPHHNF*GSGGGGS*PH HHHHH (SEQ ID NO: 435) |
| EZ-41 (SEQ ID NO: 465) | Pfl-link1-H6 | *GPGSGGAGSPGSAGGPGS*PSAQSQLPDKHSGLHERAPQRYGPEPE PEPEPIPEPPKEAPVVIEKPKPKPKPKPKPPAHDHKNQKETHQRHAA*G SGGGGS*PHHHHHH (SEQ ID NO: 431) |
| EZ-42 (SEQ ID NO: 466) | Pfl-link1-(GK)5-H6 | *GPGSGGAGSPGSAGGPGS*GKGKGKGKGKHHHHHH (SEQ ID NO: 434) |
| EZ-43 (SEQ ID NO: 467) | Pfl-link1-DenP308-H6 | *GPGSGGAGSPGSAGGPGS*TKPPRTPTANTSRPHHNF*GSGGGGS*PH HHHHH (SEQ ID NO: 435) |
| EZ-44 (SEQ ID NO: 479) | Pfl-link1-HC263-H6 | *GPGSGGAGSPGSAGGPGS*PSAQSQLPDKHSGLHERAPQRYGPEPE PEPEPIPEPPKEAPVVIEKPKPKPKPKPKPPAHDHKNQKETHQRHAA*G SGGGGS*PHHHHHH (SEQ ID NO: 431) |

[a] = flexible linker(s) are italicized.

EXAMPLE 5

Production of the Fusion Proteins

This example describes the expression and purification of perhydrolases with and without targeting sequences for binding to oral surfaces.

Strains were grown in 1 L of autoinduction medium (10 g/L tryptone, 5 g/L yeast extract, 5 g/L NaCl, 50 mM $Na_2HPO_4$, 50 mM $KH_2PO_4$, 25 mM $(NH_4)_2SO_4$, 3 mM $MgSO_4$, 0.75% glycerol, 0.075% glucose and 0.05% arabinose) containing 50 mg/L spectinomycin at 37° C. for 20 hrs under 200 rpm agitation. Production of the untargeted perhydrolase has been described previously in U.S. Patent Application Publication No. 2010-0087529 to DiCosimo et al. Production of the targeted perhydrolases followed a similar protocol. The cells were harvested by centrifugation at 8000 rpm and washed by resuspending the cell pellet in 20 mL of 50 mM potassium phosphate buffer, pH 7.1 containing 1 mM DTT. The solution was centrifuged again at 8000 rpm, the supernatant removed and the pellet redispersed again in the phosphate buffer containing DTT. The solution was then homogenized for 30 s to disperse the pellet (Brinkman Homogenizer model PCU11). The cells were then lysed by processing the solution through a French Press (SLM Instruments) at 13,000 psi (~89.6 MPa). The solution was processed through the press an additional two times to achieve complete lysis. The cell solution was then transferred to a conical tube and centrifuged at 8500 rpm for 5 min. For *T. maritime* constructs, the supernatant was removed and heated at 80° C. for 30 min. The solution was centrifuged again and the supernatant was transferred to a clean vial.

For non-thermophilic enzymes no heat treatment was used to purify the enzymes away from contaminating cell components. Instead, the samples were purified using a His6 tag fused to the C-terminal end of the enzymes by metal chelation chromatography using Co-NTA agarose (HisPur Cobalt Resin, Thermo Scientific, product number: 89965). Typically, cell extracts were loaded onto a 5 to 10 mL column of Co-NTA agarose equilibrated with 4 volumes of equilibration buffer (10 mM Tris HCl pH 7.5, 10% glycerol, 1 mM imidazole and 150 mM NaCl). The amount of each extract loaded on the column was adjusted to contain between 5 and 10 mg of perhydrolase fusion per mL of Co-NTA agarose beads. The resin was washed with two bed volumes of equilibration buffer and eluted with two volumes of elution buffer (10 mM Tris HCl pH 7.5, 10% glycerol, 150 mM imidazole, 500 mM NaCl). Fractions were collected and the presence of the full-length, purified proteins was confirmed by PAGE.

For production of constructs EZ-19- to EZ-26, after cell production, the cells were harvested by centrifugation at 8000 rpm and washed by resuspending the cell pellet in 20 mL of 50 mM potassium phosphate buffer, pH 7.2. The solution was centrifuged again at 8000 rpm, the supernatant removed and the pellet redispersed again in the phosphate buffer. The solution was then homogenized for 30 s to disperse the pellet (Brinkman Homogenizer model PCU11). The cells were then lysed by processing the solution through a French Press (SLM Instruments) at 13,000 psi (~89.6 MPa). The solution was processed through the press an additional two times to achieve complete lysis. The cell solution was then transferred to a conical tube and centrifuged at 8500 rpm for 5 min. The insoluble lysate pellets were dissolved in sarkosyl buffer (50 mM phosphate buffer at pH 7.2, 2% TRITON®-X100 and 1.5% sarkosyl) at 3 mL buffer per 50 mL cell lysate pellet. The solution was centrifuged and the supernatant was transferred to a new tube. The fusion proteins were purified by using a HisPur™ Cobalt Resin kit from Thermo Scientific (Rockford, Ill.).

The output of these production and purification protocols typically yielded 2-10 mg of protein per mL with a purity of the fusion perhydrolase between 90% and 75% of the protein as estimated by polyacrylamide gel electrophoresis (PAGE) analysis. Total protein was quantitated by the bicinchoninic acid (BCA) assay (Thermo Scientific) using a solution of Bovine Serum Albumin as a standard.

EXAMPLE 6

Binding of the Enamel-Targeted Perhydrolase Fusion to Hydroxyapatite

This example describes the binding of the perhydrolase to hydroxyapatite particles. The hydroxyapatite is an effective mimic for enamel.

Perhydrolase enzymes listed in Table 6 were assessed for binding to hydroxyapatite. A dispersion of hydroxyapatite nanoparticles (Aldrich 677418) was made at 0.5% solids in 10 mM phosphate buffer at pH 7.2. Enzyme stock solution was added to the hydroxyapatite dispersion to a final concentration of 10 μM and incubated for 30 min in a microcentrifuge tube with gentle agitation. Each sample was centrifuged for 5 min at 10000 rpm. The supernatant was removed and additional buffer was added. The particles were resuspended and transferred to a new tube. The process was repeated two additional times. Samples of the original input of enzyme, the supernatant removed from the particles with each wash step and the final particles were prepared for SDS-PAGE analysis by combining 60 μL of sample, 20 μL of LDS buffer and 8 μL of reducing agent (Nu-PAGE). Samples were heated at 85° C. for 10 min. 25 μL of each sample was loaded on a 4-12% BisTris gel (Invitrogen) and run at 115 volts for 1.5 h. The gel was removed and stained with a 1:1 dilution of Simply Blue stain (Invitrogen) overnight and destained for 4 h in deionized water. The gel was analyzed and detection of enzyme in each fraction was estimated based on the presence of a band. The results of the analysis are provided in Table 7 with an indication of the relative strength of each band in the gel compared to the enzyme input (input=1) to determine the strength of binding between the hydroxyapatite surface and each enzyme.

TABLE 7

Retention of Perhydrolase on Hydroxyapatite.

| Enzyme | Input | Unbound | Wash1 | Wash2 | HAP Particles |
|---|---|---|---|---|---|
| EZ-1 | 1 | 0.98 | 0.01 | 0.0 | 0.01 |
| EZ-2 | 1 | 0.5 | 0.0 | 0.0 | 0.5 |
| EZ-3 | 1 | 0.8 | 0.05 | 0.05 | 0.1 |
| EZ-4 | 1 | 0.5 | 0.05 | 0.05 | 0.4 |
| EZ-5 | 1 | 0.2 | 0.05 | 0.05 | 0.7 |
| EZ-7 | 1 | 0.5 | 0.01 | 0.0 | 0.5 |
| EZ-9 | 1 | 0.9 | 0.01 | 0.00 | 0.05 |

The data in Table 7 demonstrates that the perhydrolase fusions with targeting sequences were retained on hydroxyapatite after washes whereas the untargeted perhydrolase was not.

EXAMPLE 7

Quantitation of the Enzyme Perhydrolase Activity in Solution and Bound to Hydroxyapatite This example describes the method for the detection and quantitation of the perhydrolase via its perhydrolase activity using triacetin and hydrogen peroxide to generate peracetic acid.

The detection of peracetic acid followed the method described in Pinkernell et. al. (*Analyst*, 1997, 122, 567) using colorimetric detection of 2,2'-azino-bis(3-ethylbenzothiazoline(-6-sulfonate (ABTS) oxidation by peracetic acid. Following the formation of peracetic acid with the addition of triacetin and hydrogen peroxide, 90 μL of solution was added to 10 μL of 0.1 M $H_3PO_4$ in a well plate. 50 μL of 1 M acetic acid, 50 μL of 0.5 g/L ABTS and 50 μL of 0.002 g/L of KI was added. The solution was allowed to develop for 5 min. The absorbance of the solution was measured at 405 nm using a microplate reader. The peracetic acid concentration was calculated based on a standard curve developed simultaneously using peracetic acid reagent solution.

The enzyme activity in solution was measured by making a solution of 0.625 μg/mL of each enzyme in 50 mM phosphate buffer, pH 7.2. 10 μL of enzyme solution was mixed with 90 μL buffer, 30 μL of 3% triacetin in water, 30 μL of 30 mM $H_2O_2$. The solution was incubated for 5 min. A 90 μL aliquot was removed for detection via ABTS oxidation as noted above. Results are listed in Table 8.

TABLE 8

Detection of peracetic acid with ABTS oxidation for enzyme with triacetin and hydrogen peroxide in solution

| Enzyme ID | Avg Absorbance 405 nm Background subtracted |
|---|---|
| No enzyme | 0.000 |
| EZ-1 | 1.830 |
| EZ-2 | 1.577 |
| EZ-3 | 1.751 |
| EZ-5 | 1.658 |
| EZ-7 | 1.619 |

The perhydrolase activity of the fusions once bound to HAP discs surfaces was determined with the same ABTS method. Hydroxyapatite discs (HiMed Inc, Old Bethpage, N.Y.; 5 mm dia.×1.8 mm thick) were incubated in 20 μM enzyme solution (50 mM potassium phosphate buffer pH 7.2) for 60 min followed by 6 times of washes (50 mM potassium phosphate buffer pH 7.2). The discs with enzyme adsorbed were transferred to new wells and 200 μL of phosphate buffer (10 mM pH 7.2), 30 μL of 3% triacetin (final concentration of 0.346%) and 30 μL of 30 mM $H_2O_2$ (final concentration of 3.46 mM) were added. The solution was allowed to incubate at room temperature for 5 min. 90 μL of solution was pipetted to a new well containing 10 μL of 100 mM $H_3PO_4$. 50 μL of acetic acid, 50 μL KI, 50 μL ABTS were added as described above. The solution was developed for 5 min at room temperature and read at A405 nm. Results are listed in Table 9.

TABLE 9

Peracetic Acid detection with ABTS with enzyme bound to hydroxyapatite

| Enzyme | Avg Absorbance at 5 min | Avg Absorbance Background subtract | PAA conc μM per disc |
|---|---|---|---|
| No enzyme, No HAP | 0.775 | 0 | 0 |
| No enzyme control | 0.840 | 0.065 | 1.2 |
| EZ-1 | 0.901 | 0.126 | 3.5 |
| EZ-5 | 2.154 | 1.379 | 49.7 |
| EZ-7 | 1.45 | 1.450 | 23.5 |

This experiment demonstrates that EZ-5 and EZ-7 are active enzymes when bound to hydroxyapatite and produce peracetic acid with the addition of triacetin and hydrogen peroxide. The low value of peracetic acid detected with EZ-1 coincided with other observations that EZ-1 does not bind to hydroxyapatite (Example 6) and is not present on the surface to generate peracetic acid.

EXAMPLE 8

Quantitation of the Enzyme Perhydrolase Activity in Solution and Bound to Hydroxyapatite for Additional CE-7 Perhydrolase Constructs This example describes the perhydrolytic activities of the CE-7 perhydrolase and respective fusion proteins in solution and when bound to hydroxyapatite from *Thermotoga maritime*, *Bacillus pumilus* (Bpu), *Mesorhizobium loti* (Mlo) and *Lactobacillus lactis* (Lla) using triacetin and hydrogen peroxide to generate peracetic acid.

Perhydrolase enzymes listed in Table 6 were assessed for solution activities. The method to measure the perhydrolase in solution activity was described in Example 7 by making a 500 µL solution containing 0.5 µM of enzyme, 100 mM triacetin, 100 mM $H_2O_2$ in 100 mM phosphate buffer, pH 7.2. The solution was mixed and incubated for 10 min at 37° C. A 10 µL aliquot was removed and diluted for detection as described in Example 7. Peracetic acid concentration was determined using a standard curve generated with a stock solution of peracetic acid (Aldrich). The experiment was also performed with no enzyme present as a control.

TABLE 10

Peracetic acid generated in solution for a 10 min reaction for various CE-7 perhydrolase fusions.

| Enzyme ID | Description | PAA (ppm) |
|---|---|---|
| No enzyme | — | 378.9 |
| EZ-7 | C277S-DenP308 | 4877.2 |
| EZ-27 | Bpu-H6 | 2332.9 |
| EZ-28 | Bpu-HC263 | 2512.7 |
| EZ-29 | Bpu-DenP308 | 2273.5 |
| EZ-30 | Mlo-H6 | 468.8 |
| EZ-31 | Mlo-HC263 | 434.9 |
| EZ-32 | Mlo-DenP308 | 497.7 |
| EZ-33 | Lla-H6 | 1062.5 |
| EZ-34 | Lla-HC263 | 786 |
| EZ-35 | Lla-DenP308 | 998 |

To assess binding of these constructs to hydroxyapatite, 33 mg of hydroxyapatite particles (Macro-prep Ceramic Hydroxyapatite TYPE I, 80 µm size BioRad, Hercules, Calif.), were washed with 10 mM phosphate buffer at pH 7.2. After removing the supernatant, enzyme stock solution was added to the hydroxyapatite dispersion to a final concentration of 10 µM and incubated for 30 min in a microcentrifuge tube with gentle agitation. Each sample was centrifuged for 1 min at 10000 rpm. The supernatant was removed and additional buffer was added. The particles were resuspended and transferred to a new tube. The process was repeated two additional times. The hydroxyapatite bound enzyme activity was measured by adding a 500 µl solution containing 100 mM triacetin, 100 mM $H_2O_2$ in 100 mM phosphate buffer, pH 7.2. The solution was incubated for 30 min, at 37° C. An aliquot was removed and mixed with $H_3PO_4$ and properly diluted for detection via ABTS oxidation as described in Example 7. The experiments were performed at different day with no enzyme as control for each experiment. Results are listed in Table 11.

TABLE 11

Peracetic acid generation from hydroxyapatite bound CE-7 perhydrolase fusions.

| Enzyme ID | Description | Peracetic acid (ppm) |
|---|---|---|
| No enzyme | | 118.8 |
| EZ-9 | C277S-H6 | 1885.1 |
| EZ-27 | Bpu-H6 | 634.9 |
| EZ-30 | Mlo-H6 | 658.5 |
| EZ-33 | Lla-H6 | 359.1 |
| No enzyme | | 30 |
| EZ-2 | C277S-HC263 | 3666.4 |
| EZ-28 | Bpu-HC263 | 534.2 |
| EZ-31 | Mlo-HC263 | 241.4 |
| EZ-34 | Lla-HC263 | 242.2 |
| No enzyme | | 113.9 |
| EZ7 | C277S-DenP308 | 4453.7 |
| EZ-29 | Bpu-DenP308 | 1299.8 |
| EZ-32 | Mlo-DenP308 | 419.3 |
| EZ-35 | Lla-DenP308 | 260 |

The experiments demonstrated that all CE-7 perhydrolase fusions from Bpu, Mlo and Llo enzyme showed significant perhydrolase activity in solution as well as after binding to hydroxyapatite surfaces compare to a no enzyme control. All three CE-7 perhydrolases fusions from *B. pumilus* have higher enzyme activity compared to the fusion enzymes from *M. loti* or *L. lactis*. Targeted EZ-29 from *B. pumilus* showed higher binding activity compared to the untargeted EZ-27.

EXAMPLE 9

Quantitation of Enzyme Activity in Solution and Bound to Hydroxyapatite for Targeted C277S Perhydrolase Fusions with CXV Peptides This example describes the CE-7 C277S and fusions with CXH peptides and their perhydrolase activities using triacetin and hydrogen peroxide to generate peracetic acid in solution and when bound to hydroxyapatite. The hydroxyapatite is an effective mimic for enamel.

Perhydrolase enzymes EZ-19 to EZ-26 listed in Table 6 were assessed for enzyme activity in solution. The method to measure the perhydrolase in solution activity was described in Example 7. The enzyme activity in solution was measured by making a 500 µl sarkosyl buffer solution of 0.5 µM of each enzyme in 100 mM triacetin, 100 mM $H_2O_2$ and 10 mM phosphate buffer, pH 7.2. The solution was incubated for 10 min, at 37° C. After the reaction was stopped by mixing with $H_3PO_4$, a 10 µL aliquot was removed for proper dilution, and then detected via ABTS oxidation as described in Example 7. Results are listed in Table 12.

The same perhydrolase fusion enzymes were also assessed for binding to hydroxyapatite. Water hydrated hydroxyapatite discs (5 mm dia.×1.8 mm thick, from HiMed Inc) were used. The discs were equilibrated in 10 mM phosphate buffer at pH 7.2 for 10 min. 200 µL of enzyme solution was added to the hydroxyapatite discs to a final concentration of 10 µM in 10 mM phosphate buffer and incubated for 30 min in a microcentrifuge tube with gentle agitation. The supernatant was removed and used for unbound enzyme activity assays. The discs were transferred to a new tube and rinsed with phosphate buffer. The process was repeated two additional times. The enzyme activity of the hydroxyapatite discs with bound enzymes was measured by adding a 500 µl solution containing 100 mM triacetin, 100 mM $H_2O_2$ and 100 mM phosphate buffer, pH 7.2 to the disc and incubating for 30 min, at 37° C. After the reaction was stopped by mixing with $H_3PO_4$, a 10

µL aliquot was removed for proper dilution, and then detected via ABTS oxidation as described in Example 7. The experiments were performed over several days with a no enzyme solution used as a control for each day. Results after subtraction of the no enzyme control are listed in Table 12.

TABLE 12

Peracetic acid generated from C277s and CXH perhydrolase fusions proteins in solution and when bound to hydroxyapatite discs.

| Enzyme ID | Peracetic acid (ppm) | | |
|---|---|---|---|
| | In solution | Exposed to Hydroxyapatite | |
| | | Supernatant | Disc |
| EZ-7 | 5471 | 4864 | 2017 |
| EZ-19 | 4088 | 1665 | 3136 |
| EZ-20 | 2265 | 1229 | 2795 |
| EZ-21 | 2764 | 1581 | 3109 |
| EZ-22 | 2305 | 477 | 2495 |
| EZ-23 | 2212 | 1712 | 4463 |
| EZ-24 | 2951 | 719 | 3453 |
| EZ-25 | 1703 | 1029 | 1791 |
| EZ-26 | 2273 | 1636 | 1849 |

The experiments demonstrated that all the C277S variants with CXH targeting sequences are active and generate sufficient amounts of peracetic acid in solution and when bound to hydroxyapatite.

EXAMPLE 10

Quantitation of the Enzyme Per Hydrolase Activity in Solution and Bound to Hydroxyapatite for Non CE-7 Perhydrolase Constructs The purpose of this example is to demonstrate the use of targeted or untargeted aryl esterase enzyme variants from *M. smegmatis* and perhydrolase variants from *P. fluorescens* listed in Table 6 to generate peracetic acid in solution and when bound to hydroxyapatite.

For aryl esterase constructs, the enzyme activity in solution was measured by making a 1 mL solution of 0.5 µM of each enzyme, 100 mM triacetin, and 100 mM $H_2O_2$ in 100 mM phosphate buffer, pH 7.2. The solution was mixed and incubated for 30 min, at 37° C. As described in Example 7, the reaction was stopped by removing a portion to $H_3PO_4$ and a 10 µL aliquot was removed and diluted for detection via ABTS oxidation.

For assessment of binding and activity on hydroxyapatite, the aryl esterase enzymes were exposed to hydroxyapatite particles as described in Example 8 using 33 mg of buffer washed HAP particles (Macro-prep Ceramic Hydroxyapatite TYPE I, 80 µm size BioRad, Hercules, Calif.) using a 10 µM solution in 10 mM phosphate buffer. Following centrifugation and removal of the enzyme solution, the particles were rinsed with phosphate butter by centrifuging and removing the supernatant. A 200 µL solution containing 100 mM triacetin, 100 mM $H_2O_2$ and 100 mM phosphate buffer, pH 7.2 was added to the particles and incubated at 37° C. for 30 min. As described in Example 7, the reaction was stopped by removing a portion to $H_3PO_4$ and a 10 µL aliquot was removed diluted for detection via ABTS oxidation. Results for both solution and surface bound assays are listed in Table 13.

TABLE 13

Solution and surface bound generation of peracetic acid for *M. smegmatis* aryl esterase samples

| Enzyme ID | Description | Peracetic acid (ppm) | |
|---|---|---|---|
| | (SEQ ID NO.) | In Solution | On Hydroxyapatite |
| No enzyme | | 158 | 323 |
| EZ-36 | ArE (SEQ ID NO: 460) | 2697 | 452 |
| EZ-37 | ArE-H6 (SEQ ID NO: 461) | Not measured | 927 |
| EZ-39 | ArE-(GK)5H6 (SEQ ID NO: 463) | 1366 | 3553 |
| EZ-40 | ArE-DenP308-H6 (SEQ ID NO: 464) | 3605 | 2476 |

For *P. fluorescens* constructs, the solution activity was measured by mixing a 1 mL solution containing 2 µM enzyme, 100 mM $H_2O_2$ in a 1 M sodium acetate buffer, pH 5.5. The solution was incubated at 37° C. for 30 min. As described in Example 7, the reaction was stopped by removing a portion to $H_3PO_4$ and a 10 µL aliquot was removed and diluted for detection via ABTS oxidation. For assessment of binding and activity on hydroxyapatite, the *P. fluorescens* enzymes were exposed to hydroxyapatite particles at 20 µM in 10 mM phosphate buffer as described in Example 8 using 100 mg of buffer washed HAP particles (Macro-prep Ceramic Hydroxyapatite TYPE I, 80 µm size BioRad, Hercules, Calif.). Following centrifugation and removal of the enzyme solution, the particles were rinsed with phosphate butter by centrifuging and removing the supernatant. A 200 µL solution containing 300 mM $H_2O_2$ in 1 M sodium acetate buffer, pH 5.5 was added to the particles and incubated at 37° C. for 10 min. As described in Example 7, the reaction was stopped by removing a portion to $H_3PO_4$ and a 10 µL aliquot was removed and diluted for detection via ABTS oxidation. Results for both solution and surface bound assays are listed in Table 14.

TABLE 14

Solution and surface bound generation of peracetic acid for *P. fluorescens* perhydrolase samples

| Enzyme ID | Description (SEQ ID NO.) | Peracetic acid (ppm) | |
|---|---|---|---|
| | | In Solution | On Hydroxyapatite |
| No enzyme | | 9 | 17 |
| EZ-41 | Pfl-link1-H6 (SEQ ID NO: 465) | Not measured | 18 |
| EZ-42 | Pfl-link1-(GK)5-H6 (SEQ ID NO: 466) | 64 | 63 |
| EZ-43 | Pfl-link1-DenP308-H6 (SEQ ID NO: 467) | 79 | 68 |
| EZ-44 | Pfl-link1-HC263-H6 (SEQ ID NO: 479) | 58 | 97 |

These experiments demonstrate that perhydrolases from families beyond the CE-7 family are active in solution and when bound to hydroxyapatite for constructs including a targeting sequence.

EXAMPLE 11

Quantitation of Perhydrolytic Activity of Enamel-Targeted C277S and C277T Variant Perhydrolase Fusions in Solution and Bound to Bovine Enamel This example describes the binding of the perhydrolase fusion proteins to bovine enamel and measurement of enzyme activity in solution and when bound to bovine enamel.

Perhydrolase enzymes listed in Table 5 were assessed for enzyme activity in solution as described in Example 7. The enzyme activity in solution was measured by making a 500 µl solution of 0.5 µM of each enzyme in 100 mM triacetin, 100 mM $H_2O_2$ and 10 mM phosphate buffer, pH 7.2. The solution was incubated for 10 min, at 37° C. After the reaction was stopped by mixing an aliquot with $H_3PO_4$, a 10 µL aliquot was removed for proper dilution, and then detected via ABTS oxidation as described in Example 7. Results are listed in Table 15.

The perhydrolase enzymes were also assessed for binding to bovine enamel substrates. Enamel substrates were prepared as described in Example 2 and 3. Each enamel block was hydrated in water for overnight at room temperature (~22° C.). The enamel blocks were then equilibrated with 10 mM potassium phosphate buffer, pH7.2, for 10 min. The enamel substrates were rinsed 3 times the buffer. The enamel wells were filled with 500 µL of 10 µM enzyme solutions which was prepared by diluting in 10 mM phosphate buffer. The samples were incubated for 30 min with slow shaking at 37° C. The non-binding enzyme was removed by washing 4 times with phosphate buffer. Then, each enamel block was embedded inside a putty filled 24-well plate, with only the enamel top surface exposed. The perhydrolase activity from enamel bound enzyme was measured as described in Example 8. 100 µL reaction mixtures (100 mM phosphate buffer, pH7.2 and 100 mM $H_2O_2$ and 100 mM triacetin) was added on top of the enamel and incubated for 30 min at 37° C. A 90 µL aliquot was removed for detection via ABTS oxidation as noted in Example 8. Results are listed in Table 15. Each sample data point represents an average of 3 independent enamel blocks.

TABLE 15

Peracetic acid generated in solution and when bound to a bovine enamel surface for *T. maritima* constructs.

| Enzyme ID | Description (SEQ ID NO:) | Peracetic acid (ppm) In Solution | Peracetic acid (ppm) On Enamel |
|---|---|---|---|
| No enzyme | | 114 | 570 |
| EZ-1 | C277S (SEQ ID NO: 424) | 4270 | 628 |
| EZ-2 | C277S-HC263-H6 (SEQ ID NO: 425) | 4761 | 2549 |
| EZ-3 | C277S-link2-H6 (SEQ ID NO: 426) | 5187 | 733 |
| EZ-5 | C277S-(GK)5H6 (SED ID NO: 428) | 3956 | 1344 |
| EZ-7 | C277S-DenP308-H6 (SEQ ID NO: 429) | 5519 | 1040 |
| EZ-9 | C277S-H6 (SEQ ID NO: 430) | 5499 | 612 |
| EZ-12 | C277T (SEQ ID NO: 437) | 4918 | 612 |
| EZ-16 | C277T-HC263-H6 (SEQ ID NO: 440) | 6496 | 1832 |
| EZ-17 | C277T-link2-H6 (SEQ ID NO: 441) | 5360 | 616 |
| EZ-14 | C277T-(GK)5H6 (SEQ ID NO: 438) | 4689 | 1418 |
| EZ-18 | C277T-DenP308-H6 (SEQ ID NO: 442) | 5537 | 1158 |
| EZ-15 | C277T-H6 (SEQ ID NO: 439) | 5921 | 631 |

This experiment demonstrates that fusions using C227S and C277T from *T. maritima* sequence variants are active in solution and when bound to bovine enamel, for constructs including a targeting sequence, and generate sufficient levels of peracetic acid to whiten teeth.

EXAMPLE 12

Tooth Bleaching Efficacy Using Perhydrolytic Enzymes in a One-Step Application The purpose of this example is to show the tooth bleaching effect of enzymatic generated peracetic acid in a one-step application and compare to the performance achieved with chemically derived peracetic acid. Two methods were developed to use a perhydrolytic enzyme (CE-7 perhydrolase) system to achieve the target level of tooth bleaching. The first method (referred to herein as the "one-step approach") comprises combining different amounts of at least one CE-7 perhydrolase with triacetin (an example of a suitable ester substrate) and hydrogen peroxide to generate peracetic acid using model stained enamel substrates. Bovine enamel incisors were prepared as indicated in Example 1. Stained bovine enamel blocks were hydrated in water at least 1 hr prior to use to stabilize the color of the substrate. The color for each enamel block was measured after hydration prior to the start of the experiment. Three enamel samples were treated for each solution type. The solutions used were a buffer only control, 2.5% $H_2O_2$, 1% peracetic acid, a perhydrolase composition including 10 µM EZ-1 (C277S; SEQ ID NO: 424), 100 mM triacetin and 250 mM $H_2O_2$ and a no enzyme control of 100 mM triacetin and 250 mM $H_2O_2$. All solutions were prepared in 500 mM sodium phosphate buffer, pH 7.2. The high buffer strength was necessary to maintain the 1% peracetic acid solution at neutral pH. All solutions were freshly prepared for each treatment point. The enzyme-triacetin-$H_2O_2$ combination and triacetin-$H_2O_2$ combination was mixed immediately before enamel exposure. After each treatment step, each enamel block was rinsed with water and a color measurement was obtained. A total treatment time of 61 min was used with durations of exposure of 1 min, 5 min, 10 min, 15 min and 30 min. The concentration of peracetic acid in solution after the 1 min, 10 min and 30 min treatments was evaluated by colorimetric detection of ABTS oxidation. The results are provided in Table 16 and 17.

TABLE 16

Bleaching Efficacy of Perhydrolase System in a 1-step application on Stained Bovine Enamel

| | Whiteness Index | | | | | | |
|---|---|---|---|---|---|---|---|
| Sample | 0 min | 1 min | 6 min | 16 min | 31 min | 61 min | ΔWI |
| Buffer | −136.9 | −134.9 | −130.9 | −130.4 | −125.5 | −121.2 | 15.6 |
| $H_2O_2$ | −149.3 | −146.3 | −142.5 | −134.7 | −125.2 | −103.1 | 46.2 |
| Triacetin/$H_2O_2$ | −144.1 | −137.4 | −138.2 | −125.3 | −111.0 | −80.9 | 63.2 |
| 1% PAA | −145.7 | −119.6 | −73.4 | −62.9 | −59.0 | −59.4 | 86.3 |
| EZ-1/Triacetin/$H_2O_2$ | −141.2 | −115.6 | −54.0 | −37.3 | −32.4 | −27.9 | 113.3 |

Determination of the peracetic acid (PAA) concentration in the reaction mixtures by a colorimetric method was performed according to the method described by Dinu et. al. (supra). A reagent solution of 1 mM 2,2'-azino-bis(3-ethyl-benzothiazoline)-6-sulfonate (ABTS), 50 μM potassium iodide in 125 mM potassium citrate buffer at pH 5.0 was prepared. 25 μL of sample was mixed with 975 μL of this detection reagent and allowed to incubate for 5 min. The solution was analyzed for absorbance at 405 nm using a Microplate reader. A comparison of relative amounts of peracetic acid in solution was determined by comparing absorbance values directly.

TABLE 17

Assessment of peracetic acid concentration in solution at end of treatment time as indicated. Each sample is a 1:100 dilution into ABTS detection reagent measured at 405 nm.

| | Absorbance 405 nm | | |
|---|---|---|---|
| Sample | 1 min | 10 min | 30 min |
| Buffer | 0.055 | 0.059 | 0.055 |
| $H_2O_2$ | 0.056 | 0.060 | 0.054 |
| Triacetin/$H_2O_2$ | 0.061 | 0.069 | 0.052 |
| 1% PAA | 2.579 | 1.863 | 2.874 |
| EZ-1/Triacetin/$H_2O_2$ | 1.245 | 1.330 | 0.735 |

Data in Table 16 confirms that the enzyme-ester-peroxide composition is effective at whitening teeth. Data in Table 17 demonstrates that peracetic acid is produced from the combination of the EZ-1 (C277S; SEQ ID NO: 424) enzyme, triacetin and $H_2O_2$. Comparison of the absorbance data for the chemical peracetic acid also shows that surprisingly the enzymatic bleaching system shows better whitening performance with lower detectable peracetic acid. A low level of peracetic acid is also produced over time for the non-enzyme containing triacetin and $H_2O_2$ which was detected with a 1:10 dilution into the ABTS reagent (not included in Table). This results in detectable bleaching performance but at a much slower rate compared to the enzyme catalyzed production of a high level of peracetic acid.

EXAMPLE 13

Tooth Bleaching Efficacy Using Enamel Targeted Perhydrolytic Enzyme in a One-Step Application The purpose of this example is to show the tooth bleaching effect of enzymatic generated peracetic acid in a one-step application using a targeted CE-7 perhydrolase and compare to the performance achieved with chemically derived peracetic acid.

Bovine enamel incisors were prepared as indicated in Example 1. Stained bovine enamel blocks were hydrated in water at least 1 h prior to use to stabilize the color of the substrate. The color for each enamel block was measured after hydration prior to the start of the experiment. Two enamel samples were treated for each solution type. The solutions used were a buffer only control, 0.1% Peracetic Acid, a perhydrolase composition including 0.52 μM EZ-7 (C277S with enamel binding domain; SEQ ID NO: 429), 100 mM triacetin and 32.6 mM $H_2O_2$. All solutions were prepared in 100 mM sodium phosphate buffer, pH 7.2. All solutions were freshly prepared for each treatment point. The enzyme-triacetin-$H_2O_2$ combination was mixed immediately before enamel exposure. After each treatment step, each enamel block was rinsed with water and a color measurement was obtained. A treatment time of 30 min was repeated 4 times for each set of enamel substrates. The concentration of peracetic acid in solution after a 30 min treatment was evaluated by colorimetric detection of ABTS oxidation. The results are provided in Table 18 and 19.

TABLE 18

Bleaching Efficacy of a Targeted Perhydrolase in a 1-step application on Stained Bovine Enamel. Data is averaged from two substrates.

| | Whiteness Index | | | | | |
|---|---|---|---|---|---|---|
| Sample | 0 min | 30 min | 60 min | 90 min | 120 min | ΔWI |
| Buffer | −133.5 | −128.7 | −123.4 | −123.0 | −127.8 | 5.8 |
| 0.1% PAA | −125.8 | −101.9 | −91.9 | −80.2 | −70.8 | 55.0 |

TABLE 19

Assessment of peracetic acid concentration in solution at end of treatment time as indicated. Each sample is a 1:10 dilution into ABTS detection reagent measured at 405 nm.

| | Absorbance 405 nm | | [PAA] |
|---|---|---|---|
| Sample | Tooth1 | Tooth2 | (ppm) |
| Buffer | 0.073 | 0.070 | 0 |
| 0.1% PAA | 1.103 | 1.043 | 920 |
| EZ-7/Triacetin/$H_2O_2$ | 1.575 | 1.533 | 1350 |

Data in Table 18 confirms that the targeted enzyme-ester-peroxide composition is effective at whitening teeth in a 1-step process. Data in Table 19 demonstrates that peracetic acid is produced from the combination of the EZ-7 enzyme, triacetin and $H_2O_2$.

EXAMPLE 14

Peracetic Acid Production Using CE-7 Perhydrolases Against a Variety of Ester Substrates The purpose of this example was to demonstrate that a broad variety of CE-7 perhydrolases—including an enamel targeting perhydrolase—catalyze the formation of peracetic acid from a broad variety of esters under oral care specific conditions.

The variants of the *Thermotoga maritima* perhydrolase were cloned, recombinantly expressed and purified in a manner similar to that described in Example 4. The sequence changes in these perhydrolase variants are listed in Table 5.

Various ester substrates were tested against at least two or more of the perhydrolase variants listed in Table 5. With the exception of three esters that were custom synthesized, all other esters were procured from the Sigma-Aldrich (St. Louis, Mo.), TCI America (Portland, Oreg.), Alpha Aesar (Ward Hill, Mass.) or Tessendlo Company (Phoenix, Ariz.).

To test various enzymes against an ester substrate, it was convenient to run up to 4 reactions simultaneously by staggering the beginning of each individual reaction by 0.5-1 min. Each individual reaction was performed in a glass vessel (height: 76 mm; o.d.: 33 mm; i.d.: 24 mm) equipped with a magnetic stirring bar. Four reaction vessels were banded together and kept at constant temperature in a jacketed one-liter, stainless steel, tempering beaker (KGW IsoTherm, # TSS-G 1000W) with circulating water controlled by a Thermo NesLab recirculation bath (Model # RTE-7 Digital One). Buffer (6 mL, 100 mM sodium phosphate buffer, pH 7.2) was added to each reaction vessel and allowed to equilibrate to 37° C. The ester substrate of interest was added to achieve 100 mM concentration. The reaction was initiated by the simultaneous addition of 40 ppm enzyme and 60 mM $H_2O_2$ (37 μL, 30% hydrogen peroxide solution). To follow the production of peracetic acid, 80 μL samples from each reaction were removed at specific intervals from 1 to 15 minutes. The sample was immediately quenched in a microfuge filter tube (NanoSep 30K VWR cat #82031-354) containing a volume and concentration of phosphoric acid solution that was sufficient to stop the enzymatic reaction (by lowering the pH between 2 and 3) and to dilute the sample for convenient HPLC analyses. The acid-quenched samples were centrifuged for 5 minutes to remove any particulates. Once filtered, a Karst reaction and HPLC analyses for peracetic acid were immediately performed on each sample set using the method described previously in U.S. Pat. No. 7,829,315 to DiCosimo et al. The maximum peracetic acid produced by each ester substrate is listed in Table 20.

TABLE 20

Maximum Peracetic Acid Produced from Neutral Conditions.[1]

| Ester Substrate (CAS#) | No Enzyme | C277S (SEQ ID NO: 424) | C277T (SEQ ID NO: 437) | C277T/R296P (SEQ ID NO: 476) | Wild Type (SEQ ID NO: 16) |
|---|---|---|---|---|---|
| 1-thio-β-D glucose-2,3,4,6-tetraacetate (19879-84-6) | 10 | 0 | 171 | 147 | 156 |
| 1,5-pentanediol diacetate (542-59-6) | 11 | 335 | 484 | 364 | 435 |
| Diethylene glycol diacetate (628-68-2) | 17 | 469 | 653 | 530 | 424 |
| Sorbitol hexaacetate (7208-47-1) | 11 | 712 | 705 | 616 | 381 |
| Sucrose octaacetate (126-14-7) | 20 | 215 | 493 | 501 | 304 |
| 4-acetoxybenzoic acid (2345-34-8) | 299 | 604 | 426 | 485 | 398 |
| Vanillin acetate (881-68-5) | 251 | 660 | 500 | 405 | 564 |
| Propylene glycol methyl ether acetate (108-65-5) | 22 | 173 | 197 | 181 | 177 |
| 2-acetamido-2-deoxy-3,4,6 triacetyl-1-chloride-α-D-glucopyranose (3068-34-6) | 78 | 863 | 899 | 876 | 548 |
| 5-acetoxymethyl-2-furaldehyde (10551-58-3) | 67 | 1185 | 1125 | 1136 | 778 |
| Ethylene glycol diacetate (111-55-7) | 51 | 1007 | 1059 | 1020 | 794 |
| Propylene glycol diacetate (623-84-7) | 17 | 1128 | 1245 | 1202 | 780 |
| Diacetin (25395-31-7) | 20 | 1013 | 1132 | 1087 | 1160 |
| α-D-glucose pentaacetate (604-68-2) | 406 | 2091 | 2542 | 1678 | 1188 |
| β-D-glucose pentaacetate (604-69-3) | 1124 | 2178 | 2531 | 1716 | 1158 |
| 1,2,3,5-tetra-O-acetyl-ribofuranose (13035-61-5) | 2246 | 3397 | 3472 | 3270 | 2828 |
| 1,2,3,4-tetra-O-acetyl-ribopyranose (4049-34-7) | 2264 | 3525 | 3361 | 3503 | 2278 |

TABLE 20-continued

Maximum Peracetic Acid Produced from Neutral Conditions.[1]

| Ester Substrate (CAS#) | Peracetic Acid (PAA) (ppm) | | | | |
|---|---|---|---|---|---|
| | No Enzyme | C277S (SEQ ID NO: 424) | C277T (SEQ ID NO: 437) | C277T/R296P (SEQ ID NO: 476) | Wild Type (SEQ ID NO: 16) |
| Tri-O-acetyl glucal (2873-29-2) | 62 | 1047 | 1319 | 1034 | 729 |
| Triacetin (102-76-1) | 51 | 1977 | 2311 | 2291 | 937 |
| β-D-galactose pentaacetate (4163-60-4) | 176 | 2539 | 2546 | 1947 | 764 |
| 2-acetamido-2-deoxy-1,3,4,6-tetraacetyl-β-D-glucopyranose (7772-79-4) | 2574 | 3374 | 3808 | 3790 | 2687 |
| β-D-xylofuranose tetraacetate (CV Chem)[a] | 1373 | 3354 | 3481 | 3158 | 2384 |
| 3,4-diacetoxy-1-butene (18085-02-4) | 53 | 2281 | 2285 | 2478 | 1692 |
| β-D-glucopyranose,1,2,3,4-tetraacetate (13100-46-4) | 2102 | 2309 | 2225 | 2235 | 2129 |
| 2,3,4,6-tetraacetyl-β-D-glucopyranose (10343-06-3)[b] | 1500 | 2820 | 3072 | N/A | N/A |
| β-methyl xyloside triacetin (18531-01-6)[b] | 412 | 3856 | 3635 | N/A | N/A |
| 1,3,4,6-tetra-O-acetyl-mannopyranose (18968-05-3) | 1803 | 3593 | 3436 | N/A | 2361 |
| α-D-mannopyranose pentaacetate (4163-65-9) | 3659 | 4017 | 4212 | 3752 | 4023 |

TABLE NOTES:
[1][ester], 100 mM; [$H_2O_2$], 60 mM; [perhydrolase enzyme], 40 ppm with 95 mM phosphate, pH (7.2);
[a]custom synthesis by CV-Chem (CiVenti Chem, Product #CV-3146; reference Number 121-RM-134);
[b]Prepared following literature synthesis Robertson et al., (1934) *J. Chem. Soc.*, 824-9.
N/A = not tested.

These ester substrates were tested for peracetic acid production using a targeted C277S perhydrolase variant, EZ-7 under the same reaction conditions used to generate date for Table 20. Peracetic acid production using propylene glycol diacetate or sucrose octaacetate with the EZ-7 perhydrolase system is shown in Table 21. The data shown demonstrates that the alternative esters are effective substrates for targeted variants of perhydrolase as described in Example 5.

TABLE 21

Maximum peracetic acid produced by alternative substrates using targeted and untargeted CE-7 perhydrolase.

| | Peracetic Acid (ppm) | |
|---|---|---|
| Enzyme ID | Propylene glycol diacetate | Sucrose octaacetate |
| EZ-1 | 2165 | 2768 |
| EZ-7 | 2109 | 2070 |

EXAMPLE 15

Tooth Bleaching Using CE-7 Perhydrolases Against a Variety of Ester Substrates

The purpose of this example was to demonstrate tooth bleaching efficacy using a CE-7 perhydrolase that catalyzes the formation of peracetic acid from four esters under oral care relevant conditions.

For this example the C277S (EZ-1) variant of *Thermotoga maritime* perhydrolase was cloned, recombinantly expressed and purified as in Example 4. All of the substrates were purchased from Sigma-Aldrich (St. Louis, Mo.) with the exception of triacetin (Tessendlo Company (Phoenix, Ariz.)).

The substrates triacetin (TA), α-D-glucose pentaacetate (GPA), sucrose octaacetate (SOC) and propylene glycol diacetate (PGDA) were used to demonstrate enzymatic mediated tooth whitening with EZ-1 (C277S; SEQ ID NO: 424). The optimal conditions used for the generation of peracetic acid with each substrate were derived from the studies in Example 14 and are listed below as follows:

40 ppm EZ-1, 100 mM Substrate, X mM $H_2O_2$, 95 mM phosphate, pH 7.2, where X varies depending on the identity of the substrate; 100 mM $H_2O_2$ (TA), 360 mM $H_2O_2$ (PGDA and SOC), 60 mM $H_2O_2$ (GPA).

Bovine enamel incisors were prepared as indicated in Example 1. The stained enamel blocks were placed in a 24 well plate with the dentin side facing down and hydrated overnight in phosphate buffer, pH 7.2. Prior to treatment, a color measurement of each tooth was performed using a Konica-Minolta 2600d spectrophotometer and whiteness index was calculated as specified in Example 1.

Each enzyme solution was prepared in a 1.5-mL microfuge tube (Eppendorf, #2243102-1) and 1 mL of the solution was immediately transferred to the 24 well plate containing the pre-hydrated teeth. The control samples consisted of 100 mM phosphate buffer, pH 7.2 and 9% $H_2O_2$ in 100 mM citrate/phosphate buffer, pH 5.3. The teeth were incubated at room temperature for 30 minutes, removed, rinsed with 100 mM phosphate, pH 7.2 and a color measurement was taken. The teeth were placed back into the 24 well plate at which time fresh enzyme solutions were prepared and added to each well. This process was repeated for a total of 3 whitening treatments; 30 min per treatment (Table 22).

TABLE 22

Color Measurements of Coffee-Tea Stained Bovine Enamel Exposed to 40 ppm EZ-1, 100 mM Substrate, Varying $H_2O_2$[1], 95 mM Phosphate, pH 7.2.

| | Whiteness Index | | | | |
|---|---|---|---|---|---|
| Sample | Treatment 0 | Treatment 1 | Treatment 2 | Treatment 3 | ΔWI |
| Buffer[a] | −190.4 | −183.3 | −181.1 | −179.0 | 11.4 |
| 9% $H_2O_2$[a] | −167.6 | −129.6 | −117.6 | −115.2 | 52.4 |
| TA | −189.9 | −108.7 | −86.7 | −86.1 | 103.8 |
| PGDA | −181.4 | −108.0 | −80.9 | −80.1 | 101.3 |
| SOC | −172.8 | −135.2 | −135.9 | −128.8 | 44.0 |
| GPA | −225.2 | −128.7 | −105.3 | −95.9 | 129.3 |

Table notes:
[1]$H_2O_2$ concentrations vary depending on substrate and are as follows: 100 mM $H_2O_2$ (TA), 360 mM $H_2O_2$ (PGDA and SOC), 60 mM $H_2O_2$ (GPA).
[a]Control samples contained no enzyme.

As observed in Table 22, all of the enzymatically generated peracetic acid samples using TA, PGDA, SOC and GPA show a significant change in whiteness index as indicated by a shift to more positive values with each successive treatment. The change in whiteness index for the buffer control is marginal with a ΔWI of 11.4. These measurements also coincide with visual inspection of the teeth after each 30 minute treatment. This data demonstrates that enzymatically generated peracetic acid, using a variety of different substrates with EZ-1, is effective at whitening coffee-tea stained bovine teeth.

EXAMPLE 16

Tooth Bleaching Efficacy Using Perhydrolytic Enzymes in a Two-Step Application

The purpose of this example was to demonstrate the tooth bleaching efficacy of perhydrolases systems in a two-step application.

Bovine enamel incisors were prepared as indicated in Example 1. The stained enamel blocks were embedded in a 48 well plate to protect the dentin backside from solution exposure. A solution of 10 µM of each enzyme in 10 mM phosphate buffer, pH 7.2 was prepared and 500 µL of solution was incubated with each enamel substrate for 60 min. The enzyme solution was removed and each well was rinsed three times with an additional 500 µL of buffer. The enamel blocks were placed in a fresh well for the whitening process. A solution with a final concentration of 40 mM triacetin, 100 mM $H_2O_2$ in 50 mM phosphate pH 7.2 buffer was freshly prepared and 500 µL of solution was added to each enamel block. Over the course of 1 hr the enamel blocks were removed and a color measurement was obtained and then each was returned to the solution in the well plate. The whiteness index for each sample was monitored. The results are listed in Table 23.

TABLE 23

Color Measurements of Coffee-Tea Stained Bovine Enamel Exposed to a Variety of Perhydrolases and Triacetin/$H_2O_2$ in 2 steps.

| | Whiteness Index | | | | | | |
|---|---|---|---|---|---|---|---|
| Enzyme | 0 min | 5 min | 15 min | 30 min | 45 min | 60 min | ΔWI |
| No enzyme | −108.2 | −102.7 | −104.0 | −107.3 | −98.3 | −96.7 | 11.4 |
| EZ-1 | −152.7 | −126.2 | −138.9 | −144.8 | −107.3 | −96.1 | 56.6 |
| EZ-2 | −154.5 | −134.6 | −97.3 | −57.2 | −35.8 | −25.3 | 129.1 |
| EZ-3 | −159.0 | −147.4 | −161.5 | −117.3 | −104.7 | −83.8 | 75.2 |
| EZ-4 | −158.9 | −143.6 | −149.5 | −129.4 | −106.5 | −89.5 | 69.4 |
| EZ-5 | −135.8 | −129.8 | −97.4 | −65.1 | −49.9 | −42.7 | 93.2 |

This example demonstrates that a surface bound perhydrolase can be used to whiten teeth by catalyzing the formation of peracetic acid at the surface of the enamel. The bleaching performance in this example correlates to the observed retention of each enzyme on hydroxyapatite. The untargeted EZ-1 (C277S; SEQ ID NO: 424) shows poor retention on hydroxyapatite and enamel and therefore low potential to achieve suitable whitening in a 2-step process. The addition of an effective targeting sequence to retain the enzyme on the enamel enables the production of peracetic acid in a 2-step application process.

EXAMPLE 17

Tooth Bleaching Efficacy Using Perhydrolytic Enzymes in a Two-Step Application

The purpose of this example was to demonstrate the tooth bleaching efficacy of targeted and untargeted perhydrolases systems in a two-step application.

Bovine enamel incisors were prepared as indicated in Example 1. The stained enamel blocks were embedded in SILLY PUTTY® (Crayola LLC, Easton, Pa.) filled well, a 24-well plate to protect the dentin backside from solution exposure. A solution of 20 µM of each enzyme in 10 mM phosphate buffer, pH 7.2 was prepared and 500 µL of the enzyme solution was added to each enamel blocks and incubated for 10 min at 37° C. The enamel block was then rinsed three times with an additional 500 µL of buffer each time. The enamel blocks were transferred and embedded in a fresh putty well for the whitening process. A solution (200 µL) containing 100 mM phosphate buffer, 100 mM triacetin, 100 mM $H_2O_2$, pH 7.2 was added to the enamel and incubated for 10 min at 37° C. The enamel block was removed from the well using forceps, then rinsed and stored in a 1.5 mL of water filled well for color measurements. The 2-step process was repeated 5 times (50 min total). The results of color measurements of coffee-tea stained bovine enamel after the 2-step process were shown in Table 24. Each sample data point represents 2 repeats of independent enamel blocks.

For measuring the level of peracetic acid generated in the system, the ABTS method was used, 90 µL of the reaction mixtures was removed to a new well containing 10 µL stopping buffer (1.33 M $H_3PO_4$). The samples were diluted 1:100 with 100 mM phosphate buffer and added to ABTS detection reagent as noted in Example 8. Results are listed in Table 25. Each sample data point represents 2 repeats of independent enamel blocks.

TABLE 24

Color Measurements of Coffee-Tea Stained Bovine Enamel Exposed to a Variety of Perhydrolases and Triacetin/$H_2O_2$ in 2 steps

| | | Whiteness Index | | | | | | |
|---|---|---|---|---|---|---|---|---|
| Step 1 | Step 2 | Before | Rd1 | Rd2 | Rd3 | Rd4 | Rd5 | ΔWI |
| Buffer | Buffer | −122.9 | −117.9 | −116.3 | −126.7 | −118.4 | −128.6 | −5.7 |
| Buffer | Triacetin $H_2O_2$ | −130.9 | −150.4 | −136.9 | −134.4 | −145.4 | −141.9 | −11.1 |
| EZ1 | Triacetin $H_2O_2$ | −140.0 | −129.5 | −129.5 | −129.2 | −125.1 | −122.1 | 17.9 |
| EZ7 | Triacetin $H_2O_2$ | −120.8 | −106.7 | −96.0 | −88.7 | −85.7 | −76.6 | 44.2 |

TABLE 25

Level of peracetic acid generation after each round of whitening process.

| | | PAA (ppm) generated after each round of whitening | | | | |
|---|---|---|---|---|---|---|
| Step 1 | Step 2 | Rd1 | Rd2 | Rd3 | Rd4 | Rd5 |
| Buffer | Buffer | 1.2 | 0.5 | 8.7 | 1.3 | 2.0 |
| Buffer | Triacetin/$H_2O_2$ | 31.0 | 25.8 | 16.0 | 45.5 | 35.9 |
| EZ1 | Triacetin/$H_2O_2$ | 33.2 | 41.0 | 30.2 | 39.3 | 47.1 |
| EZ7 | Triacetin/$H_2O_2$ | 383.5 | 496.7 | 716.5 | 998.5 | 1224.5 |

This example demonstrates that a surface bound perhydrolase can be used to whiten teeth by catalyzing the formation of peracetic acid at the surface of the enamel. The bleaching performance in this example using bovine enamel correlates to the observed retention of each enzyme on hydroxyapatite. The untargeted EZ-1 (C277S) shows poor retention on hydroxyapatite and enamel and therefore low potential to achieve suitable whitening in a 2-step process. The addition of an effective targeting sequence to retain the enzyme on the enamel enables the production of peracetic acid in a 2-step application process.

What is claimed is:

1. A method comprising
1) providing a set of reaction components comprising:
   a) at least one substrate selected from the group consisting of:
      i) esters having the structure

[X]$_m$R$_5$ wherein X=an ester group of the formula R$_6$C(O)O
      R$_6$=C1 to C7 linear, branched or cyclic hydrocarbyl moiety, optionally substituted with hydroxyl groups or C1 to C4 alkoxy groups, wherein R$_6$ optionally comprises one or more ether linkages for R$_6$=C2 to C7;
      R$_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups;
      wherein each carbon atom in R$_5$ individually comprises no more than one hydroxyl group or no more than one ester group or carboxylic acid group;
      wherein R$_5$ optionally comprises one or more ether linkages;
      m is an integer ranging from 1 to the number of carbon atoms in R$_5$; and
      wherein said esters have solubility in water of at least 5 ppm at 25° C.;
      ii) glycerides having the structure $$R_1-\overset{O}{\overset{\|}{C}}-O-CH_2-\underset{OR_3}{CH}-CH_2-OR_4$$

wherein R$_1$=C1 to C7 straight chain or branched chain alkyl optionally substituted with an hydroxyl or a C1 to C4 alkoxy group and R$_3$ and R$_4$ are individually H or R$_1$C(O);
      iii) one or more esters of the formula $$R_1-\overset{O}{\overset{\|}{C}}-O-R_2$$

wherein R$_1$ is a C1 to C7 straight chain or branched chain alkyl optionally substituted with an hydroxyl or a C1 to C4 alkoxy group and R$_2$ is a C1 to C10 straight chain or branched chain alkyl, alkenyl, alkynyl, aryl, alkylaryl, alkylheteroaryl, heteroaryl, (CH$_2$OH$_2$O)$_n$, or (CH$_2$CH(CH$_3$)—O)$_n$H and n is 1 to 10; and
      iv) acetylated saccharides selected from the group consisting of acetylated monosaccharides, acetylated disaccharides, and acetylated polysaccharides;
   b) a source of peroxygen; and
   c) an enzyme catalyst having perhydrolytic activity, wherein said enzyme catalyst comprises a fusion protein comprising the following general structure:
   PAH-[L]y-OCBD
   or
   OCBD-[L]y-PAH
   wherein
   PAH is an enzyme having perhydrolytic activity; wherein said enzyme is a carbohydrate esterase having a CE-7 signature motif that aligns with a reference sequence SEQ ID NO: 2, said signature motif comprising:
      i) an RGQ motif at positions corresponding to positions 118-120 of SEQ ID NO:2;
      ii) a GXSQG motif at positions corresponding to positions 179-183 of SEQ ID NO:2; and
      iii) an HE motif at positions corresponding to positions 298-299 of SEQ ID NO;2; OCBD is a peptidic component having affinity for oral cavity surface; wherein the peptidic component is a single chain variable fragment (scFv) antibody or a single chain polypeptide lacking an immunoglobulin fold; L is a peptide linker ranging from 1 to 100 amino acids in length; and y is 0 or 1; and
2) combining the reaction components of (1) under suitable reaction condition whereby at least one peracid is enzymatically produced; and
3) contacting an oral cavity surface with the at least one peracid whereby the oral cavity surface receives a peracid-based benefit selected from the group consisting of bleaching, teeth whitening, disinfecting, destaining, deodorizing, decreasing or removing biofilm, and combinations thereof.

2. The method of claim 1 wherein the single chain polypeptide comprises at least one oral cavity surface-binding peptide ranging from 5 to 60 amino acids in length and having a K$_D$ value or an MB$_{50}$ value of 10$^{-5}$ M or less for the oral cavity surface.

3. The method of claim 2 wherein the single chain polypeptide comprises 2 to 50 oral cavity surface-binding peptides wherein the oral cavity surface-binding peptides are independently and optionally separated by a polypeptide spacer ranging from 1 to 100 amino acids in length.

4. The method of claim 1 wherein the oral cavity surface is a tooth surface.

5. The method of claim 4 wherein the tooth surface comprises tooth enamel, tooth pellicle or a combination thereof.

6. The method of claim 2 wherein the oral cavity surface-binding peptide is a tooth enamel-binding peptide.

7. The method of claim 2 wherein the oral cavity surface-binding peptide is a tooth pellicle-binding peptide.

8. The method of claim 2 wherein the oral cavity surface-binding peptide is a skin-binding peptide.

9. The method of claim 1 where the peracid is produced at a concentration of 500 ppb to 10,000 ppm within 5 minutes of combining the set of reaction components.

10. The method of claim 9 wherein the peracid is contacted with the oral care surface for less than 1 hour.

11. The method of claim 1 wherein the peracid is peracetic acid.

12. The method of claim 11 wherein an efficacious concentration of peracetic acid is enzymatically produced and contacted with the oral cavity surface within 5 minutes of combining the reaction components.

13. The method of claim 1 wherein the substrate comprises triacetin.

14. A fusion protein comprising the following general structure:

PAH-[L]$_y$-OCBD or

OCBD-[L]$_y$-PAH wherein
PAH is an enzyme having perhydrolytic activity; wherein said enzyme is a carbohydrate esterase having a CE-7 signature motif that aligns with a reference sequence SEQ ID NO: 2, said signature motif comprising:
1) an RGQ motif at positions corresponding to positions 118-120 of SEQ ID NO:2;
2) a GXSQG motif at positions corresponding to positions 179-183 of SEQ ID NO:2; and
3) an HE motif at positions corresponding to positions 298-299 of SEQ ID NO:2;

OCBD is a peptidic component having affinity for an oral cavity surface; wherein the peptidic component is a single chain variable fragment (scFv) antibody or a single chain polypeptide lacking an immunoglobulin fold;

L is a peptide linker ranging from 1 to 100 amino acids in length; and y is 0 or 1.

15. The fusion protein of claim 14 wherein the single chain peptide comprises at least one oral cavity surface-binding peptide ranging from 5 to 60 amino acids in length.

16. The fusion protein of claim 15 wherein said at least one oral cavity surface-binding peptide has a $K_D$ value or an $MB_{50}$ value of $10^{-5}$ M or less.

17. The fusion protein of claim 15 wherein the single chain polypeptide comprises 2 to 50 oral cavity surface-binding peptides, wherein the oral cavity surface-binding peptides are independently and optionally separated by a polypeptide spacer ranging from 1 to 100 amino acids in length.

18. The fusion protein of claim 14, wherein the peptidic component having affinity for an oral cavity surface comprises a length of no more than 200 amino acids.

19. An oral care product comprising:
1) an enzyme catalyst comprising the fusion protein of claim 14;
2) at least one substrate selected from the group consisting of:
a) esters having the structure

wherein X=an ester group of the formula $R_6C(O)O$
$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;
M is an integer ranging from 1 to the number of carbon atoms in $R_5$; and
wherein said esters have solubility in water of at least 5 ppm at 25° C.;
b) glycerides having the structure

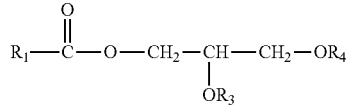

wherein $R_1$=C1 to C7 straight chain or branched chain alkyl optionally substituted with an hydroxyl or a C1 to C4 alkoxy group and $R_3$ and $R_4$ are individually H or $R_1C(O)$;

c) one or more esters of the formula

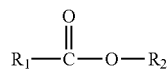

wherein $R_1$ is a C1 to C7 straight chain or branched chain alkyl optionally substituted with an hydroxyl or a C1 to C4 alkoxy group and
$R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; and
c) acetylated saccharides selected from the group consisting of acetylated monosaccharides, acetylated disaccharides, and acetylated polysaccharides;
3) a source of peroxygen; and
4) an orally acceptable carrier medium.

20. An oral care product comprising:
1) an enzyme catalyst having perhydrolytic activity, wherein said enzyme catalyst comprises an enzyme having a CE-7 signature motif that aligns with a reference sequence SEQ ID NO: 2 using CLUSTALW, said signature motif comprising:
a) an RGQ motif at positions corresponding to positions 118-120 of SEQ ID NO:2;
b) a GXSQG motif at positions corresponding to positions 179-183 of SEQ ID NO:2; and
c) an HE motif at positions corresponding to positions 298-299 of SEQ ID NO:2;
2) at least one substrate selected from the group consisting of:
a) esters having the structure

wherein X=an ester group of the formula $R_6C(O)O$
$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;
M is an integer ranging from 1 to the number of carbon atoms in $R_5$; and
wherein said esters have solubility in water of at least 5 ppm at 25° C.;
b) glycerides having the structure

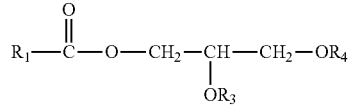

wherein $R_1$=C1 to C7 straight chain or branched chain alkyl optionally substituted with an hydroxyl or a C1 to C4 alkoxy group and $R_3$ and $R_4$ are individually H or $R_1C(O)$;

c) one or more esters of the formula

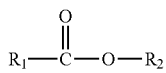

wherein $R_1$ is a C1 to C7 straight chain or branched chain alkyl optionally substituted with an hydroxyl or a C1 to C4 alkoxy group and $R_2$ is a C1 to 010 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10; and d) acetylated saccharides selected from the group consisting of acetylated monosaccharides, acetylated disaccharides, and acetylated polysaccharides;

3) a source of peroxygen; and 4) an orally acceptable carrier medium.

21. The oral care product of claim 19 wherein the single chain peptide lacking an immunoglobulin fold comprises at least one tooth enamel-binding or tooth pellicle-binding peptide.

22. The oral care product of claim 21 wherein the at least one tooth enamel-binding or tooth pellicle-binding peptides range from 5 to 60 amino acids in length.

23. The oral care product of claim 19, claim 20, claim 21 or claim 22 wherein the oral care product is in the form of a powder, paste, gel, liquid, ointment, tablet, rinse or any combination thereof.

24. The oral care product of claim 23 wherein the oral care product is a toothpaste, a dental cream, a tooth gel, a tooth powder, a mouth wash, a breath freshener, a strip or a dental floss.

25. The oral care product of claim 23 wherein the oral care product is in the form of a whitening strip or dental tray.

26. The oral care product of claim 19 or claim 20 wherein the enzyme catalyst remains separated from the substrate, the source of peroxygen or both the substrate and the source of peroxygen prior to use of the oral care product.

* * * * *

SEQUENCE LISTING

<160> NUMBER OF SEQ ID NOS: 479

<210> SEQ ID NO 1
<211> LENGTH: 960
<212> TYPE: DNA
<213> ORGANISM: Bacillus subtilis
<220> FEATURE:
<221> NAME/KEY: CDS
<222> LOCATION: (1)..(960)

<400> SEQUENCE: 1

```
atg caa cta ttc gat ctg ccg ctc gac caa ttg caa aca tat aag cct      48
Met Gln Leu Phe Asp Leu Pro Leu Asp Gln Leu Gln Thr Tyr Lys Pro
1               5                   10                  15 gaa aaa aca gca ccg aaa gat ttt tct gag ttt tgg aaa ttg tct ttg      96
Glu Lys Thr Ala Pro Lys Asp Phe Ser Glu Phe Trp Lys Leu Ser Leu
            20                  25                  30 gag gaa ctt gca aaa gtc caa gca gaa cct gat tta cag ccg gtt gac     144
Glu Glu Leu Ala Lys Val Gln Ala Glu Pro Asp Leu Gln Pro Val Asp
        35                  40                  45 tat cct gct gac gga gta aaa gtg tac cgt ctc aca tat aaa agc ttc     192
Tyr Pro Ala Asp Gly Val Lys Val Tyr Arg Leu Thr Tyr Lys Ser Phe
    50                  55                  60 gga aac gcc cgc att acc gga tgg tac gcg gtg cct gac aag caa ggc     240
Gly Asn Ala Arg Ile Thr Gly Trp Tyr Ala Val Pro Asp Lys Gln Gly
65                  70                  75                  80 ccg cat ccg gcg atc gtg aaa tat cat ggc tac aat gca agc tat gat     288
Pro His Pro Ala Ile Val Lys Tyr His Gly Tyr Asn Ala Ser Tyr Asp
                85                  90                  95 ggt gag att cat gaa atg gta aac tgg gca ctc cat ggc tac gcc gca     336
Gly Glu Ile His Glu Met Val Asn Trp Ala Leu His Gly Tyr Ala Ala
            100                 105                 110
```

| | | | | | | | | | | | | | | | | |
|---|---|---|---|---|---|---|---|---|---|---|---|---|---|---|---|---|
| ttc | ggc | atg | ctt | gtc | cgc | ggt | cag | cag | agc | agc | gag | gat | acg | agt | att | 384 |
| Phe | Gly | Met | Leu | Val | Arg | Gly | Gln | Gln | Ser | Ser | Glu | Asp | Thr | Ser | Ile | |
| | | | 115 | | | | 120 | | | | | 125 | | | | |
| tca | ctg | cac | ggt | cac | gct | ttg | ggc | tgg | atg | acg | aaa | gga | att | ctt | gat | 432 |
| Ser | Leu | His | Gly | His | Ala | Leu | Gly | Trp | Met | Thr | Lys | Gly | Ile | Leu | Asp | |
| | 130 | | | | 135 | | | | | 140 | | | | | | |
| aaa | gat | aca | tac | tat | tac | cgc | ggt | gtt | tat | ttg | gac | gcc | gtc | cgc | gcg | 480 |
| Lys | Asp | Thr | Tyr | Tyr | Tyr | Arg | Gly | Val | Tyr | Leu | Asp | Ala | Val | Arg | Ala | |
| 145 | | | | | 150 | | | | | 155 | | | | | 160 | |
| ctt | gag | gtc | atc | agc | agc | ttc | gac | gag | gtt | gac | gaa | aca | agg | atc | ggt | 528 |
| Leu | Glu | Val | Ile | Ser | Ser | Phe | Asp | Glu | Val | Asp | Glu | Thr | Arg | Ile | Gly | |
| | | | | 165 | | | | | 170 | | | | | 175 | | |
| gtg | aca | gga | gga | agc | caa | ggc | gga | ggt | tta | acc | att | gcc | gca | gca | gcg | 576 |
| Val | Thr | Gly | Gly | Ser | Gln | Gly | Gly | Gly | Leu | Thr | Ile | Ala | Ala | Ala | Ala | |
| | | 180 | | | | | 185 | | | | | 190 | | | | |
| ctg | tca | gac | att | cca | aaa | gcc | gcg | gtt | gcc | gat | tat | cct | tat | tta | agc | 624 |
| Leu | Ser | Asp | Ile | Pro | Lys | Ala | Ala | Val | Ala | Asp | Tyr | Pro | Tyr | Leu | Ser | |
| | | 195 | | | | | 200 | | | | | 205 | | | | |
| aac | ttc | gaa | cgg | gcc | att | gat | gtg | gcg | ctt | gaa | cag | ccg | tac | ctt | gaa | 672 |
| Asn | Phe | Glu | Arg | Ala | Ile | Asp | Val | Ala | Leu | Glu | Gln | Pro | Tyr | Leu | Glu | |
| | 210 | | | | | 215 | | | | | 220 | | | | | |
| atc | aat | tcc | ttc | ttc | aga | aga | aat | ggc | agc | ccg | gaa | aca | gaa | gtg | cag | 720 |
| Ile | Asn | Ser | Phe | Phe | Arg | Arg | Asn | Gly | Ser | Pro | Glu | Thr | Glu | Val | Gln | |
| 225 | | | | | 230 | | | | | 235 | | | | | 240 | |
| gcg | atg | aag | aca | ctt | tca | tat | ttc | gat | att | atg | aat | ctc | gct | gac | cga | 768 |
| Ala | Met | Lys | Thr | Leu | Ser | Tyr | Phe | Asp | Ile | Met | Asn | Leu | Ala | Asp | Arg | |
| | | | | 245 | | | | | 250 | | | | | 255 | | |
| gtg | aag | gtg | cct | gtc | ctg | atg | tca | atc | ggc | ctg | att | gac | aag | gtc | acg | 816 |
| Val | Lys | Val | Pro | Val | Leu | Met | Ser | Ile | Gly | Leu | Ile | Asp | Lys | Val | Thr | |
| | | | 260 | | | | | 265 | | | | | 270 | | | |
| ccg | ccg | tcc | acc | gtg | ttt | gcc | gcc | tac | aat | cat | ttg | gaa | aca | gag | aaa | 864 |
| Pro | Pro | Ser | Thr | Val | Phe | Ala | Ala | Tyr | Asn | His | Leu | Glu | Thr | Glu | Lys | |
| | | | 275 | | | | | 280 | | | | | 285 | | | |
| gag | ctg | aag | gtg | tac | cgc | tac | ttc | gga | cat | gag | tat | atc | cct | gct | ttt | 912 |
| Glu | Leu | Lys | Val | Tyr | Arg | Tyr | Phe | Gly | His | Glu | Tyr | Ile | Pro | Ala | Phe | |
| | 290 | | | | | 295 | | | | | 300 | | | | | |
| caa | acg | gaa | aaa | ctt | gct | ttc | ttt | aag | cag | cat | ctt | aaa | ggc | tga | taa | 960 |
| Gln | Thr | Glu | Lys | Leu | Ala | Phe | Phe | Lys | Gln | His | Leu | Lys | Gly | | | |
| 305 | | | | | 310 | | | | | 315 | | | | | | |

<210> SEQ ID NO 2
<211> LENGTH: 318
<212> TYPE: PRT
<213> ORGANISM: Bacillus subtilis

<400> SEQUENCE: 2

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Leu His Gly His Ala Leu Gly Trp Met Thr Lys Gly Ile Leu Asp
        130                 135                 140

Lys Asp Thr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
                    180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Gln Pro Tyr Leu Glu
        210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
                    260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
290                 295                 300

Gln Thr Glu Lys Leu Ala Phe Phe Lys Gln His Leu Lys Gly
305                 310                 315

```
<210> SEQ ID NO 3
<211> LENGTH: 957
<212> TYPE: DNA
<213> ORGANISM: Bacillus subtilis

<400> SEQUENCE: 3
atgcaactat tcgatctgcc gctcgaccaa ttgcaaacat ataagcctga aaaaacagca    60
ccgaaagatt tttctgagtt ttggaaattg tctttggagg aacttgcaaa agtccaagca   120
gaacctgatt tacagccggt tgactatcct gctgacggag taaaagtgta ccgtctcaca   180
tataaaagct tcggaaacgc ccgcattacc ggatggtacg cggtgcctga caaggaaggc   240
ccgcatccgg cgatcgtgaa atatcatggc tacaatgcaa gctatgatgg tgagattcat   300
gaaatggtaa actgggcact ccatggctac gccacattcg gcatgcttgt ccgcggccag   360
cagagcagcg aggatacgag tatttcaccg cacggtcacg ctttgggctg gatgacgaaa   420
ggaattcttg ataaagatac atactattac cgcggtgttt atttggacgc cgtccgcgcg   480
cttgaggtca tcagcagctt cgacgaggtt gacgaaacaa ggatcggtgt gacaggagga   540
agccaaggcg gaggtttaac cattgccgca gcagcgctgt cagacattcc aaaagccgcg   600
gttgccgatt atccttattt aagcaacttc gaacgggcca ttgatgtggc gcttgaacag   660
ccgtaccttg aaatcaattc cttcttcaga gaaatggcag gcccggaaac agaagtgcag   720
gcgatgaaga cactttcata tttcgatatt atgaatctcg ctgaccgagt gaaggtgcct   780
gtcctgatgt caatcggcct gattgacaag gtcacgccgc cgtccaccgt gtttgccgcc   840
tacaatcatt tggaaacaaa gaagagctg aaggtgtacc gctacttcgg acatgagtat   900
atccctgctt ttcaaactga aaaacttgct ttctttaagc agcatcttaa aggctga     957
```

<210> SEQ ID NO 4
<211> LENGTH: 318
<212> TYPE: PRT
<213> ORGANISM: Bacillus subtilis s

<400> SEQUENCE: 4

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Thr
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Lys Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 5
<211> LENGTH: 957
<212> TYPE: DNA
<213> ORGANISM: Bacillus subtilis

<400> SEQUENCE: 5
atgcaactat tcgatctgcc gctcgaccaa ttgcaaacgt ataagcctga aaaaacaaca     60
ccgaacgatt tttctgagtt ttggaaatcg tctttggacg aacttgcgaa agtcaaagca    120

```
gcacctgatt tacagctggt tgattatcct gctgatggag tcaaggtgta ccgcctcaca    180
tataaaagct tcggaaacgc ccgcattacc ggatggtacg cagtgcctga caaggaagga    240
ccgcatccgg cgatcgtcaa atatcatggc tacaacgcta gctatgacgg tgagattcat    300
gaaatggtaa actgggcgct ccacggttac gccgcattcg gcatgctagt ccgcggccag    360
cagagcagcg aggatacgag tatttctcca catggccatg ctttgggctg atgacgaaa    420
ggaatccttg ataaagatac atactattac cggggcgttt attggacgc tgtccgcgcg    480
cttgaggtca tcagcagctt tgacgaagtt gacgaaacaa gaatcggtgt gacaggcgga    540
agccaaggag gcggcttaac cattgccgca gccgctctgt cagacattcc aaaagccgcg    600
gttgccgatt atccttattt aagcaacttt gaacgggcca ttgatgtggc gcttgaacag    660
ccgtaccttg aaatcaattc cttctttaga agaaatggaa gcccggaaac ggaagagaag    720
gcgatgaaga cactttcata tttcgatatt atgaatctcg ctgaccgagt gaaggtccct    780
gtcctgatgt cgatcggtct gattgacaag gtcacgccgc cgtccaccgt gtttgccgca    840
tacaaccact tggagacaga gaaagagctc aaagtgtacc gctacttcgg gcatgagtat    900
atccctgcct ttcaaacaga aaaacttgct ttctttaagc agcatcttaa aggctga      957
```

<210> SEQ ID NO 6
<211> LENGTH: 318
<212> TYPE: PRT
<213> ORGANISM: Bacillus subtilis

<400> SEQUENCE: 6

```
Met Gln Leu Phe Asp Leu Pro Leu Asp Gln Leu Gln Thr Tyr Lys Pro
1               5                   10                  15

Glu Lys Thr Thr Pro Asn Asp Phe Ser Glu Phe Trp Lys Ser Ser Leu
            20                  25                  30

Asp Glu Leu Ala Lys Val Lys Ala Ala Pro Asp Leu Gln Leu Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Glu Lys
225                 230                 235                 240
```

```
Ala Met Lys Thr Leu Ser Tyr Phe Asp Ile Met Asn Leu Ala Asp Arg
            245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
            275                 280                 285

Glu Leu Lys Val Tyr Arg Tyr Phe Gly His Gly Tyr Ile Pro Ala Phe
            290                 295                 300

Gln Thr Glu Lys Leu Ala Phe Phe Lys Gln His Leu Lys Gly
305                 310                 315
```

<210> SEQ ID NO 7
<211> LENGTH: 957
<212> TYPE: DNA
<213> ORGANISM: Bacillus licheniformis

<400> SEQUENCE: 7

```
atgcagcagc ttatgatat gccgcttgaa cagctttatc agtataaacc tgaacggacg      60
gcaccggccg atttaaaga gttctggaag ggttcattgg aggaattggc aaatgaaaaa     120
gcgggaccgc agcttgaacc gcatgaatat ccggctgacg gggtaaaagt ctactggctt     180
acatacagaa gcatcggggg agcgcgaatt aaaggctggt acgcagtacc cgaccgccaa     240
gggcctcatc ctgcgatcgt caaataccac ggctataacg caagctatga cggagacatt     300
cacgatattg tcaattgggc tcttcacggc tatgcggcat tcggtatgct ggtccgcgga     360
cagaacagca gtgaagatac agagatctct catcacggac atgtaccgg ctggatgaca     420
aaaggaatcc tcgatccgaa acatattac tacagagggg tctatttaga tgccgtacga     480
gcagtcgaag tggtcagcgg ttttgctgaa gtcgatgaaa gcggatcgg ggtgatcggg     540
gcaagccaag gaggcgggct ggccgtcgcg gtttcggcgc tgtccgatat tccaaaagca     600
gccgtgtcag aataccctta tttaagcaat tttcaacgag cgatcgatac agcgatcgac     660
cagccatatc tcgaaatcaa ctccttttc agaagaaaca ccagtccgga tattgagcag     720
gcggccatgc atacctgtc ttatttcgat gtcatgaacc ttgcccaatt ggtcaaagcg     780
accgtactca tgtcgatcgg actggttgac accatcactc cgccatccac cgtctttgcg     840
gcttacaatc acttggaaac ggataaagaa ataaaagtgt accgttattt tggacacgaa     900
tacatcccgc cgttccaaac cgaaaagctg gcgtttctga aaagcatct gaaataa       957
```

<210> SEQ ID NO 8
<211> LENGTH: 318
<212> TYPE: PRT
<213> ORGANISM: Bacillus licheniformis

<400> SEQUENCE: 8

```
Met Gln Gln Pro Tyr Asp Met Pro Leu Glu Gln Leu Tyr Gln Tyr Lys
1               5                   10                  15

Pro Glu Arg Thr Ala Pro Ala Asp Phe Lys Glu Phe Trp Lys Gly Ser
            20                  25                  30

Leu Glu Glu Leu Ala Asn Glu Lys Ala Gly Pro Gln Leu Glu Pro His
        35                  40                  45

Glu Tyr Pro Ala Asp Gly Val Lys Val Tyr Trp Leu Thr Tyr Arg Ser
    50                  55                  60

Ile Gly Gly Ala Arg Ile Lys Gly Trp Tyr Ala Val Pro Asp Arg Gln
65                  70                  75                  80

Gly Pro His Pro Ala Ile Val Lys Tyr His Gly Tyr Asn Ala Ser Tyr
```

```
                85                  90                  95
Asp Gly Asp Ile His Asp Ile Val Asn Trp Ala Leu His Gly Tyr Ala
            100                 105                 110
Ala Phe Gly Met Leu Val Arg Gly Gln Asn Ser Ser Glu Asp Thr Glu
            115                 120                 125
Ile Ser His His Gly His Val Pro Gly Trp Met Thr Lys Gly Ile Leu
            130                 135                 140
Asp Pro Lys Thr Tyr Tyr Tyr Arg Gly Val Tyr Leu Asp Ala Val Arg
145                 150                 155                 160
Ala Val Glu Val Val Ser Gly Phe Ala Glu Val Asp Glu Lys Arg Ile
                165                 170                 175
Gly Val Ile Gly Ala Ser Gln Gly Gly Gly Leu Ala Val Ala Val Ser
            180                 185                 190
Ala Leu Ser Asp Ile Pro Lys Ala Ala Val Ser Glu Tyr Pro Tyr Leu
            195                 200                 205
Ser Asn Phe Gln Arg Ala Ile Asp Thr Ala Ile Asp Gln Pro Tyr Leu
            210                 215                 220
Glu Ile Asn Ser Phe Phe Arg Arg Asn Thr Ser Pro Asp Ile Glu Gln
225                 230                 235                 240
Ala Ala Met His Thr Leu Ser Tyr Phe Asp Val Met Asn Leu Ala Gln
                245                 250                 255
Leu Val Lys Ala Thr Val Leu Met Ser Ile Gly Leu Val Asp Thr Ile
            260                 265                 270
Thr Pro Pro Ser Thr Val Phe Ala Ala Tyr Asn His Leu Glu Thr Asp
            275                 280                 285
Lys Glu Ile Lys Val Tyr Arg Tyr Phe Gly His Glu Tyr Ile Pro Pro
290                 295                 300
Phe Gln Thr Glu Lys Leu Ala Phe Leu Arg Lys His Leu Lys
305                 310                 315

<210> SEQ ID NO 9
<211> LENGTH: 963
<212> TYPE: DNA
<213> ORGANISM: Bacillus pumilus

<400> SEQUENCE: 9
atgcaattgt tcgatttatc actagaagag ctaaaaaaat ataaaccaaa gaaaacagca      60
cgtcctgatt tctcagactt ttggaagaaa tcgctcgaag aactgcgcca agtggaggca     120
gagccaacac ttgaatctta tgactatcca gtgaaaggcg tcaaggtgta ccgcctgacg     180
tatcaaagct ttggacattc taaaattgaa ggcttttatg ctgtgcctga tcaaactggt     240
ccgcatccag cgctcgttcg ttttcatggc tataatgcca gctatgacgg cggcattcac     300
gacatcgtca actgggcgct gcacggctat gcaacatttg gtatgctcgt ccgcggtcaa     360
ggtggcagtg aagacacatc agtgacacca ggcgggcatg cattagggtg gatgacaaaa     420
ggcattttat cgaaagatac gtactattat cgaggcgttt atctagatgc tgttcgtgca     480
cttgaagtca ttcagtcttt ccccgaagta gatgaacacc gtatcggcgt gatcggtgga     540
agtcagggg gtgcgttagc gattgcggcc gcagcccttt cagacattcc aaaagtcgtt     600
gtggcagact atccttactt atcaaatttt gagcgtgcag ttgatgttgc cttggagcag     660
ccttatttag aaatcaattc atactttcgc agaaacagtg atccgaaagt ggaggaaaag     720
gcatttgaga cattaagcta ttttgattta atcaatttag ctggatgggt gaaacagcca     780
acattgatgg cgatcggtct gattgacaaa ataaccccac catctactgt gtttgcggca     840
```

```
tacaaccatt tagaaacaga taaagacctg aaagtatatc gctatttttgg acacgagttt    900 atccctgctt tcaaacaga gaagctgtcc tttttacaaa agcatttgct tctatcaaca    960
taa                                                                  963
```

<210> SEQ ID NO 10
<211> LENGTH: 320
<212> TYPE: PRT
<213> ORGANISM: Bacillus pumilus

<400> SEQUENCE: 10

```
Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
            20                  25                  30

Glu Glu Leu Arg Gln Val Glu Ala Glu Pro Thr Leu Glu Ser Tyr Asp
        35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
            100                 105                 110

Phe Gly Met Leu Val Arg Gly Gln Gly Gly Ser Glu Asp Thr Ser Val
        115                 120                 125

Thr Pro Gly Gly His Ala Leu Gly Trp Met Thr Lys Gly Ile Leu Ser
    130                 135                 140

Lys Asp Thr Tyr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala
            180                 185                 190

Leu Ser Asp Ile Pro Lys Val Val Ala Asp Tyr Pro Tyr Leu Ser
    195                 200                 205

Asn Phe Glu Arg Ala Val Asp Val Ala Leu Glu Gln Pro Tyr Leu Glu
210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
            260                 265                 270

Pro Pro Ser Thr Val Phe Ala Ala Tyr Asn His Leu Glu Thr Asp Lys
    275                 280                 285

Asp Leu Lys Val Tyr Arg Tyr Phe Gly His Glu Phe Ile Pro Ala Phe
290                 295                 300

Gln Thr Glu Lys Leu Ser Phe Leu Gln Lys His Leu Leu Ser Thr
305                 310                 315                 320
```

<210> SEQ ID NO 11
<211> LENGTH: 963
<212> TYPE: DNA
<213> ORGANISM: Clostridium thermocellum

<400> SEQUENCE: 11

```
atggcacaat tatatgatat gcctttggag gaattaaaaa aatataagcc tgcgcttaca     60
aaacagaaag attttgatga gttttgggaa aaaagcctta agagctggc tgaaattcct    120
ttaaaatatc aacttatacc ttatgatttt ccggcccgga gggtaaaagt tttcagagtt   180
gaatatcttg ttttaaagg tgcaaatatt gaagggtggc ttgccgttcc cgagggagaa    240
gggttgtatc ccgggcttgt acagtttcac ggatacaact gggcgatgga tggatgtgtt   300
cccgatgtgg taaattgggc tttgaatgga tatgccgcat ttcttatgct tgttcgggga   360
cagcagggaa gaagcgtgga caatattgtg cccggcagcg gtcatgcttt gggatggatg   420
tcgaaaggta ttttgtcacc ggaggaatat tattatagag gagtatatat ggatgcggtt   480
cgtgctgttg aaattttggc ttcgcttcct tgtgtggatg aatcgagaat aggagtgaca   540
gggggcagcc agggtggagg acttgcactg gcggtggctg ctctgtccgg cataccgaaa   600
gttgcagccg tgcattatcc gtttctggca cattttgagc gtgccattga cgttgcgccg   660
gacggccctt atcttgaaat taacgaatat ttaagaagaa acagcggtga agaaatagaa   720
agacaggtaa agaaaaccct ttcctatttt gatatcatga atcttgctcc ccgtataaaa   780
tgccgtactt ggatttgcac tggtcttgtg gatgagatta ctcctccgtc aacggttttt   840
gcagtgtaca atcacctcaa atgcccaaag gaaatttcgg tattcagata ttttgggcat   900
gaacatatgc caggaagcgt tgaaatcaag ctgaggatac ttatggatga gctgaatccg   960
taa                                                                  963
```

<210> SEQ ID NO 12
<211> LENGTH: 320
<212> TYPE: PRT
<213> ORGANISM: Clostridium thermocellum

<400> SEQUENCE: 12

```
Met Ala Gln Leu Tyr Asp Met Pro Leu Glu Glu Leu Lys Lys Tyr Lys
1               5                   10                  15

Pro Ala Leu Thr Lys Gln Lys Asp Phe Asp Glu Phe Trp Glu Lys Ser
            20                  25                  30

Leu Lys Glu Leu Ala Glu Ile Pro Leu Lys Tyr Gln Leu Ile Pro Tyr
        35                  40                  45

Asp Phe Pro Ala Arg Arg Val Lys Val Phe Arg Val Glu Tyr Leu Gly
    50                  55                  60

Phe Lys Gly Ala Asn Ile Glu Gly Trp Leu Ala Val Pro Glu Gly Glu
65                  70                  75                  80

Gly Leu Tyr Pro Gly Leu Val Gln Phe His Gly Tyr Asn Trp Ala Met
                85                  90                  95

Asp Gly Cys Val Pro Asp Val Val Asn Trp Ala Leu Asn Gly Tyr Ala
            100                 105                 110

Ala Phe Leu Met Leu Val Arg Gly Gln Gln Gly Arg Ser Val Asp Asn
        115                 120                 125

Ile Val Pro Gly Ser Gly His Ala Leu Gly Trp Met Ser Lys Gly Ile
    130                 135                 140

Leu Ser Pro Glu Glu Tyr Tyr Tyr Arg Gly Val Tyr Met Asp Ala Val
145                 150                 155                 160

Arg Ala Val Glu Ile Leu Ala Ser Leu Pro Cys Val Asp Glu Ser Arg
                165                 170                 175

Ile Gly Val Thr Gly Gly Ser Gln Gly Gly Gly Leu Ala Leu Ala Val
            180                 185                 190
```

```
Ala Ala Leu Ser Gly Ile Pro Lys Val Ala Val His Tyr Pro Phe
        195                 200                 205

Leu Ala His Phe Glu Arg Ala Ile Asp Val Ala Pro Asp Gly Pro Tyr
    210                 215                 220

Leu Glu Ile Asn Glu Tyr Leu Arg Arg Asn Ser Gly Glu Ile Glu
225                 230                 235                 240

Arg Gln Val Lys Lys Thr Leu Ser Tyr Phe Asp Ile Met Asn Leu Ala
                245                 250                 255

Pro Arg Ile Lys Cys Arg Thr Trp Ile Cys Thr Gly Leu Val Asp Glu
                260                 265                 270

Ile Thr Pro Pro Ser Thr Val Phe Ala Val Tyr Asn His Leu Lys Cys
                275                 280                 285

Pro Lys Glu Ile Ser Val Phe Arg Tyr Phe Gly His Glu His Met Pro
        290                 295                 300

Gly Ser Val Glu Ile Lys Leu Arg Ile Leu Met Asp Glu Leu Asn Pro
305                 310                 315                 320
```

<210> SEQ ID NO 13
<211> LENGTH: 978
<212> TYPE: DNA
<213> ORGANISM: Thermotoga neapolitana

<400> SEQUENCE: 13

```
atggccttct tcgatatgcc ccttgaggaa ctgaaaaagt accggcctga aggtacgag      60
gagaaagatt tcgatgagtt ctggagggaa acacttaaag aaagcgaagg attccctctg    120
gatcccgtct ttgaaaaggt ggactttcat ctcaaaacgg ttgaaacgta cgatgttact    180
ttctctggat acaggggca gagaataaag ggctggcttc ttgttccgaa gttggcggaa     240
gaaaagcttc catgcgtcgt gcagtacata ggttacaatg tggaagggg ttttccacac     300
gactggctgt tctggccgtc aatgggttac atctgttttg tcatggacac caggggcag     360
ggaagcggct ggatgaaggg agacacaccg gattaccctg aggtccagt cgatccacag     420
tacccccgga tcatgacgag gggcattctg gatccgggaa cctattacta caggcgagtc    480
ttcgtggatg cggtcagggc ggtggaagca gccatttcct tcccgagagt ggattccagg    540
aaggtggtgg tggccggagg cagtcagggt ggggggaatcg cccttgcggt gagtgccctg   600
tcgaacaggg tgaaggctct gctctgcgat gtgccgtttc tgtgccactt cagaagggcc    660
gtgcaacttg tcgacacaca cccatacgtg gagatcacca acttcctcaa acccacagg    720
gacaaagagg agattgtttt cagaacactt tcctacttcg atggtgtgaa ctttgcagca    780
agggcaaagg tgcccgccct gttttccgtt gggctcatgg acaccatctg tcctcccctcg   840
acggtcttcg ccgcttacaa ccactacgcc ggtccaaagg agatcagaat ctatccgtac   900
aacaaccacg aaggtggagg ttctttccag gcaattgagc aggtgaaatt cttgaagaga  960
ctatttgagg aaggctag                                                  978
```

<210> SEQ ID NO 14
<211> LENGTH: 325
<212> TYPE: PRT
<213> ORGANISM: Thermotoga neapolitana

<400> SEQUENCE: 14

```
Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30
```

```
Lys Glu Ser Glu Gly Phe Pro Leu Asp Pro Val Phe Glu Lys Val Asp
            35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ile Ser Phe Pro Arg
                165                 170                 175

Val Asp Ser Arg Lys Val Val Ala Gly Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 15
<211> LENGTH: 978
<212> TYPE: DNA
<213> ORGANISM: Thermotoga maritima

<400> SEQUENCE: 15
atggccttct tcgatttacc actcgaagaa ctgaagaaat atcgtccaga gcggtacgaa      60
gagaaagact tcgatgagtt ctgggaaagag acactcgcag agagcgaaaa gttccccta    120 gaccccgtct tcgagaggat ggagtctcac ctcaaaacag tcgaagcgta cgatgtcacc    180
ttctccggat acaggggaca gaggatcaaa gggtggctcc ttgttccaaa actggaagaa    240
gaaaaacttc cctgcgttgt gcagtacata ggatacaacg gtggaagagg attccctcac    300
gactggctgt tctggccttc tatgggttac atatgtttcg tcatggatac tcgaggtcag    360
ggaagcggct ggctgaaagg agacacaccg gattaccctg agggtccgt tgaccctcag    420 tatccaggat tcatgacaag aggaatactg gatcccagaa cttactacta cagacgagtc    480
```

```
ttcacggacg ctgtcagagc cgttgaagct gctgcttctt ttcctcaggt agatcaagaa      540
agaatcgtga tagctggagg cagtcagggt ggcggaatag cccttgcggt gagcgctctc      600
tcaaagaaag caaaggctct tctgtgcgat gtgccgtttc tgtgtcactt cagaagagca      660
gtacagcttg tggatacgca tccatacgcg gagatcacga actttctaaa gacccacaga      720
gacaaggaag aaatcgtgtt caggactctt tcctatttcg atggagtgaa cttcgcagcc      780
agagcgaaga tccctgcgct gttttctgtg gtctcatgg acaacatttg tcctccttca       840
acggttttcg ctgcctacaa ttactacgct ggaccgaagg aaatcagaat ctatccgtac      900
aacaaccacg agggaggagg ctctttccaa gcggttgaac aggtgaaatt cttgaaaaaa      960
ctatttgaga aaggctaa                                                   978
```

<210> SEQ ID NO 16
<211> LENGTH: 325
<212> TYPE: PRT
<213> ORGANISM: Thermotoga maritima

<400> SEQUENCE: 16

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285
```

```
Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 17
<211> LENGTH: 963
<212> TYPE: DNA
<213> ORGANISM: Thermoanaerobacterium sp.

<400> SEQUENCE: 17
atgggacttt tcgacatgcc attacaaaaa cttagagaat acactggtac aaatccatgc    60
cctgaagatt tcgatgagta ttggaatagg gctttagatg agatgaggtc agttgatcct   120
aaaattgaat tgaaagaaag tagctttcaa gtatcctttg cagaatgcta tgacttgtac   180
tttacaggtg ttcgtggtgc cagaattcat gcaaagtata aaaacctaa gacagaaggg    240 aaacatccag cgttgataag atttcatgga tattcgtcaa attcaggcga ctggaacgac   300
aaattaaatt acgtggcggc aggcttcacc gttgtggcta tggatgtaag aggtcaagga   360
gggcagtctc aagatgttgg cggtgtaact gggaatactt taaatgggca tattataaga   420
gggctagacg atgatgctga taatatgctt tcaggcata ttttcttaga cactgcccaa    480
ttggctggaa tagttatgaa catgccagaa gttgatgaag atagagtggg agtcatggga   540
ccttctcaag gcggagggct gtcgttggcg tgtgctgcat ggagccaag ggtacgcaaa    600 gtagtatctg aatatccttt tttatctgac tacaagagag tttgggactt agaccttgca   660
aaaaacgcct atcaagagat tacggactat ttcaggcttt tgacccaag gcatgaaagg    720 gagaatgagg tatttacaaa gcttggatat atagacgtta aaaaccttgc gaaaaggata   780
aaaggcgatg tcttaatgtg cgttgggctt atggaccaag tatgtccgcc atcaactgtt   840
tttgcagcct acaacaacat acagtcaaaa aaagatataa agtgtatcc tgattatgga   900 catgaaccta tgagaggatt tggagattta gcgatgcagt ttatgttgga actatattca   960
taa                                                                 963

<210> SEQ ID NO 18
<211> LENGTH: 320
<212> TYPE: PRT
<213> ORGANISM: Thermoanaerobacterium sp.

<400> SEQUENCE: 18

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
            20                  25                  30

Asp Glu Met Arg Ser Val Asp Pro Lys Ile Glu Leu Lys Glu Ser Ser
        35                  40                  45

Phe Gln Val Ser Phe Ala Glu Cys Tyr Asp Leu Tyr Phe Thr Gly Val
    50                  55                  60

Arg Gly Ala Arg Ile His Ala Lys Tyr Ile Lys Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110
```

```
Ala Met Asp Val Arg Gly Gln Gly Gly Gln Ser Gln Asp Val Gly Gly
        115                 120                 125

Val Thr Gly Asn Thr Leu Asn Gly His Ile Ile Arg Gly Leu Asp Asp
    130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Val Asp Glu Asp Arg Val
                165                 170                 175

Gly Val Met Gly Pro Ser Gln Gly Gly Leu Ser Leu Ala Cys Ala
            180                 185                 190

Ala Leu Glu Pro Arg Val Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300

Arg Gly Phe Gly Asp Leu Ala Met Gln Phe Met Leu Glu Leu Tyr Ser
305                 310                 315                 320

<210> SEQ ID NO 19
<211> LENGTH: 978
<212> TYPE: DNA
<213> ORGANISM: Bacillus sp.
<220> FEATURE:
<221> NAME/KEY: CDS
<222> LOCATION: (1)..(978)

<400> SEQUENCE: 19 atg aac ctt ttt gat atg ccc ctt gag gag ctg cag cat tac aag cct    48
Met Asn Leu Phe Asp Met Pro Leu Glu Glu Leu Gln His Tyr Lys Pro
1               5                   10                  15 gcc cag acc agg cag gat gat ttt gag tca ttc tgg aaa aag cgg att    96
Ala Gln Thr Arg Gln Asp Asp Phe Glu Ser Phe Trp Lys Lys Arg Ile
            20                  25                  30 gag gag aac agt caa tat ccg ctg aat ata gaa gta atg gag cgg gtt    144
Glu Glu Asn Ser Gln Tyr Pro Leu Asn Ile Glu Val Met Glu Arg Val
        35                  40                  45 tat ccg gtt ccg gga gtg aga gta tat gat att tat ttt gac ggg ttc    192
Tyr Pro Val Pro Gly Val Arg Val Tyr Asp Ile Tyr Phe Asp Gly Phe
    50                  55                  60 cgg aat tcc cgc atc cat ggg gtg tat gtt act cca gaa act ccg gga    240
Arg Asn Ser Arg Ile His Gly Val Tyr Val Thr Pro Glu Thr Pro Gly
65                  70                  75                  80 gcg gac act cct gcg gca gtg att ttt cac ggc tat aac tgg aac acg    288
Ala Asp Thr Pro Ala Ala Val Ile Phe His Gly Tyr Asn Trp Asn Thr
                85                  90                  95 ctg cag ccg cat tac agc ttc aag cac gtg att cag ggg att cct gta    336
Leu Gln Pro His Tyr Ser Phe Lys His Val Ile Gln Gly Ile Pro Val
            100                 105                 110 ctg atg gtg gag gtg cgg gga caa aat ctc ttg tct cca gat aga aat    384
```

```
                                                        -continued

Leu Met Val Glu Val Arg Gly Gln Asn Leu Leu Ser Pro Asp Arg Asn
        115                 120                 125 cat tat ggg aat gga ggt ccg gga ggc tgg atg aca ctc ggc gtg atg          432
His Tyr Gly Asn Gly Gly Pro Gly Gly Trp Met Thr Leu Gly Val Met
        130                 135                 140 gat ccc gat caa tat tat tac agc ctg gta tat atg gac tgc ttc cgc          480
Asp Pro Asp Gln Tyr Tyr Tyr Ser Leu Val Tyr Met Asp Cys Phe Arg
145                 150                 155                 160 agc att gat gct gtc agg gaa ctg tcg agg aag aga agt gtg ttt gtg          528
Ser Ile Asp Ala Val Arg Glu Leu Ser Arg Lys Arg Ser Val Phe Val
                165                 170                 175 gaa ggc gga agc cag gga ggt gca ctg gcg att gcc gca gcc gcc ctg          576
Glu Gly Gly Ser Gln Gly Gly Ala Leu Ala Ile Ala Ala Ala Ala Leu
                180                 185                 190 cag gat gac atc ctg ctt gca ctc gcc gac atc cct ttt ctc acc cat          624
Gln Asp Asp Ile Leu Leu Ala Leu Ala Asp Ile Pro Phe Leu Thr His
                195                 200                 205 ttc aag cgt tcc gtg gag ctt tcc tcg gat gga ccg tat cag gag att          672
Phe Lys Arg Ser Val Glu Leu Ser Ser Asp Gly Pro Tyr Gln Glu Ile
210                 215                 220 tcc cac tac ttc aaa gtt cat gat cct ctt cat caa acg gaa gag cag          720
Ser His Tyr Phe Lys Val His Asp Pro Leu His Gln Thr Glu Glu Gln
225                 230                 235                 240 gta tat cag acg ctc agc tat gtg gac tgc atg aac atg gcc agc atg          768
Val Tyr Gln Thr Leu Ser Tyr Val Asp Cys Met Asn Met Ala Ser Met
                245                 250                 255 gtt gaa tgt cca gtc ctt ctt tca gcc ggt ctg gaa gac atc gtt tgt          816
Val Glu Cys Pro Val Leu Leu Ser Ala Gly Leu Glu Asp Ile Val Cys
                260                 265                 270 ccc ccg tcc agt gca ttt gca ctg ttc aac cat ctc ggc ggg cca aaa          864
Pro Pro Ser Ser Ala Phe Ala Leu Phe Asn His Leu Gly Gly Pro Lys
                275                 280                 285 gaa ata cgg gcc tat ccg gaa tac gcc cat gaa gta ccg gct gtc cat          912
Glu Ile Arg Ala Tyr Pro Glu Tyr Ala His Glu Val Pro Ala Val His
            290                 295                 300 gaa gag gaa aag ctg aag ttt ata tct tca agg cta aaa aat aga gaa          960
Glu Glu Glu Lys Leu Lys Phe Ile Ser Ser Arg Leu Lys Asn Arg Glu
305                 310                 315                 320 aag agg tgc cgg cca tga                                                  978
Lys Arg Cys Arg Pro
                325

<210> SEQ ID NO 20
<211> LENGTH: 325
<212> TYPE: PRT
<213> ORGANISM: Bacillus sp.

<400> SEQUENCE: 20

Met Asn Leu Phe Asp Met Pro Leu Glu Glu Leu Gln His Tyr Lys Pro
1               5                   10                  15

Ala Gln Thr Arg Gln Asp Asp Phe Glu Ser Phe Trp Lys Lys Arg Ile
            20                  25                  30

Glu Glu Asn Ser Gln Tyr Pro Leu Asn Ile Glu Val Met Glu Arg Val
        35                  40                  45

Tyr Pro Val Pro Gly Val Arg Val Tyr Asp Ile Tyr Phe Asp Gly Phe
    50                  55                  60

Arg Asn Ser Arg Ile His Gly Val Tyr Val Thr Pro Glu Thr Pro Gly
65                  70                  75                  80

Ala Asp Thr Pro Ala Ala Val Ile Phe His Gly Tyr Asn Trp Asn Thr
                85                  90                  95
```

Leu Gln Pro His Tyr Ser Phe Lys His Val Ile Gln Gly Ile Pro Val
            100                 105                 110

Leu Met Val Glu Val Arg Gly Gln Asn Leu Leu Ser Pro Asp Arg Asn
            115                 120                 125

His Tyr Gly Asn Gly Gly Pro Gly Gly Trp Met Thr Leu Gly Val Met
130                 135                 140

Asp Pro Asp Gln Tyr Tyr Tyr Ser Leu Val Tyr Met Asp Cys Phe Arg
145                 150                 155                 160

Ser Ile Asp Ala Val Arg Glu Leu Ser Arg Lys Arg Ser Val Phe Val
                165                 170                 175

Glu Gly Gly Ser Gln Gly Gly Ala Leu Ala Ile Ala Ala Ala Ala Leu
            180                 185                 190

Gln Asp Asp Ile Leu Leu Ala Leu Ala Asp Ile Pro Phe Leu Thr His
            195                 200                 205

Phe Lys Arg Ser Val Glu Leu Ser Ser Asp Gly Pro Tyr Gln Glu Ile
210                 215                 220

Ser His Tyr Phe Lys Val His Asp Pro Leu His Gln Thr Glu Glu Gln
225                 230                 235                 240

Val Tyr Gln Thr Leu Ser Tyr Val Asp Cys Met Asn Met Ala Ser Met
                245                 250                 255

Val Glu Cys Pro Val Leu Leu Ser Ala Gly Leu Glu Asp Ile Val Cys
            260                 265                 270

Pro Pro Ser Ser Ala Phe Ala Leu Phe Asn His Leu Gly Gly Pro Lys
            275                 280                 285

Glu Ile Arg Ala Tyr Pro Glu Tyr Ala His Glu Val Pro Ala Val His
            290                 295                 300

Glu Glu Glu Lys Leu Lys Phe Ile Ser Ser Arg Leu Lys Asn Arg Glu
305                 310                 315                 320

Lys Arg Cys Arg Pro
            325

<210> SEQ ID NO 21
<211> LENGTH: 960
<212> TYPE: DNA
<213> ORGANISM: Bacillus halodurans

<400> SEQUENCE: 21
ttagagatca gataaaaatt gaaaaatccg atcacgatgg cctggcaaat cttcgtgagc      60
aaagtctgga tataactcga tacttttgt cgtcgtgagt ttgttataca tggcaaattg     120
tgtagacggc gggcaaaccg tatccattaa cccaacagca agtaagactt ctccctttac     180
gagtggagca agatgctgaa tatcaatata gcctagcttc gtaaagattt cagcctcacg     240
tcggtgctgt ggatcaaagc gacgaaaata cgtttgcaat tcgtcataag ctttctcggc     300
taaatccatc tcccatacgc gttggtaatc gctaaggaaa ggataaacag gagctacctt     360 tttaatttc ggttccaaag ccgcacaagc aatcgctaag gcccctcctt gtgaccaacc     420
tgtcactgcc acgcgctctt catcgacttc aggaaggttc atcacaatgt ggcaagctg     480 agccgtatca agaaacacat gacggaacaa taattgatca gcattatcat cgagtccgcg     540
tattatatga ccggaatgag tattccccctt cacgcctcct gtgtcttcag acaagcctcc     600
ttgcccgcga acgtccattg caagaacaga atatccgagg gctgcgtaat gaagtaaacc     660
cgtccattcc cccgcattca tcgtatatcc gtgaaaatga ataaccgccg ggtgtgtccc     720
gctcgtgtgt cttgggcgca cgtattttgc gtgaattcta gcacccctaa ccctgtaaa     780

-continued

```
atataggtgg aagcattctg catacgtggt ttgaaaatca ctcggtatga gctctacgtt    840
tggatttacc tttctcatct cttgtaaagc acgatcccaa tactcagtaa agtcatctgg    900
ctttggatta cgtcccatgt actcttttaa ttcggttaac ggcatgtcta ttagtggcat    960
```

<210> SEQ ID NO 22
<211> LENGTH: 319
<212> TYPE: PRT
<213> ORGANISM: Bacillus halodurans

<400> SEQUENCE: 22

```
Met Pro Leu Ile Asp Met Pro Leu Thr Glu Leu Lys Glu Tyr Met Gly
1               5                   10                  15

Arg Asn Pro Lys Pro Asp Asp Phe Thr Glu Tyr Trp Asp Arg Ala Leu
            20                  25                  30

Gln Glu Met Arg Lys Val Asn Pro Asn Val Glu Leu Ile Pro Ser Asp
        35                  40                  45

Phe Gln Thr Thr Tyr Ala Glu Cys Phe His Leu Tyr Phe Thr Gly Val
    50                  55                  60

Arg Gly Ala Arg Ile His Ala Lys Tyr Val Arg Pro Arg His Thr Ser
65                  70                  75                  80

Gly Thr His Pro Ala Val Ile His Phe His Gly Tyr Thr Met Asn Ala
                85                  90                  95

Gly Glu Trp Thr Gly Leu Leu His Tyr Ala Ala Leu Gly Tyr Ser Val
            100                 105                 110

Leu Ala Met Asp Val Arg Gly Gln Gly Gly Leu Ser Glu Asp Thr Gly
        115                 120                 125

Gly Val Lys Gly Asn Thr His Ser Gly His Ile Ile Arg Gly Leu Asp
    130                 135                 140

Asp Asn Ala Asp Gln Leu Leu Phe Arg His Val Phe Leu Asp Thr Ala
145                 150                 155                 160

Gln Leu Ala Asn Ile Val Met Asn Leu Pro Glu Val Asp Glu Glu Arg
                165                 170                 175

Val Ala Val Thr Gly Trp Ser Gln Gly Gly Ala Leu Ala Ile Ala Cys
            180                 185                 190

Ala Ala Leu Glu Pro Lys Ile Lys Lys Val Ala Pro Val Tyr Pro Phe
        195                 200                 205

Leu Ser Asp Tyr Gln Arg Val Trp Glu Met Asp Leu Ala Glu Lys Ala
    210                 215                 220

Tyr Asp Glu Leu Gln Thr Tyr Phe Arg Arg Phe Asp Pro Gln His Arg
225                 230                 235                 240

Arg Glu Ala Glu Ile Phe Thr Lys Leu Gly Tyr Ile Asp Ile Gln His
                245                 250                 255

Leu Ala Pro Leu Val Lys Gly Glu Val Leu Ala Val Gly Leu Met
            260                 265                 270

Asp Thr Val Cys Pro Pro Ser Thr Gln Phe Ala Met Tyr Asn Lys Leu
        275                 280                 285

Thr Thr Thr Lys Ser Ile Glu Leu Tyr Pro Asp Phe Ala His Glu Asp
    290                 295                 300

Leu Pro Gly His Arg Asp Arg Ile Phe Gln Phe Leu Ser Asp Leu
305                 310                 315
```

<210> SEQ ID NO 23
<211> LENGTH: 954
<212> TYPE: DNA
<213> ORGANISM: Bacillus clausii

```
<400> SEQUENCE: 23
atgccattag tcgatatgcc gttgcgcgag ttgttagctt atgaaggaat aaaccctaaa        60
ccagcagatt ttgaccaata ctggaaccgg gccaaaacgg aaattgaagc gattgatccc       120
gaagtcactc tagtcgaatc ttcttttcag tgttcgtttg caaactgtta ccatttctat       180
tatcgaagcg ctggaaatgc aaaaatccat gcgaaatacg tacagccaaa agcaggggag       240
aagacgccag cagttttat gttccatggg tatgggggc gttcagccga atggagcagc         300
ttgttaaatt atgtagcggc gggttttct gttttctata tggacgtgcg tggacaaggt        360
ggaacttcag aggatcctgg gggcgtaagg gggaatacat ataggggcca cattattcgc       420
ggcctcgatg ccgggccaga cgcactttt taccgcagcg ttttcttgga caccgtccaa        480
ttggttcgtg ctgctaaaac attgcctcac atcgataaaa cacggcttat ggccacaggg       540
tggtcgcaag ggggcgcctt aacgcttgcc tgtgctgccc ttgttcctga atcaagcgt        600
cttgctccag tatacccgtt tttaagcgat tacaagcgag tgtggcaaat ggatttagcg       660
gttcgttcgt ataagaatt ggctgattat ttccgttcat acgatccgca acataaacgc        720
catggcgaaa ttttttgaacg ccttggctac atcgatgtcc agcatcttgc tgaccggatt     780
caaggagatg tcctaatggg agttggttta atggatacag aatgcccgcc gtctacccaa       840
tttgctgctt ataataaaat aaaggctaaa aaatcgtatg agctctatcc tgattttggc       900
catgagcacc ttccaggaat gaacgatcat attttcgct ttcactag ttga                954

<210> SEQ ID NO 24
<211> LENGTH: 317
<212> TYPE: PRT
<213> ORGANISM: Bacillus clausii

<400> SEQUENCE: 24

Met Pro Leu Val Asp Met Pro Leu Arg Glu Leu Leu Ala Tyr Glu Gly
1               5                   10                  15

Ile Asn Pro Lys Pro Ala Asp Phe Asp Gln Tyr Trp Asn Arg Ala Lys
            20                  25                  30

Thr Glu Ile Glu Ala Ile Asp Pro Glu Val Thr Leu Val Glu Ser Ser
        35                  40                  45

Phe Gln Cys Ser Phe Ala Asn Cys Tyr His Phe Tyr Arg Ser Ala
    50                  55                  60

Gly Asn Ala Lys Ile His Ala Lys Tyr Val Gln Pro Lys Ala Gly Glu
65                  70                  75                  80

Lys Thr Pro Ala Val Phe Met Phe His Gly Tyr Gly Arg Ser Ala
                85                  90                  95

Glu Trp Ser Ser Leu Leu Asn Tyr Val Ala Ala Gly Phe Ser Val Phe
            100                 105                 110

Tyr Met Asp Val Arg Gly Gln Gly Gly Thr Ser Glu Asp Pro Gly Gly
        115                 120                 125

Val Arg Gly Asn Thr Tyr Arg Gly His Ile Ile Arg Gly Leu Asp Ala
    130                 135                 140

Gly Pro Asp Ala Leu Phe Tyr Arg Ser Val Phe Leu Asp Thr Val Gln
145                 150                 155                 160

Leu Val Arg Ala Ala Lys Thr Leu Pro His Ile Asp Lys Thr Arg Leu
                165                 170                 175

Met Ala Thr Gly Trp Ser Gln Gly Gly Ala Leu Thr Leu Ala Cys Ala
            180                 185                 190

Ala Leu Val Pro Glu Ile Lys Arg Leu Ala Pro Val Tyr Pro Phe Leu
        195                 200                 205
```

```
Ser Asp Tyr Lys Arg Val Trp Gln Met Asp Leu Ala Val Arg Ser Tyr
    210                 215                 220

Lys Glu Leu Ala Asp Tyr Phe Arg Ser Tyr Asp Pro Gln His Lys Arg
225                 230                 235                 240

His Gly Glu Ile Phe Glu Arg Leu Gly Tyr Ile Asp Val Gln His Leu
                245                 250                 255

Ala Asp Arg Ile Gln Gly Asp Val Leu Met Gly Val Gly Leu Met Asp
            260                 265                 270

Thr Glu Cys Pro Pro Ser Thr Gln Phe Ala Ala Tyr Asn Lys Ile Lys
        275                 280                 285

Ala Lys Lys Ser Tyr Glu Leu Tyr Pro Asp Phe Gly His Glu His Leu
    290                 295                 300

Pro Gly Met Asn Asp His Ile Phe Arg Phe Thr Ser
305                 310                 315
```

```
<210> SEQ ID NO 25
<211> LENGTH: 960
<212> TYPE: DNA
<213> ORGANISM: Bacillus subtilis
<220> FEATURE:
<221> NAME/KEY: CDS
<222> LOCATION: (1)..(960)

<400> SEQUENCE: 25
```

```
atg caa cta ttc gat ctg ccg ctc gac caa ttg caa aca tat aag cct      48
Met Gln Leu Phe Asp Leu Pro Leu Asp Gln Leu Gln Thr Tyr Lys Pro
1               5                   10                  15 gaa aaa aca gca ccg aaa gat ttt tct gag ttt tgg aaa ttg tct ttg      96
Glu Lys Thr Ala Pro Lys Asp Phe Ser Glu Phe Trp Lys Leu Ser Leu
                20                  25                  30 gag gaa ctt gca aaa gtc caa gca gaa cct gat cta cag ccg gtt gac     144
Glu Glu Leu Ala Lys Val Gln Ala Glu Pro Asp Leu Gln Pro Val Asp
            35                  40                  45 tat cct gct gac gga gta aaa gtg tac cgt ctc aca tat aaa agc ttc     192
Tyr Pro Ala Asp Gly Val Lys Val Tyr Arg Leu Thr Tyr Lys Ser Phe
        50                  55                  60 gga aac gcc cgc att acc gga tgg tac gcg gtg cct gac aag caa ggc     240
Gly Asn Ala Arg Ile Thr Gly Trp Tyr Ala Val Pro Asp Lys Gln Gly
65                  70                  75                  80 ccg cat ccg gcg atc gtg aaa tat cat ggc tac aat gca agc tat gat     288
Pro His Pro Ala Ile Val Lys Tyr His Gly Tyr Asn Ala Ser Tyr Asp
                85                  90                  95 ggt gag att cat gaa atg gta aac tgg gca ctc cat ggc tac gcc gca     336
Gly Glu Ile His Glu Met Val Asn Trp Ala Leu His Gly Tyr Ala Ala
            100                 105                 110 ttc ggc atg ctt gtc cgc ggc cag cag agc agc gag gat acg agt att     384
Phe Gly Met Leu Val Arg Gly Gln Gln Ser Ser Glu Asp Thr Ser Ile
        115                 120                 125 tca ccg cac ggt cac gct ttg ggc tgg atg acg aaa gga att ctt gat     432
Ser Pro His Gly His Ala Leu Gly Trp Met Thr Lys Gly Ile Leu Asp
    130                 135                 140 aaa gat aca tac tat tac cgc ggt gtt tat ttg gac gcc gtc cgc gcg     480
Lys Asp Thr Tyr Tyr Tyr Arg Gly Val Tyr Leu Asp Ala Val Arg Ala
145                 150                 155                 160 ctt gag gtc atc agc agc ttc gac gag gtt gac gaa aca agg atc ggt     528
Leu Glu Val Ile Ser Ser Phe Asp Glu Val Asp Glu Thr Arg Ile Gly
                165                 170                 175 gtg aca gga gga agc caa ggc gga ggt tta acc att gcc gca gca gcg     576
Val Thr Gly Gly Ser Gln Gly Gly Gly Leu Thr Ile Ala Ala Ala Ala
            180                 185                 190
```

```
ctg tca gac att cca aaa gcc gcg gtt gcc gat tat cct tat tta agc      624
Leu Ser Asp Ile Pro Lys Ala Ala Val Ala Asp Tyr Pro Tyr Leu Ser
        195                 200                 205 aac ttc gaa cgg gcc att gat gtg gcg ctt gaa cag ccg tac ctt gaa      672
Asn Phe Glu Arg Ala Ile Asp Val Ala Leu Glu Gln Pro Tyr Leu Glu
210                 215                 220 atc aat tcc ttc ttc aga aga aat ggc agc ccg gaa aca gaa gtg cag      720
Ile Asn Ser Phe Phe Arg Arg Asn Gly Ser Pro Glu Thr Glu Val Gln
225                 230                 235                 240 gcg atg aag aca ctt tca tat ttc gat att atg aat ctc gct gac cga      768
Ala Met Lys Thr Leu Ser Tyr Phe Asp Ile Met Asn Leu Ala Asp Arg
            245                 250                 255 gtg aag gtg cct gtc ctg atg tca atc ggc ctg att gac aag gtc acg      816
Val Lys Val Pro Val Leu Met Ser Ile Gly Leu Ile Asp Lys Val Thr
        260                 265                 270 ccg cca tcc acc gtg ttt gcc gcc tac aat cat ttg gaa aca gag aaa      864
Pro Pro Ser Thr Val Phe Ala Ala Tyr Asn His Leu Glu Thr Glu Lys
    275                 280                 285 gag ctg aag gtg tac cgc tac ttc gga cat gag tat atc cct gct ttt      912
Glu Leu Lys Val Tyr Arg Tyr Phe Gly His Glu Tyr Ile Pro Ala Phe
290                 295                 300 caa acg gaa aaa ctt gct ttc ttt aag cag cat ctt aaa ggc tga taa      960
Gln Thr Glu Lys Leu Ala Phe Phe Lys Gln His Leu Lys Gly
305                 310                 315

<210> SEQ ID NO 26
<211> LENGTH: 318
<212> TYPE: PRT
<213> ORGANISM: Bacillus subtilis

<400> SEQUENCE: 26

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205
```

```
Asn Phe Glu Arg Ala Ile Asp Val Ala Leu Glu Gln Pro Tyr Leu Glu
        210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
                260                 265                 270

Pro Pro Ser Thr Val Phe Ala Ala Tyr Asn His Leu Glu Thr Glu Lys
            275                 280                 285

Glu Leu Lys Val Tyr Arg Tyr Phe Gly His Glu Tyr Ile Pro Ala Phe
        290                 295                 300

Gln Thr Glu Lys Leu Ala Phe Phe Lys Gln His Leu Lys Gly
305                 310                 315

<210> SEQ ID NO 27
<211> LENGTH: 325
<212> TYPE: PRT
<213> ORGANISM: Thermotoga neapolitana
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 27

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Val Ala Gly Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255
```

```
Asn Phe Ala Ala Arg Ala Lys Val Pro Ala Leu Phe Ser Val Gly Leu
            260                 265                 270

Met Asp Thr Ile Xaa Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 28
<211> LENGTH: 325
<212> TYPE: PRT
<213> ORGANISM: Thermotoga maritima
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 28

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
            85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
            130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
            165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn Tyr
```

```
                     275                 280                 285
Tyr Ala Gly Pro Lys Glu Ile Arg Ile Tyr Pro Tyr Asn Asn His Glu
            290                 295                 300
Gly Gly Gly Ser Phe Gln Ala Val Glu Gln Val Lys Phe Leu Lys Lys
305                 310                 315                 320
Leu Phe Glu Lys Gly
                325

<210> SEQ ID NO 29
<211> LENGTH: 326
<212> TYPE: PRT
<213> ORGANISM: Thermotoga lettingae
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 29

Met Val Tyr Phe Asp Met Pro Leu Glu Asp Leu Arg Lys Tyr Leu Pro
1               5                   10                  15
Gln Arg Tyr Glu Glu Lys Asp Phe Asp Asp Phe Trp Lys Gln Thr Ile
            20                  25                  30
His Glu Thr Arg Gly Tyr Phe Gln Glu Pro Ile Leu Lys Lys Val Asp
        35                  40                  45
Phe Tyr Leu Gln Asn Val Glu Thr Phe Asp Val Thr Phe Ser Gly Tyr
50                  55                  60
Arg Gly Gln Lys Ile Lys Gly Trp Leu Ile Leu Pro Lys Phe Arg Asn
65                  70                  75                  80
Gly Lys Leu Pro Cys Val Val Glu Phe Val Gly Tyr Gly Gly Arg
                85                  90                  95
Gly Phe Pro Tyr Asp Trp Leu Leu Trp Ser Ala Ala Gly Tyr Ala His
            100                 105                 110
Phe Ile Met Asp Thr Arg Gly Gln Gly Ser Asn Trp Met Lys Gly Asp
        115                 120                 125
Thr Pro Asp Tyr Glu Asp Asn Pro Ser Asp Pro Gln Tyr Pro Gly Phe
130                 135                 140
Leu Thr Lys Gly Val Leu Asn Pro Glu Thr Tyr Tyr Arg Arg Val
145                 150                 155                 160
Phe Met Asp Ala Phe Met Ala Val Glu Thr Ile Ser Gln Leu Glu Gln
                165                 170                 175
Ile Asp Ser Gln Thr Ile Ile Leu Ser Gly Ala Ser Gln Gly Gly Gly
            180                 185                 190
Ile Ala Leu Ala Val Ser Ala Leu Ser Ser Lys Val Met Ala Leu Leu
        195                 200                 205
Cys Asp Val Pro Phe Leu Cys His Tyr Lys Arg Ala Val Gln Ile Thr
210                 215                 220
Asp Ser Met Pro Tyr Ala Glu Ile Thr Arg Tyr Cys Lys Thr His Ile
225                 230                 235                 240
Asp Lys Ile Gln Thr Val Phe Arg Thr Leu Ser Tyr Phe Asp Gly Val
                245                 250                 255
Asn Phe Ala Ala Arg Ala Lys Cys Pro Ala Leu Phe Ser Val Gly Leu
            260                 265                 270
Met Asp Asp Ile Xaa Pro Pro Ser Thr Val Phe Ala Ala Tyr Asn Tyr
        275                 280                 285
Tyr Ala Gly Glu Lys Asp Ile Arg Ile Tyr Pro Tyr Asn Asn His Glu
290                 295                 300
```

Gly Gly Gly Ser Phe His Thr Leu Glu Lys Leu Lys Phe Val Lys Lys
305                 310                 315                 320

Thr Ile Ser Met Arg Glu
                325

<210> SEQ ID NO 30
<211> LENGTH: 325
<212> TYPE: PRT
<213> ORGANISM: Thermotoga petrophilia
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 30

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
                20                  25                  30

Ala Glu Asn Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Met Lys Gly Asp
                115                 120                 125

Thr Pro Asp Tyr Pro Glu Asp Pro Val Asp Pro Gln Tyr Pro Gly Phe
130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
                210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Xaa Pro Pro Ser Thr Val Phe Ala Ala Tyr Asn His
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 31
<211> LENGTH: 325
<212> TYPE: PRT
<213> ORGANISM: Thermotoga sp. RQ2a
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 31

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 32
<211> LENGTH: 329
<212> TYPE: PRT

<213> ORGANISM: Thermotoga sp. RQ2b
<220> FEATURE:
<221> NAME/KEY: MISC_FEATURE
<222> LOCATION: (278)..(278)
<223> OTHER INFORMATION: Xaa is Ala, Val, Ser, or Thr.

<400> SEQUENCE: 32

```
Met Ala Leu Phe Asp Met Pro Leu Glu Lys Leu Arg Ser Tyr Leu Pro
1               5                   10                  15

Asp Arg Tyr Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
    50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
    130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Xaa Pro Pro Ser Thr Val Phe Ala Ala Tyr Asn
        275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325
```

<210> SEQ ID NO 33
<211> LENGTH: 326
<212> TYPE: PRT
<213> ORGANISM: Thermotoga lettingae

<400> SEQUENCE: 33

Met Val Tyr Phe Asp Met Pro Leu Glu Asp Leu Arg Lys Tyr Leu Pro

```
                1               5                    10                  15
Gln Arg Tyr Glu Glu Lys Asp Phe Asp Asp Phe Trp Lys Gln Thr Ile
                    20                  25                  30

His Glu Thr Arg Gly Tyr Phe Gln Glu Pro Ile Leu Lys Lys Val Asp
                    35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                      70                  75                  80

Gly Lys Leu Pro Cys Val Val Glu Phe Val Gly Tyr Gly Gly Arg
                    85                  90                  95

Gly Phe Pro Tyr Asp Trp Leu Leu Trp Ser Ala Ala Gly Tyr Ala His
                    100                 105                 110

Phe Ile Met Asp Thr Arg Gly Gln Gly Ser Asn Trp Met Lys Gly Asp
                    115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Arg Arg Val
145                     150                 155                 160

Phe Met Asp Ala Phe Met Ala Val Glu Thr Ile Ser Gln Leu Glu Gln
                    165                 170                 175

Ile Asp Ser Gln Thr Ile Ile Leu Ser Gly Ala Ser Gln Gly Gly Gly
                    180                 185                 190

Ile Ala Leu Ala Val Ser Ala Leu Ser Ser Lys Val Met Ala Leu Leu
                    195                 200                 205

Cys Asp Val Pro Phe Leu Cys His Tyr Lys Arg Ala Val Gln Ile Thr
                    210                 215                 220

Asp Ser Met Pro Tyr Ala Glu Ile Thr Arg Tyr Cys Lys Thr His Ile
225                     230                 235                 240

Asp Lys Ile Gln Thr Val Phe Arg Thr Leu Ser Tyr Phe Asp Gly Val
                    245                 250                 255

Asn Phe Ala Ala Arg Ala Lys Cys Pro Ala Leu Phe Ser Val Gly Leu
                    260                 265                 270

Met Asp Asp Ile Cys Pro Pro Ser Thr Val Phe Ala Ala Tyr Asn Tyr
                    275                 280                 285

Tyr Ala Gly Glu Lys Asp Ile Arg Ile Tyr Pro Tyr Asn Asn His Glu
                    290                 295                 300

Gly Gly Gly Ser Phe His Thr Leu Glu Lys Leu Lys Pro Val Lys Lys
305                     310                 315                 320

Thr Ile Ser Met Arg Glu
                    325

<210> SEQ ID NO 34
<211> LENGTH: 325
<212> TYPE: PRT
<213> ORGANISM: Thermotoga petrophilia

<400> SEQUENCE: 34

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
                    20                  25                  30

Ala Glu Asn Glu Lys Phe Pro Leu Asp Pro Val Phe Glu Arg Met Glu
                    35                  40                  45

Ser His Leu Lys Thr Val Glu Ala Tyr Asp Val Thr Phe Ser Gly Tyr
```

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Met Lys Gly Asp
            115                 120                 125

Thr Pro Asp Tyr Pro Glu Asp Pro Val Asp Pro Gln Tyr Pro Gly Phe
        130                 135                 140

Met Thr Arg Gly Ile Leu Asp Pro Arg Thr Tyr Tyr Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Cys Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 35
<211> LENGTH: 325
<212> TYPE: PRT
<213> ORGANISM: Thermotoga sp. RQ2

<400> SEQUENCE: 35

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Val Tyr Asp Val Thr Phe Ser Gly Tyr
        50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys

```
                100              105              110
Phe Val Met Asp Thr Arg Gly Gln Gly Ser Gly Trp Leu Lys Gly Asp
            115              120              125
Thr Pro Asp Tyr Pro Glu Asp Pro Val Asp Pro Gln Tyr Pro Gly Phe
    130              135              140
Met Thr Arg Gly Ile Leu Asp Pro Arg Thr Tyr Tyr Arg Arg Val
145              150              155              160
Phe Thr Asp Ala Val Arg Ala Val Glu Ala Ala Ser Phe Pro Arg
                165              170              175
Val Asp His Glu Arg Ile Val Ile Ala Gly Gly Ser Gln Gly Gly Gly
            180              185              190
Ile Ala Leu Ala Val Ser Ala Leu Ser Lys Lys Ala Lys Ala Leu Leu
            195              200              205
Cys Asp Val Pro Phe Leu Cys His Phe Arg Arg Ala Val Gln Leu Val
            210              215              220
Asp Thr His Pro Tyr Ala Glu Ile Thr Asn Phe Leu Lys Thr His Arg
225              230              235              240
Asp Lys Glu Glu Ile Val Phe Arg Thr Leu Ser Tyr Phe Asp Gly Val
                245              250              255
Asn Phe Ala Val Arg Ala Lys Ile Pro Ala Leu Phe Ser Val Gly Leu
            260              265              270
Met Asp Asn Ile Cys Pro Pro Ser Thr Val Phe Ala Ala Tyr Asn His
            275              280              285
Tyr Ala Gly Pro Lys Glu Ile Arg Ile Tyr Pro Tyr Asn Asn His Glu
            290              295              300
Gly Gly Gly Ser Phe Gln Ala Ile Glu Gln Val Lys Phe Leu Lys Arg
305              310              315              320
Leu Phe Glu Lys Gly
                325

<210> SEQ ID NO 36
<211> LENGTH: 329
<212> TYPE: PRT
<213> ORGANISM: Thermotoga sp. RQ2

<400> SEQUENCE: 36

Met Ala Leu Phe Asp Met Pro Leu Glu Lys Leu Arg Ser Tyr Leu Pro
1               5               10              15
Asp Arg Tyr Glu Glu Glu Asp Phe Asp Leu Phe Trp Lys Glu Thr Leu
            20              25              30
Glu Glu Ser Arg Lys Phe Pro Leu Asp Pro Ile Phe Glu Arg Val Asp
        35              40              45
Tyr Leu Leu Glu Asn Val Glu Val Tyr Asp Val Thr Phe Ser Gly Tyr
    50              55              60
Arg Gly Gln Arg Ile Lys Ala Trp Leu Ile Leu Pro Val Val Lys Lys
65              70              75              80
Glu Glu Arg Leu Pro Cys Ile Val Glu Phe Ile Gly Tyr Arg Gly Gly
                85              90              95
Arg Gly Phe Pro Phe Asp Trp Leu Phe Trp Ser Ser Ala Gly Tyr Ala
            100              105              110
His Phe Val Met Asp Thr Arg Gly Gln Gly Thr Ser Arg Val Lys Gly
            115              120              125
Asp Thr Pro Asp Tyr Cys Asp Glu Pro Ile Asn Pro Gln Phe Pro Gly
    130              135              140
Phe Met Thr Arg Gly Ile Leu Asp Pro Arg Thr Tyr Tyr Tyr Arg Arg
```

```
                145                 150                 155                 160
Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
            195                 200                 205

Val Ser Asn Val Pro Phe Leu Cys His Phe Arg Arg Ala Val Gln Ile
        210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
                260                 265                 270

Leu Met Asp Lys Thr Cys Pro Pro Ser Thr Val Phe Ala Ala Tyr Asn
            275                 280                 285

His Tyr Ala Gly Pro Lys Glu Ile Lys Val Tyr Pro Phe Asn Glu His
        290                 295                 300

Glu Gly Gly Glu Ser Phe Gln Arg Met Glu Leu Arg Phe Met Lys
305                 310                 315                 320

Arg Ile Leu Lys Gly Glu Phe Lys Ala
            325

<210> SEQ ID NO 37
<211> LENGTH: 960
<212> TYPE: DNA
<213> ORGANISM: artificial sequence
<220> FEATURE:
<223> OTHER INFORMATION: Synthetic gene - codon optimized

<400> SEQUENCE: 37
atgggtctgt tcgatatgcc actgcaaaaa ctgcgtgaat ataccggtac caacccatgt      60
cctgaggatt tcgatgaata ctgggatcgc gcactggacg aaatgcgtag cgttgatcct     120
aaaatcaaga tgaagaagag ctcctttcaa gttccgttcg cggaatgtta cgatctgtat     180
tttaccggcg ttcgtggtgc ccgcattcac gcgaaataca ttcgtccgaa accgaaggc     240 aaacacccgg cgctgattcg cttccatggt tactccagca actctggtga ttggaacgac     300
aagctgaact acgttgcggc tggttttacc gtagtagcga tggacgctcg tggccagggt     360
ggccaatctc aggacgtcgg cggtgttaat ggcaacaccc tgaacggtca catcatccgt     420
ggcctggacg atgatgcaga taacatgctg ttccgtcata ttttcctgga caccgcgcag     480
ctggctggta tcgttatgaa catgccggaa atcgatgagg accgcgtagc tgttatgggt     540
ccgtcccagg cggcggtct gtccctggcg tgtgcggctc tggaacctaa atccgtaaa       600 gtagtgtccg aatatccgtt cctgagcgac tacaagcgtg tgtgggatct ggatctggcc     660
aaaaatgcgt accaagaaat cactgactat ttccgtctgt tcgacccacg ccacgaacgt     720
gagaacgagg ttttactaa actgggttac attgacgtaa agaacctggc gaaacgtatc     780
aaaggtgatg ttctgatgtg cgtgggcctg atggatcagg tctgcccgcc gagcaccgta     840
tttgcagcat acaacaacat ccagtccaag aaggacatca agtctaccc ggactatggt      900 cacgaaccga tgcgtggctt cggtgacctg gctatgcagt tcatgctgga actgtattct     960

<210> SEQ ID NO 38
<211> LENGTH: 320
```

<212> TYPE: PRT
<213> ORGANISM: Thermoanaerobacterium saccharolyticum

<400> SEQUENCE: 38

```
Met Gly Leu Phe Asp Met Pro Leu Gln Lys Leu Arg Glu Tyr Thr Gly
1               5                   10                  15
Thr Asn Pro Cys Pro Glu Asp Phe Asp Glu Tyr Trp Asp Arg Ala Leu
            20                  25                  30
Asp Glu Met Arg Ser Val Asp Pro Lys Ile Lys Met Lys Lys Ser Ser
        35                  40                  45
Phe Gln Val Pro Phe Ala Glu Cys Tyr Asp Leu Tyr Phe Thr Gly Val
    50                  55                  60
Arg Gly Ala Arg Ile His Ala Lys Tyr Ile Arg Pro Lys Thr Glu Gly
65                  70                  75                  80
Lys His Pro Ala Leu Ile Arg Phe His Gly Tyr Ser Asn Ser Gly
                85                  90                  95
Asp Trp Asn Asp Lys Leu Asn Tyr Val Ala Ala Gly Phe Thr Val Val
            100                 105                 110
Ala Met Asp Ala Arg Gly Gln Gly Gly Gln Ser Gln Asp Val Gly Gly
        115                 120                 125
Val Asn Gly Asn Thr Leu Asn Gly His Ile Ile Arg Gly Leu Asp Asp
    130                 135                 140
Asp Ala Asp Asn Met Leu Phe Arg His Ile Phe Leu Asp Thr Ala Gln
145                 150                 155                 160
Leu Ala Gly Ile Val Met Asn Met Pro Glu Ile Asp Glu Asp Arg Val
                165                 170                 175
Ala Val Met Gly Pro Ser Gln Gly Gly Gly Leu Ser Leu Ala Cys Ala
            180                 185                 190
Ala Leu Glu Pro Lys Ile Arg Lys Val Val Ser Glu Tyr Pro Phe Leu
        195                 200                 205
Ser Asp Tyr Lys Arg Val Trp Asp Leu Asp Leu Ala Lys Asn Ala Tyr
    210                 215                 220
Gln Glu Ile Thr Asp Tyr Phe Arg Leu Phe Asp Pro Arg His Glu Arg
225                 230                 235                 240
Glu Asn Glu Val Phe Thr Lys Leu Gly Tyr Ile Asp Val Lys Asn Leu
                245                 250                 255
Ala Lys Arg Ile Lys Gly Asp Val Leu Met Cys Val Gly Leu Met Asp
            260                 265                 270
Gln Val Cys Pro Pro Ser Thr Val Phe Ala Ala Tyr Asn Asn Ile Gln
        275                 280                 285
Ser Lys Lys Asp Ile Lys Val Tyr Pro Asp Tyr Gly His Glu Pro Met
    290                 295                 300
Arg Gly Phe Gly Asp Leu Ala Met Gln Phe Met Leu Glu Leu Tyr Ser
305                 310                 315                 320
```

<210> SEQ ID NO 39
<211> LENGTH: 939
<212> TYPE: DNA
<213> ORGANISM: Lactococcus lactis

<400> SEQUENCE: 39

```
atgacaaaaa taaacaattg gcaagattat caaggaagtt cacttaaacc agaggatttt      60
gataaatttt gggatgaaaa aattaatttg gtttcaaatc atcaatttga atttgaatta     120
atagaaaaaa atcttcctc taaggtagtt aactttatc atttgtggtt tacagctatt      180
gatggagcta aaattcatgc tcagttaatt gttcccaaga atttgaaaga gaaataccca     240
```

```
gccatcttac aatttcatgg ttatcattgc gatagtgggg attgggtcga taaaataggg    300
atagttgccg aagggaatgt agttcttgcg cttgattgtc gaggacaagg tggtttaagt    360
caagataata ttcaaactat ggggatgaca atgaagggac tcattgttcg aggaattgat    420
gaagggtatg aaaatctcta ttacgttcgc caatttatgg acttaataac tgcaaccaaa    480
attttatccg agtttgattt tgttgatgaa acaaatataa gtgcacaagg tgcttctcaa    540
ggtggagcgc ttgccgttgc ttgcgccgca ctttctcctc ttataaaaaa ggtgactgcc    600
acttacccct ttctttcaga ttatcgcaaa gcttatgagc ttggtgccga ggaatctgct    660
ttcgaagaac ttccatattg gtttcagttt aaagatccac ttcatctaag agaagactgg    720
ttttttaatc agttggaata cattgatatt caaaatttag caccaagaat taaggctgag    780
gtcatttgga tcctaggcgg caaagatact gttgttcctc cgattacgca aatggcggct    840
tacaataaaa tacaaagtaa aaaatctctc tatgtcttac ctgaatacgg ccatgaatat    900
cttcctaaaa ttagcgactg gttaagagag aatcaataa                          939
```

<210> SEQ ID NO 40
<211> LENGTH: 312
<212> TYPE: PRT
<213> ORGANISM: Lactococcus lactis

<400> SEQUENCE: 40

```
Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
                20                  25                  30

Asn His Gln Phe Glu Phe Glu Leu Ile Glu Lys Asn Leu Ser Ser Lys
            35                  40                  45

Val Val Asn Phe Tyr His Leu Trp Phe Thr Ala Ile Asp Gly Ala Lys
        50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
        115                 120                 125

Met Thr Met Lys Gly Leu Ile Val Arg Gly Ile Asp Glu Gly Tyr Glu
130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
        195                 200                 205

Arg Lys Ala Tyr Glu Leu Gly Ala Glu Glu Ser Ala Phe Glu Glu Leu
    210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255
```

```
Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
        275                 280                 285

Ser Leu Tyr Val Leu Pro Glu Tyr Gly His Glu Tyr Leu Pro Lys Ile
    290                 295                 300

Ser Asp Trp Leu Arg Glu Asn Gln
305                 310

<210> SEQ ID NO 41
<211> LENGTH: 972
<212> TYPE: DNA
<213> ORGANISM: Mesorhizobium loti

<400> SEQUENCE: 41
atgccgttcc cggatctgat ccagcccgaa ctgggcgctt atgtcagcag tgtcggcatg      60
ccggacgact tgcccaatt ctggacgtcg accatcgccg aggctcgcca ggccggcggt     120
gaggtcagta tcgtgcaggc gcagacgaca ctgaaggcgg tccagtcctt cgatgtcacg     180
tttccaggat acggcggtca tccaatcaaa ggatggctga tcttgccgac gcaccacaag     240
gggcggcttc ccctcgtcgt gcagtatatc ggctatggcg gcggccgcgg cttggcgcat     300
gagcaactgc attgggcggc gtcaggcttt gcctatttcc gaatggatac acgcgggcag     360
ggaagcgact ggagcgtcgg tgagaccgcc gatcccgtcg gctcgacctc gtccattccc     420
ggctttatga cgcgtggcgt gctggacaag aatgactact attaccggcg cctgttcacc     480
gatgccgtga gggcgataga tgctctgctc ggactggact tcgtcgatcc gaacgcatc     540 gcggtttgcg gtgacagtca gggaggcggt atttcgctcg ccgttggcgg catcgacccg     600
cgcgtcaagg ccgtaatgcc cgacgttcca tttctgtgcg actttccgcg cgctgtgcag     660
actgccgtgc gcgatcccta tttggaaatc gttcgctttc tggcccagca tcgcgaaaag     720
aaggcggcag tctttgaaac gctcaactat ttcgactgcg tcaacttcgc ccggcggtcc     780
aaggcgccgg cgctgttttc ggtggccctg atggacgaag tctgcccgcc ctctaccgtg     840
tatggcgcat tcaatgccta tgcaggcgaa aagaccatca cagagtacga attcaacaat     900
catgaaggcg ggcaaggcta tcaagagcgc aacagatga cgtggctcag caggctgttc     960
ggtgtcggct ga                                                         972

<210> SEQ ID NO 42
<211> LENGTH: 323
<212> TYPE: PRT
<213> ORGANISM: Mesorhizobium loit

<400> SEQUENCE: 42

Met Pro Phe Pro Asp Leu Ile Gln Pro Glu Leu Gly Ala Tyr Val Ser
1               5                  10                   15

Ser Val Gly Met Pro Asp Asp Phe Ala Gln Phe Trp Thr Ser Thr Ile
            20                  25                  30

Ala Glu Ala Arg Gln Ala Gly Gly Glu Val Ser Ile Val Gln Ala Gln
        35                  40                  45

Thr Thr Leu Lys Ala Val Gln Ser Phe Asp Val Thr Phe Pro Gly Tyr
    50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Gly Arg
                85                  90                  95
```

```
Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
        115                 120                 125

Thr Ala Asp Pro Val Gly Ser Thr Ser Ser Ile Pro Gly Phe Met Thr
    130                 135                 140

Arg Gly Val Leu Asp Lys Asn Asp Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Ile Ser
            180                 185                 190

Leu Ala Val Gly Gly Ile Asp Pro Arg Val Lys Ala Val Met Pro Asp
        195                 200                 205

Val Pro Phe Leu Cys Asp Phe Pro Arg Ala Val Gln Thr Ala Val Arg
    210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255

Ala Arg Arg Ser Lys Ala Pro Leu Phe Ser Val Ala Leu Met Asp
            260                 265                 270

Glu Val Cys Pro Pro Ser Thr Val Tyr Gly Ala Phe Asn Ala Tyr Ala
        275                 280                 285

Gly Glu Lys Thr Ile Thr Glu Tyr Glu Phe Asn Asn His Glu Gly Gly
    290                 295                 300

Gln Gly Tyr Gln Glu Arg Gln Gln Met Thr Trp Leu Ser Arg Leu Phe
305                 310                 315                 320

Gly Val Gly

<210> SEQ ID NO 43
<211> LENGTH: 990
<212> TYPE: DNA
<213> ORGANISM: Geobacillus stearothermophilus

<400> SEQUENCE: 43
atgttcgata tgccgttagc acaattacag aaatacatgg ggacaaatcc gaagccggct     60
gattttgctg acttttggag tcgagcgttg gaggaattat ctgcccaatc gttgcattat    120
gagctgattc cggcaacatt tcaaacgaca gtggcgagtt gctaccattt gtatttcacg    180
ggagtcggcg gggctagagt ccattgtcag ttagtaaaac cgagagagca gaagcagaaa    240
ggcccggggt tggtatggtt tcatggctac catacgaata gcggcgattg ggtcgataaa    300
ctggcatatg ctgcggcagg ttttactgta ttggcgatgg attgccgcgg ccaaggagga    360
aaatcagagg ataatttgca agtgaaaggc ccaacattga agggccatat tattcgcgga    420
attgaggatc caaatcctca tcatctttat tatcgaaatg ttttttttaga tacagttcag    480 gcggtaagaa ttttatgctc tatggatcat attgatcgtg aacgaattgg tgtatatggc    540
gcttcccaag gaggagcgtt ggcattagcg tgtgctgctc tggaaccatc ggtggtgaaa    600
aaagcggttg tgctctatcc atttttatcg gattataagc gggcgcaaga gttggatatg    660 aaaaatacccg cgtatgagga aattcattat tattttcgat tttagatcc cacacatgag    720 cgggaagaag aagtatttta caaactaggc tatattgata tcaactctt agccgatcgg    780 atttgtgccg atgtttttatg gctgttgcg ctagaagacc atatttgtcc cccgtccaca    840
```

-continued

```
caatttgctg tttataataa aattaagtca aaaaaagaca tggttttgtt ttacgagtat      900
ggtcatgagt atttaccgac tatgggagac cgtgcttatc tgttttttg  cccgatcttc      960 tttccaatcc aaaagagaaa cgttaagtaa                                       990
```

```
<210> SEQ ID NO 44
<211> LENGTH: 329
<212> TYPE: PRT
<213> ORGANISM: Geobacillus stearothermophilus

<400> SEQUENCE: 44
```

| | | | | | | | | | | | | | | |
|---|---|---|---|---|---|---|---|---|---|---|---|---|---|---|
| Met | Phe | Asp | Met | Pro | Leu | Ala | Gln | Leu | Gln | Lys | Tyr | Met | Gly | Thr | Asn |
| 1 | | | | 5 | | | | | 10 | | | | | 15 | |
| Pro | Lys | Pro | Ala | Asp | Phe | Ala | Asp | Phe | Trp | Ser | Arg | Ala | Leu | Glu | Glu |
| | | | 20 | | | | | 25 | | | | | 30 | | |
| Leu | Ser | Ala | Gln | Ser | Leu | His | Tyr | Glu | Leu | Ile | Pro | Ala | Thr | Phe | Gln |
| | | 35 | | | | | 40 | | | | | 45 | | | |
| Thr | Thr | Val | Ala | Ser | Cys | Tyr | His | Leu | Tyr | Phe | Thr | Gly | Val | Gly | Gly |
| | 50 | | | | | 55 | | | | | 60 | | | | |
| Ala | Arg | Val | His | Cys | Gln | Leu | Val | Lys | Pro | Arg | Glu | Gln | Lys | Gln | Lys |
| 65 | | | | | 70 | | | | | 75 | | | | | 80 |
| Gly | Pro | Gly | Leu | Val | Trp | Phe | His | Gly | Tyr | His | Thr | Asn | Ser | Gly | Asp |
| | | | | 85 | | | | | 90 | | | | | 95 | |
| Trp | Val | Asp | Lys | Leu | Ala | Tyr | Ala | Ala | Gly | Phe | Thr | Val | Leu | Ala |
| | | | 100 | | | | | 105 | | | | | 110 | | |
| Met | Asp | Cys | Arg | Gly | Gln | Gly | Gly | Lys | Ser | Glu | Asp | Asn | Leu | Gln | Val |
| | | 115 | | | | | 120 | | | | | 125 | | | |
| Lys | Gly | Pro | Thr | Leu | Lys | Gly | His | Ile | Ile | Arg | Gly | Ile | Glu | Asp | Pro |
| 130 | | | | | 135 | | | | | 140 | | | | | |
| Asn | Pro | His | His | Leu | Tyr | Tyr | Arg | Asn | Val | Phe | Leu | Asp | Thr | Val | Gln |
| 145 | | | | | 150 | | | | | 155 | | | | | 160 |
| Ala | Val | Arg | Ile | Leu | Cys | Ser | Met | Asp | His | Ile | Asp | Arg | Glu | Arg | Ile |
| | | | 165 | | | | | 170 | | | | | 175 | | |
| Gly | Val | Tyr | Gly | Ala | Ser | Gln | Gly | Gly | Ala | Leu | Ala | Leu | Ala | Cys | Ala |
| | | | | 180 | | | | | 185 | | | | | 190 | |
| Ala | Leu | Glu | Pro | Ser | Val | Val | Lys | Lys | Ala | Val | Val | Leu | Tyr | Pro | Phe |
| | | 195 | | | | | 200 | | | | | 205 | | | |
| Leu | Ser | Asp | Tyr | Lys | Arg | Ala | Gln | Glu | Leu | Asp | Met | Lys | Asn | Thr | Ala |
| 210 | | | | | 215 | | | | | 220 | | | | | |
| Tyr | Glu | Glu | Ile | His | Tyr | Tyr | Phe | Arg | Phe | Leu | Asp | Pro | Thr | His | Glu |
| 225 | | | | | 230 | | | | | 235 | | | | | 240 |
| Arg | Glu | Glu | Glu | Val | Phe | Tyr | Lys | Leu | Gly | Tyr | Ile | Asp | Ile | Gln | Leu |
| | | | | 245 | | | | | 250 | | | | | 255 | |
| Leu | Ala | Asp | Arg | Ile | Cys | Ala | Asp | Val | Leu | Trp | Ala | Val | Ala | Leu | Glu |
| | | | 260 | | | | | 265 | | | | | 270 | | |
| Asp | His | Ile | Cys | Pro | Pro | Ser | Thr | Gln | Phe | Ala | Val | Tyr | Asn | Lys | Ile |
| | | 275 | | | | | 280 | | | | | 285 | | | |
| Lys | Ser | Lys | Lys | Asp | Met | Val | Leu | Phe | Tyr | Glu | Tyr | Gly | His | Glu | Tyr |
| | 290 | | | | | 295 | | | | | 300 | | | | |
| Leu | Pro | Thr | Met | Gly | Asp | Arg | Ala | Tyr | Leu | Phe | Phe | Cys | Pro | Ile | Phe |
| 305 | | | | | 310 | | | | | 315 | | | | | 320 |
| Phe | Pro | Ile | Gln | Lys | Arg | Asn | Val | Lys | | | | | | | |
| | | | | 325 | | | | | | | | | | | |

```
<210> SEQ ID NO 45
```

<211> LENGTH: 978
<212> TYPE: DNA
<213> ORGANISM: artificial sequence
<220> FEATURE:
<223> OTHER INFORMATION: synthetic construct

<400> SEQUENCE: 45

```
atggcgttct tcgacctgcc tctggaagaa ctgaagaaat accgtccaga gcgttacgaa      60
gagaaggaca tcgacgagtt ctgggaggaa actctggcgg agaccgaaaa gtttccgctg     120
gacccagtgt tcgagcgtat ggaatctcac ctgaaaaccg tggaggcata tgacgttact     180
ttttctggtt accgtggcca gcgtatcaaa ggctggctgc tggttccgaa actggaggaa     240
gaaaaactgc cgtgcgtagt tcagtacatc ggttacaacg gtggccgtgg ctttccgcac     300
gattggctgt tctggccgtc tatgggctac atttgcttcg tcatggatac tcgtggtcag     360
ggttccggct ggctgaaagg cgatactccg gattatccgg agggcccggt agacccgcag     420
taccctggct tcatgacgcg tggtattctg gatccgcgta cctattacta tcgccgcgtt     480
tttaccgatg cagttcgtgc cgtagaggcc gcggcttctt tccctcaggt tgacctggag     540
cgtattgtta tcgctggtgg ctcccagggt ggcggcatcg ccctggcggt atctgcgctg     600
agcaagaaag ctaaggcact gctgtgtgac gtcccgttcc tgtgtcactt ccgtcgcgct     660
gttcagctgg tagataccca tccgtacgcg gagattacta acttcctgaa aactcaccgc     720
gacaaagaag aaatcgtttt ccgcaccctg tcctatttcg acggcgttaa cttcgcggct     780
cgtgcaaaaa ttccggcact gttctctgtt ggtctgatgg acgacatcag ccctccttct     840
accgttttcg cggcatataa ctattatgcg ggtccgaaag aaatccgtat ctatccgtac     900
aacaaccacg aaggcggtgg tggctttcag gctgttgaac aagtgaaatc cctgaagaaa     960
ctgtttgaga agggctaa                                                   978
```

<210> SEQ ID NO 46
<211> LENGTH: 325
<212> TYPE: PRT
<213> ORGANISM: artificial sequence
<220> FEATURE:
<223> OTHER INFORMATION: synthetic construct

<400> SEQUENCE: 46

```
Met Ala Phe Phe Asp Leu Pro Leu Glu Glu Leu Lys Lys Tyr Arg Pro
1               5                   10                  15

Glu Arg Tyr Glu Glu Lys Asp Ile Asp Glu Phe Trp Glu Glu Thr Leu
            20                  25                  30

Ala Glu Thr Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
```

```
            145                 150                 155                 160

Phe Thr Asp Ala Val Arg Ala Val Glu Ala Ala Ser Phe Pro Gln
                165                 170                 175

Val Asp Leu Glu Arg Ile Val Ile Ala Gly Gly Ser Gln Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asp Ile Ser Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
                290                 295                 300

Gly Gly Gly Gly Phe Gln Ala Val Glu Gln Val Lys Ser Leu Lys Lys
305                 310                 315                 320

Leu Phe Glu Lys Gly
                325

<210> SEQ ID NO 47
<211> LENGTH: 978
<212> TYPE: DNA
<213> ORGANISM: artificial sequence
<220> FEATURE:
<223> OTHER INFORMATION: synthetic construct

<400> SEQUENCE: 47
atggcgttct tcgacctgcc tctggaagaa ctgaagaaat accgtccaga gcgttacgaa      60
gagaaggact cgacgagtt ctgggaggaa actctggcgg agagcgaaaa gtttccgctg      120
gacccagtgt tcgagcgtat ggaatctcac ctgaaaaccg tggaggcata tgacgttact      180
ttttctggtt accgtggcca gcgtatcaaa ggctggctgc tggttccgaa actggaggaa      240
gaaaaactgc cgtgcgtagt tcagtacatc ggttacaacg gtggccgtgg ctttccgcac      300
gattggctgt tctggccgtc tatgggctac atttgcttcg tcatggatac tcgtggtcag      360
ggttccggct ggctgaaagg cgatactccg gattatccgg agggcccggt agacccgcag      420
taccctggct tcatgacgcg tggtattctg gatccgcgta cctattacta tcgccgcgtt      480
tttaccgatg cagttcgtgc cgtagaggcc gcggcttctt tccctcaggt tgaccaggag      540
cgtattgtta tcgctggtgg ctcccagggt ggcggcatcg ccctggcggt atctgcgctg      600
agcaagaaag ctaaggcact gctgtgtgac gtcccgttcc tgtgtcactt ccgtcgcgct      660
gttcagctgg tagataccca tccgtacgcg gagattacta cttcctgaa aactcaccgc      720 gacaaagaag aaatcgtttt ccgcaccctg tcctatttcg acggcgttaa cttcgcggct      780
cgtgcaaaaa ttccggcact gttctctgtt ggtctgatgg acgacatcag ccctccttct      840
accgttttcg cggcatataa ctattatgcg ggtccgaaag aaatccgtat ctatccgtac      900
aacaaccacg aaggcggtgg tagctttcag gctgttgaac aagtgaaatt cctgaagaaa      960
ctgtttgaga agggctaa                                                    978
```

```
<210> SEQ ID NO 48
<211> LENGTH: 325
<212> TYPE: PRT
<213> ORGANISM: artificial sequence
<220> FEATURE:
<223> OTHER INFORMATION: synthetic construct

<400> SEQUENCE: 48

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asp Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 49
<211> LENGTH: 978
<212> TYPE: DNA
<213> ORGANISM: Artificial sequence
<220> FEATURE:
<223> OTHER INFORMATION: synthetic construct
```

<400> SEQUENCE: 49

```
atggcgttct tcgacctgcc tctggaagaa ctgaagaaat accgtccaga gcgttacgaa      60
gagaaggact tcgacgagtt ctgggaggaa actctggcgg agagcgaaaa gtttccgctg     120
gacccagtgt tcgagcgtat ggaatctcac ctgaaaaccg tggaggcata tgacgttact     180
ttttctggtt accgtggcca gcgtatcaaa ggctggctgc tggttccgaa actggaggaa     240
gaaaaactgc cgtgcgtagt tcagtacatc ggttacaacg gtggccgtgg ctttccgcac     300
gattggctgt tctggccgtc tatgggctac atttgcttcg tcatggatac tcgtggtcag     360
ggttccggct ggctgaaagg cgatactccg gattatccgg agggcccggt agacccgcag     420
taccctggct tcatgacgcg tggtattctg gatccgcgta cctattacta cgccgcgtt      480
tttaccgatg cagttcgtgc cgtagaggcc gcggcttctt tccctcaggt tgaccaggag     540
cgtattgtta tcgctggtgg ctcccagggt ggcggcatcg ccctggcggt atctgcgctg     600
agcaagaaag ctaaggcact gctgtgtgac gtcccgttcc tgtgtcactt ccgtcgcgct     660
gttcagctgg tagatacca tccgtacgcg gagattacta acttcctgaa aactcaccgc     720
gacaaagaag aaatcgtttt ccgcaccctg tcctatttcg acggcgttaa cttcgcggct     780
cgtgcaaaaa ttccggcact gttctctgtt ggtctgatgg acaacatcag ccctccttct     840
accgttttcg cggcatataa ctattatgcg ggtccgaaag aaatccgtat ctatccgtac     900
aacaaccacg aaggcggtgg tagctttcag gctgttgaac aagtgaaatc cctgaagaaa     960
ctgtttgaga agggctaa                                                   978
```

<210> SEQ ID NO 50
<211> LENGTH: 325
<212> TYPE: PRT
<213> ORGANISM: Artificial sequence
<220> FEATURE:
<223> OTHER INFORMATION: synthetic construct

<400> SEQUENCE: 50

```
Met Ala Phe Phe Asp Leu Pro Leu Glu Glu Leu Lys Lys Tyr Arg Pro
  1               5                  10                  15

Glu Arg Tyr Glu Glu Lys Asp Phe Asp Glu Phe Trp Glu Glu Thr Leu
             20                  25                  30

Ala Glu Ser Glu Lys Phe Pro Leu Asp Pro Val Phe Glu Arg Met Glu
         35                  40                  45

Ser His Leu Lys Thr Val Glu Ala Tyr Asp Val Thr Phe Ser Gly Tyr
     50                  55                  60

Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
```

```
                    180                 185                 190
Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Ser Leu Lys Lys
305                 310                 315                 320

Leu Phe Glu Lys Gly
                325

<210> SEQ ID NO 51
<211> LENGTH: 978
<212> TYPE: DNA
<213> ORGANISM: Artificial sequence
<220> FEATURE:
<223> OTHER INFORMATION: synthetic construct

<400> SEQUENCE: 51
atggcgttct cgacctgcc tctggaagaa ctgaagaaat accgtccaga gcgttacgaa      60
gagaaggact cgacgagtt ctgggaggaa actctggcgg agaccgaaaa gtttccgctg     120
gacccagtgt tcgagcgtat ggaatctcac ctgaaaaccg tggaggcata tgacgttact     180
ttttctggtt accgtggcca gcgtatcaaa ggctggctgc tggttccgaa actggaggaa     240
gaaaaactgc cgtgcgtagt tcagtacatc ggttacaacg gtggccgtgg ctttccgcac     300
gattggctgt tctggccgtc tatgggctac atttgcttcg tcatggatac tcgtggtcag     360
ggttccggct ggctgaaagg cgatactccg gattatccgg agggcccggt agacccgcag     420
taccctggct tcatgacgcg tggtattctg gatccgcgta cctattacta tcgccgcgtt     480
tttaccgatg cagttcgtgc cgtagaggcc gcggcttctt cccctcaggt tgaccaggag     540
cgtattgtta tcgctggtgg ctcccagggt ggcggcatcg ccctggcggt atctgcgctg     600
agcaagaaag ctaaggcact gctgtgtgac gtcccgttcc tgtgtcactt ccgtcgcgct     660
gttcagctgg tagatcccca tccgtacgcg gagattacta acttcctgaa aactcaccgc     720
gacaaagaag aaatcgtttt ccgcacccctg tcctatttcg acggcgttaa cttcgcggct     780
cgtgcaaaaa ttccggcact gttctctgtt ggtctgatgg acaacatcag ccctccttct     840
accgttttcg cggcatataa ctattatgcg ggtccgaaag aaatccgtat ctatccgtac     900
aacaaccacg aaggcggtgg tagctttcag gctgttgaac aagtgaaatt cctgaagaaa     960
ctgtttgaga agggctaa                                                    978

<210> SEQ ID NO 52
<211> LENGTH: 325
<212> TYPE: PRT
<213> ORGANISM: Artificial sequence
<220> FEATURE:
<223> OTHER INFORMATION: synthetic construct
```

```
<400> SEQUENCE: 52

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Thr Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Gly Pro Val Asp Pro Gln Tyr Pro Gly Phe
130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 53
<211> LENGTH: 978
<212> TYPE: DNA
<213> ORGANISM: Artificial sequence
<220> FEATURE:
<223> OTHER INFORMATION: synthetic construct

<400> SEQUENCE: 53
atggcgttct tcgacctgcc tctggaagaa ctgaagaaat accgtccaga gcgttacgaa      60
gagaaggact tcgacgagtt ctgggaggaa actctggcgg agagcgaaaa gtttccgctg     120
```

```
gacccagtgt tcgagcgtat ggaatctcac ctgaaaaccg tggaggcata tgacgttact    180
ttttctggtt accgtggcca gcgtatcaaa ggctggctgc tggttccgaa actggaggaa    240
gaaaaactgc cgtgcgtagt tcagtacatc ggttacaacg gtggccgtgg ctttccgcac    300
gattggctgt tctggccgtc tatgggctac atttgcttcg tcatggatac tcgtggtcag    360
ggttccggct ggctgaaagg cgatactccg gattatccgg agggcccggt agacccgcag    420
taccctggct tcatgacgcg tggtattctg gatccgcgta cctattacta tcgccgcgtt    480
tttaccgatg cagttcgtgc cgtagaggcc gcggcttctt tccctcaggt tgacctggag    540
cgtattgtta tcgctggtgg ctcccagggt ggcggcatcg ccctggcggt atctgcgctg    600
agcaagaaag ctaaggcact gctgtgtgac gtcccgttcc tgtgtcactt ccgtcgcgct    660
gttcagctgg tagataccca tccgtacgcg gagattacta cttcctgaa aactcaccgc    720 gacaaagaag aaatcgtttt ccgcaccctg tcctatttcg acggcgttaa cttcgcggct    780
cgtgcaaaaa ttccggcact gttctctgtt ggtctgatgg acaacatcag ccctccttct    840
accgttttcg cggcatataa ctattatgcg ggtccgaaag aaatccgtat ctatccgtac    900
aacaaccacg aaggcggtgg tagctttcag gctgttgaac aagtgaaatt cctgaagaaa    960
ctgtttgaga agggctaa                                                  978
```

<210> SEQ ID NO 54
<211> LENGTH: 325
<212> TYPE: PRT
<213> ORGANISM: Artificial sequence
<220> FEATURE:
<223> OTHER INFORMATION: synthetic construct

<400> SEQUENCE: 54

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Leu Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
```

```
                210                 215                 220
Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Ser Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 55
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 55 atg gcg ttc ttc gac ctg cct cgg gaa gaa ctg aag aaa tac cgt cca      48
Met Ala Phe Phe Asp Leu Pro Arg Glu Glu Leu Lys Lys Tyr Arg Pro
1               5                   10                  15 gag cgt tac gaa gag aag gac ttc gac gag ttc tgg gag gaa act ctg      96
Glu Arg Tyr Glu Glu Lys Asp Phe Asp Glu Phe Trp Glu Glu Thr Leu
                20                  25                  30 gcg gag agc gaa aag ttt ccg ctg gac cca gtg ttc gag cgt atg gaa     144
Ala Glu Ser Glu Lys Phe Pro Leu Asp Pro Val Phe Glu Arg Met Glu
            35                  40                  45 tct cac ctg aaa acc gtg gag gca tat gac gtt act ttt tct ggt tac     192
Ser His Leu Lys Thr Val Glu Ala Tyr Asp Val Thr Phe Ser Gly Tyr
        50                  55                  60 cgt ggc cag cgt atc aaa ggc tgg ctg ctg gtt ccg aaa ctg gag gaa     240
Arg Gly Gln Arg Ile Lys Gly Trp Leu Leu Val Pro Lys Leu Glu Glu
65                  70                  75                  80 gaa aaa ctg ccg tgc gta gtt cag tac atc ggt tac aac ggt ggc cgt     288
Glu Lys Leu Pro Cys Val Val Gln Tyr Ile Gly Tyr Asn Gly Gly Arg
                85                  90                  95 ggc ttt ccg cac gat tgg ctg ttc tgg ccg tct atg ggc tac att tgc     336
Gly Phe Pro His Asp Trp Leu Phe Trp Pro Ser Met Gly Tyr Ile Cys
                100                 105                 110 ttc gtc atg gat act cgt ggt cag ggt tcc ggc tgg cag aaa ggc gat     384
Phe Val Met Asp Thr Arg Gly Gln Gly Ser Gly Trp Gln Lys Gly Asp
            115                 120                 125 act ccg gat tat ccg gag ggc ccg gta gac ccg cag tac cct ggc ttc     432
Thr Pro Asp Tyr Pro Glu Gly Pro Val Asp Pro Gln Tyr Pro Gly Phe
        130                 135                 140 atg acg cgt ggt att ctg gat ccg cgt acc tat tac tat cgc cgc gtt     480
Met Thr Arg Gly Ile Leu Asp Pro Arg Thr Tyr Tyr Tyr Arg Arg Val
145                 150                 155                 160 ttt acc gat gca gtt cgt gcc gta gag gcc gcg gct tct ttc cct ctg     528
Phe Thr Asp Ala Val Arg Ala Val Glu Ala Ala Ala Ser Phe Pro Leu
                165                 170                 175
```

```
gtt gac cag gag cgt att gat atc gct ggt ggc tcc cag ggt ggc ggc       576
Val Asp Gln Glu Arg Ile Asp Ile Ala Gly Gly Ser Gln Gly Gly Gly
            180                 185                 190 atc gcc ctg gcg gta tct gcg ctg agc aaa aaa gct aag gca ctg ctg       624
Ile Ala Leu Ala Val Ser Ala Leu Ser Lys Lys Ala Lys Ala Leu Leu
        195                 200                 205 tgt gac gtc ccg ttc ctg tgt cac ttc cgt cgc gct gtt cag ctg gta       672
Cys Asp Val Pro Phe Leu Cys His Phe Arg Arg Ala Val Gln Leu Val
    210                 215                 220 gat acc cat ccg tac gcg gag att act aac ttc ctg aaa act cac cgc       720
Asp Thr His Pro Tyr Ala Glu Ile Thr Asn Phe Leu Lys Thr His Arg
225                 230                 235                 240 gac aaa gaa gaa atc gtt atc cgc acc ctg tcc tat ttc gac ggc gtt       768
Asp Lys Glu Glu Ile Val Ile Arg Thr Leu Ser Tyr Phe Asp Gly Val
                245                 250                 255 aac ttc gcg gct cgt gca aaa att ccg gca ctg ttc tct gtt ggt ctg       816
Asn Phe Ala Ala Arg Ala Lys Ile Pro Ala Leu Phe Ser Val Gly Leu
            260                 265                 270 atg gac aac atc agc cct cct tct acc gtt ttc gcg gca tat aac tat       864
Met Asp Asn Ile Ser Pro Pro Ser Thr Val Phe Ala Ala Tyr Asn Tyr
        275                 280                 285 tat gcg ggt ctg aaa gaa atc cgt atc tat ccg tac aac aac cac gaa       912
Tyr Ala Gly Leu Lys Glu Ile Arg Ile Tyr Pro Tyr Asn Asn His Glu
    290                 295                 300 ggc ggt ggt agc ttt cag gct gtt gaa caa gtg aaa ttc ctg aag aaa       960
Gly Gly Gly Ser Phe Gln Ala Val Glu Gln Val Lys Phe Leu Lys Lys
305                 310                 315                 320 ctg ttt gag aag ggc taa                                               978
Leu Phe Glu Lys Gly
                325

<210> SEQ ID NO 56
<211> LENGTH: 325
<212> TYPE: PRT
<213> ORGANISM: artificial sequence
<220> FEATURE:
<223> OTHER INFORMATION: Synthetic Construct

<400> SEQUENCE: 56

Met Ala Phe Phe Asp Leu Pro Arg Glu Glu Leu Lys Lys Tyr Arg Pro
1               5                   10                  15

Glu Arg Tyr Glu Glu Lys Asp Phe Asp Glu Phe Trp Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Gln Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160
```

```
Phe Thr Asp Ala Val Arg Ala Val Glu Ala Ala Ser Phe Pro Leu
                165                 170                 175

Val Asp Gln Glu Arg Ile Asp Ile Ala Gly Ser Gln Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Ile Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Leu Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 57
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 57 atg gcg ttc ttc gac ctg cct ctg gaa gaa ctg aag aaa tac cgt cca     48
Met Ala Phe Phe Asp Leu Pro Leu Glu Glu Leu Lys Lys Tyr Arg Pro
1               5                   10                  15 gag cgt tac gaa gag aag gac ttc gac gag ttc tgg gag gaa act ctg     96
Glu Arg Tyr Glu Glu Lys Asp Phe Asp Glu Phe Trp Glu Glu Thr Leu
            20                  25                  30 gcg gag agc gaa aag ttt ccg ctg gac cca gtg ttc gag cgt atg gaa    144
Ala Glu Ser Glu Lys Phe Pro Leu Asp Pro Val Phe Glu Arg Met Glu
        35                  40                  45 tct cac ctg aaa acc gtg gag gca tat gac gtt act ttt tct ggt tac    192
Ser His Leu Lys Thr Val Glu Ala Tyr Asp Val Thr Phe Ser Gly Tyr
    50                  55                  60 cgt ggc cag cgt atc aaa ggc tgg ctg ctg gtt ccg gaa ctg gag gaa    240
Arg Gly Gln Arg Ile Lys Gly Trp Leu Leu Val Pro Glu Leu Glu Glu
65                  70                  75                  80 gaa aaa ctg ccg tgc gta gtt cag tac atc ggt tac aac ggt ggc cgt    288
Glu Lys Leu Pro Cys Val Val Gln Tyr Ile Gly Tyr Asn Gly Gly Arg
                85                  90                  95 ggc ttt ccg cac gat tgg ctg ttc tgg ccg tct atg ggc tac att tgc    336
Gly Phe Pro His Asp Trp Leu Phe Trp Pro Ser Met Gly Tyr Ile Cys
            100                 105                 110 ttc gtc atg gat act cgt ggt cag ggt tcc ggc tgg ctg aaa ggc gat    384
Phe Val Met Asp Thr Arg Gly Gln Gly Ser Gly Trp Leu Lys Gly Asp
        115                 120                 125 act ccg gat tat ccg gag ggc ccg gta gac ccg cag tac cct ggc ttc    432
Thr Pro Asp Tyr Pro Glu Gly Pro Val Asp Pro Gln Tyr Pro Gly Phe
```

```
atg acg cgt ggt att ctg gat ccg cgt acc tat tac tat cgc cgc gtt       480
Met Thr Arg Gly Ile Leu Asp Pro Arg Thr Tyr Tyr Tyr Arg Arg Val
145                 150                 155                 160 ttt acc gat gca gtt cgt gcc gta gag gcc gcg gct tct ttc cct cag       528
Phe Thr Asp Ala Val Arg Ala Val Glu Ala Ala Ala Ser Phe Pro Gln
                165                 170                 175 gtt gac cag gag cgt att gtt atc gct ggt ggc tcc cag ggt ggc ggc       576
Val Asp Gln Glu Arg Ile Val Ile Ala Gly Gly Ser Gln Gly Gly Gly
            180                 185                 190 atc gcc ctg gcg gta tct gcg ctg agc aag aaa gct aag gca ctg ctg       624
Ile Ala Leu Ala Val Ser Ala Leu Ser Lys Lys Ala Lys Ala Leu Leu
        195                 200                 205 tgt gac gtc ccg ttc ctg tgt cac ttc cgt cgc gct gtt cag ctg gta       672
Cys Asp Val Pro Phe Leu Cys His Phe Arg Arg Ala Val Gln Leu Val
    210                 215                 220 gat acc cat ccg tac gcg gag att act aac ttc ctg aaa act cac cgc       720
Asp Thr His Pro Tyr Ala Glu Ile Thr Asn Phe Leu Lys Thr His Arg
225                 230                 235                 240 gac aaa gaa gaa atc gtt ttc cgc acc ctg tcc tat ttc gac ggc gtt       768
Asp Lys Glu Glu Ile Val Phe Arg Thr Leu Ser Tyr Phe Asp Gly Val
                245                 250                 255 aac ttc gcg gct cgt gca aaa att ccg gaa ctg ttc tct gtt ggt ctg       816
Asn Phe Ala Ala Arg Ala Lys Ile Pro Glu Leu Phe Ser Val Gly Leu
            260                 265                 270 atg gac aac atc agc cct cct tct acc gtt ttc gcg gca tat aac tat       864
Met Asp Asn Ile Ser Pro Pro Ser Thr Val Phe Ala Ala Tyr Asn Tyr
        275                 280                 285 tat gcg ggt ccg aaa gaa atc cgt atc tat ccg tac aac aac cac gaa       912
Tyr Ala Gly Pro Lys Glu Ile Arg Ile Tyr Pro Tyr Asn Asn His Glu
    290                 295                 300 ggc ggt ggt agc ttt cag gct gtt gaa caa gtg aaa ttc ctg aag aaa       960
Gly Gly Gly Ser Phe Gln Ala Val Glu Gln Val Lys Phe Leu Lys Lys
305                 310                 315                 320 ctg ttt gag aag ggc taa                                               978
Leu Phe Glu Lys Gly
                325

<210> SEQ ID NO 58
<211> LENGTH: 325
<212> TYPE: PRT
<213> ORGANISM: artificial sequence
<220> FEATURE:
<223> OTHER INFORMATION: Synthetic Construct

<400> SEQUENCE: 58

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Glu Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110
```

```
Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Glu Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 59
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 59 atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15 gag cgt tac gaa gag aag gac ttc gac gag tac tgg gag gaa act ctg      96
Glu Arg Tyr Glu Glu Lys Asp Phe Asp Glu Tyr Trp Glu Glu Thr Leu
            20                  25                  30 gcg gag agc gaa aag ttt ccg ctg gac cca gtg ttc gag cgt atg gaa     144
Ala Glu Ser Glu Lys Phe Pro Leu Asp Pro Val Phe Glu Arg Met Glu
        35                  40                  45 tct cac ctg aaa acc gtg gag gca tat gac gtt act ttt tct ggt tac     192
Ser His Leu Lys Thr Val Glu Ala Tyr Asp Val Thr Phe Ser Gly Tyr
    50                  55                  60 cgt ggc cag cgt atc aaa ggc tgg ctg ctg gtt ccg aaa ctg gag gaa     240
Arg Gly Gln Arg Ile Lys Gly Trp Leu Leu Val Pro Lys Leu Glu Glu
65                  70                  75                  80 gaa aaa ctg ccg tgc gta gtt cag tac atc ggt tac aac ggt ggc cgt     288
Glu Lys Leu Pro Cys Val Val Gln Tyr Ile Gly Tyr Asn Gly Gly Arg
                85                  90                  95
```

```
ggc ttt ccg cac gat tgg ctg ttc tgg ccg tct atg ggc tac att tgc       336
Gly Phe Pro His Asp Trp Leu Phe Trp Pro Ser Met Gly Tyr Ile Cys
            100                 105                 110 ttc gtc atg gat act cgt ggt cag ggt tcc ggc tgg ctg aaa ggc gat       384
Phe Val Met Asp Thr Arg Gly Gln Gly Ser Gly Trp Leu Lys Gly Asp
        115                 120                 125 act ccg gat tat ccg gag ggc ccg gta gac ccg cag tac cct ggc ttc       432
Thr Pro Asp Tyr Pro Glu Gly Pro Val Asp Pro Gln Tyr Pro Gly Phe
    130                 135                 140 atg acg cgt ggt gtt ctg gat ccg cgt acc tat tac tat cgc cgc gtt       480
Met Thr Arg Gly Val Leu Asp Pro Arg Thr Tyr Tyr Tyr Arg Arg Val
145                 150                 155                 160 ttt acc gat gca gtt cgt gcc gta gag gcc gcg gct tct ttc cct cag       528
Phe Thr Asp Ala Val Arg Ala Val Glu Ala Ala Ala Ser Phe Pro Gln
                165                 170                 175 gtt gac cag gag cgt att gtt atc gct ggt ggc tcc cag ggt ggc ggc       576
Val Asp Gln Glu Arg Ile Val Ile Ala Gly Gly Ser Gln Gly Gly Gly
            180                 185                 190 atc gcc ctg gcg gta tct gcg ctg agc aag aaa gct aag gca ctg ctg       624
Ile Ala Leu Ala Val Ser Ala Leu Ser Lys Lys Ala Lys Ala Leu Leu
        195                 200                 205 tgt gac gtc ccg ttc ctg tgt cac ttc cgt cgc gct gtt cag ctg gta       672
Cys Asp Val Pro Phe Leu Cys His Phe Arg Arg Ala Val Gln Leu Val
    210                 215                 220 gat acc cat ccg tac gcg gag att act aac ttc ctg aaa act cac cgc       720
Asp Thr His Pro Tyr Ala Glu Ile Thr Asn Phe Leu Lys Thr His Arg
225                 230                 235                 240 gac aaa gaa gaa atc gtt ttc cgc acc ctg tcc tat ttc gac ggc gtt       768
Asp Lys Glu Glu Ile Val Phe Arg Thr Leu Ser Tyr Phe Asp Gly Val
                245                 250                 255 aac ttc gcg gct cgt gca aaa att ccg gta ctg ttc tct gtt ggt ctg       816
Asn Phe Ala Ala Arg Ala Lys Ile Pro Val Leu Phe Ser Val Gly Leu
            260                 265                 270 atg gac aac atc agc cct cct tct acc gtt ttc gcg gca tat aac tat       864
Met Asp Asn Ile Ser Pro Pro Ser Thr Val Phe Ala Ala Tyr Asn Tyr
        275                 280                 285 tat gcg ggt ccg aaa gaa acc cgt atc tat ccg tac aac agc cac gaa       912
Tyr Ala Gly Pro Lys Glu Thr Arg Ile Tyr Pro Tyr Asn Ser His Glu
    290                 295                 300 ggc ggt ggt agc ttt cag gct gtt gaa caa gtg aaa ttc ctg aag aaa       960
Gly Gly Gly Ser Phe Gln Ala Val Glu Gln Val Lys Phe Leu Lys Lys
305                 310                 315                 320 ctg ttt gag aag ggc taa                                               978
Leu Phe Glu Lys Gly
                325
```

<210> SEQ ID NO 60
<211> LENGTH: 325
<212> TYPE: PRT
<213> ORGANISM: artificial sequence
<220> FEATURE:
<223> OTHER INFORMATION: Synthetic Construct

<400> SEQUENCE: 60

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Tyr Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
```

```
                      50                  55                  60
Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
        130                 135                 140

Met Thr Arg Gly Val Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Val Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Thr Arg Ile Tyr Pro Tyr Asn Ser His Glu
    290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 61
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 61 atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15 gag cgt tac gaa gag aag gac ttc gac gag ttc tgg gag gaa act ctg      96
Glu Arg Tyr Glu Glu Lys Asp Phe Asp Glu Phe Trp Glu Glu Thr Leu
            20                  25                  30 gcg gag agc gaa aag ttt ccg ctg gac cca gtg ttc gag cgt atg gaa     144
Ala Glu Ser Glu Lys Phe Pro Leu Asp Pro Val Phe Glu Arg Met Glu
        35                  40                  45 tct cac ctg aaa acc gtg gag gca tat gac gtt act ttt tct ggt tac     192
Ser His Leu Lys Thr Val Glu Ala Tyr Asp Val Thr Phe Ser Gly Tyr
```

```
                50                  55                  60
cgt ggc cag cgt atc aaa ggc tgg ctg ctg gtt ccg aaa ctg gag gaa       240
Arg Gly Gln Arg Ile Lys Gly Trp Leu Leu Val Pro Lys Leu Glu Glu
 65                  70                  75                  80 gaa aaa ctg ccg tgc gta gtt cag tac atc ggt tac aac ggt ggc cgt       288
Glu Lys Leu Pro Cys Val Val Gln Tyr Ile Gly Tyr Asn Gly Gly Arg
                 85                  90                  95 ggc ttt ccg cac gat tgg ctg ttc tgg ccg tct atg ggc tac att tgc       336
Gly Phe Pro His Asp Trp Leu Phe Trp Pro Ser Met Gly Tyr Ile Cys
            100                 105                 110 ttc gtc atg gat act cgt ggt cag ggt tcc ggc tgg ctg aaa ggc gat       384
Phe Val Met Asp Thr Arg Gly Gln Gly Ser Gly Trp Leu Lys Gly Asp
        115                 120                 125 act ccg gat tat ccg gag ggc ccg gta gac ccg cag tac cct ggc ttc       432
Thr Pro Asp Tyr Pro Glu Gly Pro Val Asp Pro Gln Tyr Pro Gly Phe
    130                 135                 140 atg acg cgt ggt att ctg gat ccg cgt acc tat tac tat cgc cgc gtt       480
Met Thr Arg Gly Ile Leu Asp Pro Arg Thr Tyr Tyr Tyr Arg Arg Val
145                 150                 155                 160 ttt acc gat gca gtt cgt gcc gta gag gcc gcg gct tct ttc cct cag       528
Phe Thr Asp Ala Val Arg Ala Val Glu Ala Ala Ala Ser Phe Pro Gln
                165                 170                 175 gtt gac cag gag cgt att gtt atc gct ggt ggc tcc cag ggt ggc ggc       576
Val Asp Gln Glu Arg Ile Val Ile Ala Gly Gly Ser Gln Gly Gly Gly
            180                 185                 190 atc gcc cag gcg gta tct gcg ctg agc aag aaa gct aag gca ctg ctg       624
Ile Ala Gln Ala Val Ser Ala Leu Ser Lys Lys Ala Lys Ala Leu Leu
        195                 200                 205 tgt gac gtc ccg ttc ctg tgt cac ttc cgt cgc gct gtt cag ctg gta       672
Cys Asp Val Pro Phe Leu Cys His Phe Arg Arg Ala Val Gln Leu Val
    210                 215                 220 gat acc cat ccg tac gcg gag att act aac ttc ctg aaa act cac cgc       720
Asp Thr His Pro Tyr Ala Glu Ile Thr Asn Phe Leu Lys Thr His Arg
225                 230                 235                 240 gac aaa gaa gaa atc gtt ttc cgc acc ctg tcc tat ttc gac ggc gtt       768
Asp Lys Glu Glu Ile Val Phe Arg Thr Leu Ser Tyr Phe Asp Gly Val
                245                 250                 255 aac ttc gcg gct cgt gca aaa att ccg gca ctg ttc tct gtt ggt ctg       816
Asn Phe Ala Ala Arg Ala Lys Ile Pro Ala Leu Phe Ser Val Gly Leu
            260                 265                 270 atg gac aac atc agc cct cct tct acc gtt ttc gcg gca tat aac tat       864
Met Asp Asn Ile Ser Pro Pro Ser Thr Val Phe Ala Ala Tyr Asn Tyr
        275                 280                 285 tat gcg ggt ccg aaa gaa atc cgt atc tat ccg tac aac aac cac gaa       912
Tyr Ala Gly Pro Lys Glu Ile Arg Ile Tyr Pro Tyr Asn Asn His Glu
    290                 295                 300 ggc ggt ggt agc ttt cag gct gtt gaa caa gtg aaa ttc ctg aag aaa       960
Gly Gly Gly Ser Phe Gln Ala Val Glu Gln Val Lys Phe Leu Lys Lys
305                 310                 315                 320 ctg ttt gag aag ggc taa                                               978
Leu Phe Glu Lys Gly
                325
```

<210> SEQ ID NO 62  
<211> LENGTH: 325  
<212> TYPE: PRT  
<213> ORGANISM: artificial sequence  
<220> FEATURE:  
<223> OTHER INFORMATION: Synthetic Construct

<400> SEQUENCE: 62

```
Met Ala Phe Phe Asp Leu Pro Leu Glu Glu Leu Lys Lys Tyr Arg Pro
1               5                   10                  15

Glu Arg Tyr Glu Lys Asp Phe Asp Phe Trp Glu Thr Leu
            20                  25              30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
            165                 170                 175

Val Asp Gln Glu Arg Ile Val Ile Ala Gly Ser Gln Gly Gly
            180                 185                 190

Ile Ala Gln Ala Val Ser Ala Leu Ser Lys Ala Lys Ala Leu Leu
            195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 63
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 63 atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15
```

```
gag cgt tac gaa gag aag gac ttc gac gag ttc tgg gag gaa act ctg        96
Glu Arg Tyr Glu Glu Lys Asp Phe Asp Glu Phe Trp Glu Glu Thr Leu
         20                  25                  30 gcg gag agc gaa aag ttt ccg ctg gac cca gtg ttc gag cgt atg gaa       144
Ala Glu Ser Glu Lys Phe Pro Leu Asp Pro Val Phe Glu Arg Met Glu
     35                  40                  45 tct cac ctg aaa acc gtg gag gca tat gac gtt act ttt tct ggt tac       192
Ser His Leu Lys Thr Val Glu Ala Tyr Asp Val Thr Phe Ser Gly Tyr
 50                  55                  60 cgt ggc cag cgt atc aaa ggc tgg ctg ctg gtt ccg aaa ctg gag gaa       240
Arg Gly Gln Arg Ile Lys Gly Trp Leu Leu Val Pro Lys Leu Glu Glu
65                  70                  75                  80 gaa aaa ctg ccg tgc gta gtt cag tac atc ggt tac aac ggt ggc cgt       288
Glu Lys Leu Pro Cys Val Val Gln Tyr Ile Gly Tyr Asn Gly Gly Arg
             85                  90                  95 ggc ttt ccg cac gat tgg ctg ttc tgg ccg tct atg ggc ttc att tgc       336
Gly Phe Pro His Asp Trp Leu Phe Trp Pro Ser Met Gly Phe Ile Cys
        100                 105                 110 ttc gtc atg gat act cgt ggt cag ggt tcc ggc tgg ctg aaa ggc gat       384
Phe Val Met Asp Thr Arg Gly Gln Gly Ser Gly Trp Leu Lys Gly Asp
        115                 120                 125 act ccg gat tat ccg gag ggc ccg gta gac ccg cag tac cct ggc ttc       432
Thr Pro Asp Tyr Pro Glu Gly Pro Val Asp Pro Gln Tyr Pro Gly Phe
    130                 135                 140 atg acg cgt ggt att ctg gat ccg cgt acc tat tac tat cgc cgc gtt       480
Met Thr Arg Gly Ile Leu Asp Pro Arg Thr Tyr Tyr Tyr Arg Arg Val
145                 150                 155                 160 ttt acc gat gca gtt cgt gcc gta gag gcc gcg gct tct ttc cct cag       528
Phe Thr Asp Ala Val Arg Ala Val Glu Ala Ala Ala Ser Phe Pro Gln
                165                 170                 175 gtt gac cag gag cgt att gtt atc gct ggt ggc tcc cag ggt ggc ggc       576
Val Asp Gln Glu Arg Ile Val Ile Ala Gly Gly Ser Gln Gly Gly Gly
            180                 185                 190 atc gcc ctg gcg gta tct gcg ctg agc aag aaa gct aag gca ctg ctg       624
Ile Ala Leu Ala Val Ser Ala Leu Ser Lys Lys Ala Lys Ala Leu Leu
        195                 200                 205 tgt gac gtc ccg ttc ctg tgt cac ttc cgt cgc gct gtt cag ctg gta       672
Cys Asp Val Pro Phe Leu Cys His Phe Arg Arg Ala Val Gln Leu Val
        210                 215                 220 gat acc cat ccg tac gcg gag att act aac ttc ctg aaa act cac cgc       720
Asp Thr His Pro Tyr Ala Glu Ile Thr Asn Phe Leu Lys Thr His Arg
225                 230                 235                 240 gac aaa gaa gaa atc gtt ttc cgc acc ctg tcc tat ttc gac ggc gtt       768
Asp Lys Glu Glu Ile Val Phe Arg Thr Leu Ser Tyr Phe Asp Gly Val
                245                 250                 255 aac ttc gcg gct cgt gca aaa att ccg gca ctg ttc tct gtt ggt ctg       816
Asn Phe Ala Ala Arg Ala Lys Ile Pro Ala Leu Phe Ser Val Gly Leu
            260                 265                 270 atg gac aac atc agc cct cct tct acc gtt ttc gcg gca tat aac tat       864
Met Asp Asn Ile Ser Pro Pro Ser Thr Val Phe Ala Ala Tyr Asn Tyr
        275                 280                 285 tat gcg ggt ccg aaa gaa atc cgt atc tat ccg tac aac aac cac gaa       912
Tyr Ala Gly Pro Lys Glu Ile Arg Ile Tyr Pro Tyr Asn Asn His Glu
    290                 295                 300 ggc ggt ggt agc ttt cag gct gtt gaa caa gtg aaa ttc ctg aag aaa       960
Gly Gly Gly Ser Phe Gln Ala Val Glu Gln Val Lys Phe Leu Lys Lys
305                 310                 315                 320 ctg ttt gag aag ggc taa                                               978
Leu Phe Glu Lys Gly
                325
```

<210> SEQ ID NO 64
<211> LENGTH: 325
<212> TYPE: PRT
<213> ORGANISM: artificial sequence
<220> FEATURE:
<223> OTHER INFORMATION: Synthetic Construct

<400> SEQUENCE: 64

```
Met Ala Phe Phe Asp Leu Pro Leu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
                50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                    85                  90                  95

Gly Phe Pro His Asp Trp Leu Phe Trp Pro Ser Met Gly Phe Ile Cys
                100                 105                 110

Phe Val Met Asp Thr Arg Gly Gln Gly Ser Gly Trp Leu Lys Gly Asp
                115                 120                 125

Thr Pro Asp Tyr Pro Glu Gly Pro Val Asp Pro Gln Tyr Pro Gly Phe
                130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
                210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Ser Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Val Glu Val Lys Phe Leu Lys Lys
305                 310                 315                 320

Leu Phe Glu Lys Gly
                325
```

<210> SEQ ID NO 65
<211> LENGTH: 12
<212> TYPE: PRT
<213> ORGANISM: artificial sequence
<220> FEATURE:
<223> OTHER INFORMATION: Synthetic construct

```
<400> SEQUENCE: 65

Arg Val Pro Asn Lys Thr Val Thr Val Asp Gly Ala
1               5                   10

<210> SEQ ID NO 66
<211> LENGTH: 12
<212> TYPE: PRT
<213> ORGANISM: artificial sequence
<220> FEATURE:
<223> OTHER INFORMATION: Synthetic construct

<400> SEQUENCE: 66

Asp Arg His Lys Ser Lys Tyr Ser Ser Thr Lys Ser
1               5                   10

<210> SEQ ID NO 67
<211> LENGTH: 12
<212> TYPE: PRT
<213> ORGANISM: artificial sequence
<220> FEATURE:
<223> OTHER INFORMATION: Synthetic construct

<400> SEQUENCE: 67

Lys Asn Phe Pro Gln Gln Lys Glu Phe Pro Leu Ser
1               5                   10

<210> SEQ ID NO 68
<211> LENGTH: 12
<212> TYPE: PRT
<213> ORGANISM: artificial sequence
<220> FEATURE:
<223> OTHER INFORMATION: Synthetic construct

<400> SEQUENCE: 68

Gln Arg Asn Ser Pro Ala Met Ser Arg Arg Asp
1               5                   10

<210> SEQ ID NO 69
<211> LENGTH: 12
<212> TYPE: PRT
<213> ORGANISM: artificial sequence
<220> FEATURE:
<223> OTHER INFORMATION: Synthetic construct

<400> SEQUENCE: 69

Thr Arg Lys Pro Asn Met Pro His Gly Gln Tyr Leu
1               5                   10

<210> SEQ ID NO 70
<211> LENGTH: 12
<212> TYPE: PRT
<213> ORGANISM: artificial sequence
<220> FEATURE:
<223> OTHER INFORMATION: Synthetic construct

<400> SEQUENCE: 70

Lys Pro Pro His Leu Ala Lys Leu Pro Phe Thr Thr
1               5                   10

<210> SEQ ID NO 71
<211> LENGTH: 12
<212> TYPE: PRT
<213> ORGANISM: artificial sequence
<220> FEATURE:
<223> OTHER INFORMATION: Synthetic construct

<400> SEQUENCE: 71
```

Asn Lys Arg Pro Pro Thr Ser His Arg Ile His Ala
1               5                   10

<210> SEQ ID NO 72
<211> LENGTH: 12
<212> TYPE: PRT
<213> ORGANISM: artificial sequence
<220> FEATURE:
<223> OTHER INFORMATION: Synthetic construct

<400> SEQUENCE: 72

Asn Leu Pro Arg Tyr Gln Pro Pro Cys Lys Pro Leu
1               5                   10

<210> SEQ ID NO 73
<211> LENGTH: 12
<212> TYPE: PRT
<213> ORGANISM: artificial sequence
<220> FEATURE:
<223> OTHER INFORMATION: Synthetic construct

<400> SEQUENCE: 73

Arg Pro Pro Trp Lys Lys Pro Ile Pro Pro Ser Glu
1               5                   10

<210> SEQ ID NO 74
<211> LENGTH: 12
<212> TYPE: PRT
<213> ORGANISM: artificial sequence
<220> FEATURE:
<223> OTHER INFORMATION: Synthetic construct

<400> SEQUENCE: 74

Arg Gln Arg Pro Lys Asp His Phe Phe Ser Arg Pro
1               5                   10

<210> SEQ ID NO 75
<211> LENGTH: 12
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Thr or Pro

<400> SEQUENCE: 75

Ser Val Pro Asn Lys Xaa Val Thr Val Asp Gly Xaa
1               5                   10

<210> SEQ ID NO 76
<211> LENGTH: 12
<212> TYPE: PRT
<213> ORGANISM: artificial sequence
<220> FEATURE:
<223> OTHER INFORMATION: Synthetic construct

<400> SEQUENCE: 76

Thr Thr Lys Trp Arg His Arg Ala Pro Val Ser Pro
1               5                   10

<210> SEQ ID NO 77
<211> LENGTH: 12

```
<212> TYPE: PRT
<213> ORGANISM: artificial sequence
<220> FEATURE:
<223> OTHER INFORMATION: Synthetic construct

<400> SEQUENCE: 77

Trp Leu Gly Lys Asn Arg Ile Lys Pro Arg Ala Ser
1               5                   10

<210> SEQ ID NO 78
<211> LENGTH: 12
<212> TYPE: PRT
<213> ORGANISM: artificial sequence
<220> FEATURE:
<223> OTHER INFORMATION: Synthetic construct

<400> SEQUENCE: 78

Ser Asn Phe Lys Thr Pro Leu Pro Leu Thr Gln Ser
1               5                   10

<210> SEQ ID NO 79
<211> LENGTH: 12
<212> TYPE: PRT
<213> ORGANISM: artificial sequence
<220> FEATURE:
<223> OTHER INFORMATION: Synthetic construct

<400> SEQUENCE: 79

Ser Val Ser Val Gly Met Lys Pro Ser Pro Arg Pro
1               5                   10

<210> SEQ ID NO 80
<211> LENGTH: 7
<212> TYPE: PRT
<213> ORGANISM: artificial sequence
<220> FEATURE:
<223> OTHER INFORMATION: Synthetic construct

<400> SEQUENCE: 80

Asp Leu His Thr Val Tyr His
1               5

<210> SEQ ID NO 81
<211> LENGTH: 7
<212> TYPE: PRT
<213> ORGANISM: artificial sequence
<220> FEATURE:
<223> OTHER INFORMATION: Synthetic construct

<400> SEQUENCE: 81

His Ile Lys Pro Pro Thr Arg
1               5

<210> SEQ ID NO 82
<211> LENGTH: 7
<212> TYPE: PRT
<213> ORGANISM: artificial sequence
<220> FEATURE:
<223> OTHER INFORMATION: Synthetic construct

<400> SEQUENCE: 82

His Pro Val Trp Pro Ala Ile
1               5

<210> SEQ ID NO 83
<211> LENGTH: 7
<212> TYPE: PRT
<213> ORGANISM: artificial sequence
```

```
<220> FEATURE:
<223> OTHER INFORMATION: Synthetic construct

<400> SEQUENCE: 83

Met Pro Leu Tyr Tyr Leu Gln
1               5

<210> SEQ ID NO 84
<211> LENGTH: 26
<212> TYPE: PRT
<213> ORGANISM: artificial sequence
<220> FEATURE:
<223> OTHER INFORMATION: Synthetic construct

<400> SEQUENCE: 84

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 85
<211> LENGTH: 41
<212> TYPE: PRT
<213> ORGANISM: artificial sequence
<220> FEATURE:
<223> OTHER INFORMATION: Synthetic construct

<400> SEQUENCE: 85

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
            35                  40

<210> SEQ ID NO 86
<211> LENGTH: 7
<212> TYPE: PRT
<213> ORGANISM: artificial sequence
<220> FEATURE:
<223> OTHER INFORMATION: Synthetic construct

<400> SEQUENCE: 86

Lys His Pro Thr Tyr Arg Gln
1               5

<210> SEQ ID NO 87
<211> LENGTH: 7
<212> TYPE: PRT
<213> ORGANISM: artificial sequence
<220> FEATURE:
<223> OTHER INFORMATION: Synthetic construct

<400> SEQUENCE: 87

His Pro Met Ser Ala Pro Arg
1               5

<210> SEQ ID NO 88
<211> LENGTH: 7
<212> TYPE: PRT
<213> ORGANISM: artificial sequence
<220> FEATURE:
<223> OTHER INFORMATION: Synthetic construct

<400> SEQUENCE: 88

Met Pro Lys Tyr Tyr Leu Gln
```

<210> SEQ ID NO 89
<211> LENGTH: 7
<212> TYPE: PRT
<213> ORGANISM: artificial sequence
<220> FEATURE:
<223> OTHER INFORMATION: Synthetic construct

<400> SEQUENCE: 89

Met His Ala His Ser Ile Ala
1               5

<210> SEQ ID NO 90
<211> LENGTH: 12
<212> TYPE: PRT
<213> ORGANISM: artificial sequence
<220> FEATURE:
<223> OTHER INFORMATION: Synthetic construct

<400> SEQUENCE: 90

Ala Lys Pro Ile Ser Gln His Leu Gln Arg Gly Ser
1               5                   10

<210> SEQ ID NO 91
<211> LENGTH: 12
<212> TYPE: PRT
<213> ORGANISM: artificial sequence
<220> FEATURE:
<223> OTHER INFORMATION: Synthetic construct

<400> SEQUENCE: 91

Ala Pro Pro Thr Pro Ala Ala Ala Ser Ala Thr Thr
1               5                   10

<210> SEQ ID NO 92
<211> LENGTH: 12
<212> TYPE: PRT
<213> ORGANISM: artificial sequence
<220> FEATURE:
<223> OTHER INFORMATION: Synthetic construct

<400> SEQUENCE: 92

Asp Pro Thr Glu Gly Ala Arg Arg Thr Ile Met Thr
1               5                   10

<210> SEQ ID NO 93
<211> LENGTH: 12
<212> TYPE: PRT
<213> ORGANISM: artificial sequence
<220> FEATURE:
<223> OTHER INFORMATION: Synthetic construct

<400> SEQUENCE: 93

Leu Asp Thr Ser Phe Pro Pro Val Pro Phe His Ala
1               5                   10

<210> SEQ ID NO 94
<211> LENGTH: 12
<212> TYPE: PRT
<213> ORGANISM: artificial sequence
<220> FEATURE:
<223> OTHER INFORMATION: Synthetic construct

<400> SEQUENCE: 94

Leu Asp Thr Ser Phe His Gln Val Pro Phe His Gln
1               5                   10

```
<210> SEQ ID NO 95
<211> LENGTH: 11
<212> TYPE: PRT
<213> ORGANISM: artificial sequence
<220> FEATURE:
<223> OTHER INFORMATION: Synthetic construct

<400> SEQUENCE: 95

Leu Pro Arg Ile Ala Asn Thr Trp Ser Pro Ser
1               5                   10

<210> SEQ ID NO 96
<211> LENGTH: 12
<212> TYPE: PRT
<213> ORGANISM: artificial sequence
<220> FEATURE:
<223> OTHER INFORMATION: Synthetic construct

<400> SEQUENCE: 96

Arg Thr Asn Ala Ala Asp His Pro Ala Ala Val Thr
1               5                   10

<210> SEQ ID NO 97
<211> LENGTH: 12
<212> TYPE: PRT
<213> ORGANISM: artificial sequence
<220> FEATURE:
<223> OTHER INFORMATION: Synthetic construct

<400> SEQUENCE: 97

Ser Leu Asn Trp Val Thr Ile Pro Gly Pro Lys Ile
1               5                   10

<210> SEQ ID NO 98
<211> LENGTH: 12
<212> TYPE: PRT
<213> ORGANISM: artificial sequence
<220> FEATURE:
<223> OTHER INFORMATION: Synthetic construct

<400> SEQUENCE: 98

Thr Asp Met Gln Ala Pro Thr Lys Ser Tyr Ser Asn
1               5                   10

<210> SEQ ID NO 99
<211> LENGTH: 12
<212> TYPE: PRT
<213> ORGANISM: artificial sequence
<220> FEATURE:
<223> OTHER INFORMATION: Synthetic construct

<400> SEQUENCE: 99

Thr Ile Met Thr Lys Ser Pro Ser Leu Ser Cys Gly
1               5                   10

<210> SEQ ID NO 100
<211> LENGTH: 12
<212> TYPE: PRT
<213> ORGANISM: artificial sequence
<220> FEATURE:
<223> OTHER INFORMATION: Synthetic construct

<400> SEQUENCE: 100

Thr Pro Ala Leu Asp Gly Leu Arg Gln Pro Leu Arg
1               5                   10

<210> SEQ ID NO 101
```

<211> LENGTH: 12
<212> TYPE: PRT
<213> ORGANISM: artificial sequence
<220> FEATURE:
<223> OTHER INFORMATION: Synthetic construct

<400> SEQUENCE: 101

Thr Tyr Pro Ala Ser Arg Leu Pro Leu Leu Ala Pro
1               5                   10

<210> SEQ ID NO 102
<211> LENGTH: 12
<212> TYPE: PRT
<213> ORGANISM: artificial sequence
<220> FEATURE:
<223> OTHER INFORMATION: Synthetic construct

<400> SEQUENCE: 102

Ala Lys Thr His Lys His Pro Ala Pro Ser Tyr Ser
1               5                   10

<210> SEQ ID NO 103
<211> LENGTH: 12
<212> TYPE: PRT
<213> ORGANISM: artificial sequence
<220> FEATURE:
<223> OTHER INFORMATION: Synthetic construct

<400> SEQUENCE: 103

Thr Asp Pro Thr Pro Phe Ser Ile Ser Pro Glu Arg
1               5                   10

<210> SEQ ID NO 104
<211> LENGTH: 12
<212> TYPE: PRT
<213> ORGANISM: artificial sequence
<220> FEATURE:
<223> OTHER INFORMATION: Synthetic construct

<400> SEQUENCE: 104

Ser Gln Asn Trp Gln Asp Ser Thr Ser Tyr Ser Asn
1               5                   10

<210> SEQ ID NO 105
<211> LENGTH: 12
<212> TYPE: PRT
<213> ORGANISM: artificial sequence
<220> FEATURE:
<223> OTHER INFORMATION: Synthetic construct

<400> SEQUENCE: 105

Trp His Asp Lys Pro Gln Asn Ser Ser Lys Ser Thr
1               5                   10

<210> SEQ ID NO 106
<211> LENGTH: 12
<212> TYPE: PRT
<213> ORGANISM: artificial sequence
<220> FEATURE:
<223> OTHER INFORMATION: Synthetic construct

<400> SEQUENCE: 106

Leu Asp Val Glu Ser Tyr Lys Gly Thr Ser Met Pro
1               5                   10

<210> SEQ ID NO 107
<211> LENGTH: 7
<212> TYPE: PRT

<213> ORGANISM: artificial sequence
<220> FEATURE:
<223> OTHER INFORMATION: Synthetic construct

<400> SEQUENCE: 107

Asn Thr Pro Lys Glu Asn Trp
1               5

<210> SEQ ID NO 108
<211> LENGTH: 7
<212> TYPE: PRT
<213> ORGANISM: artificial sequence
<220> FEATURE:
<223> OTHER INFORMATION: Synthetic construct

<400> SEQUENCE: 108

Asn Thr Pro Ala Ser Asn Arg
1               5

<210> SEQ ID NO 109
<211> LENGTH: 7
<212> TYPE: PRT
<213> ORGANISM: artificial sequence
<220> FEATURE:
<223> OTHER INFORMATION: Synthetic construct

<400> SEQUENCE: 109

Pro Arg Gly Met Leu Ser Thr
1               5

<210> SEQ ID NO 110
<211> LENGTH: 7
<212> TYPE: PRT
<213> ORGANISM: artificial sequence
<220> FEATURE:
<223> OTHER INFORMATION: Synthetic construct

<400> SEQUENCE: 110

Pro Pro Thr Tyr Leu Ser Thr
1               5

<210> SEQ ID NO 111
<211> LENGTH: 12
<212> TYPE: PRT
<213> ORGANISM: artificial sequence
<220> FEATURE:
<223> OTHER INFORMATION: Synthetic construct

<400> SEQUENCE: 111

Thr Ile Pro Thr His Arg Gln His Asp Tyr Arg Ser
1               5                   10

<210> SEQ ID NO 112
<211> LENGTH: 7
<212> TYPE: PRT
<213> ORGANISM: artificial sequence
<220> FEATURE:
<223> OTHER INFORMATION: Synthetic construct

<400> SEQUENCE: 112

Thr Pro Pro Thr His Arg Leu
1               5

<210> SEQ ID NO 113
<211> LENGTH: 7
<212> TYPE: PRT
<213> ORGANISM: artificial sequence
<220> FEATURE:

<223> OTHER INFORMATION: Synthetic construct

<400> SEQUENCE: 113

Leu Pro Thr Met Ser Thr Pro
1               5

<210> SEQ ID NO 114
<211> LENGTH: 7
<212> TYPE: PRT
<213> ORGANISM: artificial sequence
<220> FEATURE:
<223> OTHER INFORMATION: Synthetic construct

<400> SEQUENCE: 114

Leu Gly Thr Asn Ser Thr Pro
1               5

<210> SEQ ID NO 115
<211> LENGTH: 12
<212> TYPE: PRT
<213> ORGANISM: artificial sequence
<220> FEATURE:
<223> OTHER INFORMATION: Synthetic construct

<400> SEQUENCE: 115

Thr Pro Leu Thr Gly Ser Thr Asn Leu Leu Ser Ser
1               5                   10

<210> SEQ ID NO 116
<211> LENGTH: 7
<212> TYPE: PRT
<213> ORGANISM: artificial sequence
<220> FEATURE:
<223> OTHER INFORMATION: Synthetic construct

<400> SEQUENCE: 116

Thr Pro Leu Thr Lys Glu Thr
1               5

<210> SEQ ID NO 117
<211> LENGTH: 7
<212> TYPE: PRT
<213> ORGANISM: artificial sequence
<220> FEATURE:
<223> OTHER INFORMATION: Synthetic construct

<400> SEQUENCE: 117

Lys Gln Ser His Asn Pro Pro
1               5

<210> SEQ ID NO 118
<211> LENGTH: 7
<212> TYPE: PRT
<213> ORGANISM: artificial sequence
<220> FEATURE:
<223> OTHER INFORMATION: Synthetic construct

<400> SEQUENCE: 118

Gln Gln Ser His Asn Pro Pro
1               5

<210> SEQ ID NO 119
<211> LENGTH: 7
<212> TYPE: PRT
<213> ORGANISM: artificial sequence
<220> FEATURE:
<223> OTHER INFORMATION: Synthetic construct

```
<400> SEQUENCE: 119

Thr Gln Pro His Asn Pro Pro
1               5

<210> SEQ ID NO 120
<211> LENGTH: 12
<212> TYPE: PRT
<213> ORGANISM: artificial sequence
<220> FEATURE:
<223> OTHER INFORMATION: Synthetic construct

<400> SEQUENCE: 120

Ser Thr Asn Leu Leu Arg Thr Ser Thr Val His Pro
1               5                   10

<210> SEQ ID NO 121
<211> LENGTH: 12
<212> TYPE: PRT
<213> ORGANISM: artificial sequence
<220> FEATURE:
<223> OTHER INFORMATION: Synthetic construct

<400> SEQUENCE: 121

His Thr Gln Pro Ser Tyr Ser Ser Thr Asn Leu Phe
1               5                   10

<210> SEQ ID NO 122
<211> LENGTH: 7
<212> TYPE: PRT
<213> ORGANISM: artificial sequence
<220> FEATURE:
<223> OTHER INFORMATION: Synthetic construct

<400> SEQUENCE: 122

Ser Leu Leu Ser Ser His Ala
1               5

<210> SEQ ID NO 123
<211> LENGTH: 12
<212> TYPE: PRT
<213> ORGANISM: artificial sequence
<220> FEATURE:
<223> OTHER INFORMATION: Synthetic construct

<400> SEQUENCE: 123

Gln Gln Ser Ser Ile Ser Leu Ser Ser His Ala Val
1               5                   10

<210> SEQ ID NO 124
<211> LENGTH: 7
<212> TYPE: PRT
<213> ORGANISM: artificial sequence
<220> FEATURE:
<223> OTHER INFORMATION: Synthetic construct

<400> SEQUENCE: 124

Asn Ala Ser Pro Ser Ser Leu
1               5

<210> SEQ ID NO 125
<211> LENGTH: 7
<212> TYPE: PRT
<213> ORGANISM: artificial sequence
<220> FEATURE:
<223> OTHER INFORMATION: Synthetic construct

<400> SEQUENCE: 125
```

```
His Ser Pro Ser Ser Leu Arg
1               5

<210> SEQ ID NO 126
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= H, R or N
<220> FEATURE:
<221> NAME/KEY: MISC_FEATURE
<222> LOCATION: (2)..(2)
<223> OTHER INFORMATION: X= His, Arg or Asn

<400> SEQUENCE: 126

Lys Xaa Ser His His Thr His
1               5

<210> SEQ ID NO 127
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X = H, R or N
<220> FEATURE:
<221> NAME/KEY: MISC_FEATURE
<222> LOCATION: (2)..(2)
<223> OTHER INFORMATION: X = His, Arg or Asn

<400> SEQUENCE: 127

Glu Xaa Ser His His Thr His
1               5

<210> SEQ ID NO 128
<211> LENGTH: 12
<212> TYPE: PRT
<213> ORGANISM: artificial sequence
<220> FEATURE:
<223> OTHER INFORMATION: Synthetic construct

<400> SEQUENCE: 128

Ser His His Thr His Tyr Gly Gln Pro Gly Pro Val
1               5                   10

<210> SEQ ID NO 129
<211> LENGTH: 7
<212> TYPE: PRT
<213> ORGANISM: artificial sequence
<220> FEATURE:
<223> OTHER INFORMATION: Synthetic construct

<400> SEQUENCE: 129

Leu Glu Ser Thr Ser Leu Leu
1               5

<210> SEQ ID NO 130
<211> LENGTH: 7
<212> TYPE: PRT
<213> ORGANISM: artificial sequence
<220> FEATURE:
<223> OTHER INFORMATION: Synthetic construct

<400> SEQUENCE: 130
```

Asp Leu Thr Leu Pro Phe His
1               5

<210> SEQ ID NO 131
<211> LENGTH: 8
<212> TYPE: PRT
<213> ORGANISM: artificial sequence
<220> FEATURE:
<223> OTHER INFORMATION: Synthetic construct

<400> SEQUENCE: 131

Arg Thr Asn Ala Ala Asp His Pro
1               5

<210> SEQ ID NO 132
<211> LENGTH: 12
<212> TYPE: PRT
<213> ORGANISM: artificial sequence
<220> FEATURE:
<223> OTHER INFORMATION: Synthetic construct

<400> SEQUENCE: 132

Ile Pro Trp Trp Asn Ile Arg Ala Pro Leu Asn Ala
1               5                   10

<210> SEQ ID NO 133
<211> LENGTH: 18
<212> TYPE: PRT
<213> ORGANISM: artificial sequence
<220> FEATURE:
<223> OTHER INFORMATION: Synthetic construct

<400> SEQUENCE: 133

Glu Gln Ile Ser Gly Ser Leu Val Ala Ala Pro Trp Glu Gly Glu Gly
1               5                   10                  15

Glu Arg

<210> SEQ ID NO 134
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 134

Thr Pro Pro Glu Leu Leu His Gly Ala Pro Arg Ser
1               5                   10

<210> SEQ ID NO 135
<211> LENGTH: 18
<212> TYPE: PRT
<213> ORGANISM: artificial sequence
<220> FEATURE:
<223> OTHER INFORMATION: Synthetic construct

<400> SEQUENCE: 135

Leu Asp Thr Ser Phe His Gln Val Pro Phe His Gln Lys Arg Lys Arg
1               5                   10                  15

Lys Asp

<210> SEQ ID NO 136
<211> LENGTH: 18
<212> TYPE: PRT
<213> ORGANISM: artificial sequence
<220> FEATURE:
<223> OTHER INFORMATION: Synthetic construct

<400> SEQUENCE: 136

Glu Gln Ile Ser Gly Ser Leu Val Ala Ala Pro Trp Lys Arg Lys Arg
1               5                   10                  15

Lys Asp

<210> SEQ ID NO 137
<211> LENGTH: 18
<212> TYPE: PRT
<213> ORGANISM: artificial sequence
<220> FEATURE:
<223> OTHER INFORMATION: Synthetic construct

<400> SEQUENCE: 137

Thr Pro Pro Glu Leu Leu His Gly Asp Pro Arg Ser Lys Arg Lys Arg
1               5                   10                  15

Lys Asp

<210> SEQ ID NO 138
<211> LENGTH: 13
<212> TYPE: PRT
<213> ORGANISM: artificial sequence
<220> FEATURE:
<223> OTHER INFORMATION: Synthetic construct

<400> SEQUENCE: 138

Asn Thr Ser Gln Leu Ser Thr Glu Gly Glu Gly Glu Asp
1               5                   10

<210> SEQ ID NO 139
<211> LENGTH: 13
<212> TYPE: PRT
<213> ORGANISM: artificial sequence
<220> FEATURE:
<223> OTHER INFORMATION: Synthetic construct

<400> SEQUENCE: 139

Thr Pro Pro Glu Leu Leu His Gly Asp Pro Arg Ser Cys
1               5                   10

<210> SEQ ID NO 140
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 140

His Ile Asn Lys Thr Asn Pro His Gln Gly Asn His His Ser Glu Lys
1               5                   10                  15

Thr Gln Arg Gln
            20

<210> SEQ ID NO 141
<211> LENGTH: 15
<212> TYPE: PRT
<213> ORGANISM: artificial sequence
<220> FEATURE:
<223> OTHER INFORMATION: Synthetic construct

<400> SEQUENCE: 141

His Ala His Lys Asn Gln Lys Glu Thr His Gln Arg His Ala Ala
1               5                   10                  15

<210> SEQ ID NO 142

```
<211> LENGTH: 15
<212> TYPE: PRT
<213> ORGANISM: artificial sequence
<220> FEATURE:
<223> OTHER INFORMATION: Synthetic construct

<400> SEQUENCE: 142

His Glu His Lys Asn Gln Lys Glu Thr His Gln Arg His Ala Ala
1               5                   10                  15

<210> SEQ ID NO 143
<211> LENGTH: 20
<212> TYPE: PRT
<213> ORGANISM: artificial sequence
<220> FEATURE:
<223> OTHER INFORMATION: Synthetic construct

<400> SEQUENCE: 143

His Asn His Met Gln Glu Arg Tyr Thr Glu Pro Gln His Ser Pro Ser
1               5                   10                  15

Val Asn Gly Leu
            20

<210> SEQ ID NO 144
<211> LENGTH: 17
<212> TYPE: PRT
<213> ORGANISM: artificial sequence
<220> FEATURE:
<223> OTHER INFORMATION: Synthetic construct

<400> SEQUENCE: 144

Thr His Ser Thr His Asn His Gly Ser Pro Arg His Thr Asn Ala Asp
1               5                   10                  15

Ala

<210> SEQ ID NO 145
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 145

Gly Ser Cys Val Asp Thr His Lys Ala Asp Ser Cys Val Ala Asn Asn
1               5                   10                  15

Gly Pro Ala Thr
            20

<210> SEQ ID NO 146
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 146

Ala Gln Ser Gln Leu Pro Asp Lys His Ser Gly Leu His Glu Arg Ala
1               5                   10                  15

Pro Gln Arg Tyr
            20

<210> SEQ ID NO 147
<211> LENGTH: 20
<212> TYPE: PRT
<213> ORGANISM: artificial sequence
<220> FEATURE:
```

<223> OTHER INFORMATION: Synthetic construct

<400> SEQUENCE: 147

Ala Gln Ser Gln Leu Pro Ala Lys His Ser Gly Leu His Glu Arg Ala
1               5                   10                  15

Pro Gln Arg Tyr
            20

<210> SEQ ID NO 148
<211> LENGTH: 20
<212> TYPE: PRT
<213> ORGANISM: artificial sequence
<220> FEATURE:
<223> OTHER INFORMATION: Synthetic construct

<400> SEQUENCE: 148

Ala Gln Ser Gln Leu Pro Glu Lys His Ser Gly Leu His Glu Arg Ala
1               5                   10                  15

Pro Gln Arg Tyr
            20

<210> SEQ ID NO 149
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 149

Thr Asp Met Met His Asn His Ser Asp Asn Ser Pro Pro His Arg Arg
1               5                   10                  15

Ser Pro Arg Asn
            20

<210> SEQ ID NO 150
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 150

Thr Pro Pro Glu Leu Ala His Thr Pro His His Leu Ala Gln Thr Arg
1               5                   10                  15

Leu Thr Asp Arg
            20

<210> SEQ ID NO 151
<211> LENGTH: 12
<212> TYPE: PRT
<213> ORGANISM: artificial sequence
<220> FEATURE:
<223> OTHER INFORMATION: Synthetic construct

<400> SEQUENCE: 151

Arg Leu Leu Arg Leu Leu Arg Leu Leu Arg Leu Leu
1               5                   10

<210> SEQ ID NO 152
<211> LENGTH: 12
<212> TYPE: PRT
<213> ORGANISM: artificial sequence
<220> FEATURE:
<223> OTHER INFORMATION: Synthetic construct

<400> SEQUENCE: 152

```
Thr Pro Pro Glu Leu Leu His Gly Glu Pro Arg Ser
1               5                   10
```

<210> SEQ ID NO 153
<211> LENGTH: 12
<212> TYPE: PRT
<213> ORGANISM: artificial sequence
<220> FEATURE:
<223> OTHER INFORMATION: Synthetic construct

<400> SEQUENCE: 153

```
Thr Pro Pro Glu Leu Leu His Gly Ala Pro Arg Ser
1               5                   10
```

<210> SEQ ID NO 154
<211> LENGTH: 12
<212> TYPE: PRT
<213> ORGANISM: artificial sequence
<220> FEATURE:
<223> OTHER INFORMATION: Synthetic construct

<400> SEQUENCE: 154

```
Glu Gln Ile Ser Gly Ser Leu Val Ala Ala Pro Trp
1               5                   10
```

<210> SEQ ID NO 155
<211> LENGTH: 12
<212> TYPE: PRT
<213> ORGANISM: artificial sequence
<220> FEATURE:
<223> OTHER INFORMATION: Synthetic construct

<400> SEQUENCE: 155

```
Asn Glu Val Pro Ala Arg Asn Ala Pro Trp Leu Val
1               5                   10
```

<210> SEQ ID NO 156
<211> LENGTH: 13
<212> TYPE: PRT
<213> ORGANISM: artificial sequence
<220> FEATURE:
<223> OTHER INFORMATION: Synthetic construct

<400> SEQUENCE: 156

```
Asn Ser Pro Gly Tyr Gln Ala Asp Ser Val Ala Ile Gly
1               5                   10
```

<210> SEQ ID NO 157
<211> LENGTH: 12
<212> TYPE: PRT
<213> ORGANISM: artificial sequence
<220> FEATURE:
<223> OTHER INFORMATION: Synthetic construct

<400> SEQUENCE: 157

```
Ala Lys Pro Ile Ser Gln His Leu Gln Arg Gly Ser
1               5                   10
```

<210> SEQ ID NO 158
<211> LENGTH: 12
<212> TYPE: PRT
<213> ORGANISM: artificial sequence
<220> FEATURE:
<223> OTHER INFORMATION: Synthetic construct

<400> SEQUENCE: 158

```
Leu Asp Thr Ser Phe Pro Pro Val Pro Phe His Ala
```

<210> SEQ ID NO 159
<211> LENGTH: 12
<212> TYPE: PRT
<213> ORGANISM: artificial sequence
<220> FEATURE:
<223> OTHER INFORMATION: Synthetic construct

<400> SEQUENCE: 159

Ser Leu Asn Trp Val Thr Ile Pro Gly Pro Lys Ile
1               5                   10

<210> SEQ ID NO 160
<211> LENGTH: 12
<212> TYPE: PRT
<213> ORGANISM: artificial sequence
<220> FEATURE:
<223> OTHER INFORMATION: Synthetic construct

<400> SEQUENCE: 160

Thr Gln Asp Ser Ala Gln Lys Ser Pro Ser Pro Leu
1               5                   10

<210> SEQ ID NO 161
<211> LENGTH: 12
<212> TYPE: PRT
<213> ORGANISM: artificial sequence
<220> FEATURE:
<223> OTHER INFORMATION: Synthetic construct

<400> SEQUENCE: 161

Lys Glu Leu Gln Thr Arg Asn Val Val Gln Arg Glu
1               5                   10

<210> SEQ ID NO 162
<211> LENGTH: 12
<212> TYPE: PRT
<213> ORGANISM: artificial sequence
<220> FEATURE:
<223> OTHER INFORMATION: Synthetic construct

<400> SEQUENCE: 162

Gln Arg Asn Ser Pro Ala Met Ser Arg Arg Asp
1               5                   10

<210> SEQ ID NO 163
<211> LENGTH: 12
<212> TYPE: PRT
<213> ORGANISM: artificial sequence
<220> FEATURE:
<223> OTHER INFORMATION: Synthetic construct

<400> SEQUENCE: 163

Thr Pro Thr Ala Asn Gln Phe Thr Gln Ser Val Pro
1               5                   10

<210> SEQ ID NO 164
<211> LENGTH: 12
<212> TYPE: PRT
<213> ORGANISM: artificial sequence
<220> FEATURE:
<223> OTHER INFORMATION: Synthetic construct

<400> SEQUENCE: 164

Ala Ala Gly Leu Ser Gln Lys His Glu Arg Asn Arg
1               5                   10

<210> SEQ ID NO 165
<211> LENGTH: 12
<212> TYPE: PRT
<213> ORGANISM: artificial sequence
<220> FEATURE:
<223> OTHER INFORMATION: Synthetic construct

<400> SEQUENCE: 165

Glu Thr Val His Gln Thr Pro Leu Ser Asp Arg Pro
1               5                   10

<210> SEQ ID NO 166
<211> LENGTH: 12
<212> TYPE: PRT
<213> ORGANISM: artificial sequence
<220> FEATURE:
<223> OTHER INFORMATION: Synthetic construct

<400> SEQUENCE: 166

Lys Asn Phe Pro Gln Gln Lys Glu Phe Pro Leu Ser
1               5                   10

<210> SEQ ID NO 167
<211> LENGTH: 12
<212> TYPE: PRT
<213> ORGANISM: artificial sequence
<220> FEATURE:
<223> OTHER INFORMATION: Synthetic construct

<400> SEQUENCE: 167

Leu Pro Ala Leu His Ile Gln Arg His Pro Arg Met
1               5                   10

<210> SEQ ID NO 168
<211> LENGTH: 12
<212> TYPE: PRT
<213> ORGANISM: artificial sequence
<220> FEATURE:
<223> OTHER INFORMATION: Synthetic construct

<400> SEQUENCE: 168

Gln Pro Ser His Ser Gln Ser His Asn Leu Arg Ser
1               5                   10

<210> SEQ ID NO 169
<211> LENGTH: 12
<212> TYPE: PRT
<213> ORGANISM: artificial sequence
<220> FEATURE:
<223> OTHER INFORMATION: Synthetic construct

<400> SEQUENCE: 169

Arg Gly Ser Gln Lys Ser Lys Pro Pro Arg Pro Pro
1               5                   10

<210> SEQ ID NO 170
<211> LENGTH: 12
<212> TYPE: PRT
<213> ORGANISM: artificial sequence
<220> FEATURE:
<223> OTHER INFORMATION: Synthetic construct

<400> SEQUENCE: 170

Thr His Thr Gln Lys Thr Pro Leu Leu Tyr Tyr His
1               5                   10

<210> SEQ ID NO 171

```
<211> LENGTH: 12
<212> TYPE: PRT
<213> ORGANISM: artificial sequence
<220> FEATURE:
<223> OTHER INFORMATION: Synthetic construct

<400> SEQUENCE: 171

Thr Lys Gly Ser Ser Gln Ala Ile Leu Lys Ser Thr
1               5                   10

<210> SEQ ID NO 172
<211> LENGTH: 7
<212> TYPE: PRT
<213> ORGANISM: artificial sequence
<220> FEATURE:
<223> OTHER INFORMATION: Synthetic construct

<400> SEQUENCE: 172

Thr Ala Ala Thr Thr Ser Pro
1               5

<210> SEQ ID NO 173
<211> LENGTH: 7
<212> TYPE: PRT
<213> ORGANISM: artificial sequence
<220> FEATURE:
<223> OTHER INFORMATION: Synthetic construct

<400> SEQUENCE: 173

Leu Gly Ile Pro Gln Asn Leu
1               5

<210> SEQ ID NO 174
<211> LENGTH: 20
<212> TYPE: PRT
<213> ORGANISM: artificial sequence
<220> FEATURE:
<223> OTHER INFORMATION: Synthetic construct

<400> SEQUENCE: 174

Thr His Ser Thr His Asn His Gly Ser Pro Arg His Thr Asn Ala Asp
1               5                   10                  15

Ala Gly Asn Pro
            20

<210> SEQ ID NO 175
<211> LENGTH: 20
<212> TYPE: PRT
<213> ORGANISM: artificial sequence
<220> FEATURE:
<223> OTHER INFORMATION: Synthetic construct

<400> SEQUENCE: 175

Gln Gln His Lys Val His His Gln Asn Pro Asp Arg Ser Thr Gln Asp
1               5                   10                  15

Ala His His Ser
            20

<210> SEQ ID NO 176
<211> LENGTH: 15
<212> TYPE: PRT
<213> ORGANISM: artificial sequence
<220> FEATURE:
<223> OTHER INFORMATION: Synthetic construct

<400> SEQUENCE: 176

His His Gly Thr His His Asn Ala Thr Lys Gln Lys Asn His Val
```

```
1               5                   10                  15
```

<210> SEQ ID NO 177
<211> LENGTH: 15
<212> TYPE: PRT
<213> ORGANISM: artificial sequence
<220> FEATURE:
<223> OTHER INFORMATION: Synthetic construct

<400> SEQUENCE: 177

```
Ser Thr Leu His Lys Tyr Lys Ser Gln Asp Pro Thr Pro His His
1               5                   10                  15
```

<210> SEQ ID NO 178
<211> LENGTH: 12
<212> TYPE: PRT
<213> ORGANISM: artificial sequence
<220> FEATURE:
<223> OTHER INFORMATION: Synthetic construct

<400> SEQUENCE: 178

```
Ser Val Ser Val Gly Met Lys Pro Ser Pro Arg Pro
1               5                   10
```

<210> SEQ ID NO 179
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 179

```
Thr Pro Pro Thr Asn Val Leu Met Leu Ala Thr Lys
1               5                   10
```

<210> SEQ ID NO 180
<211> LENGTH: 12
<212> TYPE: PRT
<213> ORGANISM: artificial sequence
<220> FEATURE:
<223> OTHER INFORMATION: Synthetic construct

<400> SEQUENCE: 180

```
Thr Pro Pro Glu Leu Leu His Gly Asp Pro Arg Ser
1               5                   10
```

<210> SEQ ID NO 181
<211> LENGTH: 7
<212> TYPE: PRT
<213> ORGANISM: artificial sequence
<220> FEATURE:
<223> OTHER INFORMATION: synthetic hair-binding peptide

<400> SEQUENCE: 181

```
Asn Thr Ser Gln Leu Ser Thr
1               5
```

<210> SEQ ID NO 182
<211> LENGTH: 15
<212> TYPE: PRT
<213> ORGANISM: artificial sequence
<220> FEATURE:
<223> OTHER INFORMATION: Synthetic construct

<400> SEQUENCE: 182

```
Ser Thr Leu His Lys Tyr Lys Ser Gln Asp Pro Thr Pro His His
1               5                   10                  15
```

-continued

```
<210> SEQ ID NO 183
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 183

Gly Met Pro Ala Met His Trp Ile His Pro Phe Ala
1               5                   10

<210> SEQ ID NO 184
<211> LENGTH: 15
<212> TYPE: PRT
<213> ORGANISM: artificial sequence
<220> FEATURE:
<223> OTHER INFORMATION: synthetic hair-binding peptide

<400> SEQUENCE: 184

His Asp His Lys Asn Gln Lys Glu Thr His Gln Arg His Ala Ala
1               5                   10                  15

<210> SEQ ID NO 185
<211> LENGTH: 20
<212> TYPE: PRT
<213> ORGANISM: artificial sequence
<220> FEATURE:
<223> OTHER INFORMATION: Synthetic construct

<400> SEQUENCE: 185

His Asn His Met Gln Glu Arg Tyr Thr Asp Pro Gln His Ser Pro Ser
1               5                   10                  15

Val Asn Gly Leu
            20

<210> SEQ ID NO 186
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 186

Thr Ala Glu Ile Gln Ser Ser Lys Asn Pro Asn Pro His Pro Gln Arg
1               5                   10                  15

Ser Trp Thr Asn
            20

<210> SEQ ID NO 187
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 187

Ser Ser Ala Asp Phe Ala Ser Phe Gly Phe Phe Gly Phe Ser Ala Ala
1               5                   10                  15

Ser Ala Asp Ser Arg
            20

<210> SEQ ID NO 188
<211> LENGTH: 23
<212> TYPE: PRT
<213> ORGANISM: artificial sequence
<220> FEATURE:
```

<223> OTHER INFORMATION: Dyed-hair-bindg peptide

<400> SEQUENCE: 188

Ser Ser Phe Ala Glu Ala Trp Ser Arg Ala Trp Pro Arg Ala Glu Val
1               5                   10                  15

Phe Phe Pro Ser Arg Gly Tyr
            20

<210> SEQ ID NO 189
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 189

Ser Ser Phe Ser Val Asn Glu Pro His Ala Trp Met Ala Pro Leu Ser
1               5                   10                  15

Arg

<210> SEQ ID NO 190
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 190

Ser Ser Phe Ser Trp Val Tyr Gly His Gly Gly Leu Gly Phe Ala Ser
1               5                   10                  15

Arg

<210> SEQ ID NO 191
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 191

Ser Ser Phe Val Ser Trp Ser Pro Tyr Lys Ser Pro Pro Glu Leu Ser
1               5                   10                  15

Arg

<210> SEQ ID NO 192
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 192

Ser Ser Phe Tyr Gly Ser Ser Ala Phe Val Ser Ser Gly Val Ser Val
1               5                   10                  15

Ala Tyr Gly Ser Arg
            20

<210> SEQ ID NO 193
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 193

```
Ser Ser Gly Ser Val Ala Val Ser Ala Glu Ala Ser Trp Phe Ser Gly
1               5                   10                  15

Val Ala Ala Ser Arg
            20

<210> SEQ ID NO 194
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 194

Ser Ser His Asp Glu His Tyr Gln Tyr His Tyr Tyr Ser Ser Arg
1               5                   10                  15

<210> SEQ ID NO 195
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 195

Ser Ser His Tyr Tyr Tyr Asn Asp Tyr Asp His Gln Ser Ser Arg
1               5                   10                  15

<210> SEQ ID NO 196
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 196

Ser Ser Leu Phe Asn Met Tyr Gly His Gln Ser Val Leu Gly Pro Ser
1               5                   10                  15

Arg

<210> SEQ ID NO 197
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 197

Ser Ser Leu Phe Ser Asp Val His Tyr Gly Ser Asn Lys Ala Leu Ser
1               5                   10                  15

Arg

<210> SEQ ID NO 198
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 198

Ser Ser Leu Leu Ser Asp Phe His Tyr Gly Asp Met Trp Asp Ala Ser
1               5                   10                  15

Arg

<210> SEQ ID NO 199
```

```
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 199

Ser Ser Asn Tyr Asn Tyr Asn Tyr Asn Tyr Gln Tyr Ser Ser Arg
1               5                   10                  15

<210> SEQ ID NO 200
<211> LENGTH: 21
<212> TYPE: PRT
<213> ORGANISM: artificial sequence
<220> FEATURE:
<223> OTHER INFORMATION: synethetic construct

<400> SEQUENCE: 200

Ser Ser Asn Tyr Asn Tyr Asn Tyr Asn Tyr Gln Tyr Ser Ser Arg Glu
1               5                   10                  15

Gly Glu Gly Glu Arg
            20

<210> SEQ ID NO 201
<211> LENGTH: 21
<212> TYPE: PRT
<213> ORGANISM: ARTIFICIAL SEQUENCE
<220> FEATURE:
<223> OTHER INFORMATION: Synthetic construct

<400> SEQUENCE: 201

Ser Ser Asn Tyr Asn Tyr Asn Tyr Asn Tyr Gln Tyr Ser Ser Arg Lys
1               5                   10                  15

Arg Lys Arg Lys Asp
            20

<210> SEQ ID NO 202
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 202

Ser Ser Gln Tyr Tyr Gln Asp Tyr Gln Tyr Tyr His Ser Ser Arg
1               5                   10                  15

<210> SEQ ID NO 203
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 203

Ser Ser Ser Cys Met Gly Ser His Asn Pro Arg Met Ser Val Glu Glu
1               5                   10                  15

Ser Thr Arg Asn Cys Ser Arg
            20

<210> SEQ ID NO 204
<211> LENGTH: 23
<212> TYPE: PRT
<213> ORGANISM: artificial sequence
<220> FEATURE:
<223> OTHER INFORMATION: Dyed-hair-bindg peptide
```

-continued

```
<400> SEQUENCE: 204

Ser Ser Ser Cys Asn Asn Asn Trp Phe Tyr Ser Ser Thr Leu Pro Gly
1               5                   10                  15

Gly Asp His Ala Cys Ser Arg
            20

<210> SEQ ID NO 205
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 205

Ser Ser Ser Cys Tyr Asp Val Glu Cys Ser Ser Phe Val Ala Trp Met
1               5                   10                  15

Arg Gly Pro Ser Ser Ser Arg
            20

<210> SEQ ID NO 206
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 206

Ser Ser Ser Phe Ala Ala Ser Ser Ala Phe Ser Phe Leu Val Asp Ala
1               5                   10                  15

Val Ala Trp Ser Arg
            20

<210> SEQ ID NO 207
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 207

Ser Ser Ser Phe Ala Tyr Leu Val Pro Asp Asp Gly Trp Leu Ser Ser
1               5                   10                  15

Arg

<210> SEQ ID NO 208
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 208

Ser Ser Ser Gly Ala Val Phe Ser Gly Gly Ala Asp Ala Gly Trp
1               5                   10                  15

Gly Val Trp Ser Arg
            20

<210> SEQ ID NO 209
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 209
```

```
Ser Ser Ser Ser Ala Asp Ala Ala Tyr Gly His Cys Cys Gly Ala Gly
1               5                   10                  15

Phe Ser Thr Phe Ser Ser Arg
            20
```

<210> SEQ ID NO 210
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 210

```
Ser Ser Ser Ser Asp Val His Asn Ser Ile Ile Gly Trp Asp Phe Tyr
1               5                   10                  15

His Ser Arg Gly Ser Ser Arg
            20
```

<210> SEQ ID NO 211
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 211

```
Ser Ser Ser Ser Leu Asp Phe Phe Ser Tyr Ser Ala Phe Ser Gly Gly
1               5                   10                  15

Val Ala Glu Ser Arg
            20
```

<210> SEQ ID NO 212
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 212

```
Ser Ser Ser Ser Asn Asp Ser Asn Val Ser Trp Phe His Tyr Tyr Ala
1               5                   10                  15

Ser Gly Leu Thr Ser Ser Arg
            20
```

<210> SEQ ID NO 213
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 213

```
Ser Ser Val Asp Tyr Glu Val Pro Leu Ala Val Ala Ala Glu Trp Gly
1               5                   10                  15

Phe Ser Val Ser Arg
            20
```

<210> SEQ ID NO 214
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 214

```
Ser Ser Tyr His Tyr Asp Tyr Asp His Tyr Tyr Glu Ser Ser Arg
1               5                   10                  15
```

<210> SEQ ID NO 215
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 215

```
Ser Ser Tyr Tyr Asn Tyr His Tyr Gln Tyr Gln Asp Ser Ser Arg
1               5                   10                  15
```

<210> SEQ ID NO 216
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 216

```
Ser Ser Tyr Tyr Tyr Asp Tyr Tyr Gln Gln Asp Tyr Ser Ser Arg
1               5                   10                  15
```

<210> SEQ ID NO 217
<211> LENGTH: 12
<212> TYPE: PRT
<213> ORGANISM: artificial sequence
<220> FEATURE:
<223> OTHER INFORMATION: Synthetic construct

<400> SEQUENCE: 217

```
Lys Arg Gly Arg His Lys Arg Pro Lys Arg His Lys
1               5                   10
```

<210> SEQ ID NO 218
<211> LENGTH: 7
<212> TYPE: PRT
<213> ORGANISM: artificial sequence
<220> FEATURE:
<223> OTHER INFORMATION: Synthetic construct

<400> SEQUENCE: 218

```
Arg Leu Leu Arg Leu Leu Arg
1               5
```

<210> SEQ ID NO 219
<211> LENGTH: 12
<212> TYPE: PRT
<213> ORGANISM: artificial sequence
<220> FEATURE:
<223> OTHER INFORMATION: Synthetic construct

<400> SEQUENCE: 219

```
His Lys Pro Arg Gly Gly Arg Lys Lys Ala Leu His
1               5                   10
```

<210> SEQ ID NO 220
<211> LENGTH: 18
<212> TYPE: PRT
<213> ORGANISM: artificial sequence
<220> FEATURE:
<223> OTHER INFORMATION: Synthetic construct

<400> SEQUENCE: 220

```
Lys Pro Arg Pro Pro His Gly Lys Lys His Arg Pro Lys His Arg Pro
```

```
1               5                   10                  15
Lys Lys

<210> SEQ ID NO 221
<211> LENGTH: 18
<212> TYPE: PRT
<213> ORGANISM: artificial sequence
<220> FEATURE:
<223> OTHER INFORMATION: Synthetic construct

<400> SEQUENCE: 221

Arg Gly Arg Pro Lys Lys Gly His Gly Lys Arg Pro Gly His Arg Ala
1               5                   10                  15

Arg Lys

<210> SEQ ID NO 222
<211> LENGTH: 12
<212> TYPE: PRT
<213> ORGANISM: artificial sequence
<220> FEATURE:
<223> OTHER INFORMATION: Synthetic construct

<400> SEQUENCE: 222

Thr Pro Phe His Ser Pro Glu Asn Ala Pro Gly Ser
1               5                   10

<210> SEQ ID NO 223
<211> LENGTH: 13
<212> TYPE: PRT
<213> ORGANISM: artificial sequence
<220> FEATURE:
<223> OTHER INFORMATION: Synthetic construct

<400> SEQUENCE: 223

Thr Pro Phe His Ser Pro Glu Asn Ala Pro Gly Ser Lys
1               5                   10

<210> SEQ ID NO 224
<211> LENGTH: 16
<212> TYPE: PRT
<213> ORGANISM: artificial sequence
<220> FEATURE:
<223> OTHER INFORMATION: Synthetic construct

<400> SEQUENCE: 224

Thr Pro Phe His Ser Pro Glu Asn Ala Pro Gly Ser Gly Gly Gly Ser
1               5                   10                  15

<210> SEQ ID NO 225
<211> LENGTH: 17
<212> TYPE: PRT
<213> ORGANISM: artificial sequence
<220> FEATURE:
<223> OTHER INFORMATION: Synthetic construct

<400> SEQUENCE: 225

Thr Pro Phe His Ser Pro Glu Asn Ala Pro Gly Ser Gly Gly Gly Ser
1               5                   10                  15

Ser

<210> SEQ ID NO 226
<211> LENGTH: 15
<212> TYPE: PRT
<213> ORGANISM: artificial sequence
<220> FEATURE:
<223> OTHER INFORMATION: Synthetic construct
```

```
<400> SEQUENCE: 226

Thr Pro Phe His Ser Pro Glu Asn Ala Pro Gly Ser Gly Gly Gly
1               5                   10                  15

<210> SEQ ID NO 227
<211> LENGTH: 7
<212> TYPE: PRT
<213> ORGANISM: artificial sequence
<220> FEATURE:
<223> OTHER INFORMATION: Synthetic construct

<400> SEQUENCE: 227

Phe Thr Gln Ser Leu Pro Arg
1               5

<210> SEQ ID NO 228
<211> LENGTH: 12
<212> TYPE: PRT
<213> ORGANISM: artificial sequence
<220> FEATURE:
<223> OTHER INFORMATION: Synthetic construct

<400> SEQUENCE: 228

Lys Gln Ala Thr Phe Pro Pro Asn Pro Thr Ala Tyr
1               5                   10

<210> SEQ ID NO 229
<211> LENGTH: 12
<212> TYPE: PRT
<213> ORGANISM: artificial sequence
<220> FEATURE:
<223> OTHER INFORMATION: Synthetic construct

<400> SEQUENCE: 229

His Gly His Met Val Ser Thr Ser Gln Leu Ser Ile
1               5                   10

<210> SEQ ID NO 230
<211> LENGTH: 7
<212> TYPE: PRT
<213> ORGANISM: artificial sequence
<220> FEATURE:
<223> OTHER INFORMATION: Synthetic construct

<400> SEQUENCE: 230

Leu Ser Pro Ser Arg Met Lys
1               5

<210> SEQ ID NO 231
<211> LENGTH: 7
<212> TYPE: PRT
<213> ORGANISM: artificial sequence
<220> FEATURE:
<223> OTHER INFORMATION: Synthetic construct

<400> SEQUENCE: 231

Leu Pro Ile Pro Arg Met Lys
1               5

<210> SEQ ID NO 232
<211> LENGTH: 7
<212> TYPE: PRT
<213> ORGANISM: artificial sequence
<220> FEATURE:
<223> OTHER INFORMATION: Synthetic construct

<400> SEQUENCE: 232
```

His Gln Arg Pro Tyr Leu Thr
1               5

<210> SEQ ID NO 233
<211> LENGTH: 7
<212> TYPE: PRT
<213> ORGANISM: artificial sequence
<220> FEATURE:
<223> OTHER INFORMATION: Synthetic construct

<400> SEQUENCE: 233

Phe Pro Pro Leu Leu Arg Leu
1               5

<210> SEQ ID NO 234
<211> LENGTH: 7
<212> TYPE: PRT
<213> ORGANISM: artificial sequence
<220> FEATURE:
<223> OTHER INFORMATION: Synthetic construct

<400> SEQUENCE: 234

Gln Ala Thr Phe Met Tyr Asn
1               5

<210> SEQ ID NO 235
<211> LENGTH: 11
<212> TYPE: PRT
<213> ORGANISM: artificial sequence
<220> FEATURE:
<223> OTHER INFORMATION: Synthetic construct

<400> SEQUENCE: 235

Val Leu Thr Ser Gln Leu Pro Asn His Ser Met
1               5                   10

<210> SEQ ID NO 236
<211> LENGTH: 7
<212> TYPE: PRT
<213> ORGANISM: artificial sequence
<220> FEATURE:
<223> OTHER INFORMATION: Synthetic construct

<400> SEQUENCE: 236

His Ser Thr Ala Tyr Leu Thr
1               5

<210> SEQ ID NO 237
<211> LENGTH: 12
<212> TYPE: PRT
<213> ORGANISM: artificial sequence
<220> FEATURE:
<223> OTHER INFORMATION: Synthetic construct

<400> SEQUENCE: 237

Ala Pro Gln Gln Arg Pro Met Lys Thr Phe Asn Thr
1               5                   10

<210> SEQ ID NO 238
<211> LENGTH: 12
<212> TYPE: PRT
<213> ORGANISM: artificial sequence
<220> FEATURE:
<223> OTHER INFORMATION: Synthetic construct

<400> SEQUENCE: 238

Ala Pro Gln Gln Arg Pro Met Lys Thr Val Gln Tyr

-continued

```
1               5                   10
```

<210> SEQ ID NO 239
<211> LENGTH: 7
<212> TYPE: PRT
<213> ORGANISM: artificial sequence
<220> FEATURE:
<223> OTHER INFORMATION: Synthetic construct

<400> SEQUENCE: 239

```
Pro Pro Trp Leu Asp Leu Leu
1               5
```

<210> SEQ ID NO 240
<211> LENGTH: 7
<212> TYPE: PRT
<213> ORGANISM: artificial sequence
<220> FEATURE:
<223> OTHER INFORMATION: Synthetic construct

<400> SEQUENCE: 240

```
Pro Pro Trp Thr Phe Pro Leu
1               5
```

<210> SEQ ID NO 241
<211> LENGTH: 7
<212> TYPE: PRT
<213> ORGANISM: artificial sequence
<220> FEATURE:
<223> OTHER INFORMATION: Synthetic construct

<400> SEQUENCE: 241

```
Ser Val Thr His Leu Thr Ser
1               5
```

<210> SEQ ID NO 242
<211> LENGTH: 7
<212> TYPE: PRT
<213> ORGANISM: artificial sequence
<220> FEATURE:
<223> OTHER INFORMATION: Synthetic construct

<400> SEQUENCE: 242

```
Val Ile Thr Arg Leu Thr Ser
1               5
```

<210> SEQ ID NO 243
<211> LENGTH: 12
<212> TYPE: PRT
<213> ORGANISM: artificial sequence
<220> FEATURE:
<223> OTHER INFORMATION: Synthetic construct

<400> SEQUENCE: 243

```
Asp Leu Lys Pro Pro Leu Leu Ala Leu Ser Lys Val
1               5                   10
```

<210> SEQ ID NO 244
<211> LENGTH: 12
<212> TYPE: PRT
<213> ORGANISM: artificial sequence
<220> FEATURE:
<223> OTHER INFORMATION: Synthetic construct

<400> SEQUENCE: 244

```
Ser His Pro Ser Gly Ala Leu Gln Glu Gly Thr Phe
1               5                   10
```

<210> SEQ ID NO 245
<211> LENGTH: 12
<212> TYPE: PRT
<213> ORGANISM: artificial sequence
<220> FEATURE:
<223> OTHER INFORMATION: Synthetic construct

<400> SEQUENCE: 245

Phe Pro Leu Thr Ser Lys Pro Ser Gly Ala Cys Thr
1               5                   10

<210> SEQ ID NO 246
<211> LENGTH: 12
<212> TYPE: PRT
<213> ORGANISM: artificial sequence
<220> FEATURE:
<223> OTHER INFORMATION: Synthetic construct

<400> SEQUENCE: 246

Asp Leu Lys Pro Pro Leu Leu Ala Leu Ser Lys Val
1               5                   10

<210> SEQ ID NO 247
<211> LENGTH: 7
<212> TYPE: PRT
<213> ORGANISM: artificial sequence
<220> FEATURE:
<223> OTHER INFORMATION: Synthetic construct

<400> SEQUENCE: 247

Pro Leu Leu Ala Leu His Ser
1               5

<210> SEQ ID NO 248
<211> LENGTH: 7
<212> TYPE: PRT
<213> ORGANISM: artificial sequence
<220> FEATURE:
<223> OTHER INFORMATION: Synthetic construct

<400> SEQUENCE: 248

Val Pro Ile Ser Thr Gln Ile
1               5

<210> SEQ ID NO 249
<211> LENGTH: 12
<212> TYPE: PRT
<213> ORGANISM: artificial sequence
<220> FEATURE:
<223> OTHER INFORMATION: Synthetic construct

<400> SEQUENCE: 249

Tyr Ala Lys Gln His Tyr Pro Ile Ser Thr Phe Lys
1               5                   10

<210> SEQ ID NO 250
<211> LENGTH: 7
<212> TYPE: PRT
<213> ORGANISM: artificial sequence
<220> FEATURE:
<223> OTHER INFORMATION: Synthetic construct

<400> SEQUENCE: 250

His Ser Thr Ala Tyr Leu Thr
1               5

<210> SEQ ID NO 251

```
<211> LENGTH: 12
<212> TYPE: PRT
<213> ORGANISM: artificial sequence
<220> FEATURE:
<223> OTHER INFORMATION: Synthetic construct

<400> SEQUENCE: 251

Ser Thr Ala Tyr Leu Val Ala Met Ser Ala Ala Pro
1               5                   10

<210> SEQ ID NO 252
<211> LENGTH: 12
<212> TYPE: PRT
<213> ORGANISM: artificial sequence
<220> FEATURE:
<223> OTHER INFORMATION: Synthetic construct

<400> SEQUENCE: 252

Ser Val Ser Val Gly Met Lys Pro Ser Pro Arg Pro
1               5                   10

<210> SEQ ID NO 253
<211> LENGTH: 12
<212> TYPE: PRT
<213> ORGANISM: artificial sequence
<220> FEATURE:
<223> OTHER INFORMATION: Synthetic construct

<400> SEQUENCE: 253

Thr Met Gly Phe Thr Ala Pro Arg Phe Pro His Tyr
1               5                   10

<210> SEQ ID NO 254
<211> LENGTH: 12
<212> TYPE: PRT
<213> ORGANISM: artificial sequence
<220> FEATURE:
<223> OTHER INFORMATION: Synthetic construct

<400> SEQUENCE: 254

Asn Leu Gln His Ser Val Gly Thr Ser Pro Val Trp
1               5                   10

<210> SEQ ID NO 255
<211> LENGTH: 15
<212> TYPE: PRT
<213> ORGANISM: artificial sequence
<220> FEATURE:
<223> OTHER INFORMATION: Synthetic construct

<400> SEQUENCE: 255

Gln Leu Ser Tyr His Ala Tyr Pro Gln Ala Asn His His Ala Pro
1               5                   10                  15

<210> SEQ ID NO 256
<211> LENGTH: 12
<212> TYPE: PRT
<213> ORGANISM: artificial sequence
<220> FEATURE:
<223> OTHER INFORMATION: Synthetic construct

<400> SEQUENCE: 256

Asn Gln Ala Ala Ser Ile Thr Lys Arg Val Pro Tyr
1               5                   10

<210> SEQ ID NO 257
<211> LENGTH: 14
<212> TYPE: PRT
```

```
<213> ORGANISM: artificial sequence
<220> FEATURE:
<223> OTHER INFORMATION: Synthetic construct

<400> SEQUENCE: 257

Ser Gly Cys His Leu Val Tyr Asp Asn Gly Phe Cys Asp His
1               5                   10

<210> SEQ ID NO 258
<211> LENGTH: 14
<212> TYPE: PRT
<213> ORGANISM: artificial sequence
<220> FEATURE:
<223> OTHER INFORMATION: Synthetic construct

<400> SEQUENCE: 258

Ala Ser Cys Pro Ser Ala Ser His Ala Asp Pro Cys Ala His
1               5                   10

<210> SEQ ID NO 259
<211> LENGTH: 14
<212> TYPE: PRT
<213> ORGANISM: artificial sequence
<220> FEATURE:
<223> OTHER INFORMATION: Synthetic construct

<400> SEQUENCE: 259

Asn Leu Cys Asp Ser Ala Arg Asp Ser Pro Arg Cys Lys Val
1               5                   10

<210> SEQ ID NO 260
<211> LENGTH: 12
<212> TYPE: PRT
<213> ORGANISM: artificial sequence
<220> FEATURE:
<223> OTHER INFORMATION: Synthetic construct

<400> SEQUENCE: 260

Asn His Ser Asn Trp Lys Thr Ala Ala Asp Phe Leu
1               5                   10

<210> SEQ ID NO 261
<211> LENGTH: 12
<212> TYPE: PRT
<213> ORGANISM: artificial sequence
<220> FEATURE:
<223> OTHER INFORMATION: Synthetic construct

<400> SEQUENCE: 261

Gly Ser Ser Thr Val Gly Arg Pro Leu Ser Tyr Glu
1               5                   10

<210> SEQ ID NO 262
<211> LENGTH: 12
<212> TYPE: PRT
<213> ORGANISM: artificial sequence
<220> FEATURE:
<223> OTHER INFORMATION: Synthetic construct

<400> SEQUENCE: 262

Ser Asp Thr Ile Ser Arg Leu His Val Ser Met Thr
1               5                   10

<210> SEQ ID NO 263
<211> LENGTH: 12
<212> TYPE: PRT
<213> ORGANISM: artificial sequence
<220> FEATURE:
```

<223> OTHER INFORMATION: Synthetic construct

<400> SEQUENCE: 263

Ser Pro Leu Thr Val Pro Tyr Glu Arg Lys Leu Leu
1               5                   10

<210> SEQ ID NO 264
<211> LENGTH: 12
<212> TYPE: PRT
<213> ORGANISM: artificial sequence
<220> FEATURE:
<223> OTHER INFORMATION: Synthetic construct

<400> SEQUENCE: 264

Ser Pro Tyr Pro Ser Trp Ser Thr Pro Ala Gly Arg
1               5                   10

<210> SEQ ID NO 265
<211> LENGTH: 12
<212> TYPE: PRT
<213> ORGANISM: artificial sequence
<220> FEATURE:
<223> OTHER INFORMATION: Synthetic construct

<400> SEQUENCE: 265

Val Gln Pro Ile Thr Asn Thr Arg Tyr Glu Gly Gly
1               5                   10

<210> SEQ ID NO 266
<211> LENGTH: 12
<212> TYPE: PRT
<213> ORGANISM: artificial sequence
<220> FEATURE:
<223> OTHER INFORMATION: Synthetic construct

<400> SEQUENCE: 266

Trp Pro Met His Pro Glu Lys Gly Ser Arg Trp Ser
1               5                   10

<210> SEQ ID NO 267
<211> LENGTH: 14
<212> TYPE: PRT
<213> ORGANISM: artificial sequence
<220> FEATURE:
<223> OTHER INFORMATION: Synthetic construct

<400> SEQUENCE: 267

Asp Ala Cys Ser Gly Asn Gly His Pro Asn Asn Cys Asp Arg
1               5                   10

<210> SEQ ID NO 268
<211> LENGTH: 14
<212> TYPE: PRT
<213> ORGANISM: artificial sequence
<220> FEATURE:
<223> OTHER INFORMATION: Synthetic construct

<400> SEQUENCE: 268

Asp His Cys Leu Gly Arg Gln Leu Gln Pro Val Cys Tyr Pro
1               5                   10

<210> SEQ ID NO 269
<211> LENGTH: 14
<212> TYPE: PRT
<213> ORGANISM: artificial sequence
<220> FEATURE:
<223> OTHER INFORMATION: Synthetic construct

```
<400> SEQUENCE: 269

Asp Trp Cys Asp Thr Ile Ile Pro Gly Arg Thr Cys His Gly
1               5                   10

<210> SEQ ID NO 270
<211> LENGTH: 12
<212> TYPE: PRT
<213> ORGANISM: artificial sequence
<220> FEATURE:
<223> OTHER INFORMATION: Synthetic construct

<400> SEQUENCE: 270

Ala Leu Pro Arg Ile Ala Asn Thr Trp Ser Pro Ser
1               5                   10

<210> SEQ ID NO 271
<211> LENGTH: 12
<212> TYPE: PRT
<213> ORGANISM: artificial sequence
<220> FEATURE:
<223> OTHER INFORMATION: Synthetic construct

<400> SEQUENCE: 271

Tyr Pro Ser Phe Ser Pro Thr Tyr Arg Pro Ala Phe
1               5                   10

<210> SEQ ID NO 272
<211> LENGTH: 20
<212> TYPE: PRT
<213> ORGANISM: artificial sequence
<220> FEATURE:
<223> OTHER INFORMATION: Synthetic construct

<400> SEQUENCE: 272

Ala His Pro Glu Ser Leu Gly Ile Lys Tyr Ala Leu Asp Gly Asn Ser
1               5                   10                  15

Asp Pro His Ala
            20

<210> SEQ ID NO 273
<211> LENGTH: 20
<212> TYPE: PRT
<213> ORGANISM: artificial sequence
<220> FEATURE:
<223> OTHER INFORMATION: Synthetic construct

<400> SEQUENCE: 273

Ala Ser Val Ser Asn Tyr Pro Pro Ile His His Leu Ala Thr Ser Asn
1               5                   10                  15

Thr Thr Val Asn
            20

<210> SEQ ID NO 274
<211> LENGTH: 14
<212> TYPE: PRT
<213> ORGANISM: artificial sequence
<220> FEATURE:
<223> OTHER INFORMATION: Synthetic construct

<400> SEQUENCE: 274

Asp Glu Cys Met Glu Pro Leu Asn Ala Ala His Cys Trp Arg
1               5                   10

<210> SEQ ID NO 275
<211> LENGTH: 14
<212> TYPE: PRT
```

<213> ORGANISM: artificial sequence
<220> FEATURE:
<223> OTHER INFORMATION: Synthetic construct

<400> SEQUENCE: 275

Asp Glu Cys Met His Gly Ser Asp Val Glu Phe Cys Thr Ser
1               5                   10

<210> SEQ ID NO 276
<211> LENGTH: 14
<212> TYPE: PRT
<213> ORGANISM: artificial sequence
<220> FEATURE:
<223> OTHER INFORMATION: Synthetic construct

<400> SEQUENCE: 276

Asp Leu Cys Ser Met Gln Met Met Asn Thr Gly Cys His Tyr
1               5                   10

<210> SEQ ID NO 277
<211> LENGTH: 14
<212> TYPE: PRT
<213> ORGANISM: artificial sequence
<220> FEATURE:
<223> OTHER INFORMATION: Synthetic construct

<400> SEQUENCE: 277

Asp Leu Cys Ser Ser Pro Ser Thr Trp Gly Ser Cys Ile Arg
1               5                   10

<210> SEQ ID NO 278
<211> LENGTH: 20
<212> TYPE: PRT
<213> ORGANISM: artificial sequence
<220> FEATURE:
<223> OTHER INFORMATION: Synthetic construct

<400> SEQUENCE: 278

Asp Pro Asn Glu Ser Asn Tyr Glu Asn Ala Thr Thr Val Ser Gln Pro
1               5                   10                  15

Thr Arg His Leu
            20

<210> SEQ ID NO 279
<211> LENGTH: 20
<212> TYPE: PRT
<213> ORGANISM: artificial sequence
<220> FEATURE:
<223> OTHER INFORMATION: Synthetic construct

<400> SEQUENCE: 279

Glu Pro Thr His Pro Thr Met Arg Ala Gln Met His Gln Ser Leu Arg
1               5                   10                  15

Ser Ser Ser Pro
            20

<210> SEQ ID NO 280
<211> LENGTH: 20
<212> TYPE: PRT
<213> ORGANISM: artificial sequence
<220> FEATURE:
<223> OTHER INFORMATION: Synthetic construct

<400> SEQUENCE: 280

Gly Asn Thr Asp Thr Thr Pro Pro Asn Ala Val Met Glu Pro Thr Val
1               5                   10                  15

Gln His Lys Trp
        20

<210> SEQ ID NO 281
<211> LENGTH: 15
<212> TYPE: PRT
<213> ORGANISM: artificial sequence
<220> FEATURE:
<223> OTHER INFORMATION: Synthetic construct

<400> SEQUENCE: 281

Asn Gly Pro Asp Met Val Gln Ser Val Gly Lys His Lys Asn Ser
1               5                   10                  15

<210> SEQ ID NO 282
<211> LENGTH: 15
<212> TYPE: PRT
<213> ORGANISM: artificial sequence
<220> FEATURE:
<223> OTHER INFORMATION: Synthetic construct

<400> SEQUENCE: 282

Asn Gly Pro Glu Val Arg Gln Ile Pro Ala Asn Phe Glu Lys Leu
1               5                   10                  15

<210> SEQ ID NO 283
<211> LENGTH: 20
<212> TYPE: PRT
<213> ORGANISM: artificial sequence
<220> FEATURE:
<223> OTHER INFORMATION: Synthetic construct

<400> SEQUENCE: 283

Asn Asn Thr Ser Ala Asp Asn Pro Pro Glu Thr Asp Ser Lys His His
1               5                   10                  15

Leu Ser Met Ser
        20

<210> SEQ ID NO 284
<211> LENGTH: 20
<212> TYPE: PRT
<213> ORGANISM: artificial sequence
<220> FEATURE:
<223> OTHER INFORMATION: Synthetic construct

<400> SEQUENCE: 284

Asn Asn Thr Trp Pro Glu Gly Ala Gly His Thr Met Pro Ser Thr Asn
1               5                   10                  15

Ile Arg Gln Ala
        20

<210> SEQ ID NO 285
<211> LENGTH: 20
<212> TYPE: PRT
<213> ORGANISM: artificial sequence
<220> FEATURE:
<223> OTHER INFORMATION: Synthetic construct

<400> SEQUENCE: 285

Asn Pro Thr Ala Thr Pro His Met Lys Asp Pro Met His Ser Asn Ala
1               5                   10                  15

His Ser Ser Ala
        20

<210> SEQ ID NO 286
<211> LENGTH: 20

```
<212> TYPE: PRT
<213> ORGANISM: artificial sequence
<220> FEATURE:
<223> OTHER INFORMATION: Synthetic construct

<400> SEQUENCE: 286

Asn Pro Thr Asp His Ile Pro Ala Asn Ser Thr Asn Ser Arg Val Ser
1               5                   10                  15

Lys Gly Asn Thr
            20

<210> SEQ ID NO 287
<211> LENGTH: 15
<212> TYPE: PRT
<213> ORGANISM: artificial sequence
<220> FEATURE:
<223> OTHER INFORMATION: Synthetic construct

<400> SEQUENCE: 287

Asn Pro Thr Asp Ser Thr His Met Met His Ala Arg Asn His Glu
1               5                   10                  15

<210> SEQ ID NO 288
<211> LENGTH: 14
<212> TYPE: PRT
<213> ORGANISM: artificial sequence
<220> FEATURE:
<223> OTHER INFORMATION: Synthetic construct

<400> SEQUENCE: 288

Gln His Cys Ile Thr Glu Arg Leu His Pro Pro Cys Thr Lys
1               5                   10

<210> SEQ ID NO 289
<211> LENGTH: 14
<212> TYPE: PRT
<213> ORGANISM: artificial sequence
<220> FEATURE:
<223> OTHER INFORMATION: Synthetic construct

<400> SEQUENCE: 289

Thr Pro Cys Ala Pro Ala Ser Phe Asn Pro His Cys Ser Arg
1               5                   10

<210> SEQ ID NO 290
<211> LENGTH: 14
<212> TYPE: PRT
<213> ORGANISM: artificial sequence
<220> FEATURE:
<223> OTHER INFORMATION: Synthetic construct

<400> SEQUENCE: 290

Thr Pro Cys Ala Thr Tyr Pro His Phe Ser Gly Cys Arg Ala
1               5                   10

<210> SEQ ID NO 291
<211> LENGTH: 20
<212> TYPE: PRT
<213> ORGANISM: artificial sequence
<220> FEATURE:
<223> OTHER INFORMATION: Synthetic construct

<400> SEQUENCE: 291

Trp Cys Thr Asp Phe Cys Thr Arg Ser Thr Pro Thr Ser Thr Ser Arg
1               5                   10                  15

Ser Thr Thr Ser
            20
```

```
<210> SEQ ID NO 292
<211> LENGTH: 20
<212> TYPE: PRT
<213> ORGANISM: artificial sequence
<220> FEATURE:
<223> OTHER INFORMATION: Synthetic construct

<400> SEQUENCE: 292

Ala Pro Pro Leu Lys Thr Tyr Met Gln Glu Arg Glu Leu Thr Met Ser
1               5                   10                  15

Gln Asn Lys Asp
            20

<210> SEQ ID NO 293
<211> LENGTH: 20
<212> TYPE: PRT
<213> ORGANISM: artificial sequence
<220> FEATURE:
<223> OTHER INFORMATION: Synthetic construct

<400> SEQUENCE: 293

Glu Pro Pro Thr Arg Thr Arg Val Asn Asn His Thr Val Thr Val Gln
1               5                   10                  15

Ala Gln Gln His
            20

<210> SEQ ID NO 294
<211> LENGTH: 14
<212> TYPE: PRT
<213> ORGANISM: artificial sequence
<220> FEATURE:
<223> OTHER INFORMATION: Synthetic construct

<400> SEQUENCE: 294

Gly Tyr Cys Leu Arg Gly Asp Glu Pro Ala Val Cys Ser Gly
1               5                   10

<210> SEQ ID NO 295
<211> LENGTH: 20
<212> TYPE: PRT
<213> ORGANISM: artificial sequence
<220> FEATURE:
<223> OTHER INFORMATION: Synthetic construct

<400> SEQUENCE: 295

Leu Ser Ser Lys Asp Phe Gly Val Thr Asn Thr Asp Gln Arg Thr Tyr
1               5                   10                  15

Asp Tyr Thr Thr
            20

<210> SEQ ID NO 296
<211> LENGTH: 14
<212> TYPE: PRT
<213> ORGANISM: artificial sequence
<220> FEATURE:
<223> OTHER INFORMATION: Synthetic construct

<400> SEQUENCE: 296

Asn Phe Cys Glu Thr Gln Leu Asp Leu Ser Val Cys Thr Val
1               5                   10

<210> SEQ ID NO 297
<211> LENGTH: 14
<212> TYPE: PRT
<213> ORGANISM: artificial sequence
```

```
<220> FEATURE:
<223> OTHER INFORMATION: Synthetic construct

<400> SEQUENCE: 297

Asn Thr Cys Gln Pro Thr Lys Asn Ala Thr Pro Cys Ser Ala
1               5                   10

<210> SEQ ID NO 298
<211> LENGTH: 20
<212> TYPE: PRT
<213> ORGANISM: artificial sequence
<220> FEATURE:
<223> OTHER INFORMATION: Synthetic construct

<400> SEQUENCE: 298

Pro Ser Glu Pro Glu Arg Arg Asp Arg Asn Ile Ala Ala Asn Ala Gly
1               5                   10                  15

Arg Phe Asn Thr
            20

<210> SEQ ID NO 299
<211> LENGTH: 18
<212> TYPE: PRT
<213> ORGANISM: artificial sequence
<220> FEATURE:
<223> OTHER INFORMATION: Synthetic construct

<400> SEQUENCE: 299

Thr His Asn Met Ser His Phe Pro Pro Ser Gly His Pro Lys Arg Thr
1               5                   10                  15

Ala Thr

<210> SEQ ID NO 300
<211> LENGTH: 14
<212> TYPE: PRT
<213> ORGANISM: artificial sequence
<220> FEATURE:
<223> OTHER INFORMATION: Synthetic construct

<400> SEQUENCE: 300

Thr Thr Cys Pro Thr Met Gly Thr Tyr His Val Cys Trp Leu
1               5                   10

<210> SEQ ID NO 301
<211> LENGTH: 20
<212> TYPE: PRT
<213> ORGANISM: artificial sequence
<220> FEATURE:
<223> OTHER INFORMATION: Synthetic construct

<400> SEQUENCE: 301

Tyr Cys Ala Asp His Thr Pro Asp Pro Ala Asn Pro Asn Lys Ile Cys
1               5                   10                  15

Gly Tyr Ser His
            20

<210> SEQ ID NO 302
<211> LENGTH: 20
<212> TYPE: PRT
<213> ORGANISM: artificial sequence
<220> FEATURE:
<223> OTHER INFORMATION: Synthetic construct

<400> SEQUENCE: 302

Ala Ala Asn Pro His Thr Glu Trp Asp Arg Asp Ala Phe Gln Leu Ala
1               5                   10                  15
```

Met Pro Pro Lys
            20

<210> SEQ ID NO 303
<211> LENGTH: 20
<212> TYPE: PRT
<213> ORGANISM: artificial sequence
<220> FEATURE:
<223> OTHER INFORMATION: Synthetic construct

<400> SEQUENCE: 303

Asp Leu His Pro Met Asp Pro Ser Asn Lys Arg Pro Asp Asn Pro Ser
1               5                   10                  15

Asp Leu His Thr
            20

<210> SEQ ID NO 304
<211> LENGTH: 14
<212> TYPE: PRT
<213> ORGANISM: artificial sequence
<220> FEATURE:
<223> OTHER INFORMATION: Synthetic construct

<400> SEQUENCE: 304

Glu Ser Cys Val Ser Asn Ala Leu Met Asn Gln Cys Ile Tyr
1               5                   10

<210> SEQ ID NO 305
<211> LENGTH: 20
<212> TYPE: PRT
<213> ORGANISM: artificial sequence
<220> FEATURE:
<223> OTHER INFORMATION: Synthetic construct

<400> SEQUENCE: 305

His Asn Lys Ala Asp Ser Trp Asp Pro Asp Leu Pro Pro His Ala Gly
1               5                   10                  15

Met Ser Leu Gly
            20

<210> SEQ ID NO 306
<211> LENGTH: 20
<212> TYPE: PRT
<213> ORGANISM: artificial sequence
<220> FEATURE:
<223> OTHER INFORMATION: Synthetic construct

<400> SEQUENCE: 306

Leu Asn Asp Gln Arg Lys Pro Gly Pro Pro Thr Met Pro Thr His Ser
1               5                   10                  15

Pro Ala Val Gly
            20

<210> SEQ ID NO 307
<211> LENGTH: 14
<212> TYPE: PRT
<213> ORGANISM: artificial sequence
<220> FEATURE:
<223> OTHER INFORMATION: Synthetic construct

<400> SEQUENCE: 307

Asn Thr Cys Ala Thr Ser Pro Asn Ser Tyr Thr Cys Ser Asn
1               5                   10

<210> SEQ ID NO 308

```
<211> LENGTH: 14
<212> TYPE: PRT
<213> ORGANISM: artificial sequence
<220> FEATURE:
<223> OTHER INFORMATION: Synthetic construct

<400> SEQUENCE: 308

Ser Asp Cys Thr Ala Gly Leu Val Pro Pro Leu Cys Ala Thr
1               5                   10

<210> SEQ ID NO 309
<211> LENGTH: 20
<212> TYPE: PRT
<213> ORGANISM: artificial sequence
<220> FEATURE:
<223> OTHER INFORMATION: Synthetic construct

<400> SEQUENCE: 309

Thr Ile Glu Ser Ser Gln His Ser Arg Thr His Gln Gln Asn Tyr Gly
1               5                   10                  15

Ser Thr Lys Thr
            20

<210> SEQ ID NO 310
<211> LENGTH: 20
<212> TYPE: PRT
<213> ORGANISM: artificial sequence
<220> FEATURE:
<223> OTHER INFORMATION: Synthetic construct

<400> SEQUENCE: 310

Val Gly Thr Met Lys Gln His Pro Thr Thr Thr Gln Pro Pro Arg Val
1               5                   10                  15

Ser Ala Thr Asn
            20

<210> SEQ ID NO 311
<211> LENGTH: 20
<212> TYPE: PRT
<213> ORGANISM: artificial sequence
<220> FEATURE:
<223> OTHER INFORMATION: Synthetic construct

<400> SEQUENCE: 311

Tyr Ser Glu Thr Pro Asn Asp Gln Lys Pro Asn Pro His Tyr Lys Val
1               5                   10                  15

Ser Gly Thr Lys
            20

<210> SEQ ID NO 312
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 312

Asn Gly Asn Asn His Thr Asp Ile Pro Asn Arg Ser Ser Tyr Thr Gly
1               5                   10                  15

Gly Ser Phe Ala
            20

<210> SEQ ID NO 313
<211> LENGTH: 20
<212> TYPE: PRT
<213> ORGANISM: Artificial Sequence
```

```
<220> FEATURE:
<223> OTHER INFORMATION: Synthetic oral-surface binding peptide

<400> SEQUENCE: 313

Thr Met Thr Asn His Val Tyr Asn Ser Tyr Thr Glu Lys His Ser Ser
1               5                   10                  15

Thr His Arg Ser
            20

<210> SEQ ID NO 314
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 314

Thr Thr Tyr His Tyr Lys Asn Ile Tyr Gln Glu Ser Tyr Gln Gln Arg
1               5                   10                  15

Asn Pro Ala Val
            20

<210> SEQ ID NO 315
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 315

Val Glu Pro Ala Thr Lys Asn Met Arg Glu Ala Arg Ser Ser Thr Gln
1               5                   10                  15

Met Arg Arg Ile
            20

<210> SEQ ID NO 316
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 316

Tyr Leu Leu Pro Lys Asp Gln Thr Thr Ala Pro Gln Val Thr Pro Ile
1               5                   10                  15

Val Gln His Lys
            20

<210> SEQ ID NO 317
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 317

Ala Ser Asn Leu Asp Ser Thr Phe Thr Ala Ile Asn Thr Pro Ala Cys
1               5                   10                  15

Cys Thr

<210> SEQ ID NO 318
<211> LENGTH: 18
<212> TYPE: PRT
<213> ORGANISM: Artificial Sequence
<220> FEATURE:
```

-continued

<223> OTHER INFORMATION: Synthetic oral-surface binding peptide

<400> SEQUENCE: 318

Glu Phe Pro Tyr Tyr Asn Asp Asn Pro Pro Asn Pro Glu Arg His Thr
1               5                   10                  15

Leu Arg

<210> SEQ ID NO 319
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 319

Gly Met Pro Thr Arg Tyr Tyr His Asn Thr Pro Pro His Leu Thr Pro
1               5                   10                  15

Lys Phe

<210> SEQ ID NO 320
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 320

His Lys Asn Ala Ile Gln Pro Val Asn Asp Ala Thr Thr Leu Asp Thr
1               5                   10                  15

Thr Met

<210> SEQ ID NO 321
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 321

Ala Val Val Pro Ala Asp Leu Asn Asp His Ala Asn His Leu Ser
1               5                   10                  15

<210> SEQ ID NO 322
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 322

Asp Leu Gly Thr Phe Pro Asn Arg Thr Leu Lys Met Ala Ala His
1               5                   10                  15

<210> SEQ ID NO 323
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 323

Phe Asp Gly Ile Gly Leu Gly Thr Ala Thr Arg His Gln Asn Arg
1               5                   10                  15

<210> SEQ ID NO 324

```
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 324

Gln Ala Ala Gln Val His Met Met Gln His Ser Arg Pro Thr Thr
1               5                   10                  15

<210> SEQ ID NO 325
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 325

Ser Glu Ala Arg Ala Arg Thr Phe Asn Asp His Thr Thr Pro Met Pro
1               5                   10                  15

Ile Ile

<210> SEQ ID NO 326
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 326

Glu Leu Asp His Asp Ser Arg His Tyr Met Asn Gly Leu Gln Arg Lys
1               5                   10                  15

Val Thr

<210> SEQ ID NO 327
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 327

Gly Pro Gln His Val Leu Met Gln Asp Thr His Gln Gly Tyr Ala Phe
1               5                   10                  15

Asp Asn

<210> SEQ ID NO 328
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 328

Thr Thr Gly Ser Ser Ser Gln Ala Asp Thr Ser Ala Ser Met Ser Ile
1               5                   10                  15

Val Pro Ala His
            20

<210> SEQ ID NO 329
<211> LENGTH: 18
<212> TYPE: PRT
<213> ORGANISM: Artificial Sequence
<220> FEATURE:
<223> OTHER INFORMATION: Synthetic oral-surface binding peptide
```

```
<400> SEQUENCE: 329

Lys Ala Pro Ile Ala Asn Met Leu Gln Pro His Ser Tyr Gln Tyr Ser
1               5                   10                  15

Val Ala

<210> SEQ ID NO 330
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 330

Thr Tyr Gln Gly Val Pro Ser Trp Pro Ala Val Ile Asp Asp Ala Ile
1               5                   10                  15

Arg Arg

<210> SEQ ID NO 331
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 331

Val Asn Pro Asn Trp Val Glu Thr Gln Ala Leu His Gln Pro Pro Gly
1               5                   10                  15

Asn Thr

<210> SEQ ID NO 332
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 332

Asp His Asn Asn Arg Gln His Ala Val Glu Val Arg Glu Asn Lys Thr
1               5                   10                  15

His Thr Ala Arg
            20

<210> SEQ ID NO 333
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 333

Ile Tyr Pro Asn Glu Ser Met Ser Thr Ser Asn Val Arg Gly Pro Tyr
1               5                   10                  15

His Pro

<210> SEQ ID NO 334
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 334

His Asp Pro Asn His Leu Thr His Gln Ala Arg Thr Ile Tyr Arg Asn
1               5                   10                  15
```

Ala Asn His Thr
            20

<210> SEQ ID NO 335
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 335

Ser Asn Ala Thr Met Tyr Asn Ile Gln Ser His Ser His His Gln
1               5                   10                  15

<210> SEQ ID NO 336
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 336

Ala Asn Glu Leu Ser Thr Tyr Ala Gln Thr Asn Pro Gly Ser Gly
1               5                   10                  15

<210> SEQ ID NO 337
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 337

Asp Thr Ile His Pro Asn Lys Met Lys Ser Pro Ser Ser Pro Leu
1               5                   10                  15

<210> SEQ ID NO 338
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 338

Ala Pro Pro Thr Tyr Gln Thr Ala Ser Tyr Pro His Asn Leu Pro Ser
1               5                   10                  15

Lys Arg Lys Met
            20

<210> SEQ ID NO 339
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 339

Gln Val Pro Asp Tyr Leu Ser Pro Thr His Gln Lys Lys Ala Phe Leu
1               5                   10                  15

Glu Ile Pro Thr
            20

<210> SEQ ID NO 340
<211> LENGTH: 20
<212> TYPE: PRT
<213> ORGANISM: Artificial Sequence

```
<220> FEATURE:
<223> OTHER INFORMATION: Synthetic oral-surface binding peptide

<400> SEQUENCE: 340

Thr Asn Asp Leu His Ala Asn Pro Phe Thr Gly Thr Tyr Ile Ala Pro
1               5                   10                  15

Asp Pro Thr Ser
            20

<210> SEQ ID NO 341
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 341

His Lys Asn Glu Asn Ile Met Gln Tyr Asn Val Asn Asp Arg Trp His
1               5                   10                  15

Ile Thr Pro Ala
            20

<210> SEQ ID NO 342
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 342

Ile Asp Gly Pro His His Ser Pro Val His Arg Tyr His Thr Pro Ser
1               5                   10                  15

Ile Thr

<210> SEQ ID NO 343
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 343

Ala Ile Glu Tyr Gln His Ser Ala Thr Thr Pro Trp Thr Met Arg Thr
1               5                   10                  15

Arg Leu Pro Pro
            20

<210> SEQ ID NO 344
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 344

Glu Phe Tyr Pro Phe Ala Glu Val Pro Pro Glu Lys Ser Gly Ile Gly
1               5                   10                  15

Arg Gln Val Phe
            20

<210> SEQ ID NO 345
<211> LENGTH: 20
<212> TYPE: PRT
<213> ORGANISM: Artificial Sequence
<220> FEATURE:
```

<223> OTHER INFORMATION: Synthetic oral-surface binding peptide

<400> SEQUENCE: 345

Gly Val His Gln Tyr Ser Arg Pro Thr Val Pro Ser Tyr Leu Trp Thr
1               5                   10                  15

Ser Gly Gln His
            20

<210> SEQ ID NO 346
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 346

Gly Tyr Gln Pro His Tyr Val Asp His Thr Ile Gly Trp Gln Pro Met
1               5                   10                  15

Ile Arg Pro Asn
            20

<210> SEQ ID NO 347
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 347

Gln Phe Asn Gln Thr Ser His Ser Phe Met His Gly Thr Ser Gly Tyr
1               5                   10                  15

Val Pro Gly Lys
            20

<210> SEQ ID NO 348
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 348

Ser Phe Ser Trp His Arg Gly Asp Trp Glu Leu Gly His Gln Ser Lys
1               5                   10                  15

Thr Met Gly Met
            20

<210> SEQ ID NO 349
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 349

Ser Met Trp His Asp Ile Thr Lys Arg Tyr Arg Asn Pro Ser Glu Met
1               5                   10                  15

Val Ser Ala Tyr
            20

<210> SEQ ID NO 350
<211> LENGTH: 20
<212> TYPE: PRT
<213> ORGANISM: Artificial Sequence
<220> FEATURE:

<223> OTHER INFORMATION: Synthetic oral-surface binding peptide

<400> SEQUENCE: 350

Thr His Gly Asn Lys His Gln Ser Trp Thr Tyr Pro Ser Glu Ile Asn
1               5                   10                  15

His Lys Asn Tyr
            20

<210> SEQ ID NO 351
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 351

Trp His Glu Pro His Gln Phe Ser Gly Glu Asn Thr Asp Tyr Ser Ser
1               5                   10                  15

Ser Met Gly Thr
            20

<210> SEQ ID NO 352
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 352

Thr His Gly Asn Lys His Gln Ser Trp Thr Tyr Pro Ser Glu Ile Asn
1               5                   10                  15

His Lys Asn Tyr
            20

<210> SEQ ID NO 353
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 353

Asp Gly Tyr Lys Leu Gln Thr Ser Leu Asp Trp Gln Met Trp Asn Pro
1               5                   10                  15

<210> SEQ ID NO 354
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 354

Phe Pro Ser Lys Trp Tyr Asn His His Arg His Ile Thr Gly His Val
1               5                   10                  15

<210> SEQ ID NO 355
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 355

Gly Gly Met Gly Ala Leu Glu Ser Tyr Arg Gln Trp Asn His Leu Ala
1               5                   10                  15

```
<210> SEQ ID NO 356
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 356

Gly Ile Asn Lys Gly Gln Arg Pro Pro Trp Glu Ser Trp His Glu Asn
1               5                   10                  15

<210> SEQ ID NO 357
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 357

Gly Tyr Gly Gln Tyr Val Ser Gln Gln Thr Trp Ala His Ser Asn Lys
1               5                   10                  15

<210> SEQ ID NO 358
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 358

His Asp His Leu Ser Trp Trp Gly Gln Phe Asp Arg Gln Asn Leu Leu
1               5                   10                  15

<210> SEQ ID NO 359
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 359

Met Pro Gly His Gln Glu Ser Ile Lys Val Gln Asn Trp Asn Arg Val
1               5                   10                  15

<210> SEQ ID NO 360
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 360

Asn Leu His Ser Pro Trp Pro Ser His Ala Ala His Trp Ser Thr
1               5                   10                  15

<210> SEQ ID NO 361
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 361

Asn Gln Gln Met Lys Leu Val Pro Gln His Trp His Arg Ala Gln Pro
1               5                   10                  15
```

```
<210> SEQ ID NO 362
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 362

Ser Glu Lys Trp Phe Asn Pro Gly Pro Trp Pro Lys Leu Ala Thr Gln
1               5                   10                  15

<210> SEQ ID NO 363
<211> LENGTH: 25
<212> TYPE: PRT
<213> ORGANISM: Artificial Sequence
<220> FEATURE:
<223> OTHER INFORMATION: synthetic construct

<400> SEQUENCE: 363

Ser Ser Arg Pro Asn Gly Asn Asn His Thr Asp Ile Pro Asn Arg Ser
1               5                   10                  15

Ser Tyr Thr Gly Gly Ser Phe Ala Lys
            20                  25

<210> SEQ ID NO 364
<211> LENGTH: 25
<212> TYPE: PRT
<213> ORGANISM: Artificial Sequence
<220> FEATURE:
<223> OTHER INFORMATION: synthetic construct

<400> SEQUENCE: 364

Ser Ser Arg Pro Thr Met Thr Asn His Val Tyr Asn Ser Tyr Thr Glu
1               5                   10                  15

Lys His Ser Ser Thr His Arg Ser Lys
            20                  25

<210> SEQ ID NO 365
<211> LENGTH: 25
<212> TYPE: PRT
<213> ORGANISM: Artificial Sequence
<220> FEATURE:
<223> OTHER INFORMATION: synthetic construct

<400> SEQUENCE: 365

Ser Ser Arg Pro Thr Thr Tyr His Tyr Lys Asn Ile Tyr Gln Glu Ser
1               5                   10                  15

Tyr Gln Gln Arg Asn Pro Ala Val Lys
            20                  25

<210> SEQ ID NO 366
<211> LENGTH: 25
<212> TYPE: PRT
<213> ORGANISM: Artificial Sequence
<220> FEATURE:
<223> OTHER INFORMATION: synthetic construct

<400> SEQUENCE: 366

Ser Ser Arg Pro Val Glu Pro Ala Thr Lys Asn Met Arg Glu Ala Arg
1               5                   10                  15

Ser Ser Thr Gln Met Arg Arg Ile Lys
            20                  25

<210> SEQ ID NO 367
<211> LENGTH: 25
<212> TYPE: PRT
```

```
<213> ORGANISM: Artificial Sequence
<220> FEATURE:
<223> OTHER INFORMATION: synthetic construct

<400> SEQUENCE: 367

Ser Ser Arg Pro Tyr Leu Leu Pro Lys Asp Gln Thr Thr Ala Pro Gln
1               5                   10                  15

Val Thr Pro Ile Val Gln His Lys Lys
            20                  25

<210> SEQ ID NO 368
<211> LENGTH: 23
<212> TYPE: PRT
<213> ORGANISM: Artificial Sequence
<220> FEATURE:
<223> OTHER INFORMATION: synthetic construct

<400> SEQUENCE: 368

Ser Ser Arg Pro Glu Phe Pro Tyr Tyr Asn Asp Asn Pro Pro Asn Pro
1               5                   10                  15

Glu Arg His Thr Leu Arg Lys
            20

<210> SEQ ID NO 369
<211> LENGTH: 20
<212> TYPE: PRT
<213> ORGANISM: Artificial Sequence
<220> FEATURE:
<223> OTHER INFORMATION: synthetic construct

<400> SEQUENCE: 369

Ser Ser Arg Pro Asp Leu Gly Thr Phe Pro Asn Arg Thr Leu Lys Met
1               5                   10                  15

Ala Ala His Lys
            20

<210> SEQ ID NO 370
<211> LENGTH: 20
<212> TYPE: PRT
<213> ORGANISM: Artificial Sequence
<220> FEATURE:
<223> OTHER INFORMATION: synthetic construct

<400> SEQUENCE: 370

Ser Ser Arg Pro Phe Asp Gly Ile Gly Leu Gly Thr Ala Thr Arg His
1               5                   10                  15

Gln Asn Arg Lys
            20

<210> SEQ ID NO 371
<211> LENGTH: 20
<212> TYPE: PRT
<213> ORGANISM: Artificial Sequence
<220> FEATURE:
<223> OTHER INFORMATION: synthetic construct

<400> SEQUENCE: 371

Ser Ser Arg Pro Gln Ala Ala Gln Val His Met Met Gln His Ser Arg
1               5                   10                  15

Pro Thr Thr Lys
            20

<210> SEQ ID NO 372
<211> LENGTH: 23
<212> TYPE: PRT
```

<213> ORGANISM: Artificial Sequence
<220> FEATURE:
<223> OTHER INFORMATION: synthetic construct

<400> SEQUENCE: 372

Ser Ser Arg Pro Ser Glu Ala Arg Ala Arg Thr Phe Asn Asp His Thr
1               5                   10                  15

Thr Pro Met Pro Ile Ile Lys
            20

<210> SEQ ID NO 373
<211> LENGTH: 23
<212> TYPE: PRT
<213> ORGANISM: Artificial Sequence
<220> FEATURE:
<223> OTHER INFORMATION: synthetic construct

<400> SEQUENCE: 373

Ser Ser Arg Pro Glu Leu Asp His Asp Ser Arg His Tyr Met Asn Gly
1               5                   10                  15

Leu Gln Arg Lys Val Thr Lys
            20

<210> SEQ ID NO 374
<211> LENGTH: 23
<212> TYPE: PRT
<213> ORGANISM: Artificial Sequence
<220> FEATURE:
<223> OTHER INFORMATION: synthetic construct

<400> SEQUENCE: 374

Ser Ser Arg Pro Gly Pro Gln His Val Leu Met Gln Asp Thr His Gln
1               5                   10                  15

Gly Tyr Ala Phe Asp Asn Lys
            20

<210> SEQ ID NO 375
<211> LENGTH: 25
<212> TYPE: PRT
<213> ORGANISM: Artificial Sequence
<220> FEATURE:
<223> OTHER INFORMATION: synthetic construct

<400> SEQUENCE: 375

Ser Ser Arg Pro Thr Thr Gly Ser Ser Gln Ala Asp Thr Ser Ala
1               5                   10                  15

Ser Met Ser Ile Val Pro Ala His Lys
            20                  25

<210> SEQ ID NO 376
<211> LENGTH: 23
<212> TYPE: PRT
<213> ORGANISM: Artificial Sequence
<220> FEATURE:
<223> OTHER INFORMATION: synthetic construct

<400> SEQUENCE: 376

Ser Ser Arg Pro Thr Tyr Gln Gly Val Pro Ser Trp Pro Ala Val Ile
1               5                   10                  15

Asp Asp Ala Ile Arg Arg Lys
            20

<210> SEQ ID NO 377
<211> LENGTH: 23
<212> TYPE: PRT

```
<213> ORGANISM: Artificial Sequence
<220> FEATURE:
<223> OTHER INFORMATION: synthetic construct

<400> SEQUENCE: 377

Ser Ser Arg Pro Val Asn Pro Asn Trp Val Glu Thr Gln Ala Leu His
1               5                  10                  15

Gln Pro Pro Gly Asn Thr Lys
            20

<210> SEQ ID NO 378
<211> LENGTH: 23
<212> TYPE: PRT
<213> ORGANISM: Artificial Sequence
<220> FEATURE:
<223> OTHER INFORMATION: synthetic construct

<400> SEQUENCE: 378

Ser Ser Arg Pro Ile Tyr Pro Asn Glu Ser Met Ser Thr Ser Asn Val
1               5                  10                  15

Arg Gly Pro Tyr His Pro Lys
            20

<210> SEQ ID NO 379
<211> LENGTH: 25
<212> TYPE: PRT
<213> ORGANISM: Artificial Sequence
<220> FEATURE:
<223> OTHER INFORMATION: synthetic construct

<400> SEQUENCE: 379

Ser Ser Arg Pro His Asp Pro Asn His Leu Thr His Gln Ala Arg Thr
1               5                  10                  15

Ile Tyr Arg Asn Ala Asn His Thr Lys
            20                  25

<210> SEQ ID NO 380
<211> LENGTH: 25
<212> TYPE: PRT
<213> ORGANISM: Artificial Sequence
<220> FEATURE:
<223> OTHER INFORMATION: synthetic construct

<400> SEQUENCE: 380

Ser Ser Arg Pro Ala Pro Pro Thr Tyr Gln Thr Ala Ser Tyr Pro His
1               5                  10                  15

Asn Leu Pro Ser Lys Arg Lys Met Lys
            20                  25

<210> SEQ ID NO 381
<211> LENGTH: 25
<212> TYPE: PRT
<213> ORGANISM: Artificial Sequence
<220> FEATURE:
<223> OTHER INFORMATION: synthetic construct

<400> SEQUENCE: 381

Ser Ser Arg Pro Gln Val Pro Asp Tyr Leu Ser Pro Thr His Gln Lys
1               5                  10                  15

Lys Ala Phe Leu Glu Ile Pro Thr Lys
            20                  25

<210> SEQ ID NO 382
<211> LENGTH: 25
<212> TYPE: PRT
```

-continued

<213> ORGANISM: Artificial Sequence
<220> FEATURE:
<223> OTHER INFORMATION: synthetic construct

<400> SEQUENCE: 382

Ser Ser Arg Pro His Lys Asn Glu Asn Ile Met Gln Tyr Asn Val Asn
1               5                   10                  15

Asp Arg Trp His Ile Thr Pro Ala Lys
            20                  25

<210> SEQ ID NO 383
<211> LENGTH: 8
<212> TYPE: PRT
<213> ORGANISM: Artificial Sequence
<220> FEATURE:
<223> OTHER INFORMATION: Synthetic construct - caspace 3 cleavable
      linker

<400> SEQUENCE: 383

Leu Glu Ser Gly Asp Glu Val Asp
1               5

<210> SEQ ID NO 384
<211> LENGTH: 37
<212> TYPE: PRT
<213> ORGANISM: Artificial Sequence
<220> FEATURE:
<223> OTHER INFORMATION: synthetic construct

<400> SEQUENCE: 384

Thr Ser Thr Ser Lys Ala Ser Thr Thr Thr Ser Ser Lys Thr Thr Thr
1               5                   10                  15

Thr Thr Ser Ser Lys Thr Thr Thr Thr Thr Ser Lys Thr Ser Thr Thr
            20                  25                  30

Ser Ser Ser Ser Thr
            35

<210> SEQ ID NO 385
<211> LENGTH: 22
<212> TYPE: PRT
<213> ORGANISM: Artificial Sequence
<220> FEATURE:
<223> OTHER INFORMATION: synthetic construct

<400> SEQUENCE: 385

Gly Gln Gly Gly Tyr Gly Gly Leu Gly Ser Gln Gly Ala Gly Arg Gly
1               5                   10                  15

Gly Leu Gly Gly Gln Gly
            20

<210> SEQ ID NO 386
<211> LENGTH: 10
<212> TYPE: PRT
<213> ORGANISM: Artificial Sequence
<220> FEATURE:
<223> OTHER INFORMATION: synthetic construct

<400> SEQUENCE: 386

Gly Pro Gly Gly Tyr Gly Pro Gly Gln Gln
1               5                   10

<210> SEQ ID NO 387
<211> LENGTH: 9
<212> TYPE: PRT
<213> ORGANISM: Artificial Sequence
<220> FEATURE:

<223> OTHER INFORMATION: synthetic construct

<400> SEQUENCE: 387

Gly Gly Ser Gly Pro Gly Ser Gly Gly
1               5

<210> SEQ ID NO 388
<211> LENGTH: 5
<212> TYPE: PRT
<213> ORGANISM: Artificial Sequence
<220> FEATURE:
<223> OTHER INFORMATION: synthetic construct

<400> SEQUENCE: 388

Gly Gly Pro Lys Lys
1               5

<210> SEQ ID NO 389
<211> LENGTH: 5
<212> TYPE: PRT
<213> ORGANISM: Artificial Sequence
<220> FEATURE:
<223> OTHER INFORMATION: synthetic construct

<400> SEQUENCE: 389

Gly Pro Gly Val Gly
1               5

<210> SEQ ID NO 390
<211> LENGTH: 7
<212> TYPE: PRT
<213> ORGANISM: Artificial Sequence
<220> FEATURE:
<223> OTHER INFORMATION: synthetic construct

<400> SEQUENCE: 390

Gly Gly Gly Cys Gly Gly Gly
1               5

<210> SEQ ID NO 391
<211> LENGTH: 4
<212> TYPE: PRT
<213> ORGANISM: Artificial Sequence
<220> FEATURE:
<223> OTHER INFORMATION: synthetic construct

<400> SEQUENCE: 391

Gly Gly Gly Cys
1

<210> SEQ ID NO 392
<211> LENGTH: 14
<212> TYPE: PRT
<213> ORGANISM: Artificial Sequence
<220> FEATURE:
<223> OTHER INFORMATION: synthetic construct

<400> SEQUENCE: 392

Pro His Met Ala Ser Met Thr Gly Gly Gln Gln Met Gly Ser
1               5                   10

<210> SEQ ID NO 393
<211> LENGTH: 16
<212> TYPE: PRT
<213> ORGANISM: Artificial Sequence
<220> FEATURE:
<223> OTHER INFORMATION: synthetic construct -continued

<400> SEQUENCE: 393

Gly Pro Glu Ala Ala Lys Lys Glu Glu Ala Ala Lys Lys Pro Ala
1               5                   10                  15

<210> SEQ ID NO 394
<211> LENGTH: 14
<212> TYPE: PRT
<213> ORGANISM: Artificial Sequence
<220> FEATURE:
<223> OTHER INFORMATION: synthetic construct

<400> SEQUENCE: 394

Gly Ser Gly Gly Gly Gly Ser Gly Ser Gly Gly Gly Gly Ser
1               5                   10

<210> SEQ ID NO 395
<211> LENGTH: 37
<212> TYPE: PRT
<213> ORGANISM: Artificial Sequence
<220> FEATURE:
<223> OTHER INFORMATION: synthetic construct

<400> SEQUENCE: 395

Gly Pro Glu Pro Glu Pro Glu Pro Glu Pro Ile Pro Glu Pro Pro Lys
1               5                   10                  15

Glu Ala Pro Val Val Ile Glu Lys Pro Lys Pro Lys Pro Lys Pro Lys
            20                  25                  30

Pro Lys Pro Pro Ala
        35

<210> SEQ ID NO 396
<211> LENGTH: 18
<212> TYPE: PRT
<213> ORGANISM: artificial sequence
<220> FEATURE:
<223> OTHER INFORMATION: synthetic construct

<400> SEQUENCE: 396

Gly Pro Gly Ser Gly Gly Ala Gly Ser Pro Gly Ser Ala Gly Gly Pro
1               5                   10                  15

Gly Ser

<210> SEQ ID NO 397
<211> LENGTH: 6368
<212> TYPE: DNA
<213> ORGANISM: artificial sequence
<220> FEATURE:
<223> OTHER INFORMATION: synthetic construct

<400> SEQUENCE: 397

```
agatctcgat cccgcgaaat taatacgact cactataggg agaccacaac ggtttccctc    60
tagaaataat tttgtttaac tttaagaagg agatatacat atgcacactc agaacatat    120 caccgcagta gtacagcgtt ttgtggcagc tctgaacgcg ggcgagctgg aaggtattgt    180
ggcgctgttc gcggaagaag ccaccgtgga agaaccggtg ggttctgaac cgcgttccgg    240
caccgcagcc tgccgtgaat tttacgcaaa cagcctgaag ctgccgctgg cggttgaact    300
gacccaagaa tgtcgtgcgg tggctaacga agccgctttc gcgttcaccg tgtccttcga    360
ataccagggt cgtaagaccg ttgtggcgcc atgcgaacac tttcgtttca acggcgcagg    420
caaagtggtt tccatccgcg cactgttcgg tgaaaagaac atccatgctt gtcagggatc    480
cgatccgact ccgccgacga atgtactgat gctggcaacc aaaggcggtg gtacgcattc    540
```

-continued

```
cacgcacaac catggcagcc cgcgccacac gaatgctgac gcaggcaatc cgggcggcgg    600
caccccacca accaatgtcc tgatgctggc tactaaaggc ggcggcacgc attctaccca    660
caaccatggt agcccgcgcc atactaatgc agatgccggc aacccgggcg gtggtacccc    720
gccaaccaac gttctgatgc tggcgacgaa aggtggcggt acccattcca cgcataatca    780
tggcagccct cgccacacca acgctgatgc tggtaatcct ggtggcggta agaagaaata    840
ataaggcgcg ccgacccagc tttcttgtac aaagtggttg attcgaggct gctaacaaag    900
cccgaaagga agctgagttg gctgctgcca ccgctgagca ataactagca taaccccttg    960
gggcctctaa acgggtcttg aggggttttt tgctgaaagg aggaactata tccggatatc   1020
cacaggacgg gtgtggtcgc catgatcgcg tagtcgatag tggctccaag tagcgaagcg   1080
agcaggactg ggcggcggcc aaagcggtcg acagtgctc cgagaacggg tgcgcataga   1140
aattgcatca acgcatatag cgctagcagc acgccatagt gactggcgat gctgtcggaa   1200
tggacgatat cccgcaagag gcccggcagt accggcataa ccaagcctat gcctacagca   1260
tccagggtga cggtgccgag gatgacgatg agcgcattgt tagatttcat acacggtgcc   1320
tgactgcgtt agcaatttaa ctgtgataaa ctaccgcatt aaagcttgca gtggcggttt   1380
tcatggcttg ttatgactgt tttttgggg tacagtctat gcctcgggca tccaagcagc   1440
aagcgcgtta cgccgtgggt cgatgtttga tgttatggag cagcaacgat gttacgcagc   1500
agggcagtcg ccctaaaaca aagttaaaca tcatgaggga agcggtgatc gccgaagtat   1560
cgactcaact atcagaggta gttggcgtca tcgagcgcca tctcgaaccg acgttgctgg   1620
ccgtacattt gtacggctcc gcagtggatg gcggcctgaa gccacacagt gatattgatt   1680
tgctggttac ggtgaccgta aggcttgatg aaacaacgcg gcgagctttg atcaacgacc   1740
ttttggaaac ttcggcttcc cctggagaga gcgagattct ccgcgctgta gaagtcacca   1800
ttgttgtgca cgacgacatc attccgtggc gttatccagc taagcgcgaa ctgcaatttg   1860
gagaatggca gcgcaatgac attcttgcag gtatcttcga gccagccacg atcgacattg   1920
atctggctat cttgctgaca aaagcaagag aacatagcgt tgccttggta ggtccagcgg   1980
cggaggaact ctttgatccg gttcctgaac aggatctatt tgaggcgcta atgaaacct   2040 taacgctatg gaactcgccg cccgactggg ctggcgatga gcgaaatgta gtgcttacgt   2100
tgtcccgcat ttggtacagc gcagtaaccg gcaaaatcgc gccgaaggat gtcgctgccg   2160
actgggcaat ggagcgcctg ccggcccagt atcagcccgt catacttgaa gctagacagg   2220
cttatcttgg acaagaagaa gatcgcttgg cctcgcgcgc agatcagttg gaagaatttg   2280
tccactacgt gaaaggcgag atcaccaagg tagtcggcaa ataatgtcta acaattcgtt   2340
caagcttatc gatgataagc tgtcaaacat gagaattctt gaagacgaaa gggcctcgtg   2400
atacgcctat ttttataggt taatgtcatg ataataatgg tttcttagac gtcaggtggc   2460
acttttcggg gaaatgtgcg cggaacccct atttgtttat ttttctaaat acattcaaat   2520
atgtatccgc tcatgagaca ataaccctga taaatgcttc aataatattg aaaaaggaag   2580
agtatgagta ttcaacattt ccgtgtcgcc cttattccct ttttttgcggc attttgcctt   2640 cctgtttttg ctcacccaga aacgctggtg aaagtaaaag atgctgaaga tcagttgggt   2700
gcacgagtgg gttacatcga actggatctc aacagcggta agatccttga gttttcgc   2760 cccgaagaac gttttccaat gatgagcact tttaaagttc tgctatgtgg cgcggtatta   2820
tcccgtgttg acgccgggca agagcaactc ggtcgccgca tacactattc tcagaatgac   2880
ttggttgagt actcaccagt cacagaaaag catcttacgg atggcatgac agtaagagaa   2940
```

```
ttatgcagtg ctgccataac catgagtgat aacactgcgg ccaacttact tctgacaacg    3000
atcggaggac cgaaggagct aaccgctttt ttgcacaaca tgggggatca tgtaactcgc    3060
cttgatcgtt gggaaccgga gctgaatgaa gccataccaa acgacgagcg tgacaccacg    3120
atgcctgcag caatggcaac aacgttgcgc aaactattaa ctggcgaact acttactcta    3180
gcttcccggc aacaattaat agactggatg gaggcggata agttgcagg accacttctg     3240 cgctcggccc ttccggctgg ctggtttatt gctgataaat ctggagccgg tgagcgtggg    3300
tctcgcggta tcattgcagc actggggcca gatggtaagc cctcccgtat cgtagttatc    3360
tacacgacgg ggagtcaggc aactatggat gaacgaaata cagatcgc tgagataggt      3420 gcctcactga ttaagcattg gtaactgtca gaccaagttt actcatatat actttagatt    3480
gatttaaaac ttcatttta atttaaaagg atctaggtga agatccttttt tgataatctc    3540 atgaccaaaa tcccttaacg tgagttttcg ttccactgag cgtcagaccc cgtagaaaag    3600
atcaaaggat cttcttgaga tccttttttt ctgcgcgtaa tctgctgctt gcaaacaaaa    3660
aaaccaccgc taccagcggt ggtttgtttg ccggatcaag agctaccaac tcttttttccg   3720 aaggtaactg gcttcagcag agcgcagata ccaaatactg tccttctagt gtagccgtag    3780
ttaggccacc acttcaagaa ctctgtagca ccgcctacat acctcgctct gctaatcctg    3840
ttaccagtgg ctgctgccag tggcgataag tcgtgtctta ccgggttgga ctcaagacga    3900
tagttaccgg ataaggcgca gcggtcgggc tgaacgggggg gttcgtgcac acagcccagc   3960
ttggagcgaa cgacctacac cgaactgaga tacctacagc gtgagctatg agaaagcgcc    4020
acgcttcccg aagggagaaa ggcggacagg tatccggtaa gcggcagggt cggaacagga    4080
gagcgcacga gggagcttcc agggggaaac gcctggtatc tttatagtcc tgtcgggttt    4140
cgccacctct gacttgagcg tcgatttttg tgatgctcgt caggggggcg gagcctatgg    4200
aaaaacgcca gcaacgcggc ctttttacgg ttcctggcct tttgctggcc ttttgctcac    4260
atgttctttc ctgcgttatc ccctgattct gtggataacc gtattaccgc ctttgagtga    4320
gctgataccg ctcgccgcag ccgaacgacc gagcgcagcg agtcagtgag cgaggaagcg    4380
gaagagcgcc tgatgcggta ttttctcctt acgcatctgt gcggtatttc acaccgcata    4440
tatggtgcac tctcagtaca atctgctctg atgccgcata gttaagccag tatacactcc    4500
gctatcgcta cgtgactggg tcatggctgc gccccgacac ccgccaacac ccgctgacgc    4560
gccctgacgg gcttgtctgc tcccggcatc cgcttacaga caagctgtga ccgtctccgg    4620
gagctgcatg tgtcagaggt tttcaccgtc atcaccgaaa cgcgcgaggc agctgcggta    4680
aagctcatca gcgtggtcgt gaagcgattc acagatgtct gcctgttcat ccgcgtccag    4740
ctcgttgagt ttctccagaa gcgttaatgt ctggcttctg ataaagcggg ccatgttaag    4800
ggcggttttt tcctgtttgg tcactgatgc ctccgtgtaa gggggatttc tgttcatggg    4860
ggtaatgata ccgatgaaac gagagaggat gctcacgata cgggttactg atgatgaaca    4920
tgcccggtta ctggaacgtt gtgagggtaa acaactggcg gtatggatgc ggcgggacca    4980
gagaaaaatc actcagggtc aatgccagcg cttcgttaat acagatgtag gtgttccaca    5040
gggtagccag cagcatcctg cgatgcagat ccggaacata atggtgcagg cgctgactt     5100 ccgcgtttcc agactttacg aaacacgaaa accgaagacc attcatgttg ttgctcaggt    5160
cgcagacgtt ttgcagcagc agtcgcttca cgttcgctcg cgtatcggtg attcattctg    5220
ctaaccagta aggcaacccc gccagcctag ccgggtcctc aacgacagga gcacgatcat    5280
gcgcacccgt ggccaggacc caacgctgcc cgagatgcgc cgcgtgcggc tgctggagat    5340
```

-continued

```
ggcggacgcg atggatatgt tctgccaagg gttggtttgc gcattcacag ttctccgcaa    5400
gaattgattg gctccaattc ttggagtggt gaatccgtta gcgaggtgcc gccggcttcc    5460
attcaggtcg aggtggcccg gctccatgca ccgcgacgca acgcggggag gcagacaagg    5520
tatagggcgg cgcctacaat ccatgccaac ccgttccatg tgctcgccga ggcggcataa    5580
atcgccgtga cgatcagcgg tccagtgatc gaagttaggc tggtaagagc cgcgagcgat    5640
ccttgaagct gtccctgatg gtcgtcatct acctgcctgg acagcatggc ctgcaacgcg    5700
ggcatcccga tgccgccgga agcgagaaga atcataatgg ggaaggccat ccagcctcgc    5760
gtcgcgaacg ccagcaagac gtagcccagc gcgtcggccg ccatgccggc gataatggcc    5820
tgcttctcgc cgaaacgttt ggtggcggga ccagtgacga aggcttgagc gagggcgtgc    5880
aagattccga ataccgcaag cgacaggccg atcatcgtcg cgctccagcg aaagcggtcc    5940
tcgccgaaaa tgacccagag cgctgccggc acctgtccta cgagttgcat gataaagaag    6000
acagtcataa gtcggcgac gatagtcatg ccccgcgccc accggaagga gctgactggg    6060
ttgaaggctc tcaagggcat cggtcgatcg acgctctccc ttatgcgact cctgcattag    6120
gaagcagccc agtagtaggt tgaggccgtt gagcaccgcc gccgcaagga atggtgcatg    6180
caaggagatg gcgcccaaca gtcccccggc cacggggcct gccaccatac ccacgccgaa    6240
acaagcgctc atgagcccga agtggcgagc ccgatcttcc ccatcggtga tgtcggcgat    6300
ataggcgcca gcaaccgcac ctgtggcgcc ggtgatgccg gccacgatgc gtccggcgta    6360
gaggatcg                                                            6368
```

<210> SEQ ID NO 398
<211> LENGTH: 20
<212> TYPE: DNA
<213> ORGANISM: artificial sequence
<220> FEATURE:
<223> OTHER INFORMATION: primer

<400> SEQUENCE: 398

```
ccctcatagt tagcgtaacg                                                  20
```

<210> SEQ ID NO 399
<211> LENGTH: 15
<212> TYPE: PRT
<213> ORGANISM: artificial sequence
<220> FEATURE:
<223> OTHER INFORMATION: synthetic construct

<400> SEQUENCE: 399

```
Ser Asn Ala Thr Met Tyr Asn Ile Gln Ser His Ser His His Gln
1               5                   10                  15
```

<210> SEQ ID NO 400
<211> LENGTH: 15
<212> TYPE: PRT
<213> ORGANISM: artificial sequence
<220> FEATURE:
<223> OTHER INFORMATION: synthetic construct

<400> SEQUENCE: 400

```
Gln Ala Ala Gln Val His Met Met Gln His Ser Arg Pro Thr Thr
1               5                   10                  15
```

<210> SEQ ID NO 401
<211> LENGTH: 15
<212> TYPE: PRT
<213> ORGANISM: artificial sequence
<220> FEATURE:

<223> OTHER INFORMATION: synthetic construct

<400> SEQUENCE: 401

His Asp Pro Tyr Thr Met Lys Ser Ala Leu Arg Gln Ser Thr Ser
1               5                   10                  15

<210> SEQ ID NO 402
<211> LENGTH: 15
<212> TYPE: PRT
<213> ORGANISM: artificial sequence
<220> FEATURE:
<223> OTHER INFORMATION: synthetic construct

<400> SEQUENCE: 402

Asp Leu Gly Thr Phe Pro Asn Arg Thr Leu Lys Met Ala Ala His
1               5                   10                  15

<210> SEQ ID NO 403
<211> LENGTH: 15
<212> TYPE: PRT
<213> ORGANISM: artificial sequence
<220> FEATURE:
<223> OTHER INFORMATION: synthetic construct

<400> SEQUENCE: 403

Asp Thr Ile His Pro Asn Lys Met Lys Ser Pro Ser Ser Pro Leu
1               5                   10                  15

<210> SEQ ID NO 404
<211> LENGTH: 15
<212> TYPE: PRT
<213> ORGANISM: artificial sequence
<220> FEATURE:
<223> OTHER INFORMATION: synthetic construct

<400> SEQUENCE: 404

Gly Ser Asn Asn His Leu Pro Ser Thr Val Pro Arg Leu Thr Val
1               5                   10                  15

<210> SEQ ID NO 405
<211> LENGTH: 18
<212> TYPE: PRT
<213> ORGANISM: artificial sequence
<220> FEATURE:
<223> OTHER INFORMATION: synthetic construct

<400> SEQUENCE: 405

Ser Asn Pro Ile Pro Asn Phe Ala His Asp Leu Arg His Ser Lys Tyr
1               5                   10                  15
Asn Ser

<210> SEQ ID NO 406
<211> LENGTH: 18
<212> TYPE: PRT
<213> ORGANISM: artificial sequence
<220> FEATURE:
<223> OTHER INFORMATION: synthetic construct

<400> SEQUENCE: 406

Thr Lys Pro Pro Arg Thr Pro Thr Ala Asn Thr Ser Arg Pro His His
1               5                   10                  15
Asn Phe

<210> SEQ ID NO 407
<211> LENGTH: 20
<212> TYPE: PRT

<213> ORGANISM: artificial sequence
<220> FEATURE:
<223> OTHER INFORMATION: synthetic construct

<400> SEQUENCE: 407

Ala Asn Ser Gly Phe Pro Ile Trp Leu Gln Lys Tyr Pro Trp Ser Glu
1               5                   10                  15

Val Gln Gln Glu
            20

<210> SEQ ID NO 408
<211> LENGTH: 19
<212> TYPE: PRT
<213> ORGANISM: artificial sequence
<220> FEATURE:
<223> OTHER INFORMATION: synthetic construct

<400> SEQUENCE: 408

Ala Thr Pro Arg Leu Thr Pro Glu Ala His His Lys Ala Gly Asn Trp
1               5                   10                  15

Tyr Ala Ser

<210> SEQ ID NO 409
<211> LENGTH: 20
<212> TYPE: PRT
<213> ORGANISM: artificial sequence
<220> FEATURE:
<223> OTHER INFORMATION: synthetic construct

<400> SEQUENCE: 409

Ala Thr Pro Ser Gln His Arg Tyr Gly Leu Met Gln Asn His Ala Pro
1               5                   10                  15

Asn Gly Ile Glu
            20

<210> SEQ ID NO 410
<211> LENGTH: 16
<212> TYPE: PRT
<213> ORGANISM: artificial sequence
<220> FEATURE:
<223> OTHER INFORMATION: synthetic construct

<400> SEQUENCE: 410

Gly Met Gly Ser Glu Val Leu Ser Gln Tyr Pro Gln Ala Pro Val Gly
1               5                   10                  15

<210> SEQ ID NO 411
<211> LENGTH: 21
<212> TYPE: PRT
<213> ORGANISM: artificial sequence
<220> FEATURE:
<223> OTHER INFORMATION: synthetic construct

<400> SEQUENCE: 411

Thr Thr Tyr His Tyr Lys Asn Ile Tyr Gln Glu Ser Tyr Gln Gln Arg
1               5                   10                  15

Asn Pro Ala Val Lys
            20

<210> SEQ ID NO 412
<211> LENGTH: 16
<212> TYPE: PRT
<213> ORGANISM: artificial sequence
<220> FEATURE:
<223> OTHER INFORMATION: synthetic construct -continued

```
<400> SEQUENCE: 412

Ser Asn Ala Thr Met Tyr Asn Ile Gln Ser His Ser His His Gln Lys
1               5                   10                  15

<210> SEQ ID NO 413
<211> LENGTH: 16
<212> TYPE: PRT
<213> ORGANISM: artificial sequence
<220> FEATURE:
<223> OTHER INFORMATION: synthetic construct

<400> SEQUENCE: 413

Gln Ala Ala Gln Val His Met Met Gln His Ser Arg Pro Thr Thr Lys
1               5                   10                  15

<210> SEQ ID NO 414
<211> LENGTH: 16
<212> TYPE: PRT
<213> ORGANISM: artificial sequence
<220> FEATURE:
<223> OTHER INFORMATION: synthetic construct

<400> SEQUENCE: 414

His Asp Pro Tyr Thr Met Lys Ser Ala Leu Arg Gln Ser Thr Ser Lys
1               5                   10                  15

<210> SEQ ID NO 415
<211> LENGTH: 16
<212> TYPE: PRT
<213> ORGANISM: artificial sequence
<220> FEATURE:
<223> OTHER INFORMATION: synthetic construct

<400> SEQUENCE: 415

Asp Leu Gly Thr Phe Pro Asn Arg Thr Leu Lys Met Ala Ala His Lys
1               5                   10                  15

<210> SEQ ID NO 416
<211> LENGTH: 16
<212> TYPE: PRT
<213> ORGANISM: artificial sequence
<220> FEATURE:
<223> OTHER INFORMATION: synthetic construct

<400> SEQUENCE: 416

Asp Thr Ile His Pro Asn Lys Met Lys Ser Pro Ser Ser Pro Leu Lys
1               5                   10                  15

<210> SEQ ID NO 417
<211> LENGTH: 16
<212> TYPE: PRT
<213> ORGANISM: artificial sequence
<220> FEATURE:
<223> OTHER INFORMATION: synthetic construct

<400> SEQUENCE: 417

Gly Ser Asn Asn His Leu Pro Ser Thr Val Pro Arg Leu Thr Val Lys
1               5                   10                  15

<210> SEQ ID NO 418
<211> LENGTH: 19
<212> TYPE: PRT
<213> ORGANISM: artificial sequence
<220> FEATURE:
<223> OTHER INFORMATION: synthetic construct

<400> SEQUENCE: 418
```

```
Ser Asn Pro Ile Pro Asn Phe Ala His Asp Leu Arg His Ser Lys Tyr
1               5                   10                  15

Asn Ser Lys

<210> SEQ ID NO 419
<211> LENGTH: 19
<212> TYPE: PRT
<213> ORGANISM: artificial sequence
<220> FEATURE:
<223> OTHER INFORMATION: synthetic construct

<400> SEQUENCE: 419

Thr Lys Pro Pro Arg Thr Pro Thr Ala Asn Thr Ser Arg Pro His His
1               5                   10                  15

Asn Phe Lys

<210> SEQ ID NO 420
<211> LENGTH: 21
<212> TYPE: PRT
<213> ORGANISM: artificial sequence
<220> FEATURE:
<223> OTHER INFORMATION: synthetic construct

<400> SEQUENCE: 420

Ala Asn Ser Gly Phe Pro Ile Trp Leu Gln Lys Tyr Pro Trp Ser Glu
1               5                   10                  15

Val Gln Gln Glu Lys
            20

<210> SEQ ID NO 421
<211> LENGTH: 21
<212> TYPE: PRT
<213> ORGANISM: artificial sequence
<220> FEATURE:
<223> OTHER INFORMATION: synthetic construct

<400> SEQUENCE: 421

Ala Thr Pro Ser Gln His Arg Tyr Gly Leu Met Gln Asn His Ala Pro
1               5                   10                  15

Asn Gly Ile Glu Lys
            20

<210> SEQ ID NO 422
<211> LENGTH: 17
<212> TYPE: PRT
<213> ORGANISM: artificial sequence
<220> FEATURE:
<223> OTHER INFORMATION: synthetic construct

<400> SEQUENCE: 422

Gly Met Gly Ser Glu Val Leu Ser Gln Tyr Pro Gln Ala Pro Val Gly
1               5                   10                  15

Lys

<210> SEQ ID NO 423
<211> LENGTH: 88
<212> TYPE: PRT
<213> ORGANISM: artificial sequence
<220> FEATURE:
<223> OTHER INFORMATION: synthetic construct

<400> SEQUENCE: 423

Pro Ser Ala Gln Ser Gln Leu Pro Asp Lys His Ser Gly Leu His Glu
1               5                   10                  15
```

Arg Ala Pro Gln Arg Tyr Gly Pro Glu Pro Glu Pro Glu Pro
                20                  25                  30

Ile Pro Glu Pro Pro Lys Glu Ala Pro Val Val Ile Glu Lys Pro Lys
            35                  40                  45

Pro Lys Pro Lys Pro Lys Pro Lys Pro Ala His Asp His Lys Asn
    50                  55                  60

Gln Lys Glu Thr His Gln Arg His Ala Ala Gly Ser Gly Gly Gly Gly
65                  70                  75                  80

Ser Pro His His His His His His
            85

<210> SEQ ID NO 424
<211> LENGTH: 325
<212> TYPE: PRT
<213> ORGANISM: Thermotoga maritima

<400> SEQUENCE: 424

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Thr Leu
            20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
    195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
    275                 280                 285

Tyr Ala Gly Pro Lys Glu Ile Arg Ile Tyr Pro Tyr Asn Asn His Glu
290                 295                 300

```
Gly Gly Gly Ser Phe Gln Ala Val Glu Gln Val Lys Phe Leu Lys Lys
305                 310                 315                 320

Leu Phe Glu Lys Gly
            325

<210> SEQ ID NO 425
<211> LENGTH: 431
<212> TYPE: PRT
<213> ORGANISM: artificial sequence
<220> FEATURE:
<223> OTHER INFORMATION: synthetic construct

<400> SEQUENCE: 425

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Pro Ser Ala Gln Ser Gln Leu Pro Asp
```

```
                340             345             350
Lys His Ser Gly Leu His Glu Arg Ala Pro Gln Arg Tyr Gly Pro Glu
            355                 360                 365
Pro Glu Pro Glu Pro Glu Pro Ile Pro Glu Pro Pro Lys Glu Ala Pro
        370                 375                 380
Val Val Ile Glu Lys Pro Lys Pro Lys Pro Lys Pro Lys Pro Lys Pro
385                 390                 395                 400
Pro Ala His Asp His Lys Asn Gln Lys Glu Thr His Gln Arg His Ala
                405                 410                 415
Ala Gly Ser Gly Gly Gly Gly Ser Pro His His His His His His
            420                 425                 430

<210> SEQ ID NO 426
<211> LENGTH: 333
<212> TYPE: PRT
<213> ORGANISM: artificial sequence
<220> FEATURE:
<223> OTHER INFORMATION: synthetic construct

<400> SEQUENCE: 426

Met Ala Phe Phe Asp Leu Pro Leu Glu Glu Leu Lys Lys Tyr Arg Pro
1               5                   10                  15
Glu Arg Tyr Glu Glu Lys Asp Phe Asp Glu Phe Trp Glu Glu Thr Leu
            20                  25                  30
Ala Glu Ser Glu Lys Phe Pro Leu Asp Pro Val Phe Glu Arg Met Glu
        35                  40                  45
Ser His Leu Lys Thr Val Glu Ala Tyr Asp Val Thr Phe Ser Gly Tyr
    50                  55                  60
Arg Gly Gln Arg Ile Lys Gly Trp Leu Leu Val Pro Lys Leu Glu Glu
65                  70                  75                  80
Glu Lys Leu Pro Cys Val Val Gln Tyr Ile Gly Tyr Asn Gly Gly Arg
                85                  90                  95
Gly Phe Pro His Asp Trp Leu Phe Trp Pro Ser Met Gly Tyr Ile Cys
            100                 105                 110
Phe Val Met Asp Thr Arg Gly Gln Gly Ser Gly Trp Leu Lys Gly Asp
        115                 120                 125
Thr Pro Asp Tyr Pro Glu Gly Pro Val Asp Pro Gln Tyr Pro Gly Phe
    130                 135                 140
Met Thr Arg Gly Ile Leu Asp Pro Arg Thr Tyr Tyr Arg Arg Val
145                 150                 155                 160
Phe Thr Asp Ala Val Arg Ala Val Glu Ala Ala Ala Ser Phe Pro Gln
                165                 170                 175
Val Asp Gln Glu Arg Ile Val Ile Ala Gly Gly Ser Gln Gly Gly Gly
            180                 185                 190
Ile Ala Leu Ala Val Ser Ala Leu Ser Lys Lys Ala Lys Ala Leu Leu
        195                 200                 205
Cys Asp Val Pro Phe Leu Cys His Phe Arg Arg Ala Val Gln Leu Val
    210                 215                 220
Asp Thr His Pro Tyr Ala Glu Ile Thr Asn Phe Leu Lys Thr His Arg
225                 230                 235                 240
Asp Lys Glu Glu Ile Val Phe Arg Thr Leu Ser Tyr Phe Asp Gly Val
                245                 250                 255
Asn Phe Ala Ala Arg Ala Lys Ile Pro Ala Leu Phe Ser Val Gly Leu
            260                 265                 270
Met Asp Asn Ile Ser Pro Pro Ser Thr Val Phe Ala Ala Tyr Asn Tyr
        275                 280                 285
```

```
Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly Gly Ser His His His His His His
                325                 330

<210> SEQ ID NO 427
<211> LENGTH: 353
<212> TYPE: PRT
<213> ORGANISM: artificial sequence
<220> FEATURE:
<223> OTHER INFORMATION: synthetic construct

<400> SEQUENCE: 427

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
        260                 265                 270

Met Asp Asn Ile Ser Pro Pro Ser Thr Val Phe Ala Ala Tyr Asn Tyr
    275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320
```

```
Leu Phe Glu Lys Gly Gly Pro Gly Ser Gly Gly Ala Gly Ser Pro Gly
                325                 330                 335

Ser Ala Gly Gly Pro Gly Ser Gly Lys Gly Lys Gly Lys Gly Lys Gly
                340                 345                 350

Lys

<210> SEQ ID NO 428
<211> LENGTH: 359
<212> TYPE: PRT
<213> ORGANISM: artificial sequence
<220> FEATURE:
<223> OTHER INFORMATION: synthetic construct

<400> SEQUENCE: 428

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Gly Ala Gly Ser Pro Gly
                325                 330                 335
```

```
Ser Ala Gly Gly Pro Gly Ser Gly Lys Gly Lys Gly Lys Gly
            340                 345                 350

Lys His His His His His
        355

<210> SEQ ID NO 429
<211> LENGTH: 375
<212> TYPE: PRT
<213> ORGANISM: artificial sequence
<220> FEATURE:
<223> OTHER INFORMATION: synthetic construct

<400> SEQUENCE: 429

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335
```

Ser Ala Gly Gly Pro Gly Ser Thr Lys Pro Pro Arg Thr Pro Thr Ala
            340                 345                 350

Asn Thr Ser Arg Pro His His Asn Phe Gly Ser Gly Gly Gly Ser
            355                 360                 365

Pro His His His His His His
            370                 375

<210> SEQ ID NO 430
<211> LENGTH: 349
<212> TYPE: PRT
<213> ORGANISM: artificial sequence
<220> FEATURE:
<223> OTHER INFORMATION: synthetic construct

<400> SEQUENCE: 430

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Gly Ala Gly Ser Pro Gly

```
                    325                 330                 335
Ser Ala Gly Gly Pro Gly Ser His His His His His His
            340                 345

<210> SEQ ID NO 431
<211> LENGTH: 106
<212> TYPE: PRT
<213> ORGANISM: artificial sequence
<220> FEATURE:
<223> OTHER INFORMATION: synthetic construct

<400> SEQUENCE: 431

Gly Pro Gly Ser Gly Gly Ala Gly Ser Pro Gly Ser Ala Gly Gly Pro
1               5                   10                  15

Gly Ser Pro Ser Ala Gln Ser Gln Leu Pro Asp Lys His Ser Gly Leu
            20                  25                  30

His Glu Arg Ala Pro Gln Arg Tyr Gly Pro Glu Pro Glu Pro Glu Pro
        35                  40                  45

Glu Pro Ile Pro Glu Pro Pro Lys Glu Ala Pro Val Val Ile Glu Lys
    50                  55                  60

Pro Lys Pro Lys Pro Lys Pro Lys Pro Lys Pro Pro Ala His Asp His
65                  70                  75                  80

Lys Asn Gln Lys Glu Thr His Gln Arg His Ala Ala Gly Ser Gly Gly
                85                  90                  95

Gly Gly Ser Pro His His His His His His
            100                 105

<210> SEQ ID NO 432
<211> LENGTH: 8
<212> TYPE: PRT
<213> ORGANISM: artificial sequence
<220> FEATURE:
<223> OTHER INFORMATION: synthetic construct

<400> SEQUENCE: 432

Gly Ser His His His His His His
1               5

<210> SEQ ID NO 433
<211> LENGTH: 28
<212> TYPE: PRT
<213> ORGANISM: artificial sequence
<220> FEATURE:
<223> OTHER INFORMATION: synthetic construct

<400> SEQUENCE: 433

Gly Pro Gly Ser Gly Gly Ala Gly Ser Pro Gly Ser Ala Gly Gly Pro
1               5                   10                  15

Gly Ser Gly Lys Gly Lys Gly Lys Gly Lys Gly Lys
            20                  25

<210> SEQ ID NO 434
<211> LENGTH: 34
<212> TYPE: PRT
<213> ORGANISM: artificial sequence
<220> FEATURE:
<223> OTHER INFORMATION: synthetic construct

<400> SEQUENCE: 434

Gly Pro Gly Ser Gly Gly Ala Gly Ser Pro Gly Ser Ala Gly Gly Pro
1               5                   10                  15

Gly Ser Gly Lys Gly Lys Gly Lys Gly Lys Gly Lys His His His His
            20                  25                  30
```

His His

<210> SEQ ID NO 435
<211> LENGTH: 50
<212> TYPE: PRT
<213> ORGANISM: artificial sequence
<220> FEATURE:
<223> OTHER INFORMATION: synthetic construct

<400> SEQUENCE: 435

Gly Pro Gly Ser Gly Gly Ala Gly Ser Pro Gly Ser Ala Gly Gly Pro
1               5                   10                  15

Gly Ser Thr Lys Pro Pro Arg Thr Pro Thr Ala Asn Thr Ser Arg Pro
            20                  25                  30

His His Asn Phe Gly Ser Gly Gly Gly Ser Pro His His His His
        35                  40                  45

His His
    50

<210> SEQ ID NO 436
<211> LENGTH: 24
<212> TYPE: PRT
<213> ORGANISM: artificial sequence
<220> FEATURE:
<223> OTHER INFORMATION: synthetic construct

<400> SEQUENCE: 436

Gly Pro Gly Ser Gly Gly Ala Gly Ser Pro Gly Ser Ala Gly Gly Pro
1               5                   10                  15

Gly Ser His His His His His His
            20

<210> SEQ ID NO 437
<211> LENGTH: 325
<212> TYPE: PRT
<213> ORGANISM: artificial sequence
<220> FEATURE:
<223> OTHER INFORMATION: synthetic construct

<400> SEQUENCE: 437

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
             165                 170                 175

Val Asp Gln Glu Arg Ile Val Ile Ala Gly Ser Gln Gly Gly Gly
         180                 185                 190

Ile Ala Leu Ala Val Ser Ala Leu Ser Lys Lys Ala Lys Ala Leu Leu
             195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                 245                 250                 255

Asn Phe Ala Ala Arg Ala Lys Ile Pro Ala Leu Phe Ser Val Gly Leu
             260                 265                 270

Met Asp Asn Ile Thr Pro Pro Ser Thr Val Phe Ala Ala Tyr Asn Tyr
             275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
             325

<210> SEQ ID NO 438
<211> LENGTH: 375
<212> TYPE: PRT
<213> ORGANISM: artificial sequence
<220> FEATURE:
<223> OTHER INFORMATION: synthetic construct

<400> SEQUENCE: 438

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
             20                  25                  30

Ala Glu Ser Glu Lys Phe Pro Leu Asp Pro Val Phe Glu Arg Met Glu
         35                  40                  45

Ser His Leu Lys Thr Val Glu Ala Tyr Asp Val Thr Phe Ser Gly Tyr
     50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
             100                 105                 110

Phe Val Met Asp Thr Arg Gly Gln Gly Ser Gly Trp Leu Lys Gly Asp
         115                 120                 125

Thr Pro Asp Tyr Pro Glu Gly Pro Val Asp Pro Gln Tyr Pro Gly Phe
     130                 135                 140

Met Thr Arg Gly Ile Leu Asp Pro Arg Thr Tyr Tyr Arg Val
145                 150                 155                 160

Phe Thr Asp Ala Val Arg Ala Val Glu Ala Ala Ser Phe Pro Gln
             165                 170                 175

Val Asp Gln Glu Arg Ile Val Ile Ala Gly Ser Gln Gly Gly Gly
         180                 185                 190

```
Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Thr Lys Pro Pro Arg Thr Pro Thr Ala
            340                 345                 350

Asn Thr Ser Arg Pro His His Asn Phe Gly Ser Gly Gly Gly Ser
        355                 360                 365

Pro His His His His His His
    370                 375

<210> SEQ ID NO 439
<211> LENGTH: 349
<212> TYPE: PRT
<213> ORGANISM: artificial sequence
<220> FEATURE:
<223> OTHER INFORMATION: synthetic construct

<400> SEQUENCE: 439

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
```

```
              180                 185                 190
Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser His His His His His
            340                 345

<210> SEQ ID NO 440
<211> LENGTH: 431
<212> TYPE: PRT
<213> ORGANISM: artificial sequence
<220> FEATURE:
<223> OTHER INFORMATION: synthetic construct

<400> SEQUENCE: 440

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205
```

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Pro Ser Ala Gln Ser Gln Leu Pro Asp
            340                 345                 350

Lys His Ser Gly Leu His Glu Arg Ala Pro Gln Arg Tyr Gly Pro Glu
    355                 360                 365

Pro Glu Pro Glu Pro Glu Pro Ile Pro Glu Pro Pro Lys Glu Ala Pro
        370                 375                 380

Val Val Ile Glu Lys Pro Lys Pro Lys Pro Lys Pro Lys Pro Lys Pro
385                 390                 395                 400

Pro Ala His Asp His Lys Asn Gln Lys Glu Thr His Gln Arg His Ala
                405                 410                 415

Ala Gly Ser Gly Gly Gly Gly Ser Pro His His His His His
            420                 425                 430

<210> SEQ ID NO 441
<211> LENGTH: 333
<212> TYPE: PRT
<213> ORGANISM: artificial sequence
<220> FEATURE:
<223> OTHER INFORMATION: synthetic construct

<400> SEQUENCE: 441

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

```
Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
290                 295                 300

Gly Gly Gly Ser Phe Gln Ala Val Glu Gln Val Lys Phe Leu Lys Lys
305                 310                 315                 320

Leu Phe Glu Lys Gly Gly Ser His His His His His
                325                 330

<210> SEQ ID NO 442
<211> LENGTH: 359
<212> TYPE: PRT
<213> ORGANISM: artificial sequence
<220> FEATURE:
<223> OTHER INFORMATION: synthetic construct

<400> SEQUENCE: 442

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
```

```
                    180                 185                 190
Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Thr Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Gly Lys Gly Lys Gly Lys Gly Lys Gly
                340                 345                 350

Lys His His His His His His
            355

<210> SEQ ID NO 443
<211> LENGTH: 386
<212> TYPE: PRT
<213> ORGANISM: artificial sequence
<220> FEATURE:
<223> OTHER INFORMATION: synthetic construct

<400> SEQUENCE: 443

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190
```

```
Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Val Lys Phe Leu Lys Lys
305                 310                 315                 320

Leu Phe Glu Lys Gly Glu Pro Glu Pro Glu Gly Pro Gly Ser Gly Gly
                325                 330                 335

Ala Gly Ser Pro Gly Ser Ala Gly Gly Pro Gly Ser Glu Pro Glu Pro
                340                 345                 350

Glu Trp Lys Thr Lys Lys Ile Leu Leu Ser Arg Thr Arg Arg Ile Met
        355                 360                 365

Arg Gln Val Val Arg Ser Val Met His Lys Ile Trp His His His His
        370                 375                 380

His His
385

<210> SEQ ID NO 444
<211> LENGTH: 387
<212> TYPE: PRT
<213> ORGANISM: artificial sequence
<220> FEATURE:
<223> OTHER INFORMATION: synthetic construct

<400> SEQUENCE: 444

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Tyr Arg Arg Val
145                 150                 155                 160
```

```
Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Glu Pro Glu Pro Glu
                325                 330                 335

Gly Pro Gly Ser Gly Gly Ala Gly Ser Pro Gly Ser Ala Gly Gly Pro
            340                 345                 350

Gly Ser Trp Lys Thr Lys Lys Ile Leu Leu Ser Arg Thr Arg Arg Ile
            355                 360                 365

Met Arg Gln Val Val Arg Ser Val Met His Lys Ile Trp His His His
370                 375                 380

His His His
385

<210> SEQ ID NO 445
<211> LENGTH: 386
<212> TYPE: PRT
<213> ORGANISM: artificial sequence
<220> FEATURE:
<223> OTHER INFORMATION: synthetic construct

<400> SEQUENCE: 445

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
```

```
                130                 135                 140
Met Thr Arg Gly Ile Leu Asp Pro Arg Thr Tyr Tyr Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Ser Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Gly Pro Gly Ser Gly Gly
                325                 330                 335

Ala Gly Ser Pro Gly Ser Ala Gly Gly Pro Gly Ser Glu Pro Glu Pro
                340                 345                 350

Glu Pro Leu Trp Arg Arg Ile Thr Lys Arg Lys Leu Val Arg Pro Val
                355                 360                 365

Ala Thr Leu Met Trp Tyr Trp Phe Thr Ser Lys Arg His His His
                370                 375                 380

His His
385

<210> SEQ ID NO 446
<211> LENGTH: 387
<212> TYPE: PRT
<213> ORGANISM: artificial sequence
<220> FEATURE:
<223> OTHER INFORMATION: synthetic construct

<400> SEQUENCE: 446

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
                50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110
```

```
Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly Pro Glu Pro Glu Pro Glu Pro Glu Pro Glu
                325                 330                 335

Gly Pro Gly Ser Gly Gly Ala Gly Ser Pro Gly Ser Ala Gly Gly Pro
            340                 345                 350

Gly Ser Pro Leu Trp Arg Arg Ile Thr Lys Arg Lys Leu Val Arg Pro
            355                 360                 365

Val Ala Thr Leu Met Trp Tyr Trp Phe Thr Ser Lys Arg His His
            370                 375                 380

His His His
385

<210> SEQ ID NO 447
<211> LENGTH: 382
<212> TYPE: PRT
<213> ORGANISM: artificial sequence
<220> FEATURE:
<223> OTHER INFORMATION: synthetic construct

<400> SEQUENCE: 447

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Arg Gly Gln Arg Ile Lys Gly Trp Leu Leu Val Pro Lys Leu Glu Glu
65                  70                  75                  80
```

```
Glu Lys Leu Pro Cys Val Val Gln Tyr Ile Gly Tyr Asn Gly Gly Arg
            85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
            130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
            165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Gly Pro Gly Ser Gly Gly Ala Gly
            325                 330                 335

Ser Pro Gly Ser Ala Gly Gly Pro Gly Ser Gly Pro Glu Arg Met Leu
            340                 345                 350

Ser Arg Ile Leu Arg Met Phe Val Arg Ile Leu Lys Arg Glu Arg Leu
            355                 360                 365

Ser Gln Val Arg Gly Leu Phe Val His His His His His
            370                 375                 380

<210> SEQ ID NO 448
<211> LENGTH: 383
<212> TYPE: PRT
<213> ORGANISM: artificial sequence
<220> FEATURE:
<223> OTHER INFORMATION: synthetic construct

<400> SEQUENCE: 448

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
            50                  55                  60

Arg Gly Gln Arg Ile Lys Gly Trp Leu Leu Val Pro Lys Leu Glu Glu
```

```
                65                  70                  75                  80
Glu Lys Leu Pro Cys Val Val Gln Tyr Ile Gly Tyr Asn Gly Gly Arg
                    85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
                210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Ser Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Glu Gly Pro Gly Ser
                325                 330                 335

Gly Gly Ala Gly Ser Pro Gly Ser Ala Gly Gly Pro Gly Ser Arg Met
            340                 345                 350

Leu Ser Arg Ile Leu Arg Met Phe Val Arg Ile Leu Lys Arg Glu Arg
                355                 360                 365

Leu Ser Gln Val Arg Gly Leu Phe Val His His His His His His
        370                 375                 380
```

<210> SEQ ID NO 449
<211> LENGTH: 390
<212> TYPE: PRT
<213> ORGANISM: artificial sequence
<220> FEATURE:
<223> OTHER INFORMATION: synthetic construct

<400> SEQUENCE: 449

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60
```

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Gly Pro Gly Pro Ser
                325                 330                 335

Gly Gly Ala Gly Ser Pro Gly Ser Ala Gly Pro Gly Ser Glu Pro
            340                 345                 350

Glu Pro Glu Pro Glu Leu Arg Phe Leu Ala Arg Arg Phe Leu Lys Leu
        355                 360                 365

Arg Arg Ala Arg Lys Trp Trp Asn Ala Trp Lys Val Trp Val Thr Arg
    370                 375                 380

His His His His His His
385                 390

<210> SEQ ID NO 450
<211> LENGTH: 391
<212> TYPE: PRT
<213> ORGANISM: artificial sequence
<220> FEATURE:
<223> OTHER INFORMATION: synthetic construct

<400> SEQUENCE: 450

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

```
Ala Glu Ser Glu Lys Phe Pro Leu Asp Pro Val Phe Glu Arg Met Glu
         35                  40                  45

Ser His Leu Lys Thr Val Glu Ala Tyr Asp Val Thr Phe Ser Gly Tyr
     50                  55                  60

Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Glu Pro Glu Pro Glu
                325                 330                 335

Pro Glu Pro Glu Gly Pro Gly Ser Gly Gly Ala Gly Ser Pro Gly Ser
            340                 345                 350

Ala Gly Gly Pro Gly Ser Leu Arg Phe Leu Ala Arg Arg Phe Leu Lys
        355                 360                 365

Leu Arg Arg Ala Arg Lys Trp Trp Asn Ala Trp Lys Val Trp Val Thr
    370                 375                 380

Arg His His His His His His
385                 390

<210> SEQ ID NO 451
<211> LENGTH: 344
<212> TYPE: PRT
<213> ORGANISM: artificial sequence
<220> FEATURE:
<223> OTHER INFORMATION: synthetic construct

<400> SEQUENCE: 451

Met Gln Leu Phe Asp Leu Ser Leu Glu Glu Leu Lys Lys Tyr Lys Pro
```

```
                1               5              10              15
Lys Lys Thr Ala Arg Pro Asp Phe Ser Asp Phe Trp Lys Lys Ser Leu
                20                          25                  30

Glu Glu Leu Arg Gln Val Glu Ala Glu Pro Thr Leu Glu Ser Tyr Asp
                35                  40                      45

Tyr Pro Val Lys Gly Val Lys Val Tyr Arg Leu Thr Tyr Gln Ser Phe
    50                      55                  60

Gly His Ser Lys Ile Glu Gly Phe Tyr Ala Val Pro Asp Gln Thr Gly
65                      70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
                100                 105                 110

Phe Gly Met Leu Val Arg Gly Gln Gly Gly Ser Glu Asp Thr Ser Val
                115                 120                 125

Thr Pro Gly Gly His Ala Leu Gly Trp Met Thr Lys Gly Ile Leu Ser
            130                 135                 140

Lys Asp Thr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala Ala
                180                 185                 190

Leu Ser Asp Ile Pro Lys Val Val Ala Asp Tyr Pro Tyr Leu Ser
            195                 200                 205

Asn Phe Glu Arg Ala Val Asp Val Ala Leu Glu Gln Pro Tyr Leu Glu
    210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
                260                 265                 270

Pro Pro Ser Thr Val Phe Ala Ala Tyr Asn His Leu Glu Thr Asp Lys
            275                 280                 285

Asp Leu Lys Val Tyr Arg Tyr Phe Gly His Glu Phe Ile Pro Ala Phe
        290                 295                 300

Gln Thr Glu Lys Leu Ser Phe Leu Gln Lys His Leu Leu Leu Ser Thr
305                 310                 315                 320

Gly Pro Gly Ser Gly Gly Ala Gly Ser Pro Gly Ser Ala Gly Gly Pro
                325                 330                 335

Gly Ser His His His His His His
            340
```

<210> SEQ ID NO 452
<211> LENGTH: 426
<212> TYPE: PRT
<213> ORGANISM: artificial sequence
<220> FEATURE:
<223> OTHER INFORMATION: synthetic construct

<400> SEQUENCE: 452

```
Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
                20                  25                  30
```

Glu Glu Leu Arg Gln Val Glu Ala Glu Pro Thr Leu Glu Ser Tyr Asp
                35                  40                  45

Tyr Pro Val Lys Gly Val Lys Val Tyr Arg Leu Thr Tyr Gln Ser Phe
 50                  55                  60

Gly His Ser Lys Ile Glu Gly Phe Tyr Ala Val Pro Asp Gln Thr Gly
 65                  70                  75                  80

Pro His Pro Ala Leu Val Arg Phe His Gly Tyr Asn Ala Ser Tyr Asp
                 85                  90                  95

Gly Gly Ile His Asp Ile Val Asn Trp Ala Leu His Gly Tyr Ala Thr
                100                 105                 110

Phe Gly Met Leu Val Arg Gly Gln Gly Ser Glu Asp Thr Ser Val
                115                 120                 125

Thr Pro Gly Gly His Ala Leu Gly Trp Met Thr Lys Gly Ile Leu Ser
                130                 135                 140

Lys Asp Thr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala Ala
                180                 185                 190

Leu Ser Asp Ile Pro Lys Val Val Ala Asp Tyr Pro Tyr Leu Ser
                195                 200                 205

Asn Phe Glu Arg Ala Val Asp Val Ala Leu Glu Gln Pro Tyr Leu Glu
                210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
                260                 265                 270

Pro Pro Ser Thr Val Phe Ala Ala Tyr Asn His Leu Glu Thr Asp Lys
                275                 280                 285

Asp Leu Lys Val Tyr Arg Tyr Phe Gly His Glu Phe Ile Pro Ala Phe
                290                 295                 300

Gln Thr Glu Lys Leu Ser Phe Leu Gln Lys His Leu Leu Leu Ser Thr
305                 310                 315                 320

Gly Pro Gly Ser Gly Gly Ala Gly Ser Pro Gly Ser Ala Gly Gly Pro
                325                 330                 335

Gly Ser Pro Ser Ala Gln Ser Gln Leu Pro Asp Lys His Ser Gly Leu
                340                 345                 350

His Glu Arg Ala Pro Gln Arg Tyr Gly Pro Glu Pro Glu Pro Glu Pro
                355                 360                 365

Glu Pro Ile Pro Glu Pro Pro Lys Glu Ala Pro Val Val Ile Glu Lys
                370                 375                 380

Pro Lys Pro Lys Pro Lys Pro Lys Pro Lys Pro Ala His Asp His
385                 390                 395                 400

Lys Asn Gln Lys Glu Thr His Gln Arg His Ala Ala Gly Ser Gly Gly
                405                 410                 415

Gly Gly Ser Pro His His His His His
                420                 425

<210> SEQ ID NO 453
<211> LENGTH: 372
<212> TYPE: PRT

<213> ORGANISM: artificial sequence
<220> FEATURE:
<223> OTHER INFORMATION: synthetic construct

<400> SEQUENCE: 453

Met Gln Leu Phe Asp Leu Ser Leu Glu Leu Lys Lys Tyr Lys Pro
1               5                   10                  15

Lys Lys Thr Ala Arg Pro Asp Phe Ser Asp Phe Trp Lys Lys Ser Leu
            20                  25                  30

Glu Glu Leu Arg Gln Val Gly Ala Glu Pro Thr Leu Glu Ser Tyr Asp
                35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
                100                 105                 110

Phe Gly Met Leu Val Arg Gly Gln Gly Gly Ser Glu Asp Thr Ser Val
            115                 120                 125

Thr Pro Gly Gly His Ala Leu Gly Trp Met Thr Lys Gly Ile Leu Ser
130                 135                 140

Lys Asp Thr Tyr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala Ala
            180                 185                 190

Leu Ser Asp Ile Pro Lys Val Val Ala Asp Tyr Pro Tyr Leu Ser
            195                 200                 205

Asn Phe Glu Arg Ala Val Asp Val Ala Leu Glu Gln Pro Tyr Leu Glu
210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
            245                 250                 255

Val Lys Gln Pro Thr Leu Met Ala Ile Gly Leu Ile Asp Lys Ile Thr
            260                 265                 270

Pro Pro Ser Thr Val Phe Ala Ala Tyr Asn His Leu Glu Thr Asp Lys
            275                 280                 285

Asp Leu Lys Val Tyr Arg Tyr Phe Gly His Glu Phe Ile Pro Ala Phe
    290                 295                 300

Gln Thr Glu Lys Leu Ser Phe Leu Gln Lys His Leu Leu Ser Thr
305                 310                 315                 320

Gly Pro Gly Ser Gly Gly Ala Gly Ser Pro Gly Ser Ala Gly Gly Pro
            325                 330                 335

Gly Ser Asp Pro Thr Lys Pro Arg Thr Pro Thr Ala Asn Thr Ser
            340                 345                 350

Arg Pro His His Asn Phe Gly Ser Gly Gly Gly Ser Pro His His
            355                 360                 365

His His His His
    370

<210> SEQ ID NO 454

```
<211> LENGTH: 347
<212> TYPE: PRT
<213> ORGANISM: artificial sequence
<220> FEATURE:
<223> OTHER INFORMATION: synthetic construct

<400> SEQUENCE: 454

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
            20                  25                  30

Ala Glu Ala Arg Gln Ala Gly Gly Glu Val Ser Ile Val Gln Ala Gln
        35                  40                  45

Thr Thr Leu Lys Ala Val Gln Ser Phe Asp Val Thr Phe Pro Gly Tyr
    50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Arg
                85                  90                  95

Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
        115                 120                 125

Thr Ala Asp Pro Val Gly Ser Thr Ser Ser Ile Pro Gly Phe Met Thr
    130                 135                 140

Arg Gly Val Leu Asp Lys Asn Asp Tyr Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Gly Ile Ser
            180                 185                 190

Leu Ala Val Gly Gly Ile Asp Pro Arg Val Lys Ala Val Met Pro Asp
        195                 200                 205

Val Pro Phe Leu Cys Asp Phe Pro Arg Ala Val Gln Thr Ala Val Arg
    210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255

Ala Arg Arg Ser Lys Ala Pro Ala Leu Phe Ser Val Ala Leu Met Asp
            260                 265                 270

Glu Val Cys Pro Pro Ser Thr Val Tyr Gly Ala Phe Asn Ala Tyr Ala
        275                 280                 285

Gly Glu Lys Thr Ile Thr Glu Tyr Glu Phe Asn Asn His Glu Gly Gly
    290                 295                 300

Gln Gly Tyr Gln Glu Arg Gln Gln Met Thr Trp Leu Ser Arg Leu Phe
305                 310                 315                 320

Gly Val Gly Gly Pro Gly Ser Gly Gly Ala Gly Ser Pro Gly Ser Ala
                325                 330                 335

Gly Gly Pro Gly Ser His His His His His His
            340                 345

<210> SEQ ID NO 455
<211> LENGTH: 429
<212> TYPE: PRT
<213> ORGANISM: artificial sequence
<220> FEATURE:
```

-continued

<223> OTHER INFORMATION: synthetic construct

<400> SEQUENCE: 455

```
Met Pro Phe Pro Asp Leu Ile Gln Pro Glu Leu Gly Ala Tyr Val Ser
1               5                   10                  15
Ser Val Gly Met Pro Asp Asp Phe Ala Gln Phe Trp Thr Ser Thr Ile
            20                  25                  30
Ala Glu Ala Arg Gln Ala Gly Gly Glu Val Ser Ile Val Gln Ala Gln
        35                  40                  45
Thr Thr Leu Lys Ala Val Gln Ser Phe Asp Val Thr Phe Pro Gly Tyr
    50                  55                  60
Gly Gly His Pro Ile Lys Gly Trp Leu Ile Leu Pro Thr His His Lys
65                  70                  75                  80
Gly Arg Leu Pro Leu Val Val Gln Tyr Ile Gly Tyr Gly Gly Arg
                85                  90                  95
Gly Leu Ala His Glu Gln Leu His Trp Ala Ala Ser Gly Phe Ala Tyr
            100                 105                 110
Phe Arg Met Asp Thr Arg Gly Gln Gly Ser Asp Trp Ser Val Gly Glu
        115                 120                 125
Thr Ala Asp Pro Val Gly Ser Thr Ser Ser Ile Pro Gly Phe Met Thr
    130                 135                 140
Arg Gly Val Leu Asp Lys Asn Asp Tyr Tyr Tyr Arg Arg Leu Phe Thr
145                 150                 155                 160
Asp Ala Val Arg Ala Ile Asp Ala Leu Leu Gly Leu Asp Phe Val Asp
                165                 170                 175
Pro Glu Arg Ile Ala Val Cys Gly Asp Ser Gln Gly Gly Gly Ile Ser
            180                 185                 190
Leu Ala Val Gly Gly Ile Asp Pro Arg Val Lys Ala Val Met Pro Asp
        195                 200                 205
Val Pro Phe Leu Cys Asp Phe Pro Arg Ala Val Gln Thr Ala Val Arg
    210                 215                 220
Asp Pro Tyr Leu Glu Ile Val Arg Phe Leu Ala Gln His Arg Glu Lys
225                 230                 235                 240
Lys Ala Ala Val Phe Glu Thr Leu Asn Tyr Phe Asp Cys Val Asn Phe
                245                 250                 255
Ala Arg Arg Ser Lys Ala Pro Ala Leu Phe Ser Val Ala Leu Met Asp
            260                 265                 270
Glu Val Cys Pro Pro Ser Thr Val Tyr Gly Ala Phe Asn Ala Tyr Ala
        275                 280                 285
Gly Glu Lys Thr Ile Thr Glu Tyr Glu Phe Asn Asn His Glu Gly Gly
    290                 295                 300
Gln Gly Tyr Gln Glu Arg Gln Gln Met Thr Trp Leu Ser Arg Leu Phe
305                 310                 315                 320
Gly Val Gly Gly Pro Gly Ser Gly Gly Ala Gly Ser Pro Gly Ser Ala
                325                 330                 335
Gly Gly Pro Gly Ser Pro Ser Ala Gln Ser Gln Leu Pro Asp Lys His
            340                 345                 350
Ser Gly Leu His Glu Arg Ala Pro Gln Arg Tyr Gly Pro Glu Pro Glu
        355                 360                 365
Pro Glu Pro Glu Pro Ile Pro Glu Pro Pro Lys Glu Ala Pro Val Val
    370                 375                 380
Ile Glu Lys Pro Lys Pro Lys Pro Lys Pro Lys Pro Lys Pro Pro Ala
385                 390                 395                 400
His Asp His Lys Asn Gln Lys Glu Thr His Gln Arg His Ala Ala Gly
```

```
                         405                 410                 415
Ser Gly Gly Gly Gly Ser Pro His His His His His
                420                 425

<210> SEQ ID NO 456
<211> LENGTH: 375
<212> TYPE: PRT
<213> ORGANISM: artificial sequence
<220> FEATURE:
<223> OTHER INFORMATION: synthetic construct

<400> SEQUENCE: 456

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
            20                  25                  30

Ala Glu Ala Arg Gln Ala Gly Gly Glu Val Ser Ile Val Gln Ala Gln
        35                  40                  45

Thr Thr Leu Lys Ala Val Gln Ser Phe Asp Val Thr Phe Pro Gly Tyr
    50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Arg
                85                  90                  95

Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
        115                 120                 125

Thr Ala Asp Pro Val Gly Ser Thr Ser Ser Ile Pro Gly Phe Met Thr
    130                 135                 140

Arg Gly Val Leu Asp Lys Asn Asp Tyr Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Gly Ile Ser
            180                 185                 190

Leu Ala Val Gly Gly Ile Asp Pro Arg Val Lys Ala Val Met Pro Asp
        195                 200                 205

Val Pro Phe Leu Cys Asp Phe Pro Arg Ala Val Gln Thr Ala Val Arg
    210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255

Ala Arg Arg Ser Lys Ala Pro Ala Leu Phe Ser Val Ala Leu Met Asp
            260                 265                 270

Glu Val Cys Pro Pro Ser Thr Val Tyr Gly Ala Phe Asn Ala Tyr Ala
        275                 280                 285

Gly Glu Lys Thr Ile Thr Glu Tyr Glu Phe Asn Asn His Glu Gly Gly
    290                 295                 300

Gln Gly Tyr Gln Glu Arg Gln Gln Met Thr Trp Leu Ser Arg Leu Phe
305                 310                 315                 320

Gly Val Gly Gly Pro Gly Ser Gly Gly Ala Gly Ser Pro Gly Ser Ala
                325                 330                 335

Gly Gly Pro Gly Ser Asp Pro Thr Lys Pro Pro Arg Thr Pro Thr Ala
            340                 345                 350
```

```
Asn Thr Ser Arg Pro His His Asn Phe Gly Ser Gly Gly Gly Gly Ser
        355                 360                 365

Pro His His His His His
        370                 375

<210> SEQ ID NO 457
<211> LENGTH: 336
<212> TYPE: PRT
<213> ORGANISM: artificial sequence
<220> FEATURE:
<223> OTHER INFORMATION: synthetic construct

<400> SEQUENCE: 457

Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
            20                  25                  30

Asn His Gln Phe Glu Phe Glu Leu Ile Glu Lys Asn Leu Ser Ser Lys
        35                  40                  45

Val Val Asn Phe Tyr His Leu Trp Phe Thr Ala Ile Asp Gly Ala Lys
    50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
        115                 120                 125

Met Thr Met Lys Gly Leu Ile Val Arg Gly Ile Asp Glu Gly Tyr Glu
    130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
        195                 200                 205

Arg Lys Ala Tyr Glu Leu Gly Ala Glu Glu Ser Ala Phe Glu Glu Leu
    210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
        275                 280                 285

Ser Leu Tyr Val Leu Pro Glu Tyr Gly His Glu Tyr Leu Pro Lys Ile
    290                 295                 300

Ser Asp Trp Leu Arg Glu Asn Gln Gly Pro Gly Ser Gly Gly Ala Gly
305                 310                 315                 320

Ser Pro Gly Ser Ala Gly Gly Pro Gly Ser His His His His His His
                325                 330                 335
```

<210> SEQ ID NO 458
<211> LENGTH: 418
<212> TYPE: PRT
<213> ORGANISM: artificial sequence
<220> FEATURE:
<223> OTHER INFORMATION: synthetic construct

<400> SEQUENCE: 458

```
Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
                20                  25                  30

Asn His Gln Phe Glu Phe Glu Leu Ile Glu Lys Asn Leu Ser Ser Lys
            35                  40                  45

Val Val Asn Phe Tyr His Leu Trp Phe Thr Ala Ile Asp Gly Ala Lys
        50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
        115                 120                 125

Met Thr Met Lys Gly Leu Ile Val Arg Gly Ile Asp Glu Gly Tyr Glu
130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
        195                 200                 205

Arg Lys Ala Tyr Glu Leu Gly Ala Glu Glu Ser Ala Phe Glu Glu Leu
210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
        275                 280                 285

Ser Leu Tyr Val Leu Pro Glu Tyr Gly His Glu Tyr Leu Pro Lys Ile
290                 295                 300

Ser Asp Trp Leu Arg Glu Asn Gln Gly Pro Gly Ser Gly Gly Ala Gly
305                 310                 315                 320

Ser Pro Gly Ser Ala Gly Gly Pro Gly Ser Pro Ser Ala Gln Ser Gln
                325                 330                 335

Leu Pro Asp Lys His Ser Gly Leu His Glu Arg Ala Pro Gln Arg Tyr
            340                 345                 350

Gly Pro Glu Pro Glu Pro Glu Pro Ile Pro Glu Pro Pro Lys
        355                 360                 365

Glu Ala Pro Val Val Ile Glu Lys Pro Lys Pro Lys Pro Lys Pro Lys
```

```
                370                 375                 380
Pro Lys Pro Pro Ala His Asp His Lys Asn Gln Lys Glu Thr His Gln
385                 390                 395                 400

Arg His Ala Ala Gly Ser Gly Gly Gly Ser Pro His His His His
                    405                 410                 415

His His
```

<210> SEQ ID NO 459
<211> LENGTH: 363
<212> TYPE: PRT
<213> ORGANISM: artificial sequence
<220> FEATURE:
<223> OTHER INFORMATION: synthetic construct

<400> SEQUENCE: 459

```
Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
                20                  25                  30

Asn His Gln Phe Glu Phe Glu Leu Ile Glu Lys Asn Leu Ser Ser Lys
            35                  40                  45

Val Val Asn Phe Tyr His Leu Trp Phe Thr Ala Ile Asp Gly Ala Lys
50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
                100                 105                 110

Cys Arg Gly Gln Gly Gly Leu Ser Gln Asp Asn Ile Gln Thr Met Gly
            115                 120                 125

Met Thr Met Lys Gly Leu Ile Val Arg Gly Ile Asp Glu Gly Tyr Glu
130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
            195                 200                 205

Arg Lys Ala Tyr Glu Leu Gly Ala Glu Glu Ser Ala Phe Glu Glu Leu
210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
                260                 265                 270

Pro Pro Ile Thr Gln Met Ala Ala Tyr Asn Lys Ile Gln Ser Lys Lys
            275                 280                 285

Ser Leu Tyr Val Leu Pro Glu Tyr Gly His Glu Tyr Leu Pro Lys Ile
            290                 295                 300

Ser Asp Trp Leu Arg Glu Asn Gln Gly Pro Gly Ser Gly Gly Ala Gly
305                 310                 315                 320
```

```
Ser Pro Gly Ser Ala Gly Pro Gly Ser Asp Pro Thr Lys Pro Pro
            325                 330                 335

Arg Thr Pro Thr Ala Asn Thr Ser Arg Pro His His Asn Phe Gly Ser
            340                 345                 350

Gly Gly Gly Gly Ser Pro His His His His
            355                 360

<210> SEQ ID NO 460
<211> LENGTH: 216
<212> TYPE: PRT
<213> ORGANISM: Mycobacterium smegmatis

<400> SEQUENCE: 460

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Val Ala Arg Thr Thr Asn Ile Asp Asp Pro Thr
50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Leu Ala Pro
130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu
    210                 215

<210> SEQ ID NO 461
<211> LENGTH: 240
<212> TYPE: PRT
<213> ORGANISM: artificial sequence
<220> FEATURE:
<223> OTHER INFORMATION: synthetic construct

<400> SEQUENCE: 461

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Val Ala Arg Thr Thr Asn Ile Asp Asp Pro Thr
50                  55                  60
```

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Ser Pro Pro Leu Ala Pro
130                 135                 140

Met Pro His Pro Trp Phe Gln Leu Ile Phe Glu Gly Glu Gln Lys
145                 150                 155                 160

Thr Thr Glu Leu Ala Arg Val Tyr Ser Ala Leu Ala Ser Phe Met Lys
            165                 170                 175

Val Pro Phe Phe Asp Ala Gly Ser Val Ile Ser Thr Asp Gly Val Asp
        180                 185                 190

Gly Ile His Phe Thr Glu Ala Asn Asn Arg Asp Leu Gly Val Ala Leu
        195                 200                 205

Ala Glu Gln Val Arg Ser Leu Leu Gly Pro Gly Ser Gly Ala Gly
210                 215                 220

Ser Pro Gly Ser Ala Gly Gly Pro Gly Ser His His His His His His
225                 230                 235                 240

<210> SEQ ID NO 462
<211> LENGTH: 322
<212> TYPE: PRT
<213> ORGANISM: artificial sequence
<220> FEATURE:
<223> OTHER INFORMATION: synthetic construct

<400> SEQUENCE: 462

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Val Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Ser Pro Pro Leu Ala Pro
130                 135                 140

Met Pro His Pro Trp Phe Gln Leu Ile Phe Glu Gly Glu Gln Lys
145                 150                 155                 160

Thr Thr Glu Leu Ala Arg Val Tyr Ser Ala Leu Ala Ser Phe Met Lys
            165                 170                 175

Val Pro Phe Phe Asp Ala Gly Ser Val Ile Ser Thr Asp Gly Val Asp
        180                 185                 190

```
Gly Ile His Phe Thr Glu Ala Asn Asn Arg Asp Leu Gly Val Ala Leu
        195                 200                 205

Ala Glu Gln Val Arg Ser Leu Leu Gly Pro Gly Ser Gly Gly Ala Gly
    210                 215                 220

Ser Pro Gly Ser Ala Gly Gly Pro Gly Ser Pro Ser Ala Gln Ser Gln
225                 230                 235                 240

Leu Pro Asp Lys His Ser Gly Leu His Glu Arg Ala Pro Gln Arg Tyr
                245                 250                 255

Gly Pro Glu Pro Glu Pro Glu Pro Ile Pro Glu Pro Pro Lys
            260                 265                 270

Glu Ala Pro Val Val Ile Glu Lys Pro Lys Pro Lys Pro Lys Pro Lys
                275                 280                 285

Pro Lys Pro Pro Ala His Asp His Lys Asn Gln Lys Glu Thr His Gln
            290                 295                 300

Arg His Ala Ala Gly Ser Gly Gly Gly Ser Pro His His His His
305                 310                 315                 320

His His

<210> SEQ ID NO 463
<211> LENGTH: 250
<212> TYPE: PRT
<213> ORGANISM: artificial sequence
<220> FEATURE:
<223> OTHER INFORMATION: synthetic construct

<400> SEQUENCE: 463

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Val Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu Gly Pro Gly Ser Gly Gly Ala Gly
    210                 215                 220

Ser Pro Gly Ser Ala Gly Gly Pro Gly Ser Gly Lys Gly Lys Gly Lys
225                 230                 235                 240
```

```
Gly Lys Gly Lys His His His His His His
            245                 250

<210> SEQ ID NO 464
<211> LENGTH: 268
<212> TYPE: PRT
<213> ORGANISM: artificial sequence
<220> FEATURE:
<223> OTHER INFORMATION: synthetic construct

<400> SEQUENCE: 464

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Val Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu Gly Pro Gly Ser Gly Gly Ala Gly
    210                 215                 220

Ser Pro Gly Ser Ala Gly Gly Pro Gly Ser Asp Pro Thr Lys Pro Pro
225                 230                 235                 240

Arg Thr Pro Thr Ala Asn Thr Ser Arg Pro His His Asn Phe Gly Ser
                245                 250                 255

Gly Gly Gly Gly Ser Pro His His His His His His
            260                 265

<210> SEQ ID NO 465
<211> LENGTH: 296
<212> TYPE: PRT
<213> ORGANISM: artificial sequence
<220> FEATURE:
<223> OTHER INFORMATION: synthetic construct

<400> SEQUENCE: 465

Met Ser Thr Phe Val Ala Lys Asp Gly Thr Gln Ile Tyr Phe Lys Asp
1               5                   10                  15

Trp Gly Ser Gly Lys Pro Val Leu Phe Ser His Gly Trp Pro Leu Asp
            20                  25                  30
```

Ala Asp Met Trp Glu Tyr Gln Met Glu Tyr Leu Ser Ser Arg Gly Tyr
             35                  40                  45

Arg Thr Ile Ala Phe Asp Arg Arg Gly Phe Gly Arg Ser Asp Gln Pro
     50                  55                  60

Trp Thr Gly Asn Asp Tyr Asp Thr Phe Ala Asp Ile Ala Gln Leu
 65                  70                  75                  80

Ile Glu His Leu Asp Leu Lys Glu Val Thr Leu Val Gly Phe Ser Met
                 85                  90                  95

Gly Gly Gly Asp Val Ala Arg Tyr Ile Ala Arg His Gly Ser Ala Arg
            100                 105                 110

Val Ala Gly Leu Val Leu Leu Gly Ala Val Thr Pro Leu Phe Gly Gln
            115                 120                 125

Lys Pro Asp Tyr Pro Gln Gly Val Pro Leu Asp Val Phe Ala Arg Phe
            130                 135                 140

Lys Thr Glu Leu Leu Lys Asp Arg Ala Gln Phe Ile Ser Asp Phe Asn
145                 150                 155                 160

Ala Pro Phe Tyr Gly Ile Asn Lys Gly Gln Val Val Ser Gln Gly Val
                165                 170                 175

Gln Thr Gln Thr Leu Gln Ile Ala Leu Leu Ala Ser Leu Lys Ala Thr
            180                 185                 190

Val Asp Cys Val Thr Ala Phe Ala Glu Thr Asp Phe Arg Pro Asp Met
            195                 200                 205

Ala Lys Ile Asp Val Pro Thr Leu Val Ile His Gly Asp Gly Asp Gln
            210                 215                 220

Ile Val Pro Phe Glu Thr Thr Gly Lys Val Ala Ala Glu Leu Ile Lys
225                 230                 235                 240

Gly Ala Glu Leu Lys Val Tyr Lys Asp Ala Pro His Gly Phe Ala Val
                245                 250                 255

Thr His Ala Gln Gln Leu Asn Glu Asp Leu Leu Ala Phe Leu Lys Arg
            260                 265                 270

Gly Pro Gly Ser Gly Gly Ala Gly Ser Pro Gly Ser Ala Gly Gly Pro
            275                 280                 285

Gly Ser His His His His His His
            290                 295

<210> SEQ ID NO 466
<211> LENGTH: 306
<212> TYPE: PRT
<213> ORGANISM: artificial sequence
<220> FEATURE:
<223> OTHER INFORMATION: synthetic construct

<400> SEQUENCE: 466

Met Ser Thr Phe Val Ala Lys Asp Gly Thr Gln Ile Tyr Phe Lys Asp
1                5                  10                  15

Trp Gly Ser Gly Lys Pro Val Leu Phe Ser His Gly Trp Pro Leu Asp
                 20                  25                  30

Ala Asp Met Trp Glu Tyr Gln Met Glu Tyr Leu Ser Ser Arg Gly Tyr
             35                  40                  45

Arg Thr Ile Ala Phe Asp Arg Arg Gly Phe Gly Arg Ser Asp Gln Pro
     50                  55                  60

Trp Thr Gly Asn Asp Tyr Asp Thr Phe Ala Asp Ile Ala Gln Leu
 65                  70                  75                  80

Ile Glu His Leu Asp Leu Lys Glu Val Thr Leu Val Gly Phe Ser Met
                 85                  90                  95

```
Gly Gly Gly Asp Val Ala Arg Tyr Ile Ala Arg His Gly Ser Ala Arg
            100                 105                 110

Val Ala Gly Leu Val Leu Leu Gly Ala Val Thr Pro Leu Phe Gly Gln
            115                 120                 125

Lys Pro Asp Tyr Pro Gln Gly Val Pro Leu Asp Val Phe Ala Arg Phe
130                 135                 140

Lys Thr Glu Leu Leu Lys Asp Arg Ala Gln Phe Ile Ser Asp Phe Asn
145                 150                 155                 160

Ala Pro Phe Tyr Gly Ile Asn Lys Gly Gln Val Val Ser Gln Gly Val
                165                 170                 175

Gln Thr Gln Thr Leu Gln Ile Ala Leu Leu Ala Ser Leu Lys Ala Thr
            180                 185                 190

Val Asp Cys Val Thr Ala Phe Ala Glu Thr Asp Phe Arg Pro Asp Met
            195                 200                 205

Ala Lys Ile Asp Val Pro Thr Leu Val Ile His Gly Asp Gly Asp Gln
210                 215                 220

Ile Val Pro Phe Glu Thr Thr Gly Lys Val Ala Ala Glu Leu Ile Lys
225                 230                 235                 240

Gly Ala Glu Leu Lys Val Tyr Lys Asp Ala Pro His Gly Phe Ala Val
                245                 250                 255

Thr His Ala Gln Gln Leu Asn Glu Asp Leu Leu Ala Phe Leu Lys Arg
            260                 265                 270

Gly Pro Gly Ser Gly Gly Ala Gly Ser Pro Gly Ser Ala Gly Gly Pro
            275                 280                 285

Gly Ser Gly Lys Gly Lys Gly Lys Gly Lys His His His
            290                 295                 300

His His
305

<210> SEQ ID NO 467
<211> LENGTH: 324
<212> TYPE: PRT
<213> ORGANISM: artificial sequence
<220> FEATURE:
<223> OTHER INFORMATION: synthetic construct

<400> SEQUENCE: 467

Met Ser Thr Phe Val Ala Lys Asp Gly Thr Gln Ile Tyr Phe Lys Asp
1               5                   10                  15

Trp Gly Ser Gly Lys Pro Val Leu Phe Ser His Gly Trp Pro Leu Asp
            20                  25                  30

Ala Asp Met Trp Glu Tyr Gln Met Glu Tyr Leu Ser Ser Arg Gly Tyr
        35                  40                  45

Arg Thr Ile Ala Phe Asp Arg Arg Gly Phe Gly Arg Ser Asp Gln Pro
    50                  55                  60

Trp Thr Gly Asn Asp Tyr Asp Thr Phe Ala Asp Asp Ile Ala Gln Leu
65                  70                  75                  80

Ile Glu His Leu Asp Leu Lys Glu Val Thr Leu Val Gly Phe Ser Met
                85                  90                  95

Gly Gly Gly Asp Val Ala Arg Tyr Ile Ala Arg His Gly Ser Ala Arg
            100                 105                 110

Val Ala Gly Leu Val Leu Leu Gly Ala Val Thr Pro Leu Phe Gly Gln
            115                 120                 125

Lys Pro Asp Tyr Pro Gln Gly Val Pro Leu Asp Val Phe Ala Arg Phe
130                 135                 140

Lys Thr Glu Leu Leu Lys Asp Arg Ala Gln Phe Ile Ser Asp Phe Asn
```

```
              145                 150                 155                 160
Ala Pro Phe Tyr Gly Ile Asn Lys Gly Gln Val Val Ser Gln Gly Val
                165                 170                 175

Gln Thr Gln Thr Leu Gln Ile Ala Leu Leu Ala Ser Leu Lys Ala Thr
                180                 185                 190

Val Asp Cys Val Thr Ala Phe Ala Glu Thr Asp Phe Arg Pro Asp Met
                195                 200                 205

Ala Lys Ile Asp Val Pro Thr Leu Val Ile His Gly Asp Gly Asp Gln
210                 215                 220

Ile Val Pro Phe Glu Thr Thr Gly Lys Val Ala Ala Glu Leu Ile Lys
225                 230                 235                 240

Gly Ala Glu Leu Lys Val Tyr Lys Asp Ala Pro His Gly Phe Ala Val
                245                 250                 255

Thr His Ala Gln Gln Leu Asn Glu Asp Leu Leu Ala Phe Leu Lys Arg
                260                 265                 270

Gly Pro Gly Ser Gly Gly Ala Gly Ser Pro Gly Ser Ala Gly Gly Pro
                275                 280                 285

Gly Ser Asp Pro Thr Lys Pro Pro Arg Thr Pro Thr Ala Asn Thr Ser
                290                 295                 300

Arg Pro His His Asn Phe Gly Ser Gly Gly Gly Ser Pro His His
305                 310                 315                 320

His His His His

<210> SEQ ID NO 468
<211> LENGTH: 61
<212> TYPE: PRT
<213> ORGANISM: artificial sequence
<220> FEATURE:
<223> OTHER INFORMATION: synthetic construct

<400> SEQUENCE: 468

Glu Pro Glu Pro Glu Gly Pro Gly Ser Gly Gly Ala Gly Ser Pro Gly
1               5                   10                  15

Ser Ala Gly Gly Pro Gly Ser Glu Pro Glu Pro Glu Trp Lys Thr Lys
                20                  25                  30

Lys Ile Leu Leu Ser Arg Thr Arg Arg Ile Met Arg Gln Val Val Arg
            35                  40                  45

Ser Val Met His Lys Ile Trp His His His His His
        50                  55                  60

<210> SEQ ID NO 469
<211> LENGTH: 62
<212> TYPE: PRT
<213> ORGANISM: artificial sequence
<220> FEATURE:
<223> OTHER INFORMATION: synthetic construct

<400> SEQUENCE: 469

Glu Pro Glu Pro Glu Pro Glu Pro Glu Pro Glu Gly Pro Gly Ser Gly
1               5                   10                  15

Gly Ala Gly Ser Pro Gly Ser Ala Gly Gly Pro Gly Ser Trp Lys Thr
                20                  25                  30

Lys Lys Ile Leu Leu Ser Arg Thr Arg Arg Ile Met Arg Gln Val Val
            35                  40                  45

Arg Ser Val Met His Lys Ile Trp His His His His His
        50                  55                  60

<210> SEQ ID NO 470
```

<211> LENGTH: 61
<212> TYPE: PRT
<213> ORGANISM: artificial sequence
<220> FEATURE:
<223> OTHER INFORMATION: synthetic construct

<400> SEQUENCE: 470

Glu Pro Glu Pro Glu Gly Pro Gly Ser Gly Gly Ala Gly Ser Pro Gly
1               5                   10                  15

Ser Ala Gly Gly Pro Gly Ser Glu Pro Glu Pro Glu Pro Leu Trp Arg
            20                  25                  30

Arg Ile Thr Lys Arg Lys Leu Val Arg Pro Val Ala Thr Leu Met Trp
        35                  40                  45

Tyr Trp Phe Thr Ser Lys Arg His His His His His His
    50                  55                  60

<210> SEQ ID NO 471
<211> LENGTH: 62
<212> TYPE: PRT
<213> ORGANISM: artificial sequence
<220> FEATURE:
<223> OTHER INFORMATION: synthetic construct

<400> SEQUENCE: 471

Glu Pro Glu Pro Glu Pro Glu Pro Glu Pro Glu Gly Pro Gly Ser Gly
1               5                   10                  15

Gly Ala Gly Ser Pro Gly Ser Ala Gly Gly Pro Gly Ser Pro Leu Trp
            20                  25                  30

Arg Arg Ile Thr Lys Arg Lys Leu Val Arg Pro Val Ala Thr Leu Met
        35                  40                  45

Trp Tyr Trp Phe Thr Ser Lys Arg His His His His His His
    50                  55                  60

<210> SEQ ID NO 472
<211> LENGTH: 57
<212> TYPE: PRT
<213> ORGANISM: artificial sequence
<220> FEATURE:
<223> OTHER INFORMATION: synthetic construct

<400> SEQUENCE: 472

Glu Pro Glu Gly Pro Gly Ser Gly Gly Ala Gly Ser Pro Gly Ser Ala
1               5                   10                  15

Gly Gly Pro Gly Ser Glu Pro Glu Arg Met Leu Ser Arg Ile Leu Arg
            20                  25                  30

Met Phe Val Arg Ile Leu Lys Arg Glu Arg Leu Ser Gln Val Arg Gly
        35                  40                  45

Leu Phe Val His His His His His His
    50                  55

<210> SEQ ID NO 473
<211> LENGTH: 58
<212> TYPE: PRT
<213> ORGANISM: artificial sequence
<220> FEATURE:
<223> OTHER INFORMATION: synthetic construct

<400> SEQUENCE: 473

Glu Pro Glu Pro Glu Pro Glu Gly Pro Gly Ser Gly Gly Ala Gly Ser
1               5                   10                  15

Pro Gly Ser Ala Gly Gly Pro Gly Ser Arg Met Leu Ser Arg Ile Leu
            20                  25                  30

```
Arg Met Phe Val Arg Ile Leu Lys Arg Glu Arg Leu Ser Gln Val Arg
        35                  40                  45

Gly Leu Phe Val His His His His His His
    50                  55
```

<210> SEQ ID NO 474
<211> LENGTH: 65
<212> TYPE: PRT
<213> ORGANISM: artificial sequence
<220> FEATURE:
<223> OTHER INFORMATION: synthetic construct

<400> SEQUENCE: 474

```
Glu Pro Glu Pro Glu Pro Gly Pro Gly Ser Gly Ala Gly Ser
1               5                   10                  15

Pro Gly Ser Ala Gly Gly Pro Gly Ser Glu Pro Glu Pro Glu Pro Glu
            20                  25                  30

Leu Arg Phe Leu Ala Arg Arg Phe Leu Lys Leu Arg Arg Ala Arg Lys
        35                  40                  45

Trp Trp Asn Ala Trp Lys Val Trp Val Thr Arg His His His His
    50                  55                  60

His
65
```

<210> SEQ ID NO 475
<211> LENGTH: 66
<212> TYPE: PRT
<213> ORGANISM: artificial sequence
<220> FEATURE:
<223> OTHER INFORMATION: synthetic construct

<400> SEQUENCE: 475

```
Glu Pro Glu Pro Glu Pro Glu Pro Glu Pro Glu Pro Glu Pro Glu Gly
1               5                   10                  15

Pro Gly Ser Gly Gly Ala Gly Ser Pro Gly Ser Ala Gly Gly Pro Gly
            20                  25                  30

Ser Leu Arg Phe Leu Ala Arg Arg Phe Leu Lys Leu Arg Arg Ala Arg
        35                  40                  45

Lys Trp Trp Asn Ala Trp Lys Val Trp Val Thr Arg His His His His
    50                  55                  60

His His
65
```

<210> SEQ ID NO 476
<211> LENGTH: 325
<212> TYPE: PRT
<213> ORGANISM: artificial sequence
<220> FEATURE:
<223> OTHER INFORMATION: synthetic construct

<400> SEQUENCE: 476

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80
```

Glu Lys Leu Pro Cys Val Val Gln Tyr Ile Gly Tyr Asn Gly Gly Arg
            85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
            130                 135                 140

Met Thr Arg Gly Ile Leu Asp Pro Arg Thr Tyr Tyr Arg Val
145                 150                 155                 160

Phe Thr Asp Ala Val Arg Ala Val Glu Ala Ala Ser Phe Pro Gln
            165                 170                 175

Val Asp Gln Glu Arg Ile Val Ile Ala Gly Ser Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
            275                 280                 285

Tyr Ala Gly Pro Lys Glu Ile Pro Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 477
<211> LENGTH: 272
<212> TYPE: PRT
<213> ORGANISM: Pseudomonas fluorescens

<400> SEQUENCE: 477

Met Ser Thr Phe Val Ala Lys Asp Gly Thr Gln Ile Tyr Phe Lys Asp
1               5                   10                  15

Trp Gly Ser Gly Lys Pro Val Leu Phe Ser His Gly Trp Pro Leu Asp
            20                  25                  30

Ala Asp Met Trp Glu Tyr Gln Met Glu Tyr Leu Ser Ser Arg Gly Tyr
            35                  40                  45

Arg Thr Ile Ala Phe Asp Arg Arg Gly Phe Gly Arg Ser Asp Gln Pro
        50                  55                  60

Trp Thr Gly Asn Asp Tyr Asp Thr Phe Ala Asp Ile Ala Gln Leu
65                  70                  75                  80

Ile Glu His Leu Asp Leu Lys Glu Val Thr Leu Val Gly Phe Ser Met
            85                  90                  95

Gly Gly Gly Asp Val Ala Arg Tyr Ile Ala Arg His Gly Ser Ala Arg
            100                 105                 110

Val Ala Gly Leu Val Leu Leu Gly Ala Val Thr Pro Leu Phe Gly Gln
            115                 120                 125

```
Lys Pro Asp Tyr Pro Gln Gly Val Pro Leu Asp Val Phe Ala Arg Phe
    130                 135                 140

Lys Thr Glu Leu Leu Lys Asp Arg Ala Gln Phe Ile Ser Asp Phe Asn
145                 150                 155                 160

Ala Pro Phe Tyr Gly Ile Asn Lys Gly Gln Val Val Ser Gln Gly Val
                165                 170                 175

Gln Thr Gln Thr Leu Gln Ile Ala Leu Leu Ala Ser Leu Lys Ala Thr
            180                 185                 190

Val Asp Cys Val Thr Ala Phe Ala Glu Thr Asp Phe Arg Pro Asp Met
        195                 200                 205

Ala Lys Ile Asp Val Pro Thr Leu Val Ile His Gly Asp Gly Asp Gln
    210                 215                 220

Ile Val Pro Phe Glu Thr Thr Gly Lys Val Ala Ala Glu Leu Ile Lys
225                 230                 235                 240

Gly Ala Glu Leu Lys Val Tyr Lys Asp Ala Pro His Gly Phe Ala Val
                245                 250                 255

Thr His Ala Gln Gln Leu Asn Glu Asp Leu Leu Ala Phe Leu Lys Arg
            260                 265                 270

<210> SEQ ID NO 478
<211> LENGTH: 216
<212> TYPE: PRT
<213> ORGANISM: Mycobacterium smegmatis

<400> SEQUENCE: 478

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
                20                  25                  30

Arg Trp Thr Gly Val Leu Ala Gln Gln Leu Gly Ala Asp Phe Glu Val
            35                  40                  45

Ile Glu Glu Gly Leu Ser Ala Arg Thr Thr Asn Ile Asp Asp Pro Thr
        50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Ser Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu
    210                 215

<210> SEQ ID NO 479
```

```
<211> LENGTH: 376
<212> TYPE: PRT
<213> ORGANISM: artificial sequence
<220> FEATURE:
<223> OTHER INFORMATION: synthetic construct

<400> SEQUENCE: 479
```

| | | | | | | | | | | | | | | | |
|---|---|---|---|---|---|---|---|---|---|---|---|---|---|---|---|
| Met | Ser | Thr | Phe | Val | Ala | Lys | Asp | Gly | Thr | Gln | Ile | Tyr | Phe | Lys | Asp |
| 1 | | | | 5 | | | | | 10 | | | | | 15 | |
| Trp | Gly | Ser | Gly | Lys | Pro | Val | Leu | Phe | Ser | His | Gly | Trp | Pro | Leu | Asp |
| | | | 20 | | | | | 25 | | | | | 30 | | |
| Ala | Asp | Met | Trp | Glu | Tyr | Gln | Met | Glu | Tyr | Leu | Ser | Ser | Arg | Gly | Tyr |
| | | 35 | | | | | 40 | | | | | 45 | | | |
| Arg | Thr | Ile | Ala | Phe | Asp | Arg | Arg | Gly | Phe | Gly | Arg | Ser | Asp | Gln | Pro |
| | 50 | | | | | 55 | | | | | 60 | | | | |
| Trp | Thr | Gly | Asn | Asp | Tyr | Asp | Thr | Phe | Ala | Asp | Asp | Ile | Ala | Gln | Leu |
| 65 | | | | | 70 | | | | | 75 | | | | | 80 |
| Ile | Glu | His | Leu | Asp | Leu | Lys | Glu | Val | Thr | Leu | Val | Gly | Phe | Ser | Met |
| | | | | 85 | | | | | 90 | | | | | 95 | |
| Gly | Gly | Gly | Asp | Val | Ala | Arg | Tyr | Ile | Ala | Arg | His | Gly | Ser | Ala | Arg |
| | | | 100 | | | | | 105 | | | | | 110 | | |
| Val | Ala | Gly | Leu | Val | Leu | Gly | Ala | Val | Thr | Pro | Leu | Phe | Gly | Gln |
| | | 115 | | | | | 120 | | | | | 125 | | | |
| Lys | Pro | Asp | Tyr | Pro | Gln | Gly | Val | Pro | Leu | Asp | Val | Phe | Ala | Arg | Phe |
| | 130 | | | | | 135 | | | | | 140 | | | | |
| Lys | Thr | Glu | Leu | Leu | Lys | Asp | Arg | Ala | Gln | Phe | Ile | Ser | Asp | Phe | Asn |
| 145 | | | | | 150 | | | | | 155 | | | | | 160 |
| Ala | Pro | Phe | Tyr | Gly | Ile | Asn | Lys | Gly | Gln | Val | Val | Ser | Gln | Gly | Val |
| | | | | 165 | | | | | 170 | | | | | 175 | |
| Gln | Thr | Gln | Thr | Leu | Gln | Ile | Ala | Leu | Leu | Ala | Ser | Leu | Lys | Ala | Thr |
| | | | 180 | | | | | 185 | | | | | 190 | | |
| Val | Asp | Cys | Val | Thr | Ala | Phe | Ala | Glu | Thr | Asp | Phe | Arg | Pro | Asp | Met |
| | | 195 | | | | | 200 | | | | | 205 | | | |
| Ala | Lys | Ile | Asp | Val | Pro | Thr | Leu | Val | Ile | His | Gly | Asp | Gly | Asp | Gln |
| | 210 | | | | | 215 | | | | | 220 | | | | |
| Ile | Val | Pro | Phe | Glu | Thr | Thr | Gly | Lys | Val | Ala | Ala | Glu | Leu | Ile | Lys |
| 225 | | | | | 230 | | | | | 235 | | | | | 240 |
| Gly | Ala | Glu | Leu | Lys | Val | Tyr | Lys | Asp | Ala | Pro | His | Gly | Phe | Ala | Val |
| | | | | 245 | | | | | 250 | | | | | 255 | |
| Thr | His | Ala | Gln | Gln | Leu | Asn | Glu | Asp | Leu | Leu | Ala | Phe | Leu | Lys | Arg |
| | | | 260 | | | | | 265 | | | | | 270 | | |
| Gly | Pro | Gly | Ser | Gly | Gly | Ala | Gly | Ser | Pro | Gly | Ser | Ala | Gly | Gly | Pro |
| | | 275 | | | | | 280 | | | | | 285 | | | |
| Gly | Ser | Pro | Ser | Ala | Gln | Ser | Gln | Leu | Pro | Asp | Lys | His | Ser | Gly | Leu |
| | 290 | | | | | 295 | | | | | 300 | | | | |
| His | Glu | Arg | Ala | Pro | Gln | Arg | Tyr | Gly | Pro | Glu | Pro | Glu | Pro | Glu | Pro |
| 305 | | | | | 310 | | | | | 315 | | | | | 320 |
| Glu | Pro | Ile | Pro | Glu | Pro | Pro | Lys | Glu | Ala | Pro | Val | Val | Ile | Glu | Lys |
| | | | | 325 | | | | | 330 | | | | | 335 | |
| Pro | Lys | Pro | Lys | Pro | Lys | Pro | Lys | Pro | Lys | Pro | Pro | Ala | His | Asp | His |
| | | | 340 | | | | | 345 | | | | | 350 | | |
| Lys | Asn | Gln | Lys | Glu | Thr | His | Gln | Arg | His | Ala | Ala | Gly | Ser | Gly | Gly |
| | | 355 | | | | | 360 | | | | | 365 | | | |
| Gly | Gly | Ser | Pro | His | His | His | His |
| | 370 | | | | | 375 | | |